US009826129B2

(12) United States Patent
Inasaki et al.

(10) Patent No.: US 9,826,129 B2
(45) Date of Patent: Nov. 21, 2017

(54) NEAR-INFRARED-RAY-ABSORBING COMPOSITION, NEAR-INFRARED-RAY CUT FILTER USING SAME, MANUFACTURING METHOD THEREFOR, CAMERA MODULE, AND MANUFACTURING METHOD THEREFOR

(71) Applicant: FUJIFILM CORPORATION, Tokyo (JP)

(72) Inventors: Takeshi Inasaki, Haibara-gun (JP); Takashi Kawashima, Haibara-gun (JP); Seiichi Hitomi, Haibara-gun (JP); Kouitsu Sasaki, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/876,287

(22) Filed: Oct. 6, 2015

(65) Prior Publication Data
US 2016/0037034 A1 Feb. 4, 2016

Related U.S. Application Data

(63) Continuation of application No. PCT/JP2014/060439, filed on Apr. 10, 2014.

(30) Foreign Application Priority Data

| Apr. 11, 2013 | (JP) | 2013-083139 |
| Jul. 24, 2013 | (JP) | 2013-153988 |
| Jan. 21, 2014 | (JP) | 2014-008918 |

(51) Int. Cl.
| H04N 5/225 | (2006.01) |
| C07F 9/30 | (2006.01) |
| C07F 7/18 | (2006.01) |
| C07F 9/40 | (2006.01) |
| G02B 5/20 | (2006.01) |
| C07F 9/12 | (2006.01) |
| C07F 9/09 | (2006.01) |
| C07F 9/143 | (2006.01) |
| C07F 9/58 | (2006.01) |
| C07F 1/08 | (2006.01) |
| C07F 9/06 | (2006.01) |
| C09B 57/10 | (2006.01) |
| G02B 5/22 | (2006.01) |
| H04N 5/33 | (2006.01) |

(52) U.S. Cl.
CPC ............ *H04N 5/2254* (2013.01); *C07F 1/08* (2013.01); *C07F 7/1804* (2013.01); *C07F 9/06* (2013.01); *C07F 9/098* (2013.01); *C07F 9/12* (2013.01); *C07F 9/143* (2013.01); *C07F 9/304* (2013.01); *C07F 9/4021* (2013.01); *C07F 9/582* (2013.01); *C09B 57/10* (2013.01); *G02B 5/208* (2013.01); *G02B 5/22* (2013.01); *H04N 5/2257* (2013.01); *H04N 5/33* (2013.01)

(58) Field of Classification Search
CPC .. C07F 1/08; C07F 7/1804; C07F 9/06; C07F 9/098; C07F 9/12; C07F 9/143; C07F 9/304; C07F 9/4021; C07F 9/582; C09B 57/10; G02B 5/208; G02B 5/22; H04N 5/2254; H04N 5/2257; H04N 5/33
USPC .......................................................... 252/587
See application file for complete search history.

(56) References Cited

U.S. PATENT DOCUMENTS 5,354,514 A 10/1994 Satake et al.

FOREIGN PATENT DOCUMENTS

| JP | 02-034682 A | 2/1990 | |
| JP | H 07-033981 A | 2/1995 | |
| JP | 11-052127 A | 2/1999 | |
| JP | 11-101911 A | 4/1999 | |
| JP | 2000-007870 A | 1/2000 | |
| JP | 2002-006101 A | 1/2002 | |
| JP | 2002-069305 A | 3/2002 | |
| JP | 2003-221523 A | 8/2003 | |
| JP | 2007-191602 A | 8/2007 | |
| JP | 2008-091535 A | 4/2008 | |
| JP | 2010-134457 A | 6/2010 | |
| JP | 2010-160380 A | 7/2010 | |
| JP | 2011-063814 A | 3/2011 | |
| JP | 2013-087233 A | 5/2013 | |
| TW | 201428052 A | 7/2014 | |
| WO | WO1999026952 | * 3/1999 | ............... C07F 9/09 |
| WO | 2009/133668 A1 | 11/2009 | |

OTHER PUBLICATIONS

International Preliminary Report on Patentability dated Oct. 22, 2015 from the International Bureau in counterpart International Application No. PCT/JP2014/060439.
International Search Report of PCT/JP2014/060439, dated Jul. 8, 2014. [PCT/ISA/210].
Written Opinion of PCT/JP2014/060439, dated Jul. 8, 2014. [PCT/ISA/237].
Extended European Search Report dated Mar. 31, 2016 from the European Patent Office in counterpart European Application No. 14782890.9.
Office Action dated Feb. 20, 2017 from the Korean Intellectual Property Office in counterpart Korean Application No. 10-2015-7027279.
Office Action dated May 18, 2017, issued from the Intellectual Property Office of Taiwan in counterpart Taiwanese Application No. 103113423.

(Continued)

*Primary Examiner* — Ling Choi
*Assistant Examiner* — Chun-Cheng Wang
(74) *Attorney, Agent, or Firm* — Sughrue Mion, PLLC

(57) ABSTRACT

Provided are a near-infrared-ray-absorbing composition having strong near-infrared shielding properties when a cured film is produced, a near-infrared-ray cut filter, a manufacturing method therefor, a camera module, and a manufacturing method therefor. The near-infrared-ray-absorbing composition includes a copper complex obtained by reacting a compound (A) having at least two coordination sites with a copper component.

12 Claims, 2 Drawing Sheets

(56) References Cited

OTHER PUBLICATIONS

Office Action dated Nov. 1, 2016, from the Japanese Patent Office in counterpart Japanese Application No. 2014-081393.
Katsuhira Yoshida et al. "The effect of Metal Chelate Complexation on the Reactivity and Absorption Spectra of 1,2-Naphthoquinones: New Types of Near-infrared-absorbing Metal Complex Dyes", J. Chem. Soc. Perkin Trans. 1, Jul. 1990, No. 7, pp. 1891-1895 (8 pages total).
Office Action dated Jul. 3, 2017, from the State Intellectual Property Office of People's Republic of China in counterpart Chinese Application No. 201480020247.8.
Office Action dated Aug. 17, 2017 from the Korean Intellectual Property Office in counterpart Korean Application No. 10-2015-7027279.

* cited by examiner

NEAR-INFRARED-RAY-ABSORBING COMPOSITION, NEAR-INFRARED-RAY CUT FILTER USING SAME, MANUFACTURING METHOD THEREFOR, CAMERA MODULE, AND MANUFACTURING METHOD THEREFOR

CROSS-REFERENCE TO RELATED APPLICATIONS

This application is a Continuation of PCT International Application No. PCT/JP2014/060439 filed on Apr. 10, 2014, which claims priority under 35 U.S.C §119(a) to Japanese Patent Application No. 2013-083139 filed on Apr. 11, 2013, Japanese Patent Application No. 2013-153988 filed on Jul. 24, 2013 and Japanese Patent Application No. 2014-008918 filed on Jan. 21, 2014. Each of the above application(s) is hereby expressly incorporated by reference, in its entirety, into the present application.

BACKGROUND OF THE INVENTION

1. Field of the Invention

The present invention relates to a near-infrared-ray-absorbing composition, a near-infrared-ray cut filter using the same, a manufacturing method therefor, a camera module, and a manufacturing method therefor.

2. Description of the Related Art

A CCD or CMOS that is a solid-state imaging element for color images has been used for video cameras, digital still cameras, mobile phones equipped with a camera function, and the like. In the solid-state imaging element, since a silicon photodiode having sensitivity to near-infrared rays is used in the light-receiving section, it is necessary to revise the luminosity factor and a near-infrared-ray cut filter is frequently used.

As a material for forming the above-described near-infrared-ray cut filter, for example, near-infrared-ray-absorbing compositions in which a phosphoric acid ester copper complex is used (JP2002-69305A, JP1999-52127A (JP-H11-52127A), and JP2011-63814A) are known.

SUMMARY OF THE INVENTION

However, as a result of the present inventors' studies, it was found that, when the copper complex described in JP2002-69305A, JP1999-52127A (JP-H11-52127A), and JP2011-63814A is used, the solubility in a solvent is low or, when a near-infrared-ray cut filter is formed using a composition including the copper complex, there are cases in which near-infrared shielding properties cannot be enhanced.

The present invention aims to solve the above-described problems and an object of the present invention is to provide a near-infrared-ray-absorbing composition having strong near-infrared shielding properties when a cured film is produced.

As a result of intensive studies on the basis of the above-described circumstances, the present inventors found that the above-described problems can be solved using a specific copper complex.

In addition, it was found that, when a copper complex obtained by reacting a compound having two monoanionic coordination sites or a compound having a salt thereof is blended into a near-infrared-ray-absorbing composition, the above-described problems can be solved.

These results are not confined by any theories, but it is assumed that the structure of the copper complex obtained using the compound having the two monoanionic coordination sites becomes distorted, and the color valency improves (light in a visible range is not absorbed, and the light-absorbing capability in the near-infrared range (spectral characteristics) improves), and consequently, the near-infrared-shielding properties can be enhanced when a cured film is produced.

Specifically, the above-described problems have been solved by means <1> described below and preferably means <2> to <19>.

<1> A near-infrared-ray-absorbing composition including a copper complex obtained by reacting a compound (A) having at least two coordination sites with a copper component.

<2> A near-infrared-ray-absorbing composition including a copper complex obtained by reacting a compound (A1) having two monoanionic coordination sites or a compound having a salt thereof with a copper component.

<3> The near-infrared-ray-absorbing composition according to <1>, in which the compound (A) is a compound (A2) respectively having at least one coordination site to be coordinated with an anion and at least one coordinating atom to be coordinated with an unshared electron pair.

<4> The near-infrared-ray-absorbing composition according to <1>, in which the compound (A) is a compound (A3) having two or more coordinating atoms to be coordinated with an unshared electron pair.

<5> The near-infrared-ray-absorbing composition according to <2>, in which the compound (A1) is represented by General Formula (10) described below:

$$X^1\text{-}L^1\text{-}X^2 \qquad \text{General Formula (10)}$$

In General Formula (10), each of $X^1$ and $X^2$ independently represents the monoanionic coordination site, and $L^1$ represents an alkylene group, an alkenylene group, an arylene group, a heterocyclic group, —O—, —S—, —NR$^{N1}$—, —CO—, —CS—, —SO$_2$—, or a divalent linking group formed of a combination thereof; here, $R^{N1}$ represents a hydrogen atom, an alkyl group, an aryl group, or an aralkyl group.

<6> The near-infrared-ray-absorbing composition according to <5>, in which $X^1$ and $X^2$ are represented by General Formula (12), (13) or (13A) described below:

General Formula (12)

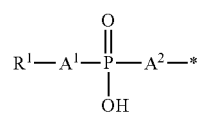

General Formula (13)

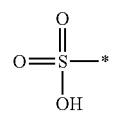

General Formula (13A)

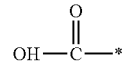

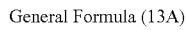

In General Formula (12), $R^1$ represents an alkyl group, an alkenyl group, an aryl group, or an aralkyl group; each of $A^1$ and $A^2$ independently represents an oxygen atom, a sulfur atom, or a single bond; and, in General Formulae (12), (13) and (13A), * represents a connecting portion to $L^1$.

<7> The near-infrared-ray-absorbing composition according to <5>, in which $X^1$ and $X^2$ are represented by General Formula (12) or (13) described below:

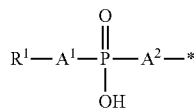

General Formula (12)

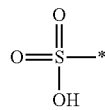

General Formula (13)

In General Formula (12), $R^1$ represents an alkyl group, an alkenyl group, an aryl group, or an aralkyl group; each of $A^1$ and $A^2$ independently represents an oxygen atom, a sulfur atom, or a single bond; and, in General Formulae (12) and (13), * represents a connecting portion to $L^1$.

<8> The near-infrared-ray-absorbing composition according to any one of <5> to <7>, in which $L^1$ is the following structure or a group formed of a combination thereof;

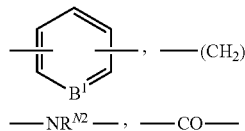

n1 represents an integer from 1 to 10, $B^1$ represents —CH— or —N—, and $R^{N2}$ represents a hydrogen atom, an alkyl group, an aryl group, or an aralkyl group.

<9> The near-infrared-ray-absorbing composition according to <8>, in which $L^1$ includes at least one of the following structures.

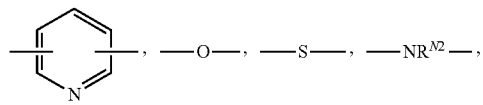

<10> The near-infrared-ray-absorbing composition according to <8> or <9>, in which $L^1$ is represented by any of General Formulae (14) to (17) described below:

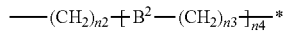
(14)

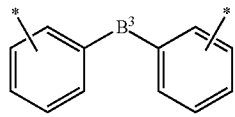
(15)

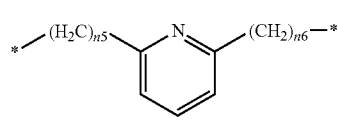
(16)

(17)

In General Formula (14), $B^2$ represents —S—, —O—, or —NR$^{N3}$—, each of n2 and n3 independently represents an integer from 0 to 5, and n4 represents an integer from 1 to 5; in General Formula (15), $B^3$ represents —S—, —O—, or —NR$^{N4}$—; each of $R^{N3}$ and $R^{N4}$ independently represents a hydrogen atom, an alkyl group, an aryl group, or an aralkyl group; in General Formula (16), each of n5 and n6 independently represents an integer from 1 to 5; and, in General Formula (17), n7 represents an integer from 1 to 10; and * represents a connecting portion to $X^1$ or $X^2$.

<11> The near-infrared-ray-absorbing composition according to any one of <6> to <10>, in which $A^1$ and $A^2$ are single bonds.

<12> The near-infrared-ray-absorbing composition according to <3>, in which the compound (A2) is represented by General Formula (1);

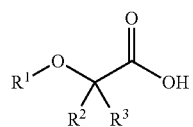

General Formula (1)

In General Formula (1), $R^1$ represents a hydrocarbon group; $R^2$ and $R^3$ represent hydrogen atoms.

<13> The near-infrared-ray-absorbing composition according to any one of <1> to <12>, further including a curable compound and a solvent.

<14> The near-infrared-ray-absorbing composition according to <13>, in which the curable compound is at least one of a trifunctional or higher acrylate, a trifunctional or higher methacrylate, and a trifunctional or higher epoxy resin.

<15> A near-infrared-ray-absorbing composition including a copper as a central metal and a compound having two monoanionic coordination sites as a ligand, or a copper complex including a structure having two monoanionic coordination sites.

<16> A near-infrared-ray cut filter obtained using the near-infrared-ray-absorbing composition according to any one of <1> to <15>.

<17> A method for manufacturing a near-infrared-ray cut filter, including a step of forming a film by applying the near-infrared-ray-absorbing composition according to any one of <1> to <15> to a light-receiving side of a solid-state imaging element.

<18> A camera module having a solid-state imaging element and a near-infrared-ray cut filter disposed in a light-receiving side of the solid-state imaging element, in which the near-infrared-ray cut filter is formed by curing the near-infrared-ray-absorbing composition according to any one of <1> to <15>.

<19> A method for manufacturing a camera module having a solid-state imaging element and a near-infrared-ray cut filter disposed in a light-receiving side of the solid-state imaging element, including a step of forming the near-infrared-ray cut filter by applying the near-infrared-ray-absorbing composition according to any one of <1> to <15> to the light-receiving side of the solid-state imaging element.

According to the present invention, it is possible to provide a near-infrared-ray-absorbing composition having strong near-infrared shielding properties when a cured film is produced.

DESCRIPTION OF THE PREFERRED EMBODIMENTS

Figure 1:
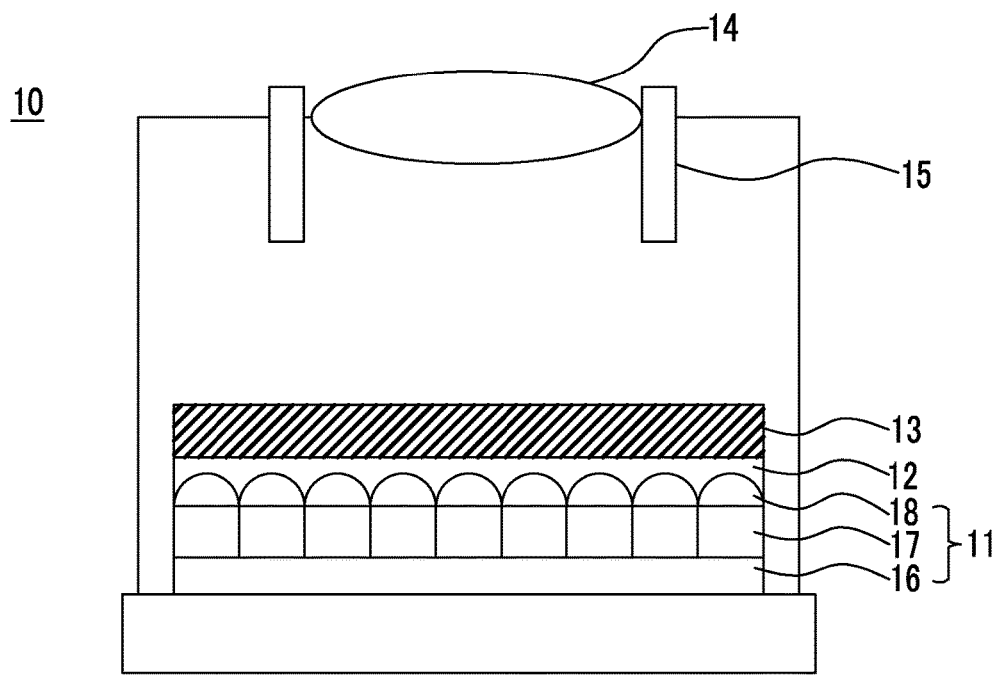
FIG. 1 is a schematic sectional view illustrating a configuration of a camera module including a near-infrared-ray cut filter according to an embodiment of the present invention.

Hereinafter, the contents of the present invention will be described in detail. In the present specification, "to" used to express numerical ranges will be used with a meaning that numerical values before and after the "to" are included in the numerical ranges as the lower limit value and the upper limit value.

In the present specification, "(meth)acrylates" represent acrylates and methacrylates, "(meth)acrylic" represents acrylic and methacrylic, and "(meth)acryloyl" represents acryloyl and methacryloyl. In addition, in the present specification, "monomers" and "monomers" refer to the same thing. Monomers are classified into oligomers and polymers and refer to compounds having a weight-average molecular weight of 2,000 or less. In the present specification, polymerizing compounds refer to compounds having a polymerizable functional group and may be monomers or polymers. Polymerizable functional groups refer to groups that participate in polymerization reactions.

Furthermore, regarding the denoting of a group (atomic group) in the present specification, a group not denoted using 'substituted' and 'unsubstituted' refers to both a group (atomic group) having no substituents and a group (atomic group) having a substituent. For example, an "alkyl group" refers not only to an alkyl group having no substituents (unsubstituted alkyl group) but also to an alkyl group having a substituent (substituted alkyl group).

Regarding the method for measuring the weight-average molecular weight and number-average molecular weight of a compound used in the present invention, the molecular weights can be measured using gel permeation chromatography (GPC) and are defined as polystyrene-equivalent values obtained from the measurement through GPC. For example, the molecular weight can be obtained using an HLC-8220 (manufactured by Tosoh Corporation), a TSKgel Super AWM-H (manufactured by Tosoh Corporation), 6.0 mm ID×15.0 cm as a column, and an N-methylpyrrolidinone (NMP) solution of 10 mmol/L of lithium bromide as an eluent).

A near-infrared ray refers to a light ray (electromagnetic wave) having a maximum absorption wavelength in a range of 700 nm to 2500 nm.

In the present specification, the total solid content refers to the total mass of components remaining after a solvent is removed from the total composition of a composition. The solid content in the present invention refers to the solid content at 25° C.

<Near-infrared-ray-absorbing Composition>

The near-infrared-ray-absorbing composition of the present invention (hereinafter, also referred to as the composition of the present invention) includes a copper complex obtained by reacting a compound (A) having at least two coordination sites with a copper component. When the composition is provided with the above-described configuration, it is possible to enhance the near-infrared shielding properties when a cured film is produced. In addition, according to the composition of the present invention, it is possible to improve the solubility of the copper complex in the composition of the present invention in a solvent.

The composition of the present invention may include a copper complex in which copper is a central metal and a compound having at least two coordination sites is a ligand, or a copper complex including a structure having at least two coordination sites.

According to the composition of the present invention, it is possible to obtain a near-infrared-ray cut filter having a high transmissivity in a visible range and capable of realizing strong near-infrared shielding properties. In addition, according to the present invention, it is possible to decrease the film thickness of the near-infrared-ray cut filter and to contribute to a decrease in the height of the camera module.

The composition of the present invention includes at least the copper complex obtained by reacting the above-described compound (A) used in the present invention. The copper complex has a form of a copper complex (copper compound) in which the copper central metal is coordinated with the above-described compound (A) used in the present invention or the compound having a salt thereof. In the copper complex used in the present invention, copper is generally divalent copper, and the copper complex can be obtained by, for example, mixing, reacting, and the like the above-described compound (A) used in the present invention or the compound having a salt thereof with a copper component (copper or a compound including copper). The compound (A) can be used singly or a combination of two or more compounds can be used.

Here, when the structures of the copper component and the compound (A) used in the present invention can be detected in the composition of the present invention, it can be said that a copper complex having the above-described compound (A) used in the present invention as a ligand is formed in the composition of the present invention. Examples of a method for detecting copper and the compound (A) used in the present invention in the composition of the present invention include ICP atomic emission spectroscopy, and copper and the compound (A) used in the present invention can be detected using this method.

Specific aspects of the compound having at least two coordination sites (hereinafter, also referred to as the compound (A)) include a compound having two monoanionic coordination sites (hereinafter, also referred to as the compound (A1)), a compound respectively having at least one coordination site to be coordinated with an anion and at least one coordinating atom to be coordinated with an unshared electron pair (hereinafter, also referred to as the compound (A2)), a compound having two or more coordinating atoms to be coordinated with an unshared electron pair (hereinafter, also referred to as the compound (A3)), and the like. Each of the compounds (A1) to (A3) can be independently used singly or a combination of two or more compounds can be used.

<<Compound (A1)>>

A first preferred embodiment of the compound (A) is a compound having two monoanionic coordination sites.

Here, the monoanionic coordination site refers to a site to be coordinated with a copper atom through a functional group having one negative charge in the coordination with a copper atom. Examples of a structure having the above-described monoanionic coordination site include structures illustrated below (a carboxyl group, a phosphoric acid diester group, a phosphonic acid monoester group, a phosphinic acid group, a sulfo group, and a hydroxyl group) or salts thereof.

Here, a compound having a site to be coordinated with a copper atom through a functional group having two negative charges as the anionic coordination site, that is, a compound having one dianionic coordination site is not the compound (A1) having two monoanionic coordination sites. For example, a phosphonic acid compound represented by General Formula (1) described in Paragraph [0026] in JP2011-63814A is not the compound (A1) used in the present invention.

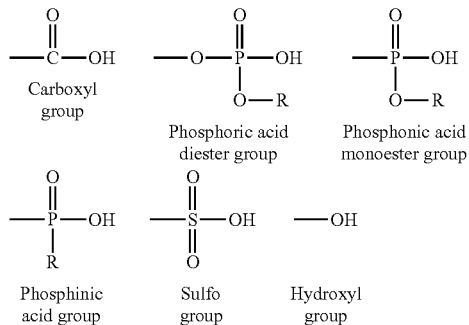

The structure having the monoanionic coordination site forms a copper complex when, for example, being coordinated with a copper atom as described below. For example, (1) a carboxyl group-copper complex, (2) a phosphoric acid diester group-copper complex, (3) a phosphonic acid monoester group-copper complex, (4) a phosphinic acid group-copper complex, (5) a sulfo group-copper complex, and (6) a hydroxyl group-copper complex are formed.

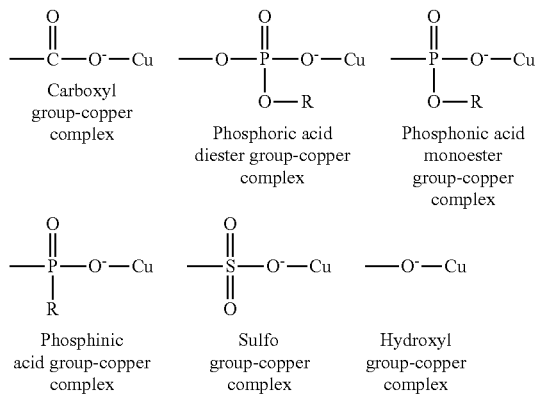

The compound (A1) used in the present invention is, more specifically, preferably represented by General Formula (10) described below.

$X^1$-$L^1$-$X^2$    General Formula (10)

(in General Formula (10), each of $X^1$ and $X^2$ independently represents the monoanionic coordination site, and $L^1$ represents an alkylene group, an alkenylene group, an arylene group, a heterocyclic group, —O—, —S—, —$NR^{N1}$—, —CO—, —CS—, —$SO_2$—, or a divalent linking group formed of a combination thereof; here, $R^{N1}$ represents a hydrogen atom, an alkyl group, an aryl group, or an aralkyl group.)

In General Formula (10), $L^1$ represents an alkylene group, an alkenylene group, an arylene group, a heterocyclic group, —O—, —S—, —$NR^{N1}$—, —CO—, —CS—, —$SO_2$—, or a divalent linking group formed of a combination thereof. Here, $NR^{N1}$ represents a hydrogen atom, an alkyl group, an aryl group, or an aralkyl group.

Examples of the alkylene group include a substituted or unsubstituted linear or branched alkylene group having 1 to 20 carbon atoms, a substituted or unsubstituted cyclic alkylene group having 3 to 20 carbon atoms, and the like.

The alkenylene group is preferably a substituted or unsubstituted alkenylene group having 2 to 10 carbon atoms and more preferably a substituted or unsubstituted alkenylene group having 2 to 8 carbon atoms.

The arylene group is preferably a substituted or unsubstituted arylene group having 6 to 18 carbon atoms and more preferably a substituted or unsubstituted arylene group having 6 to 14 carbon atoms. In addition, the arylene group is a monocyclic ring or a condensed ring, is preferably a monocyclic ring or a condensed ring having 2 to 8 condensations, and more preferably a monocyclic ring or a condensed ring having 2 to 4 condensations. Specific examples thereof include a phenylene group and a naphthylene group.

Examples of the heterocyclic group include a ring having a hetero atom in an alicyclic group or an aromatic heterocyclic group. The heterocyclic group is preferably a 5-membered ring or a 6-membered ring. In addition, the heterocyclic group is a monocyclic ring or a condensed ring, preferably a monocyclic ring or a condensed ring having 2 to 8 condensations, and more preferably a monocyclic ring or a condensed ring having 2 to 4 condensations. Specifically, the heterocyclic group is a monocyclic ring containing at least one of nitrogen, oxygen, and sulfur atoms or a heteroarylene group derived from a polycyclic aromatic ring. Examples of a heterocycle include an oxolane ring, an oxane ring, a thiolane ring, an oxizole ring, a thiophene ring, a thianthrene ring, a furan ring, a pyran ring, an isobenzofuran ring, a chromene ring, a xanthene ring, a phenoxazine ring, a pyrrole ring, a pyrazole ring, an isothiazole ring, an isoxazole ring, a pyrazine ring, a pyrimidine ring, a pyridazine ring, an indolizine ring, an isoindolizine ring, an indole ring, an indazole ring, a purine ring, a quinolizine ring, an isoquinoline ring, a phthalazine ring, a naphthyridine ring, a quinazoline ring, a shinorine ring, a pteridine ring, a carbazole ring, a carboline ring, a phenanthrene ring, an acridine ring, a perimidine ring, a phenanthroline ring, a phthalazine ring, a furazan ring, and the like.

In —$NR^{N1}$—, $R^{N1}$ represents a hydrogen atom, an alkyl group, an aryl group, or an aralkyl group.

The alkyl group as $R^{N1}$ may have any of a linear shape, a branched shape, and a ring shape. The linear or branched alkyl group is preferably a substituted or unsubstituted alkyl group having 1 to 20 carbon atoms and more preferably a substituted or unsubstituted alkyl group having 1 to 12 carbon atoms. The cyclic alkyl group may be either a monocyclic ring or a polycyclic ring. The cyclic alkyl group is preferably a substituted or unsubstituted cycloalkyl group having 3 to 20 carbon atoms and more preferably a substituted or unsubstituted cycloalkyl group having 4 to 14 carbon atoms.

The aryl group as $R^{N1}$ is preferably a substituted or unsubstituted aryl group having 6 to 18 carbon atoms, more preferably a substituted or unsubstituted aryl group having 6 to 14 carbon atoms, and still more preferably an unsubstituted aryl group having 6 to 14 carbon atoms. Specific examples thereof include a phenyl group and a naphthyl group.

The aralkyl group as $R^{N1}$ is preferably a substituted or unsubstituted aralkyl group having 7 to 20 carbon atoms and more preferably an unsubstituted aralkyl group having 7 to 15 carbon atoms.

Examples of a substituent that the above-described groups may have include a polymerizable group (preferably a polymerizable group having a carbon-carbon double bond), a halogen atom (a fluorine atom, a chlorine atom, a bromine atom, or an iodine atom), an alkyl group, a carboxylic acid ester group, a halogenated alkyl group, an alkoxy group, a methacryloyloxy group, an acryloyloxy group, an ether group, a sulfonyl group, a sulfide group, an amide group, an acyl group, a hydroxy group, a carboxyl group, an aralkyl group, $-Si-(OR^{N22})_3$, and the like.

In addition, the substituent that the above-described groups may have may be a combination of at least any one of the above-described substituents and at least one of —O—, —CO—, —COO—, and —COOR'. Here, R' is preferably a linear alkyl group having 1 to 10 carbon atoms, a branched alkyl group having 3 to 10 carbon atoms, or a cyclic alkyl group having 3 to 10 carbon atoms.

Examples of the polymerizable group include polymerizable groups having a carbon-carbon double bond (preferably a vinyl group and a (meth)acryloyloxy group), (meth) acryloyl groups, epoxy groups, aziridinyl groups, and the like.

The alkyl group may have any of a linear shape, a branched shape, and a ring shape. The linear or branched alkyl group is preferably an alkyl group having 1 to 10 carbon atoms, still more preferably an alkyl group having 1 to 8 carbon atoms, and still more preferably an alkyl group having 1 to 4 carbon atoms. The cyclic alkyl group may be either a monocyclic ring or a polycyclic ring. The cyclic alkyl group is preferably a cycloalkyl group having 3 to 20 carbon atoms and more preferably a cycloalkyl group having 4 to 10 carbon atoms.

The halogenated alkyl group is preferably an alkyl group substituted with a fluorine atom. Particularly, the halogenated alkyl group is preferably an alkyl group having two or more fluorine atoms and 1 to 10 carbon atoms, and may have any of a linear shape, a branched shape, and a ring shape and preferably has a linear shape or a branched shape. The number of carbon atoms in the alkyl group substituted with fluorine atoms is more preferably in a range of 1 to 10, more preferably in a range of 1 to 5, and more preferably in a range of 1 to 3. In the alkyl group substituted with a fluorine atom, the structure at the terminal is preferably (—CF$_3$). The fluorine atom substitution fraction of the alkyl group substituted with fluorine atoms is preferably in a range of 50% to 100% and more preferably in a range of 80% to 100%. Here, the fluorine atom substitution fraction refers to the fraction (%) of hydrogen atoms substituted with fluorine atoms in the alkyl group substituted with fluorine atoms.

Particularly, the halogenated alkyl group is more preferably a perfluoroalkyl group and still more preferably a perfluoroalkyl group having 1 to 10 carbon atoms.

In —Si—(OR$^{N22}$)$_3$, R$^{N22}$ is an alkyl group or phenyl group having 1 to 3 carbon atoms, and n is an integer from 1 to 3.

Specifically, in General Formula (10), in a case in which $L^1$ is a group formed of a combination of an arylene group and —O—, the substituent that the arylene group may have is preferably an alkyl group.

In the compound (A1) used in the present invention, $L^1$ in General Formula (10) is preferably the following structures or a group formed of a combination thereof;

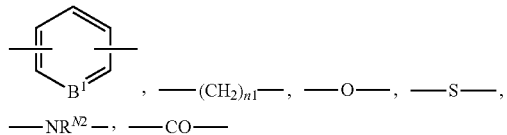

(n1 represents an integer from 1 to 10, $B^1$ represents —CH— or —N—, and $R^{N2}$ represents a hydrogen atom, an alkyl group, an aryl group, or an aralkyl group.).

The n1 represents an integer from 1 to 10, is preferably an integer from 1 to 8, and more preferably an integer from 1 to 6.

The $B^1$ represents —CH— or —N— and is preferably —N—.

$R^{N2}$ represents a hydrogen atom, an alkyl group, an aryl group, or an aralkyl group. The alkyl group, the aryl group, and the aralkyl group are identical to $R^{N1}$ in —NR$^{N1}$— in General Formula (10), and the preferred range thereof is also identical.

In addition, the compound (A1) used in the present invention preferably includes at least one of the following structures as the $L^1$ out of the above-described structures and groups formed of a combination thereof.

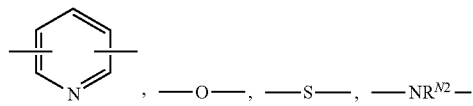

In addition, in the compound (A1) used in the present invention, $L^1$ in General Formula (10) is preferably represented by any of General Formulae (14) to (17) described below:

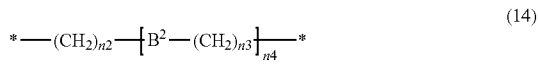

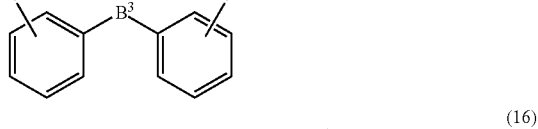

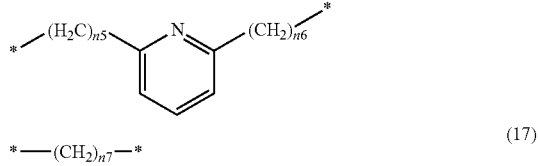

(in General Formula (14), $B^2$ represents —S—, —O—, or —NR$^{N3}$—, each of n2 and n3 independently represents an integer from 0 to 5, and n4 represents an integer from 1 to 5; in General Formula (15), $B^3$ represents —S—, —O—, or —NR$^{N4}$—; each of R$^{N3}$ and R$^{N4}$ independently represents a hydrogen atom, an alkyl group, an aryl group, or an aralkyl group; in General Formula (16), each of n5 and n6 independently represents an integer from 1 to 5; in General Formula (17), n7 represents an integer from 1 to 10; and * represents a connecting portion to X$^1$ or X$^2$).

In General Formula (14), B$^2$ represents —S—, —O—, or —NR$^{N3}$—. In —NR$^{N3}$—, R$^{N3}$ represents a hydrogen atom, an alkyl group, an aryl group, or an aralkyl group. The alkyl group, the aryl group, and the aralkyl group are identical to R$^{N1}$ in —NR$^{N1}$— in General Formula (10), and the preferred range thereof is also identical.

In General Formula (14), each of n2 and n3 independently represents an integer from 0 to 5, preferably represents an integer from 0 to 3, and more preferably represents an integer from 0 to 2.

In General Formula (14), n4 represents an integer from 1 to 5, preferably represents an integer from 1 to 3, more preferably represents 1 or 2, and particularly preferably represents 1.

In General Formula (15), B$^3$ represents —S—, —O—, or —NR$^{N4}$—. In —NR$^{N4}$—, R$^{N4}$ represents a hydrogen atom, an alkyl group, a cycloalkyl group, an aryl group, or an aralkyl group. The alkyl group, the aryl group, and the aralkyl group are identical to R$^{N1}$ in —NR$^{N1}$— in General Formula (10), and the preferred range thereof is also identical.

In General Formula (16), each of n5 and n6 independently represents an integer from 1 to 5, preferably represents an integer from 1 to 3, more preferably represents 1 or 2, and particularly preferably represents 1.

In General Formula (17), n7 represents an integer from 1 to 10, preferably represents an integer from 1 to 8, and more preferably represents an integer from 1 to 6.

Hereinafter, specific examples of the structure represented by L$^1$ in General Formal (10) will be illustrated, but the present invention is not limited thereto. Meanwhile, in the following structures, * represents a connecting portion to X$^1$ or X$^2$ in General Formula (10).

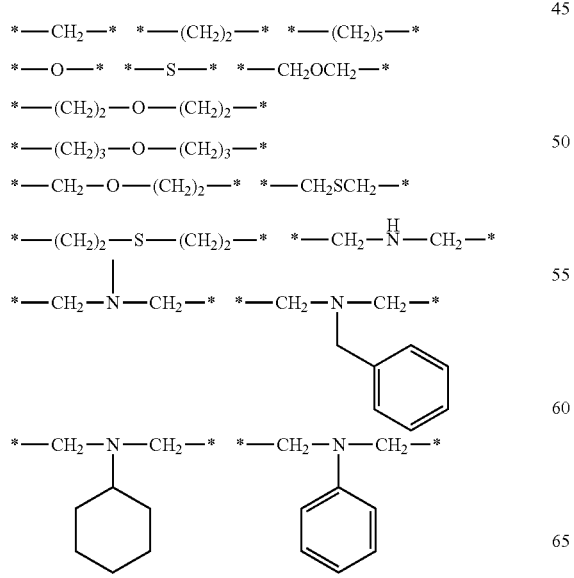

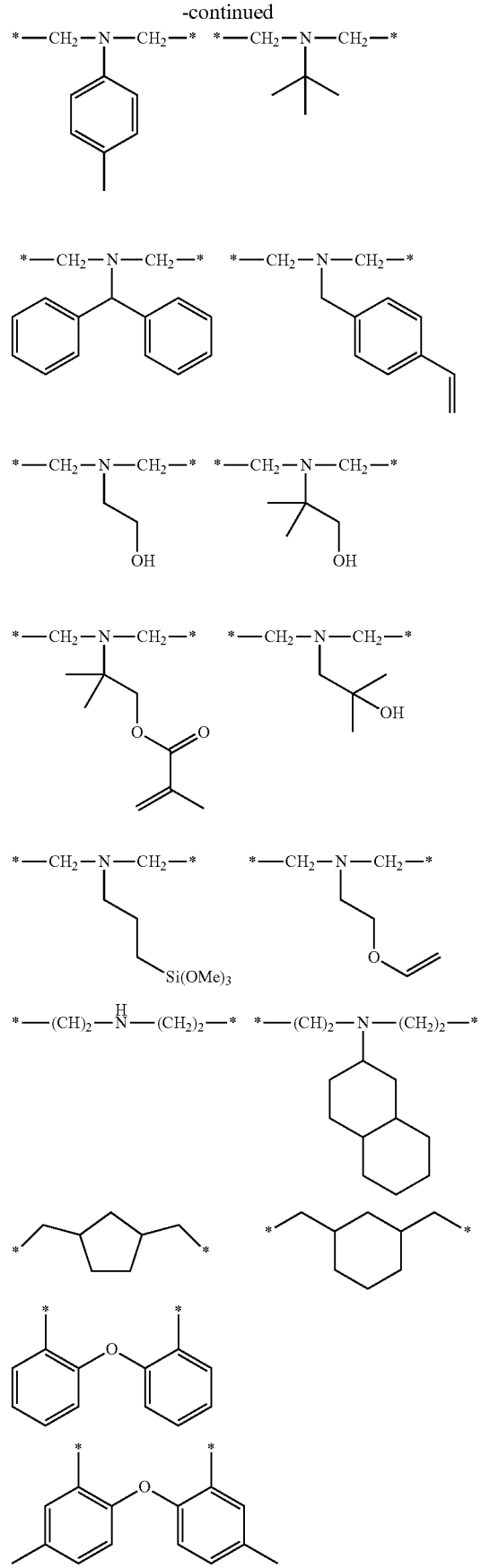

-continued
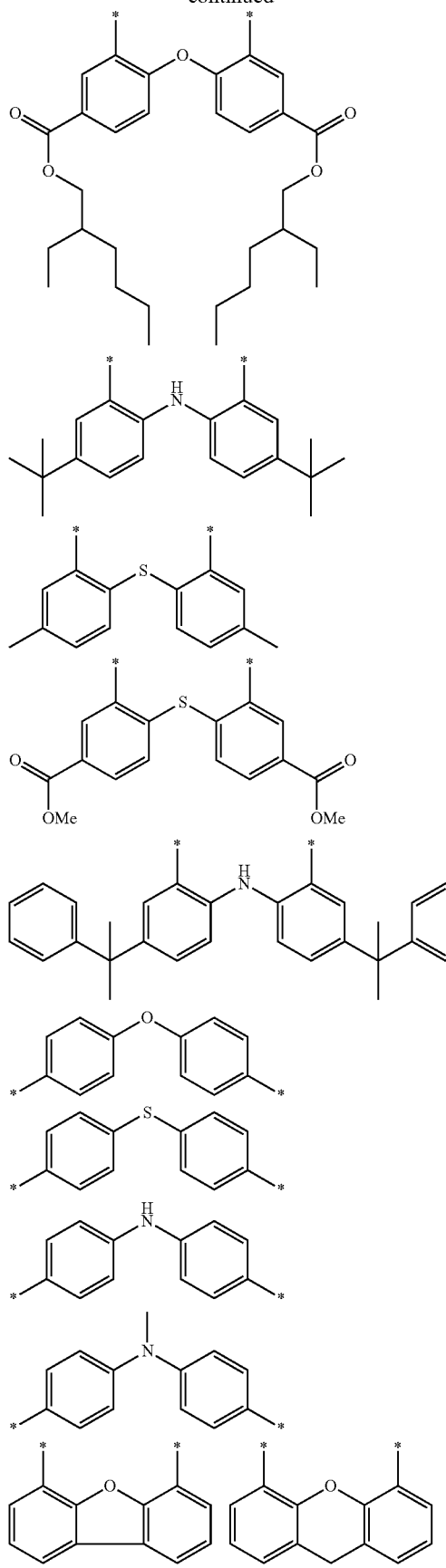
-continued
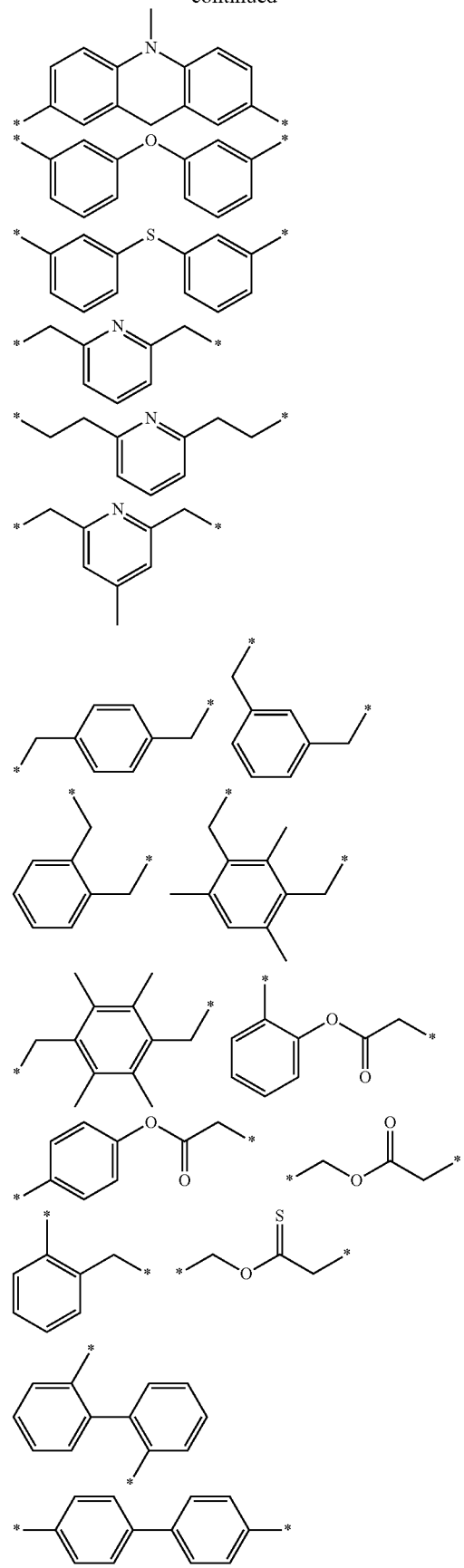

-continued

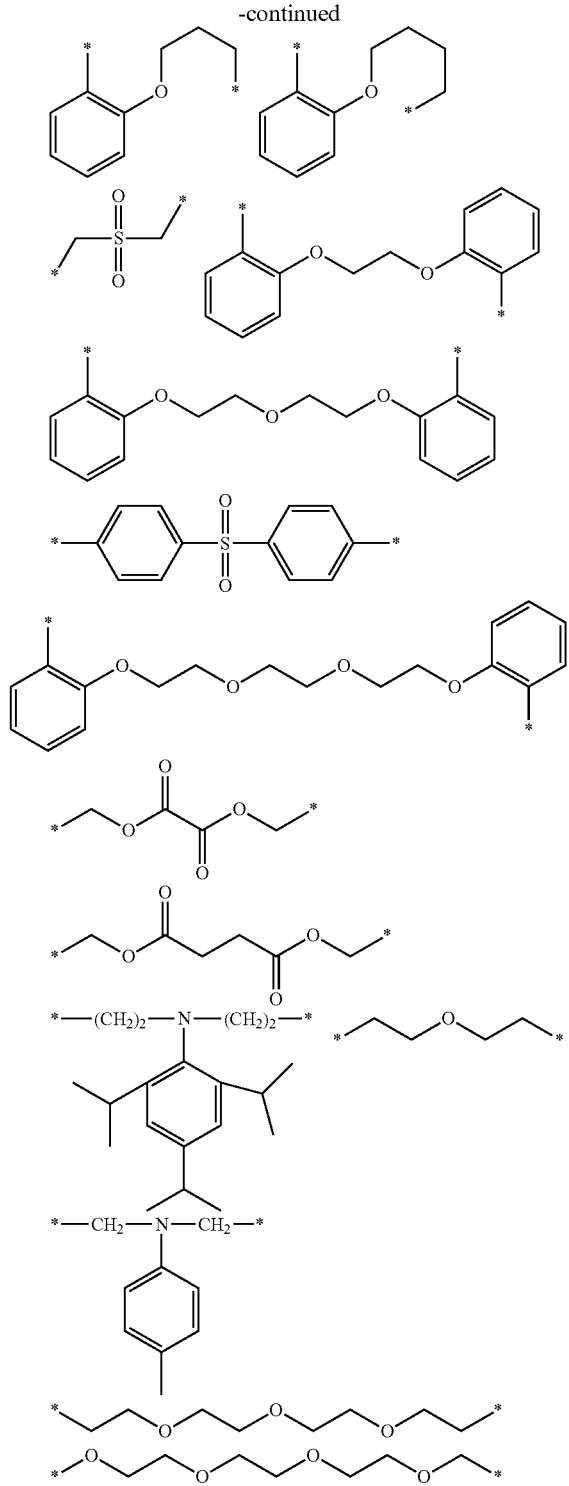

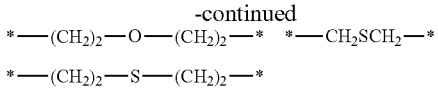
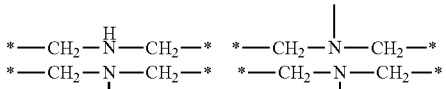
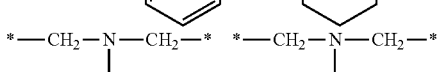
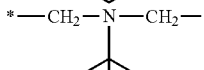
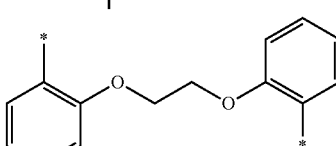
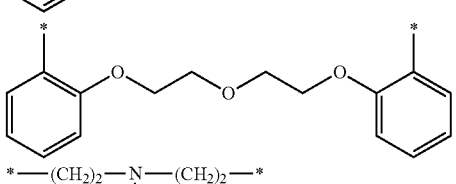
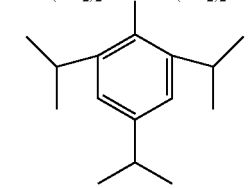
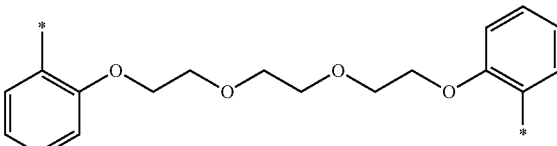
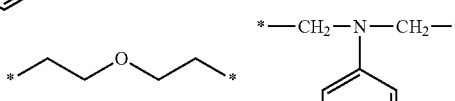
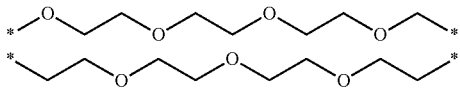

Among the specific examples of the structure represented by $L^1$ in General Formal (10), the following structures are preferred.

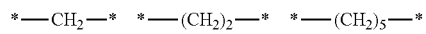
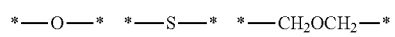

In General Formula (10), $X^1$ and $X^2$ represent the monoanionic coordination sites, and specific examples thereof include the above-described structures (a carboxyl group, a phosphoric acid diester group, a phosphonic acid monoester group, a phosphinic acid group, a sulfo group, and a hydroxyl group).

In General Formula (10), $X^1$ and $X^2$ may have mutually identical monoanionic coordination sites or may have mutually different monoanionic coordination sites.

In General Formula (10), each of $X^1$ and $X^2$ is preferably, independently, a structure represented by General Formula (12), (13) or (13A) described below:

General Formula (12)
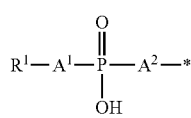

General Formula (13)
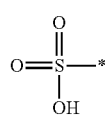

General Formula (13A)
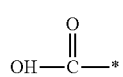

(In General Formula (12), $R^1$ represents an alkyl group, an alkenyl group, an aryl group, or an aralkyl group. Each of $A^1$ and $A^2$ independently represents an oxygen atom, a sulfur atom, or a single bond. In General Formulae (12), (13) and (13A), * represents a connecting portion to $L^1$.)

In General Formula (12), $R^1$ represents an alkyl group, an alkenyl group, an aryl group, or an aralkyl group.

The alkyl group may have any of a linear shape, a branched shape, and a ring shape. The linear or branched alkyl group is preferably a substituted or unsubstituted alkyl group having 1 to 20 carbon atoms, more preferably a substituted or unsubstituted alkyl group having 1 to 15 carbon atoms, and more preferably a substituted or unsubstituted alkyl group having 1 to 6 carbon atoms. The cyclic alkyl group may be either a monocyclic ring or a polycyclic ring. The cyclic alkyl group is preferably a substituted or unsubstituted cycloalkyl group having 3 to 20 carbon atoms, more preferably a substituted or unsubstituted cycloalkyl group having 4 to 10 carbon atoms, and particularly preferably an unsubstituted cycloalkyl group having 4 to 8 carbon atoms.

The alkenyl group is preferably a substituted or unsubstituted alkenyl group having 2 to 10 carbon atoms and more preferably a substituted or unsubstituted alkenyl group having 2 to 8 carbon atoms.

The aryl group is preferably a substituted or unsubstituted aryl group having 6 to 18 carbon atoms and more preferably a substituted or unsubstituted aryl group having 6 to 14 carbon atoms. Specific examples thereof include a phenyl group and a naphthyl group.

The aralkyl group is preferably a substituted or unsubstituted aralkyl group having 7 to 20 carbon atoms and more preferably a substituted or unsubstituted aralkyl group having 7 to 16 carbon atoms.

A substituent that $R^1$ in General Formula (12) may have is identical to the substituent that $L^1$ in General Formula (10) may have, and is preferably an alkyl group, an aryl group, an ether group, $-Si-(OR^{N22})_3$, or the like.

In General Formula (12), each of $A^1$ and $A^2$ independently represents an oxygen atom, a sulfur atom, or a single bond. Particularly, $A^1$ and $A^2$ independently are preferably single bonds from the viewpoint of further improving the heat resistance of the composition of the present invention.

Hereinafter, specific examples of the structure represented by $R^1$ in General Formal (12) will be illustrated, but the present invention is not limited thereto. Meanwhile, in the following structures, * represents a connecting portion to $A^1$ in General Formula (12).

 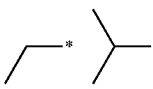 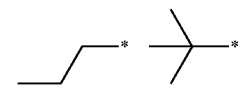

-continued
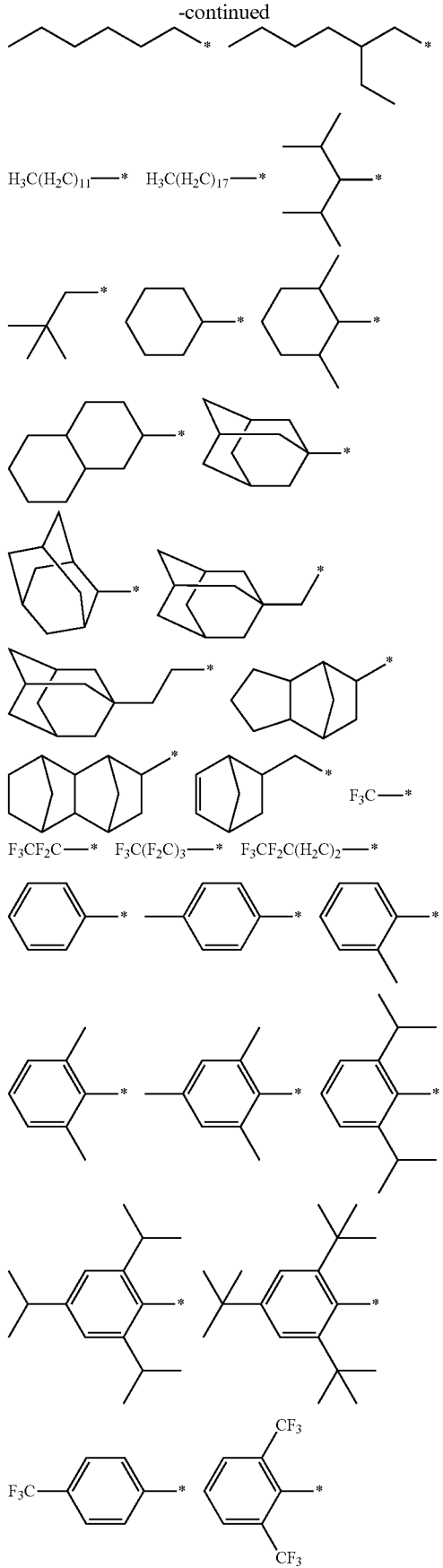

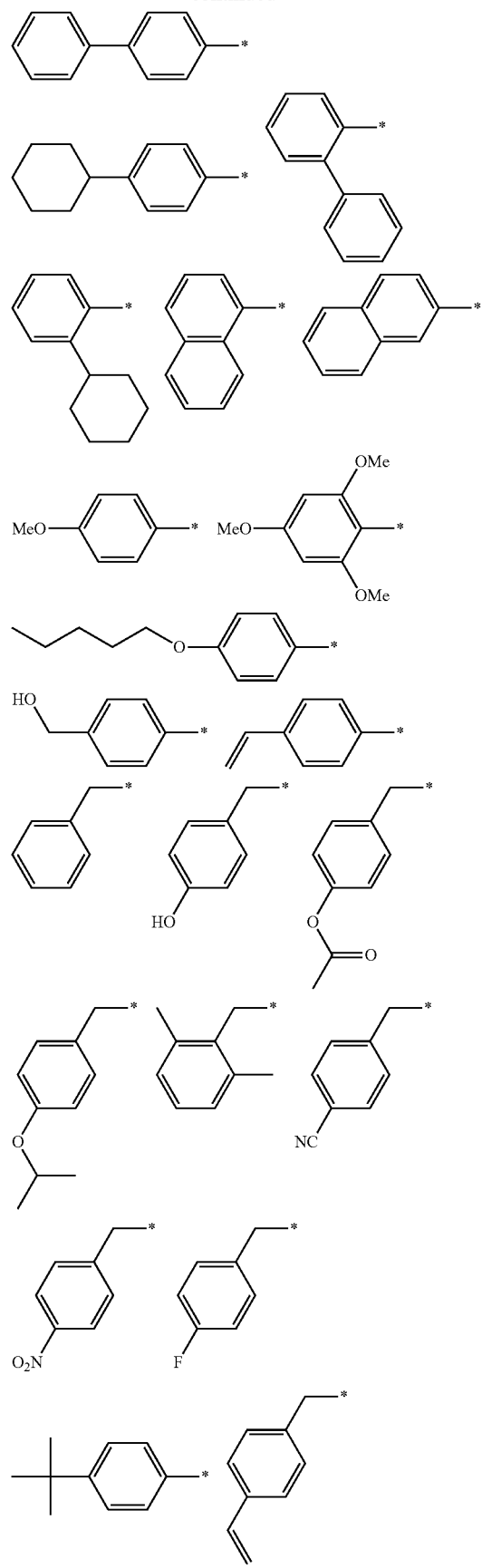
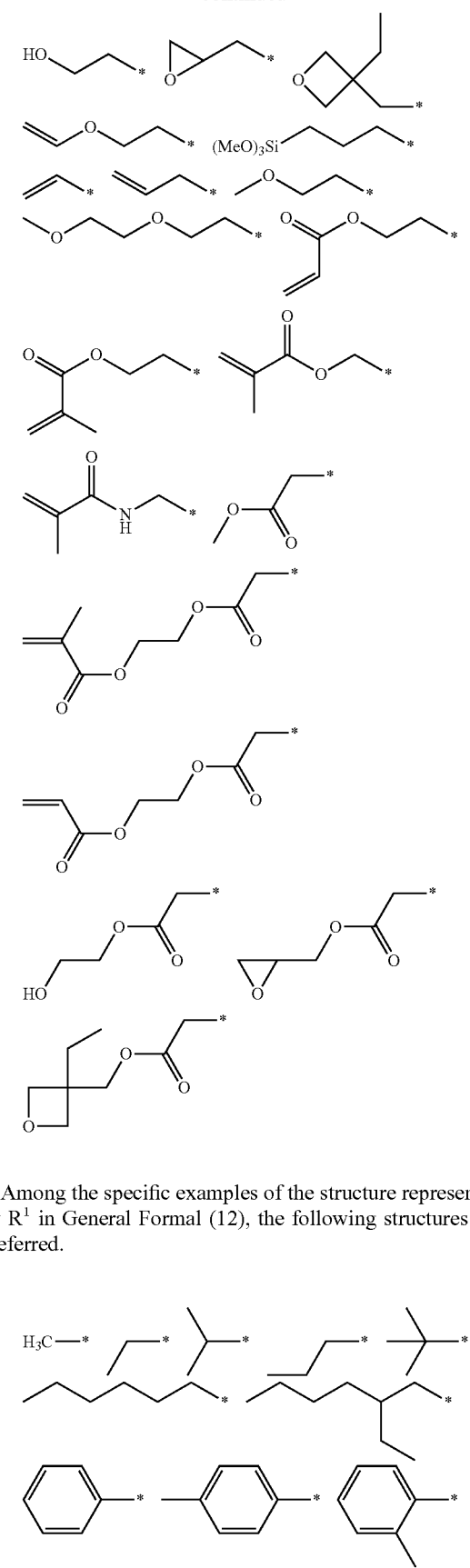
Among the specific examples of the structure represented by $R^1$ in General Formal (12), the following structures are preferred.

-continued
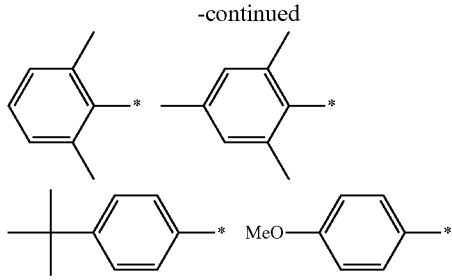
-continued
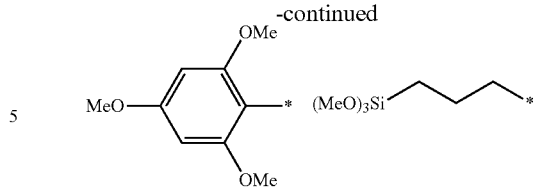
Hereinafter, specific examples of the compound (A1) used in the present invention will be illustrated, but the present invention is not limited thereto.
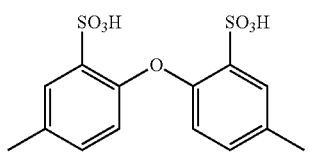
A-1
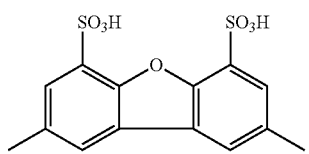
A-2
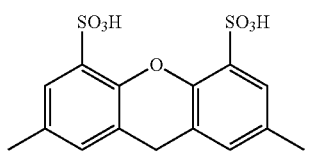
A-3
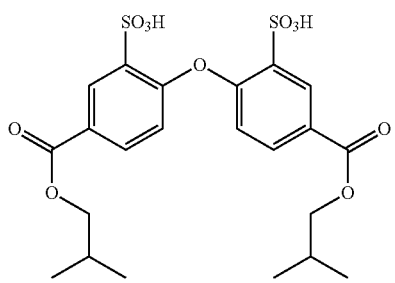
A-4
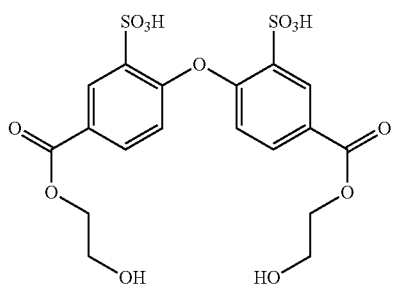
A-5
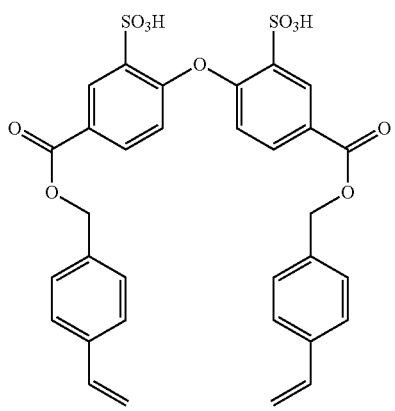
A-6
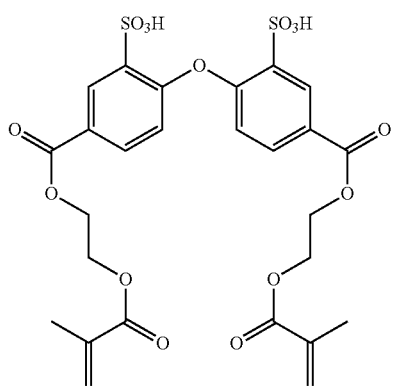
A-7
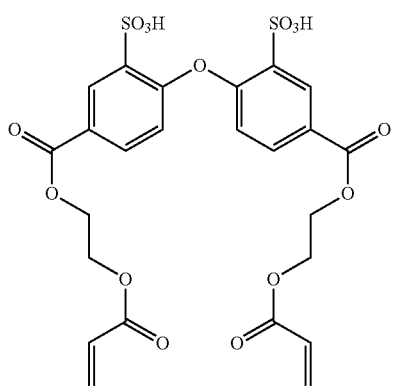
A-8

-continued
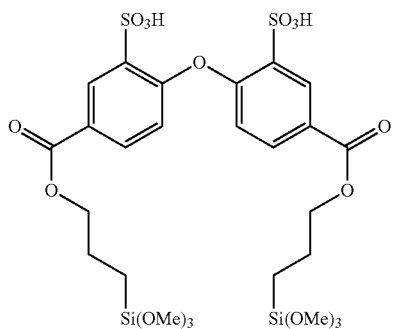
A-9
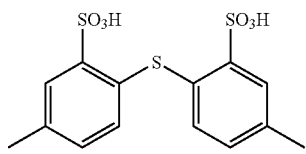
A-10
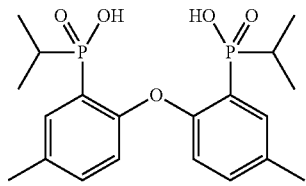
A-11
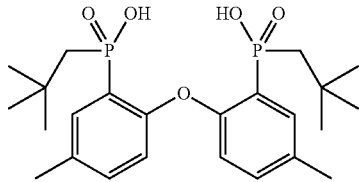
A-12
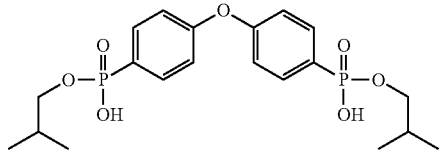
A-13
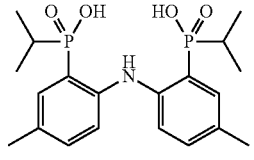
A-14
A-15
A-16
A-17
A-18
A-19
A-20
A-21
A-22

-continued
A-23
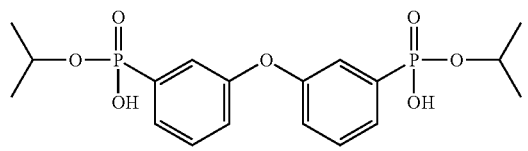
A-24
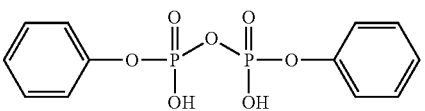
A-25
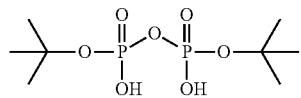
A-26
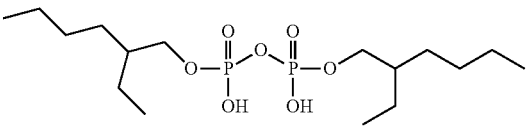
A-27
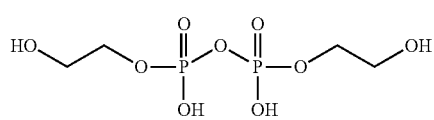
A-28
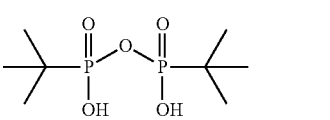
A-29
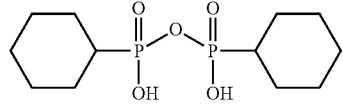
A-30
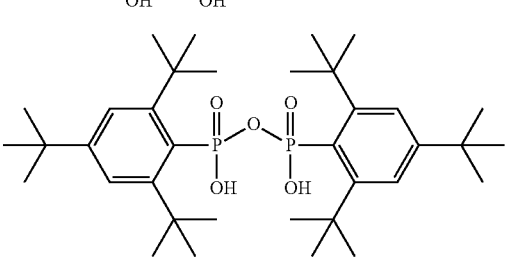
A-31
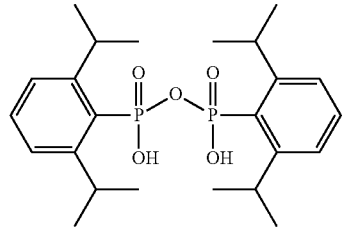
A-32
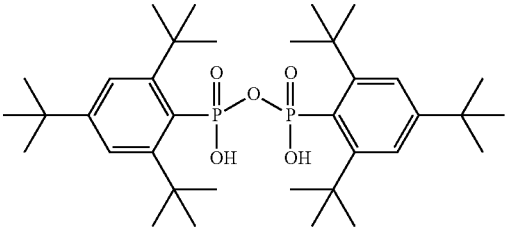
A-33
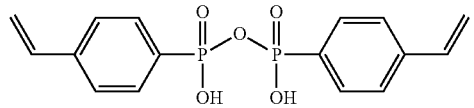
A-34
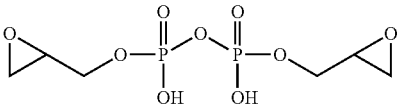
A-35
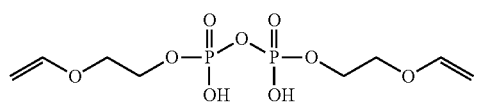
A-36
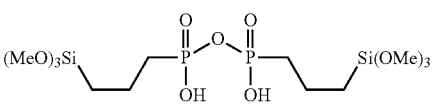
A-37
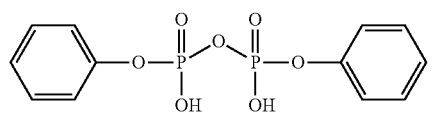
A-38
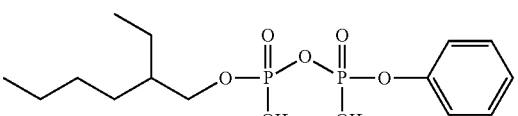
A-39
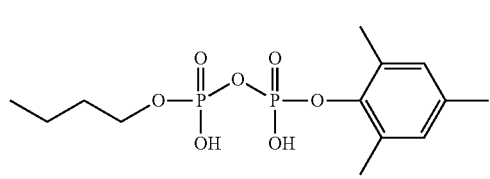
A-40
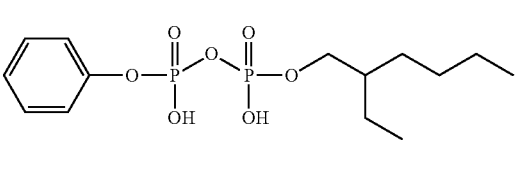
A-41
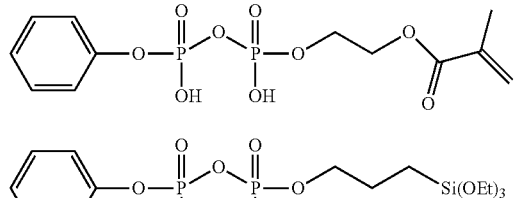
A-42
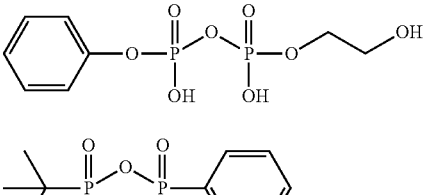
A-43
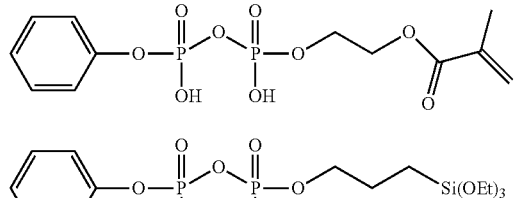
A-44
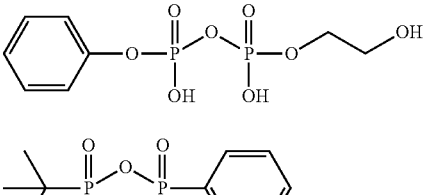

-continued
A-45 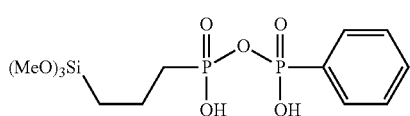
A-46 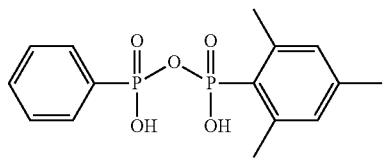
A-47 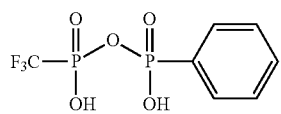
A-48 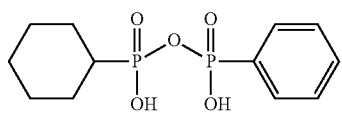
A-49 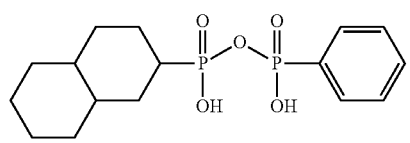
A-50 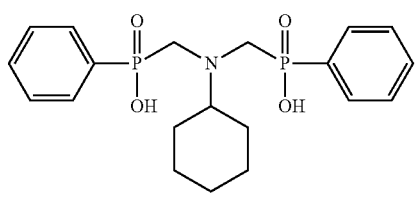
A-51 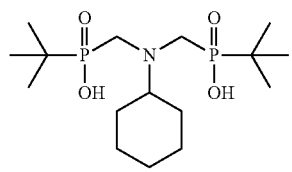
A-52 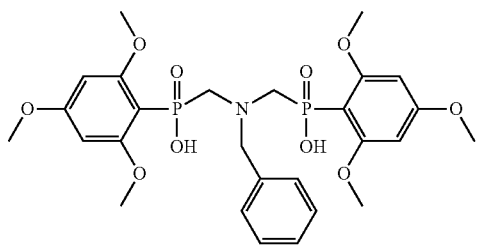
A-54 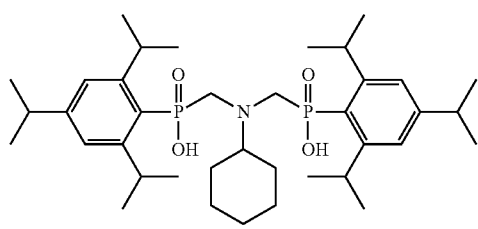
A-53 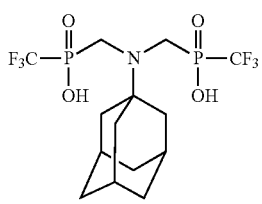
A-55 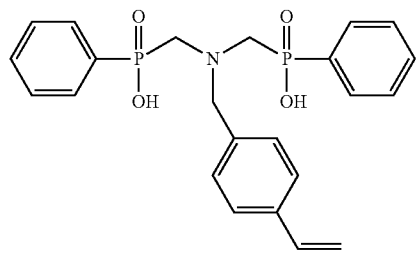
A-56 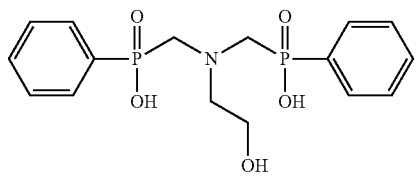
A-57 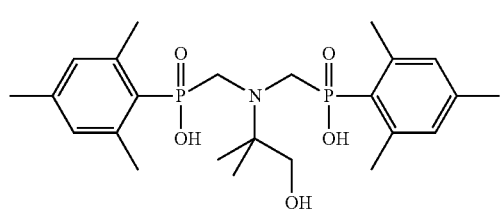
A-58 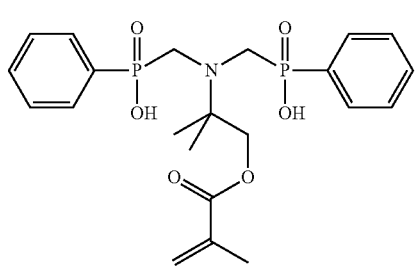

-continued
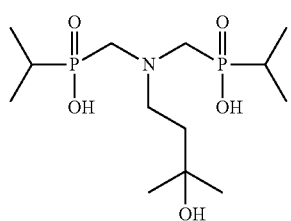
A-59
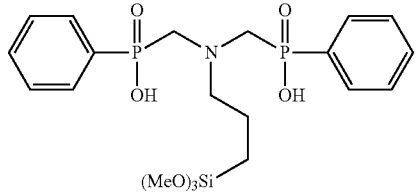
A-60
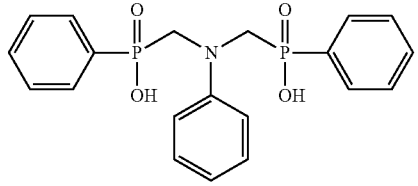
A-62
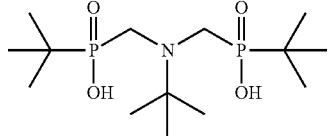
A-64
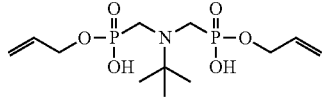
A-65
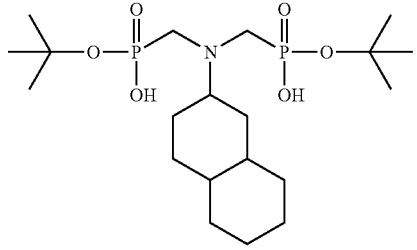
A-68
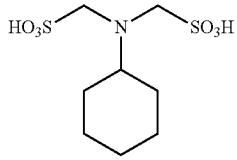
A-70
A-72
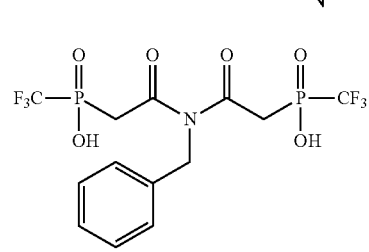
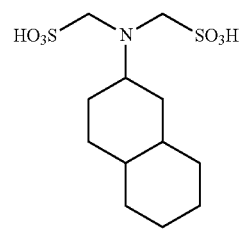

-continued

-continued
A-91
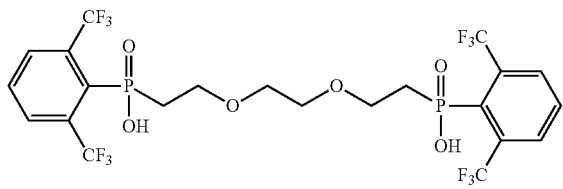
A-92
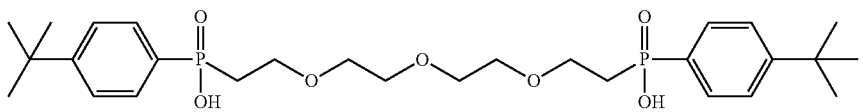
A-93
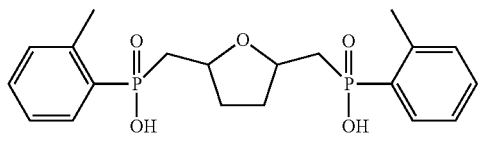
A-94
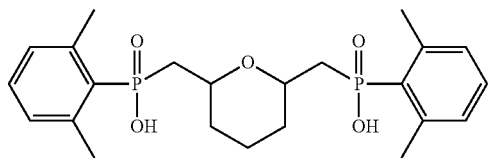
A-95
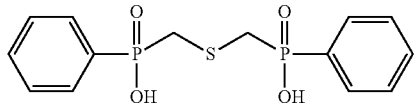
A-96
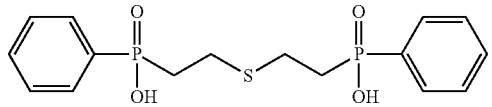
A-97
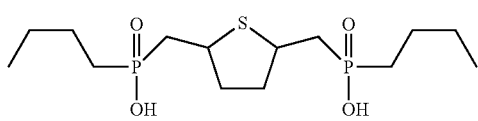
A-98
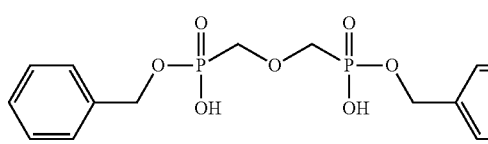
A-99
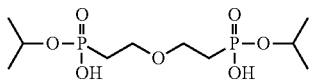
A-100
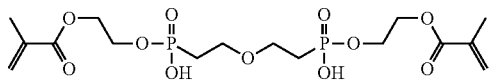
A-101
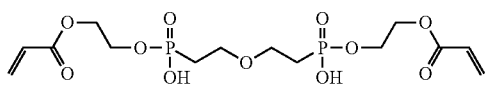
A-102
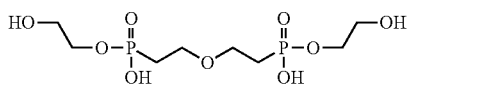
A-103
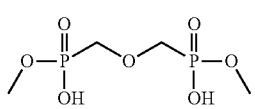
A-104
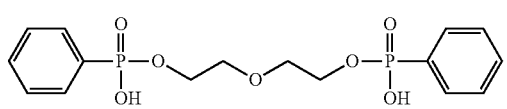
A-105
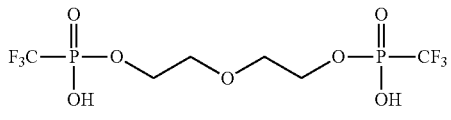
A-106
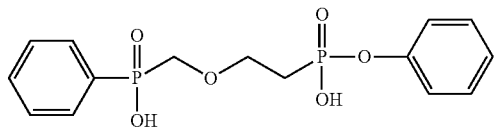
A-107
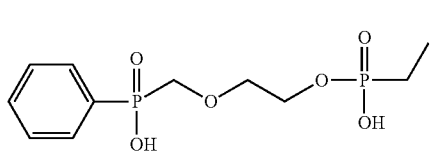
A-108
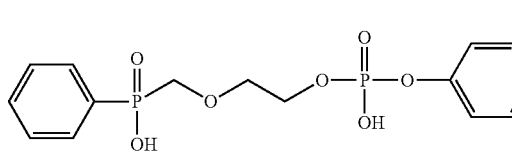
A-109
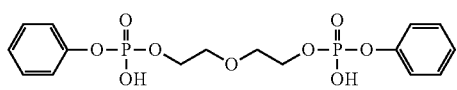
A-110
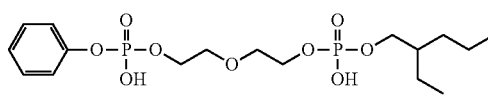

-continued
| | |
|---|---|
| A-111 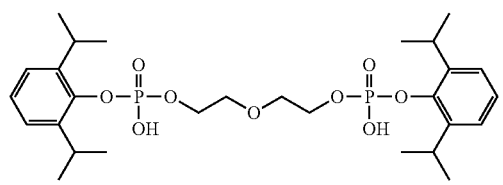 | A-112 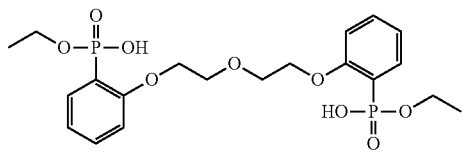 |
| A-113 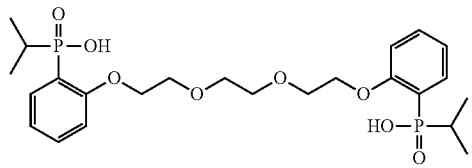 | A-114 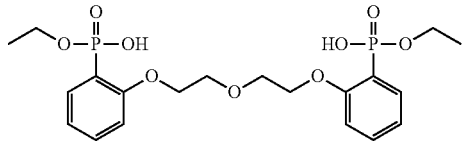 |
| A-115 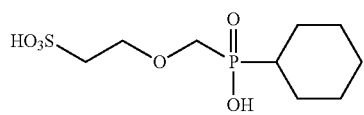 | A-116 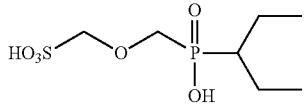 |
| A-117 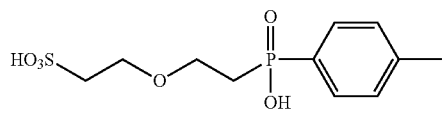 | A-118 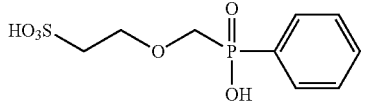 |
| A-119 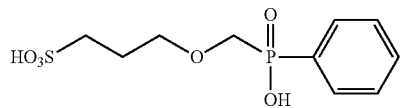 | A-120 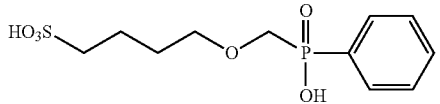 |
| A-121 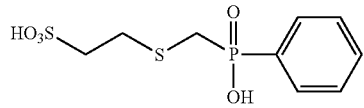 | A-122 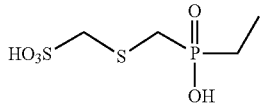 |
| A-124 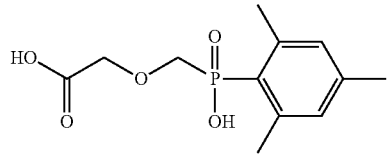 | A-123 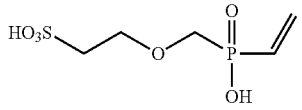 |
| A-125 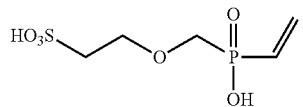 | A-126 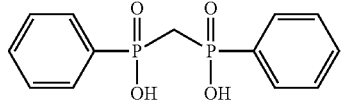 |
| A-127 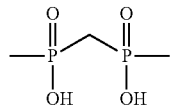 | A-128 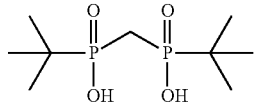 |
| A-129 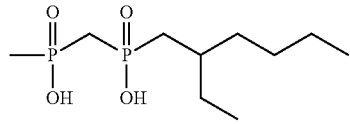 | A-130 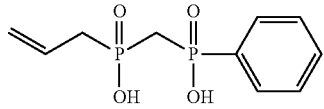 |
| A-131 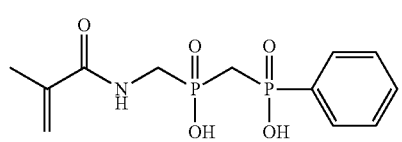 | A-132 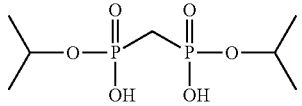 |

-continued
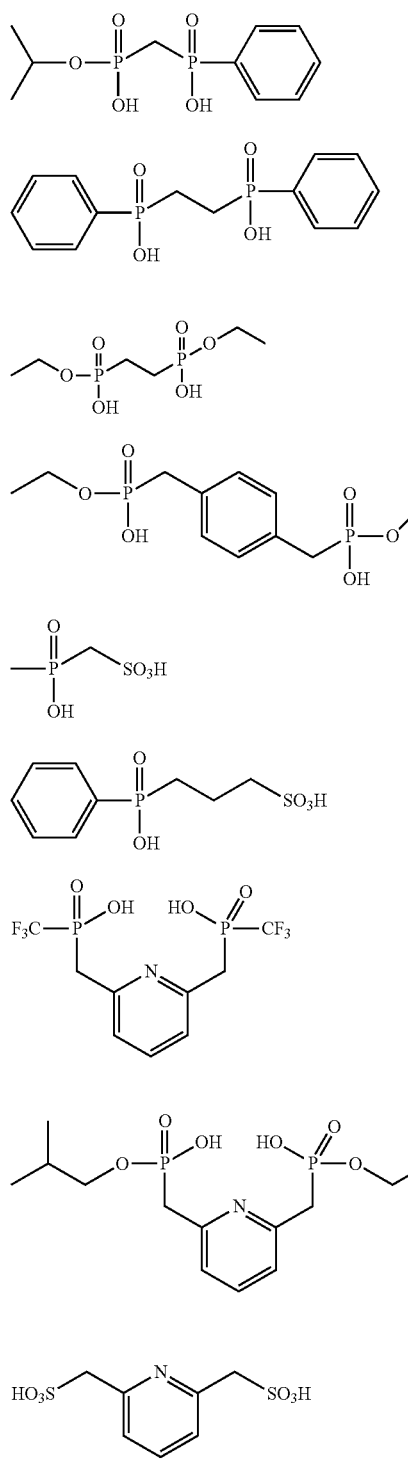
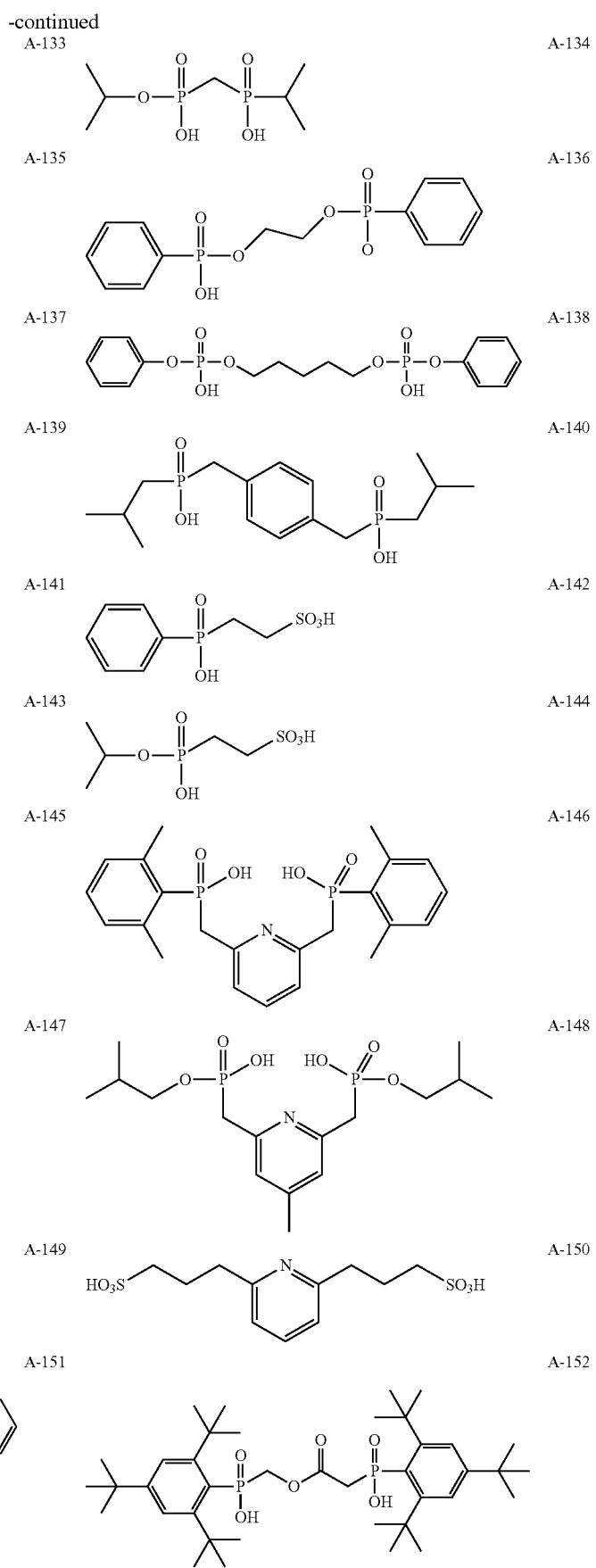

-continued
A-153
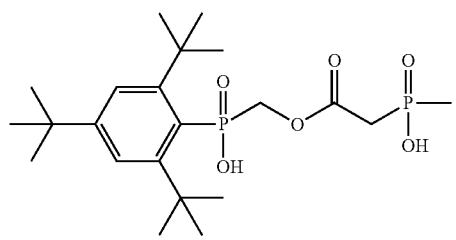
A-154
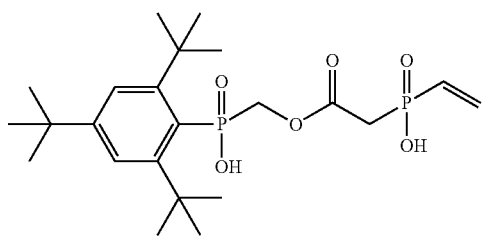
A-155
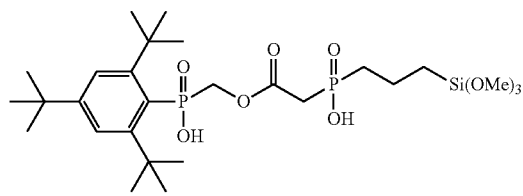
A-156
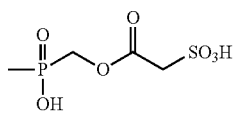
A-157
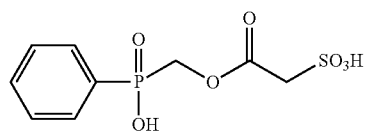
A-158
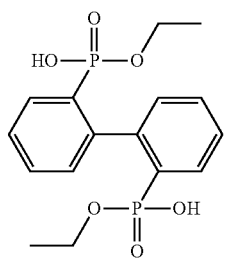
A-159
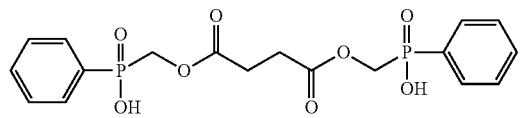
A-160
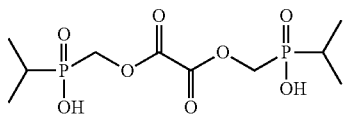
A-161
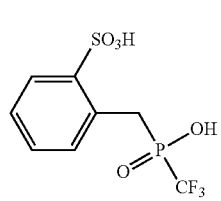
A-162
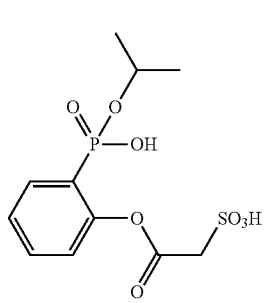
A-163
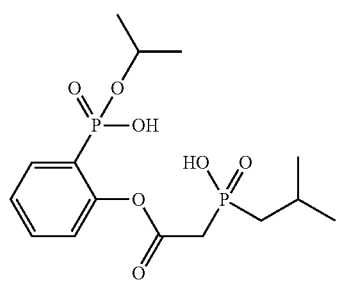
A-164
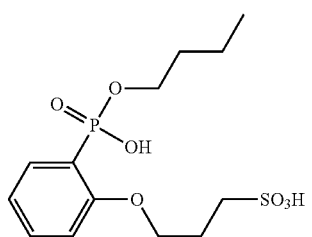
A-165
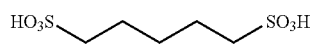
A-166
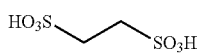
A-167
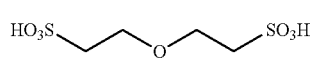
A-168
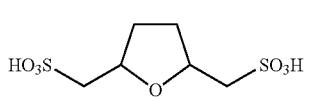

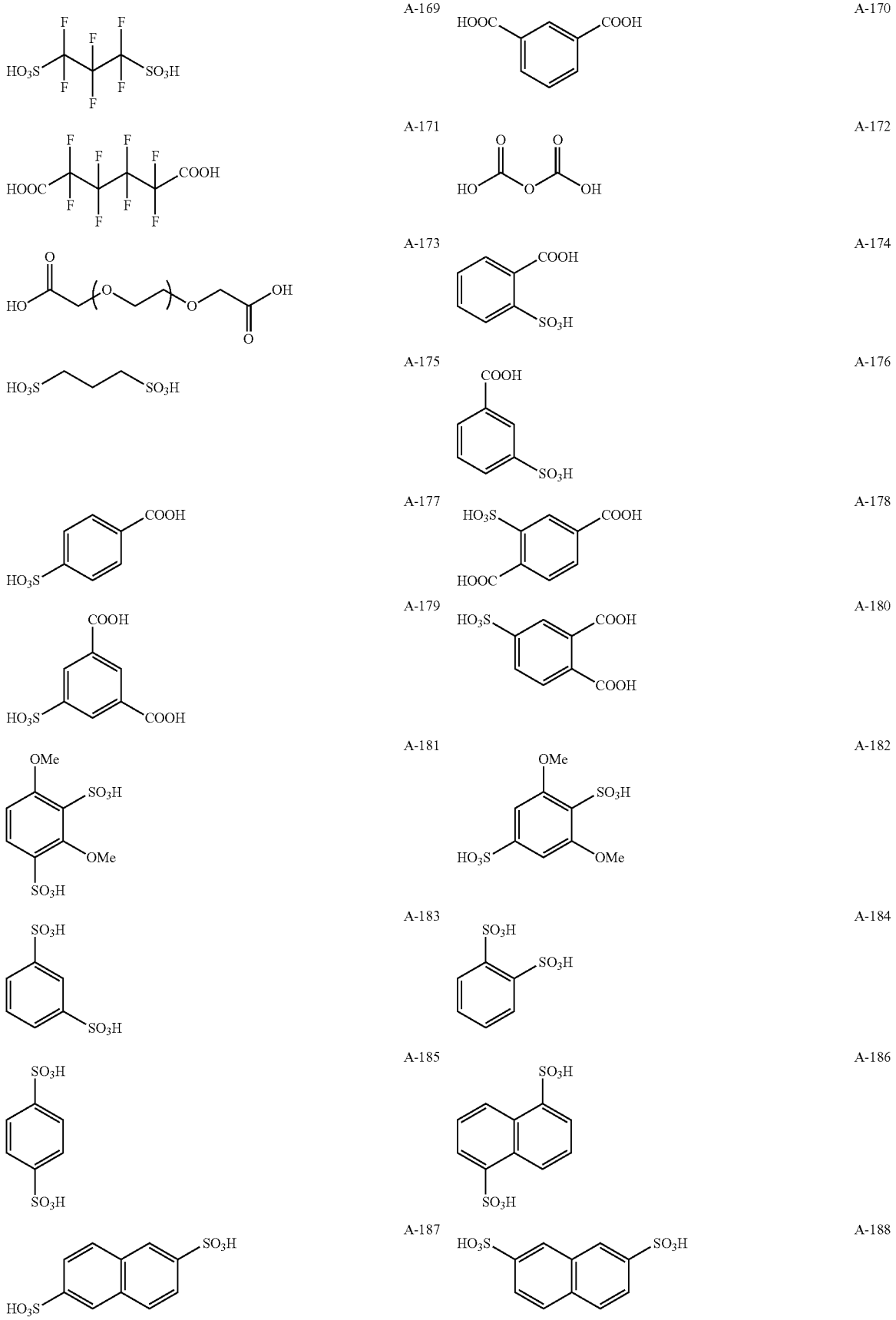

A-189
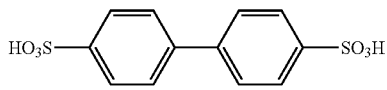

A-190
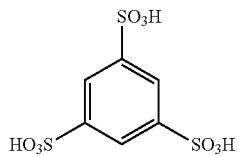

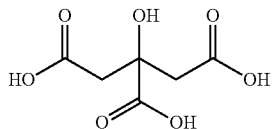

A-191

<<Salt of Compound (A1)>>

The salt of the compound (A1), which is used in the present invention, that is, the compound having the salts of the two monoanionic coordination sites is preferably, for example, a metal salt, and specific examples thereof include a sodium salt, a potassium salt, a magnesium salt, and a calcium salt.

<<Compound (A2)>>

A second preferred embodiment of the compound (A) is a compound (A2) respectively having at least one coordination site to be coordinated with an anion and at least one coordinating atom to be coordinated with an unshared electron pair. The compound (A2) has at least one coordination site to be coordinated with an anion in one molecule and may have two coordination sites. In the compound (A2), the total number of the coordination sites to be coordinated with an anion and the coordinating atoms to be coordinated with an unshared electron pair in one molecule may be two or more and may be three or four.

Examples of an aspect in which the total number of the coordination sites to be coordinated with an anion and the coordinating atoms to be coordinated with an unshared electron pair is three include a compound having two coordination sites to be coordinated with an anion and one coordinating atom to be coordinated with an unshared electron pair and a compound having one coordination site to be coordinated with an anion and two coordinating atoms to be coordinated with an unshared electron pair.

Examples of an aspect in which the total number of the coordination sites to be coordinated with an anion and the coordinating atoms to be coordinated with an unshared electron pair is four include a compound having two coordination sites to be coordinated with an anion and two coordinating atoms to be coordinated with an unshared electron pair and a compound having one coordination site to be coordinated with an anion and three coordinating atoms to be coordinated with an unshared electron pair.

In the compound (A2), the number of atoms linking an anion configuring the coordination site to be coordinated with an anion and the coordinating atom to be coordinated with an unshared electron pair is preferably in a range of 1 to 6 and more preferably in a range of 1 to 3. When the compound (A2) is provided with the above-described constitution, the structure of the copper complex becomes easily distorted, and thus it is possible to further improve the color valency.

The number of kinds of the atoms linking the anion configuring the coordination site to be coordinated with an anion and the coordinating atom to be coordinated with an unshared electron pair may be one or more. The atom linking the anion configuring the coordination site to be coordinated with an anion and the coordinating atom to be coordinated with an unshared electron pair is preferably a carbon atom.

In the following exemplary compounds, the anion configuring the coordination site to be coordinated with an anion is an oxygen anion, the coordinating atom to be coordinated with an unshared electron pair is a nitrogen atom, and the atom linking the anion configuring the coordination site to be coordinated with an anion and the coordinating atom to be coordinated with an unshared electron pair is a carbon atom. In addition, the number of the atoms linking the anions configuring the coordination sites to be coordinated with an anion and the coordinating atoms to be coordinated with an unshared electron pair is two.

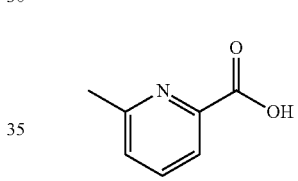

The molecular weight of the compound (A2) is preferably in a range of 50 to 1000 and more preferably in a range of 50 to 600.

In the compound (A2), the anion configuring the coordination site to be coordinated with an anion may be an anion capable of coordinating a copper atom in the copper component and is preferably an oxygen anion, a nitrogen anion, or a sulfur anion.

The coordination site to be coordinated with the anion is preferably at least one selected from the following group (AN).

Group (AN)

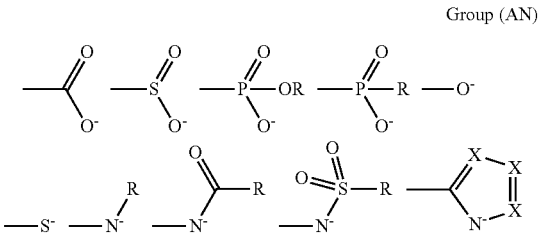

In the coordination site to be coordinated with the anion, X represents N or CR, and each of Rs preferably, independently, represents a hydrogen atom, an alkyl group, an alkenyl group, an alkynyl group, an aryl group, or a heteroaryl group.

The alkyl group may have a linear shape, a branched shape, or a ring shape, but preferably has a linear shape. The number of carbon atoms in the alkyl group is preferably in a range of 1 to 10, more preferably in a range of 1 to 6, and still more preferably in a range of 1 to 4. Examples of the alkyl group include a methyl group. The alkyl group may have a substituent, and examples of the substituent include a halogen atom, a carboxyl group, and a heterocyclic group. The heterocyclic group as the substituent may be a monocyclic ring or a polycyclic ring and may be an aromatic group or a non-aromatic group. The number of hetero atoms configuring the heterocycle is preferably in a range of 1 to 3 and preferably 1 or 2. The hetero atom configuring the heterocycle is preferably a nitrogen atom. In a case in which the alkyl group has a substituent, the alkyl group may have another substituent.

The number of carbon atoms in the alkenyl group is preferably in a range of 1 to 10 and more preferably in a range of 1 to 6.

The number of carbon atoms in the alkynyl group is preferably in a range of 1 to 10 and more preferably in a range of 1 to 6.

The aryl group may be a monocyclic ring or a polycyclic ring, but is preferably a monocyclic ring. The number of carbon atoms in the aryl group is preferably in a range of 6 to 18, more preferably in a range of 6 to 12, and still more preferably 6.

The heteroaryl group may be a monocyclic ring or a polycyclic ring. The number of hetero atoms configuring the heteroaryl group is preferably in a range of 1 to 3. The hetero atom configuring the heteroaryl group is preferably a nitrogen atom, a sulfur atom, or an oxygen atom. The number of carbon atoms in the heteroaryl group is preferably in a range of 6 to 18 and more preferably in a range of 6 to 12.

In the compound (A2), the coordinating atom to be coordinated with an unshared electron pair is preferably an oxygen atom, a nitrogen atom, a sulfur atom, or a phosphorus atom, more preferably an oxygen atom, a nitrogen atom, or a sulfur atom, and still more preferably a nitrogen atom.

In the compound (A2), in a case in which the coordinating atom to be coordinated with an unshared electron pair is a nitrogen atom, it is preferable that an atom adjacent to the nitrogen atom is a carbon atom and the carbon atom has a substituent.

The coordinating atom to be coordinated with an unshared electron pair is preferably included in a ring or at least one partial structure selected from the following group (UE).

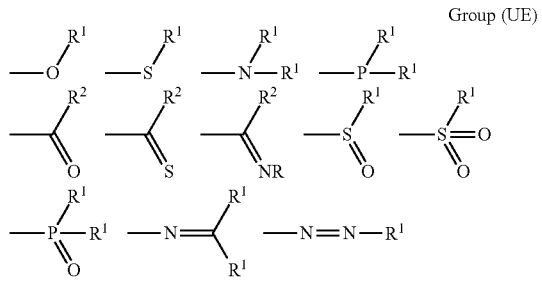

Group (UE)

In the group (UE), each of $R^1$s independently represents a hydrogen atom, an alkyl group, an alkenyl group, an alkynyl group, an aryl group, or a heteroaryl group, and each of $R^2$s independently represents a hydrogen atom, an alkyl group, an alkenyl group, an alkynyl group, an aryl group, a heteroaryl group, an alkoxy group, an aryloxy group, a heteroaryloxy group, an alkylthio group, an arylthio group, a heteroarylthio group, an amino group, or an acyl group.

In a case in which the coordinating atom to be coordinated with an unshared electron pair is included in a ring, the ring including the coordinating atom to be coordinated with an unshared electron pair may be a monocyclic ring or a polycyclic ring and may be aromatic or non-aromatic. The ring including the coordinating atom to be coordinated with an unshared electron pair is preferably a 5- to 12-membered ring and more preferably a 5- to 7-membered ring.

The ring including the coordinating atom to be coordinated with an unshared electron pair may have a substituent, and examples of the substituent include a linear, branched, or cyclic alkyl group having 1 to 10 carbon atoms, an aryl group having 6 to 12 carbon atoms, a halogen atom, a silicon atom, an alkoxy group having 1 to 12 carbon atoms, an acyl group having 1 to 12 carbon atoms, an alkylthio group having 1 to 12 carbon atoms, and a carboxyl group.

In a case in which the ring including the coordinating atom to be coordinated with an unshared electron pair has a substituent, the ring may have another substituent, and examples of the substituent include a group formed of a ring including a coordinating atom to be coordinated with an unshared electron pair, a group formed of at least one partial structure selected from the above-described group (UE), an alkyl group having 1 to 12 carbon atoms, an acyl group having 2 to 12 carbon atoms, and a hydroxy group.

In a case in which the coordinating atom to be coordinated with an unshared electron pair is included in a partial structure represented by the group (UE), each of $R^1$s preferably represents a hydrogen atom, an alkyl group, an alkenyl group, an alkynyl group, an aryl group, or a heteroaryl group.

The alkyl group, the alkynyl group, the aryl group, and the heteroaryl group are identical to the alkyl group, the alkynyl group, the aryl group, and the heteroaryl group described in the section of the coordination site to be coordinated with the anion, and the preferred range thereof is also identical.

The alkyl group is identical to the alkyl group described in the section of the coordination site to be coordinated with the anion, and the preferred range thereof is also identical.

The alkynyl group is identical to the alkynyl group described in the section of the coordination site to be coordinated with the anion, and the preferred range thereof is also identical.

The aryl group is identical to the aryl group described in the section of the coordination site to be coordinated with the anion, and the preferred range thereof is also identical.

The heteroaryl group is identical to the heteroaryl group described in the section of the coordination site to be coordinated with the anion, and the preferred range thereof is also identical.

In a case in which the coordinating atom to be coordinated with an unshared electron pair is included in a partial structure represented by the group (UE), each of $R^2$s preferably, independently, represents a hydrogen atom, an alkyl group, an alkenyl group, an alkynyl group, an aryl group, a heteroaryl group, an alkoxy group, an aryloxy group, a heteroaryloxy group, an alkylthio group, an arylthio group, a heteroarylthio group, an amino group, or an acyl group.

The number of carbon atoms in the alkoxy group is preferably in a range of 1 to 12 and more preferably in a range of 3 to 9.

The number of carbon atoms in the aryloxy group is preferably in a range of 6 to 18 and more preferably in a range of 6 to 12.

The heteroaryloxy group may be a monocyclic ring or a polycyclic ring. The heteroaryl group configuring the heteroaryloxy group is identical to the heteroaryl group described in the section of the coordination site to be coordinated with the anion, and the preferred range thereof is also identical.

The number of carbon atoms in the alkylthio group is preferably in a range of 1 to 12 and more preferably in a range of 1 to 9.

The number of carbon atoms in the arylthio group is preferably in a range of 6 to 18 and more preferably in a range of 6 to 12.

The heteroarylthio group may be a single bond or a polycyclic ring. The heteroaryl group configuring the heteroarylthio group is identical to the heteroaryl group described in the section of the coordination site to be coordinated with the anion, and the preferred range thereof is also identical.

The number of carbon atoms in the acyl group is preferably in a range of 2 to 12 and more preferably in a range of 2 to 9.

The compound (A2) is also preferably represented by General Formula (IV) described below.)

$$X^1\text{-}L^1\text{-}Y^1 \qquad \text{General Formula (IV)}$$

(In General Formula (IV), $X^1$ represents a coordination site represented by the group (AN). $Y^1$ represents a ring including a coordinating atom to be coordinated with an unshared electron pair or the partial structure represented by the group (UE). $L^1$ represents a single bond or a divalent linking group.)

In General Formula (IV), $X^1$ is identical to the above-described coordination site to be coordinated with the anion, and the preferred range thereof is also identical.

In General Formula (IV), $Y^1$ is identical to the above-described ring including the coordinating atom to be coordinated with an unshared electron pair or the above-described partial structure including the coordinating atom to be coordinated with an unshared electron pair, and the preferred range thereof is also identical.

In General Formula (IV), in a case in which $L^1$ represents a divalent linking group, an alkylene group having 1 to 12 carbon atoms, an arylene group having 6 to 12 carbon atoms, —SO—, —O—, —SO$_2$—, or a group formed of a combination thereof is preferred, and an alkylene group having 1 to 3 carbon atoms, a phenylene group, or —SO$_2$— is preferred.

More detailed examples of the compound (A2) also include compounds represented by General Formulae (IV-1) to (IV-8) described below.

$$X^2\text{-}L^2\text{-}Y^2\text{-}L^3\text{-}X^3 \qquad \text{(IV-1)}$$

$$Y^3\text{-}L^4\text{-}Y^4\text{-}L^5\text{-}X^4 \qquad \text{(IV-2)}$$

$$Y^5\text{-}L^6\text{-}X^5\text{-}L^7\text{-}X^6 \qquad \text{(IV-3)}$$

$$Y^6\text{-}L^7\text{-}X^7\text{-}L^8\text{-}Y^7 \qquad \text{(IV-4)}$$

$$X^8\text{-}L^9\text{-}Y^8\text{-}L^{10}\text{-}Y^9\text{-}L^{11}\text{-}X^9 \qquad \text{(IV-5)}$$

$$X^9\text{-}L^{12}\text{-}Y^{10}\text{-}L^{13}\text{-}Y^{11}\text{-}L^{14}\text{-}Y^{12} \qquad \text{(IV-6)}$$

$$Y^{13}\text{-}L^{15}\text{-}X^{10}\text{-}L^{16}\text{-}X^{11}\text{-}L^{17}\text{-}Y^{14} \qquad \text{(IV-7)}$$

$$Y^{15}\text{-}L^{18}\text{-}X^{12}\text{-}L^{19}\text{-}Y^{16}\text{-}L^{20}\text{-}Y^{17} \qquad \text{(IV-8)}$$

In General Formulae (IV-1) to (IV-8), each of $X^2$ to $X^4$, $X^8$, and $X^9$ independently represents at least one selected from the above-described group (AN). In addition, each of $X^5$, $X^7$, and $X^{10}$ to $X^{12}$ is independently at least one selected from the following group (AN-1). X in the group (AN-1) represents N or CR, and R is identical to R described in the section of CR in the above-described group (AN).

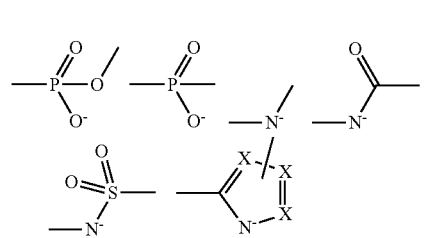

Group (AN-1)

In General Formulae (IV-1) to (IV-8), each of $Y^3$, $Y^5$ to $Y^7$, and $Y^{12}$ to $Y^{15}$ independently represents a ring including a coordinating atom to be coordinated with an unshared electron pair or at least one partial structure selected from the above-described group (UE). In addition, each of $Y^2$, $Y^4$, $Y^8$ to $Y^{11}$, and $Y^{16}$ is independently a ring including a coordinating atom to be coordinated with an unshared electron pair or at least one selected from the following group (UE-1). R in the group (UE-1) is identical to R in a case in which the coordinating atom to be coordinated with an unshared electron pair is included in the partial structure represented by the above-described group (UE).

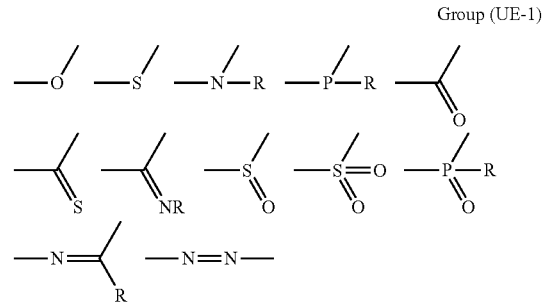

Group (UE-1)

In General Formulae (IV-1) to (IV-8), each of $L^2$ to $L^{20}$ independently represents a single bond or a divalent linking group. The divalent linking group is identical to that in a case in which $L^1$ in General Formula (IV) represents a divalent linking group, and the preferred range thereof is also identical.

Meanwhile, in the compound (A2), it is preferable that a plurality of π conjugate systems such as aromatic groups are not continuously bonded to each other in order to improve the visible transmission.

The compound (A2) is also preferably a compound having a 5-membered or 6-membered ring, and the coordinating atoms to be coordinated with an unshared electron pair also preferably configures a 5-membered or 6-membered ring.

The coordinating atom to be coordinated with an unshared electron pair included in the compound (A2) is also preferably a nitrogen atom. In addition, it is also preferred that an atom adjacent to a nitrogen atom which is the coordinating atom to be coordinated with an unshared electron pair included in the compound (A2) is a carbon atom and the carbon atom has a substituent. When the compound (A2) is provided with the above-described constitution, the structure of the copper complex becomes easily distorted, and thus it is possible to further improve the color valency. The substituent is identical to the substituent that the ring including the above-described coordinating atom to be coordinated with an unshared electron pair may include and is preferably an alkyl group having 1 to 10 carbon atoms, an aryl group having 6 to 12 carbon atoms, a carboxyl group, an alkoxy group having 1 to 12 carbon atoms, an acyl group having 1 to 12 carbon atoms, an alkylthio group having 1 to 12 carbon atoms, or a halogen atom. Particularly, an alkyl group, an aryl group, a carboxyl group, and a halogen atom are preferred.

The compound (A2) is also preferably represented by Formula (II) or (III).

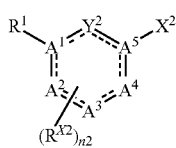

Formula (II)

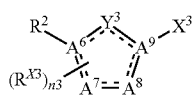

Formula (III)

(In Formula (II), $X^2$ represents a group including the coordination site to be coordinated with the anion. $Y^2$ represents an oxygen atom, a nitrogen atom, a sulfur atom, or a phosphorus atom. Each of $A^1$ and $A^5$ independently represents a carbon atom, a nitrogen atom, or a phosphorus atom. Each of $A^2$ to $A^4$ independently represents a carbon atom, an oxygen atom, a nitrogen atom, a sulfur atom, or a phosphorus atom. $R^1$ represents a substituent. $R^{X2}$ represents a substituent. n2 represents an integer from 0 to 3.

In Formula (III), $X^3$ represents the coordination site to be coordinated with the anion. $Y^3$ represents an oxygen atom, a nitrogen atom, a sulfur atom, or a phosphorus atom. Each of $A^6$ and $A^9$ independently represents a carbon atom, a nitrogen atom, or a phosphorus atom. Each of $A^7$ to $A^8$ independently represents a carbon atom, an oxygen atom, a nitrogen atom, a sulfur atom, or a phosphorus atom. $R^2$ represents a substituent. $R^{X3}$ represents a substituent. n3 represents an integer from 0 to 2.)

In Formula (II), $X^2$ represents the above-described group including the coordination site to be coordinated with the anion and, for example, may be formed only of the group including the coordination site to be coordinated with the anion, and the group including the coordination site to be coordinated with the anion may have a substituent. Examples of the substituent that the group including the coordination site to be coordinated with the anion may have include a halogen atom, a carboxyl group, and a heterocyclic group. The heterocyclic group as the substituent may be a monocyclic ring or a polycyclic ring and may be aromatic or non-aromatic. The number of hetero atoms configuring the heterocycle is preferably in a range of 1 to 3 and preferably 1 or 2. The hetero atom configuring the heterocycle is preferably a nitrogen atom.

In Formula (II), $Y^2$ represents an oxygen atom, a nitrogen atom, a sulfur atom, or a phosphorus atom and preferably represents an oxygen atom, a nitrogen atom, or a sulfur atom, more preferably an oxygen atom or a nitrogen atom, and still more preferably a nitrogen atom.

In Formula (II), independently represents a carbon atom, a nitrogen atom, or a phosphorus atom and is preferably a carbon atom.

In Formula (II), each of $A^2$ to $A^4$ independently represents a carbon atom, an oxygen atom, a nitrogen atom, a sulfur atom, or a phosphorus atom. $A^2$ and $A^3$ preferably represent carbon atoms. $A^4$ preferably represents a carbon atom or a nitrogen atom.

In Formula (II), $R^1$ represents a substituent, and the substituent is identical to the substituent that the carbon atom has in a case in which an atom adjacent to the nitrogen atom which is the coordinating atom to be coordinated with an unshared electron pair included in the above-described compound (A2) is a carbon atom, and the preferred range thereof is also identical.

In Formula (II), $R^{X2}$ represents a substituent, and the substituent is identical to the substituent that the ring including the above-described coordinating atom to be coordinated with an unshared electron pair may have, and the preferred range thereof is also identical. $R^{X2}$ is preferably any substituent of $A^2$ to $A^4$ in Formula (II), and the substituent preferably does not substitute $Y^2$.

In Formula (II), n2 represents an integer from 0 to 3 and is preferably 0 or 1, and more preferably 0.

In Formula (III), $X^3$ represents a group including the coordination site to be coordinated with the anion and is identical to $X^2$ in Formula (II), and the preferred range thereof is also identical.

In Formula (III), $Y^3$ represents an oxygen atom, a nitrogen atom, a sulfur atom, or a phosphorus atom and preferably represents an oxygen atom, a nitrogen atom, or a sulfur atom, and more preferably an oxygen atom or a nitrogen atom.

In Formula (III), each of $A^6$ and $A^9$ independently represents a carbon atom, a nitrogen atom, or a phosphorus atom. $A^6$ is preferably a carbon atom or a nitrogen atom. $A^9$ is preferably a carbon atom.

In Formula (III), each of $A^7$ and $A^8$ independently represents a carbon atom, an oxygen atom, a nitrogen atom, a sulfur atom, or a phosphorus atom. $A^7$ is preferably a carbon atom. $A^8$ is preferably a carbon atom, a nitrogen atom, or a sulfur atom.

In Formula (III), $R^2$ represents a substituent, and the substituent is identical to $R^1$ in Formula (II), and the preferred range thereof is also identical.

In Formula (III), $R^{X3}$ represents a substituent, and the substituent is identical to $R^{X2}$ in Formula (II), and the preferred range thereof is also identical.

In Formula (III), n3 represents an integer from 0 to 2 and is preferably 0 or 1, and more preferably 0.

Meanwhile, $R^{X3}$ and $R^{X2}$ are preferably not substituents in which a plurality of π conjugate systems are not continuously bonded to each other in order to improve the visible transmission.

The compound (A2) is also preferably represented by Formula (I) described below. When the compound is provided with the above-described configuration, it is possible to further improve the heat resistance.

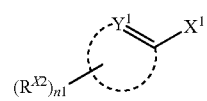

Formula (I)

(In General Formula (I), $X^1$ represents a group including the coordination site to be coordinated with the anion. $Y^1$ represents a nitrogen atom or a phosphorus atom and configures a 4- to 7-membered ring together with a carbon atom adjacent thereto. $R^{X1}$ represents a substituent, and n1 represents an integer from 0 to 6.)

In Formula (I), $X^1$ represents a group including the coordination site to be coordinated with the anion and is identical to $X^2$ in Formula (II), and the preferred range thereof is also identical.

In Formula (I), $Y^1$ represents a nitrogen atom or a phosphorus atom and configures a 4- to 7-membered ring together with a carbon atom adjacent thereto. Particularly, $Y^1$ in Formula (I) preferably represents a nitrogen atom and preferably configures a 5- or 6-membered ring together with a carbon atom adjacent thereto.

In Formula (I), $R^{X1}$ represents a substituent and is identical to the substituent that the compound may have in a case in which the above-described coordinating atom to be coordinated with an unshared electron pair is included in the ring, and the preferred range thereof is also identical.

In Formula (I), n1 represents an integer from 0 to 6 and is preferably in a range of 0 to 2 and more preferably 0 or 1.

Meanwhile, $R^{X1}$ is preferably not a substituent in which a plurality of π conjugate systems are not continuously bonded to each other in order to improve the visible transmission.

In addition, the compound (A2) is also preferably represented by Formula (1).

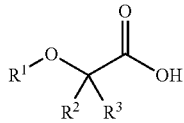

Formula (1)

(In Formula (1), $R^1$ represents a hydrocarbon group. Each of $R^2$ and $R^3$ independently represents a hydrogen atom, a halogen atom, or a monovalent organic group. $R^1$ and $R^2$ or $R^3$ may be bonded to each other so as to form a ring.)

When a composition including the compound represented by Formula (1) is used, it is possible to decrease the transmission in the visible light range when a cured film is produced and to enhance the near-infrared shielding properties.

In Formula (1), $R^1$ represents a hydrocarbon group and preferably represents an alkyl group or an aryl group.

In a case in which $R^1$ in Formula (1) represents an alkyl group, the alkyl group may have any of a linear shape, a branched shape, and a ring shape. The number of carbon atoms in the alkyl group is preferably in a range of 1 to 12, more preferably in a range of 1 to 10, and still more preferably in a range of 1 to 5. Specifically, the alkyl group is preferably a methyl group, an ethyl group, or a propyl group. In a case in which $R^1$ in Formula (1) represents an alkyl group, the alkyl group may further have a substituent. Examples of the substituent that the alkyl group may have include an alkyloxy group, an alkylcarbonyl group, an acyl group, an alkoxycarbonyl group, a halogen atom (for example, a fluorine atom), a heterocyclic group (for example, an oxolane ring, an oxane ring, a dioxolane ring, a furan ring, a dioxane ring, or a pyran ring), and a polymerizable group (for example, a vinyl group or a (meth)acryloyl group). The alkyl group having the substituent may have another substituent.

In a case in which $R^1$ in Formula (1) represents an aryl group, the number of carbon atoms in the aryl group is preferably in a range of 6 to 18 and more preferably in a range of 6 to 12. The aryl group is preferably a phenyl group. In a case in which $R^1$ in Formula (1) represents an aryl group, the aryl group may further have a substituent. The substituent that the alkyl group may have is identical to that in a case in which $R^1$ in Formula (1) represents an alkyl group.

In Formula (1), each of $R^2$ and $R^3$ independently represents a hydrogen atom, a halogen atom, or a monovalent organic group.

A first aspect of the compound represented by Formula (1) is an aspect in which $R^2$ and $R^3$ in Formula (1) are both hydrogen atoms, and a second aspect thereof is an aspect in which either or both $R^2$ and $R^3$ in Formula (1) represent halogen atoms or monovalent organic groups. The compound is preferably either the first aspect or the second aspect.

In a case in which $R^2$ and $R^3$ in Formula (1) represent halogen atoms, fluorine atoms are preferred.

In a case in which $R^2$ and $R^3$ in Formula (1) represent monovalent organic groups, an alkyl group or an aryl group is preferred, and an alkyl group is more preferred. The alkyl group may have a linear shape, a branched shape, or a ring shape, but preferably has a linear shape or a branched shape. The number of carbon atoms in the alkyl group is preferably in a range of 1 to 8 and more preferably in a range of 1 to 5. Particularly, the alkyl group is preferably a methyl group, an ethyl group, or a propyl group. The number of carbon atoms in the aryl group is preferably in a range of 6 to 18 and more preferably in a range of 6 to 12. The aryl group is preferably a phenyl group.

In Formula (1), $R^1$ and $R^2$ are bonded to each other so as to form a 5-membered ring or 6-membered ring having an oxygen atom, and $R^3$ is also preferably a hydrogen atom.

The 5-membered ring or 6-membered ring having an oxygen atom may be an aromatic ring or a non-aromatic ring, but is preferably a non-aromatic ring. Atoms configuring the 5-membered ring or 6-membered ring having an oxygen atom are preferably an oxygen atom or a carbon atom. The number of oxygen atoms in the 5-membered ring or 6-membered ring having an oxygen atom is preferably in a range of 1 to 3, more preferably 1 or 2, and still more preferably 1. The number of carbon atoms in the 5-membered ring or 6-membered ring having an oxygen atom is preferably in a range of 1 to 5 and more preferably 4 or 5. Specific examples of the 5-membered ring or 6-membered ring having an oxygen atom include an oxolane ring, an oxane ring, a dioxolane ring, a furan ring, a dioxane ring, and a pyran ring.

The compound represented by Formula (1) is also preferably represented by Formula (2).

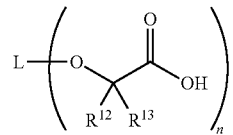

(In Formula (2), each of $R^{12}$ and $R^{13}$ independently represents a hydrogen atom, a halogen atom, or a monovalent organic group. L represents an n-valent hydrocarbon group or an n-valent group formed of a combination of a hydrocarbon group and —O—. n represents an integer from 2 to 6.)

In Formula (2), $R^{12}$ and $R^{13}$ are identical to $R^2$ and $R^3$ in Formula (1), and both preferably represent hydrogen atoms.

In Formula (2), L represents an n-valent hydrocarbon group or an n-valent group formed of a combination of a hydrocarbon group and —O—. The hydrocarbon group may have a linear shape, a branched shape, or a ring shape. The number of carbon atoms in a case in which the hydrocarbon group has a linear shape is preferably in a range of 2 to 12 and more preferably in a range of 2 to 5. The number of carbon atoms in a case in which the hydrocarbon group has a branched shape is preferably in a range of 3 to 12 and more preferably in a range of 6 to 10. The number of carbon atoms in a case in which the hydrocarbon group has a ring shape is preferably in a range of 3 to 12, more preferably in a range of 6 to 12, and more preferably 6. In a case in which the hydrocarbon group has a ring shape, the hydrocarbon group may be an aromatic ring or a non-aromatic ring, but is preferably a non-aromatic ring.

In Formula (2), n represents an integer from 2 to 6 and is preferably an integer from 2 to 4, more preferably 2 or 3, and still more preferably 2.

The carboxyl group equivalent of the compound represented by Formula (1) is preferably in a range of 1 to 3 and more preferably in a range of 1 to 2.

Specific examples of the compound (A2) include the following compounds and salts of the following compounds (for example, metal salts of sodium and the like (alkali metal salts)), but the compound is not limited thereto.

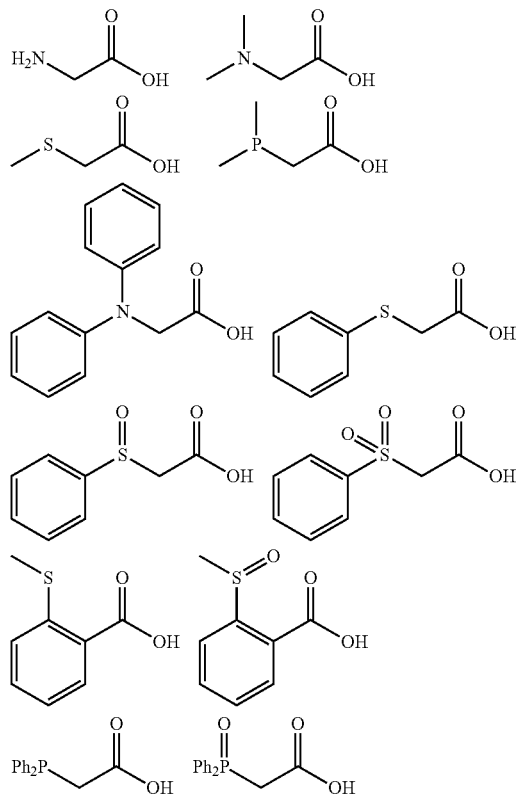

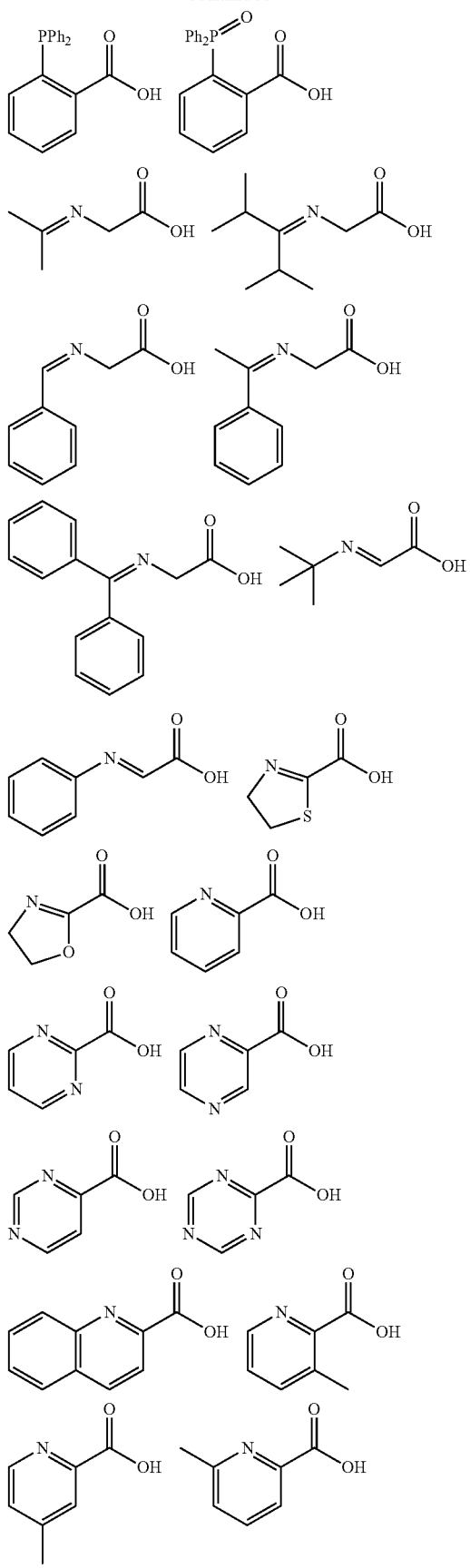

-continued
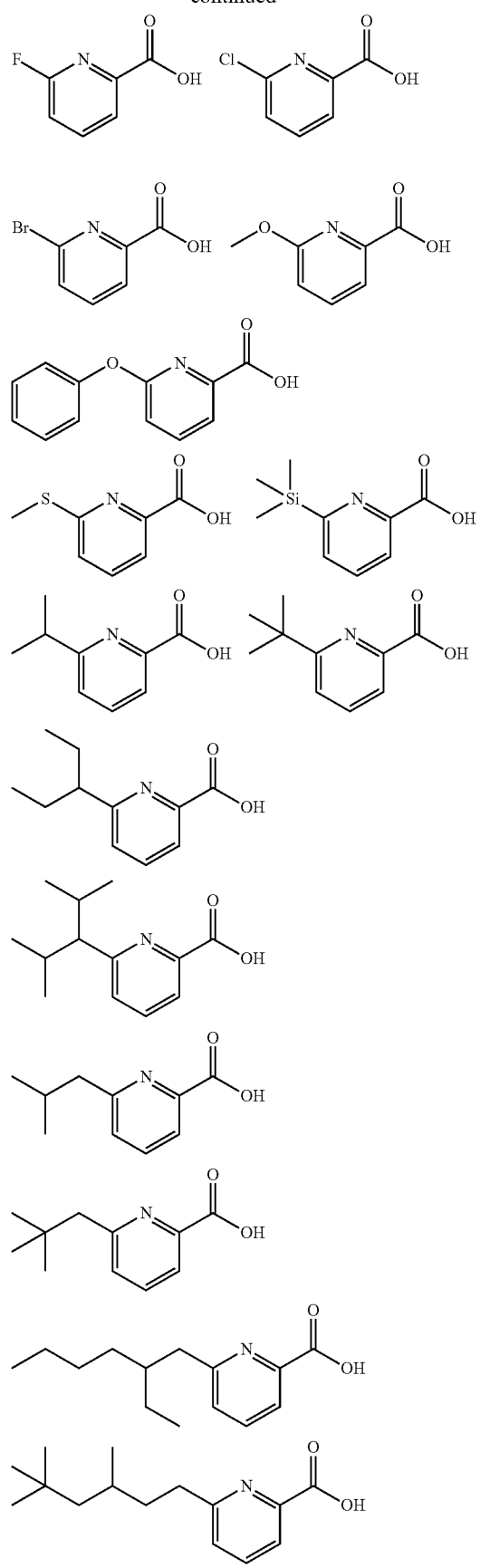
-continued
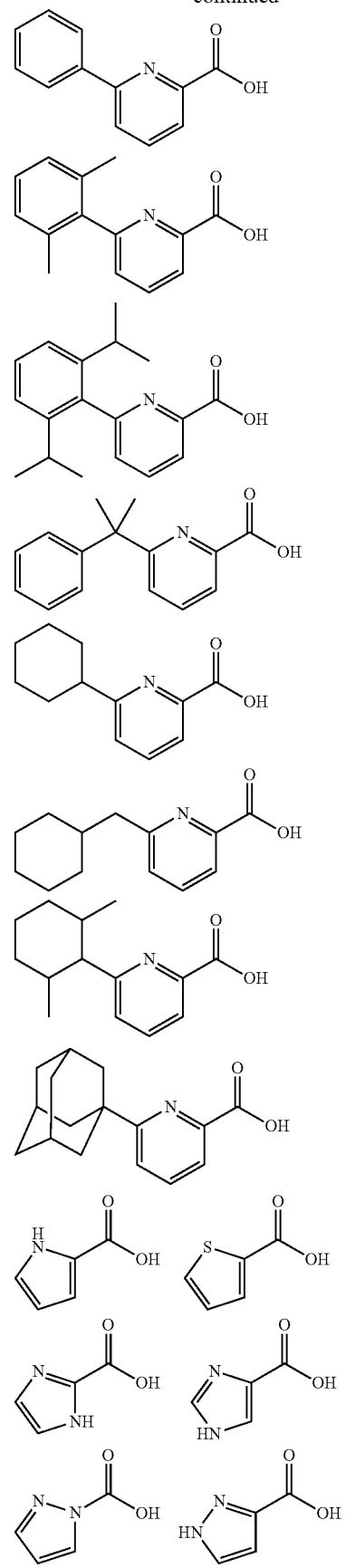

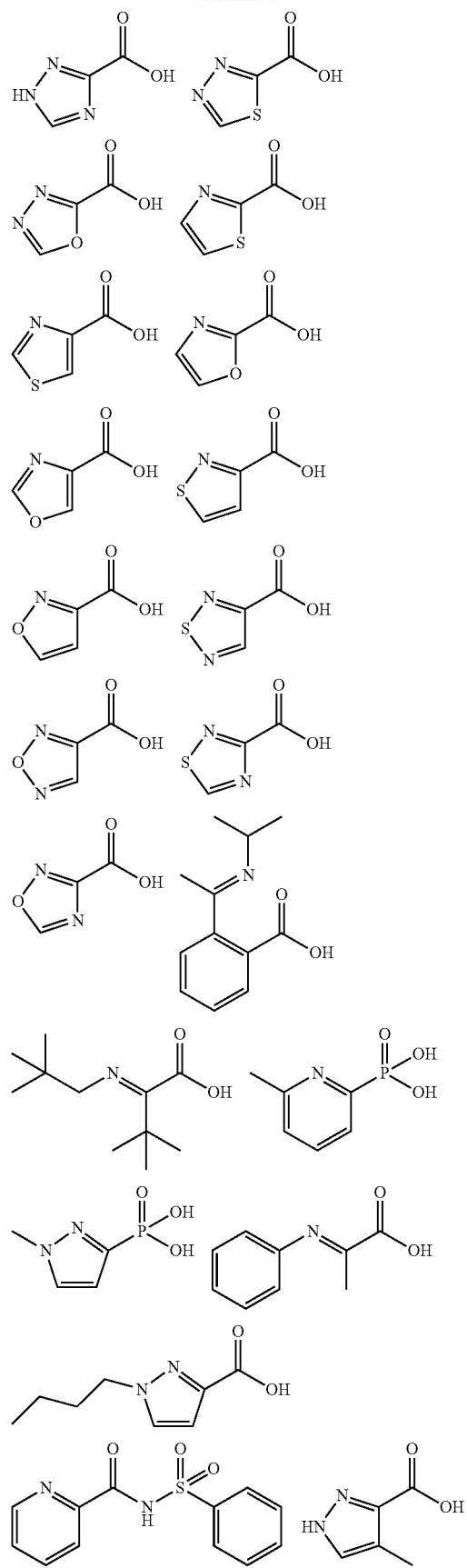
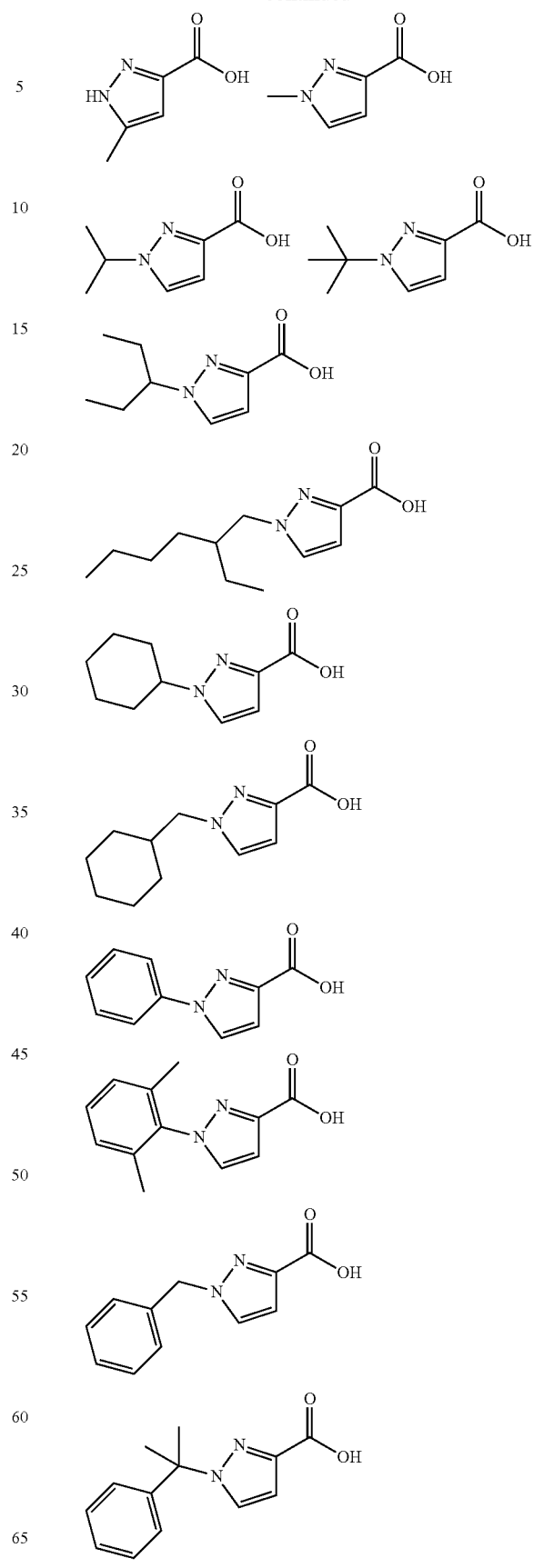

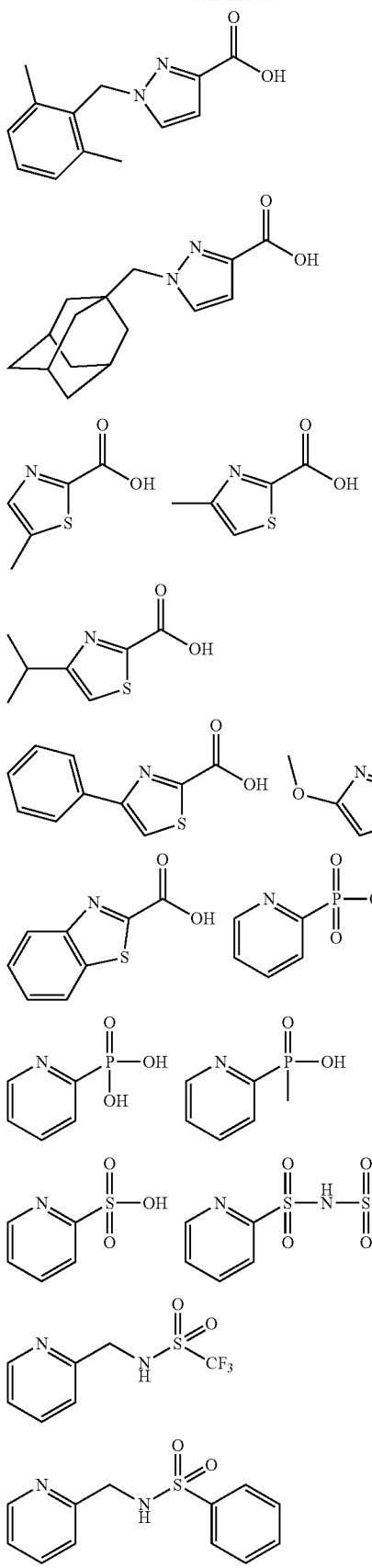
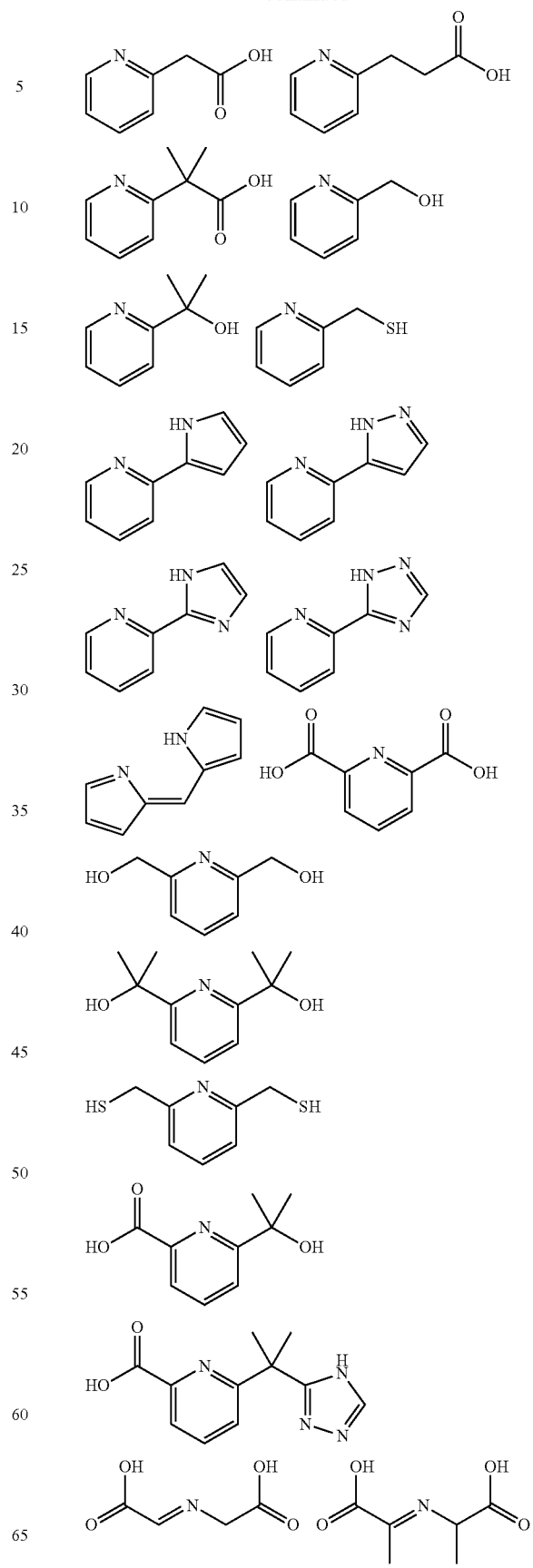

-continued
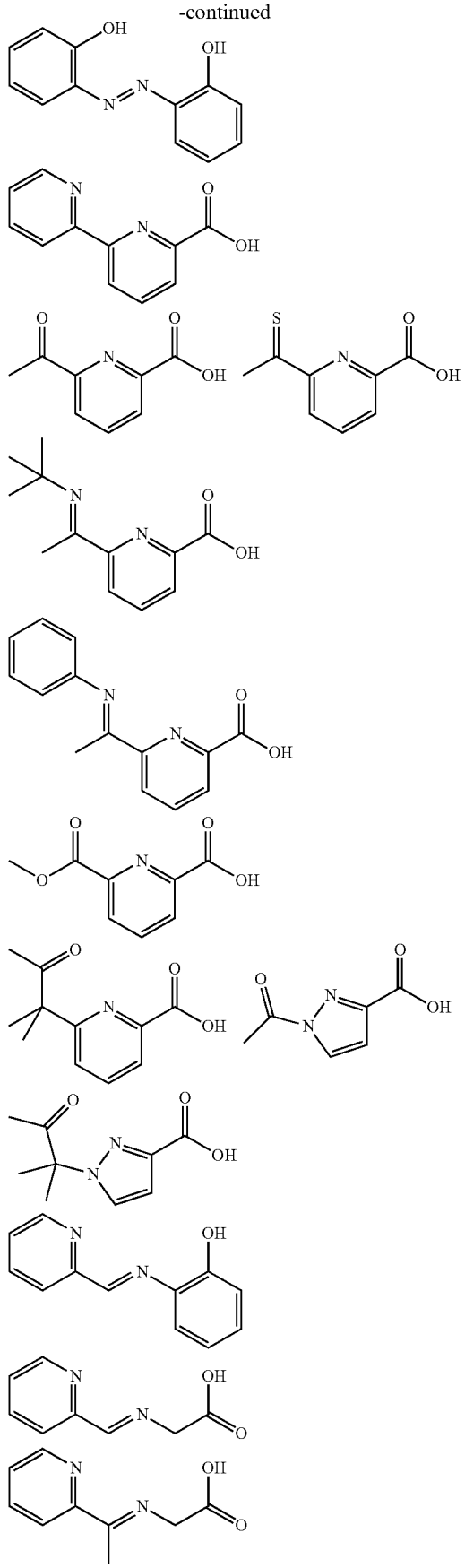
-continued
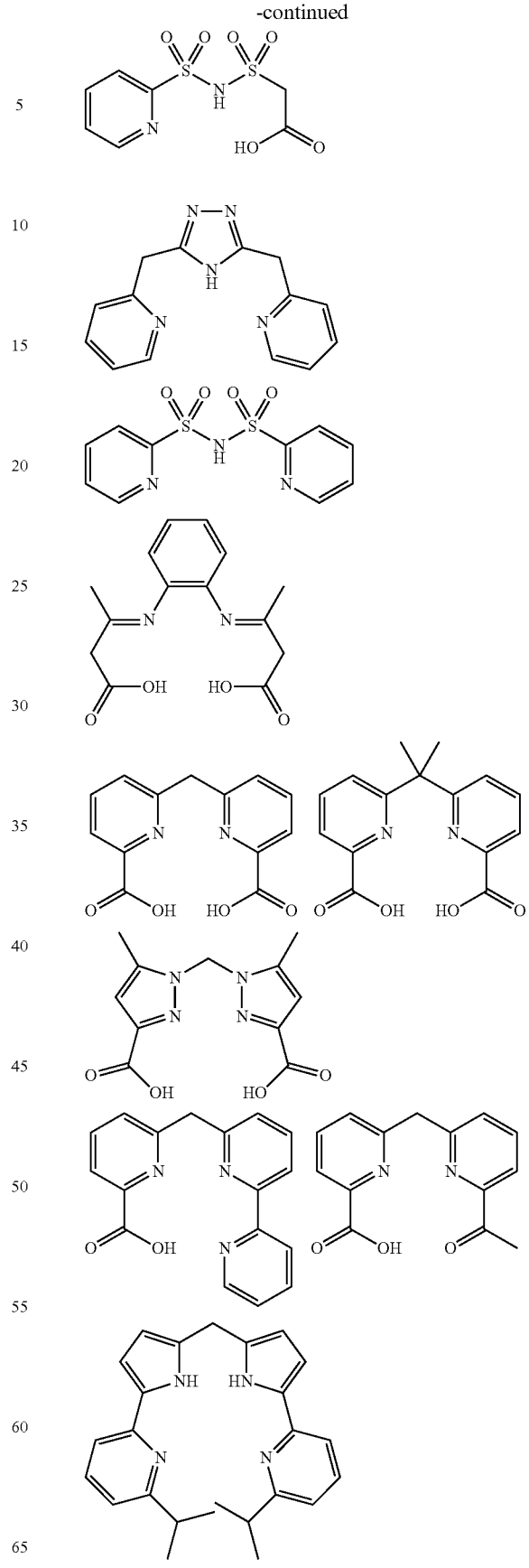

-continued
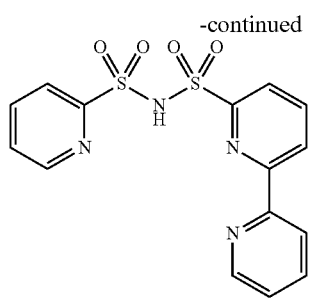
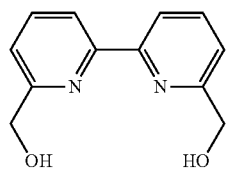
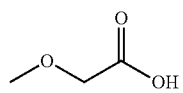
(A2-2-1)
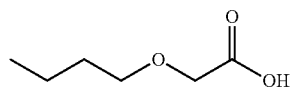
(A2-2-2)
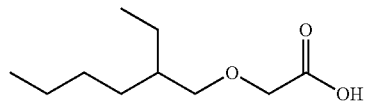
(A2-2-3)
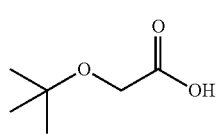
(A2-2-4)
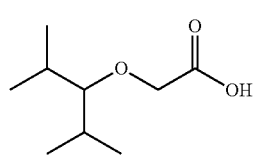
(A2-2-5)
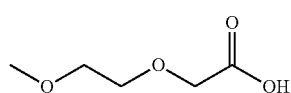
(A2-2-6)
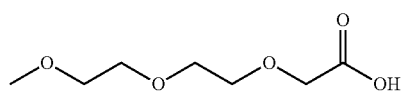
(A2-2-7)
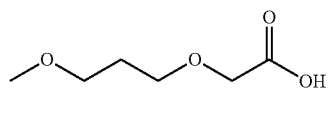
(A2-2-8)
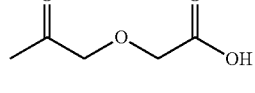
(A2-2-9)
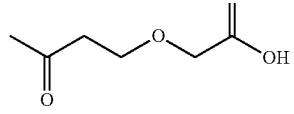
(A2-2-10)
-continued
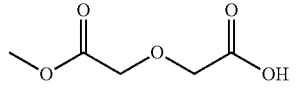
(A2-2-11)
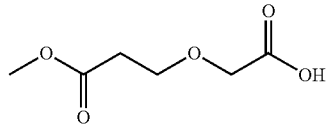
(A2-2-12)
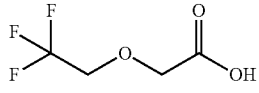
(A2-2-13)
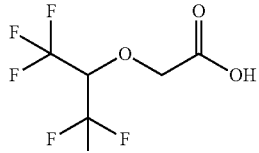
(A2-2-14)
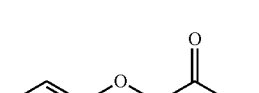
(A2-2-15)
(A2-2-16)
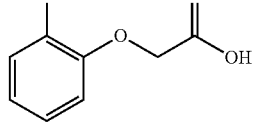
(A2-2-17)
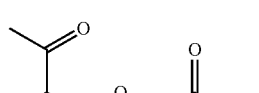
(A2-2-18)
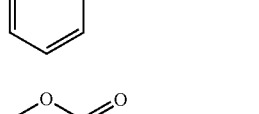
(A2-2-19)
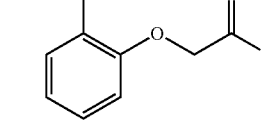
(A2-2-20)
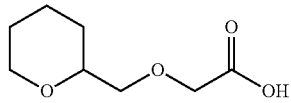
(A2-2-21)

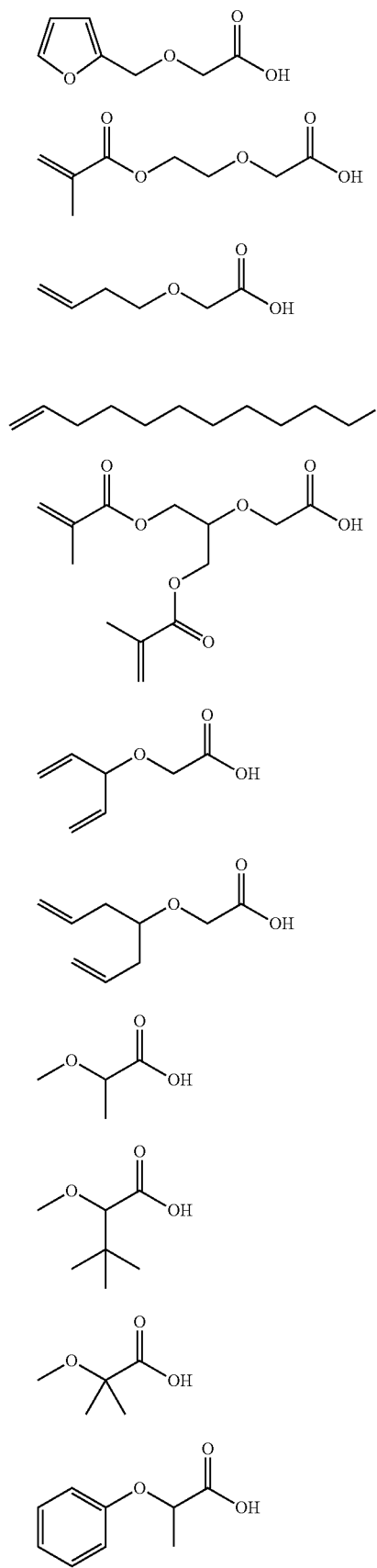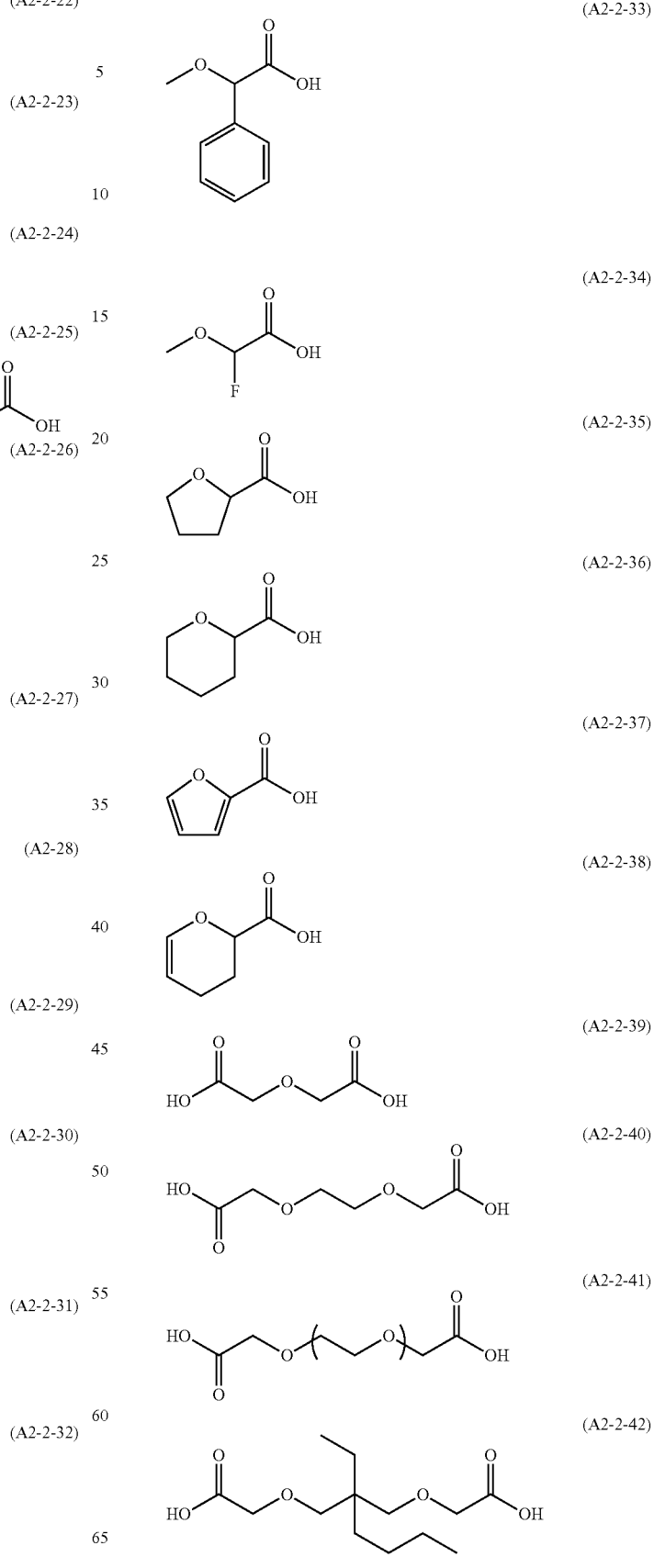

(A2-2-43)

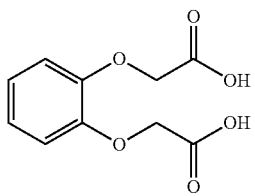

(A2-2-44)

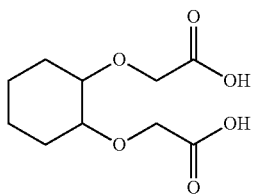

(A2-2-45)

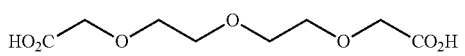

<<Salt of Compound (A2)>>

The salt of the compound (A2), which is used in the present invention, that is, the salt in the monoanionic coordination site is preferably, for example, a metal salt, and specific examples thereof include a sodium salt, a potassium salt, a magnesium salt, and a calcium salt.

<<Compound (A3)>>

A third preferred embodiment of the compound (A) is a compound (A3) having two or more coordinating atoms to be coordinated with an unshared electron pair. The compound (A3) may have, in one molecule, two or more coordinating atoms to be coordinated with an unshared electron pair, may have three or more coordinating atoms, and preferably has 2 to 4 coordinating atoms, and more preferably has 2 or 3 coordinating atoms.

The compound (A3) may or may not have the coordination site to be coordinated with the anion in the molecule. Here, the coordination site to be coordinated with the anion refers to a coordination site having an anion capable of coordinating a copper atom in the copper component, and examples thereof include coordination sites having an oxygen anion, a nitrogen anion, or a sulfur anion.

In the compound (A3), the number of atoms linking the coordinating atoms to be coordinated with an unshared electron pair is preferably in a range of 1 to 6 and more preferably in a range of 1 to 3. When the compound (A3) is provided with the above-described configuration, the structure of the copper complex becomes easily distorted, and thus it is possible to further improve the color valency.

The number of kinds of the atoms linking the coordinating atoms to be coordinated with an unshared electron pair may be one or more. The atom linking the coordinating atoms to be coordinated with an unshared electron pair is preferably a carbon atom.

In the following exemplary compounds, the coordinating atom to be coordinated with an unshared electron pair is a nitrogen atom, the atom linking the coordinating atoms to be coordinated with an unshared electron pair is a carbon atom, and the number of carbon atoms linking the nitrogen atoms is two.

The number of unsaturated bonds that the compound (A3) may have is preferably 9 or smaller, and preferably in a range of 1 to 9.

The molecular weight of the compound (A3) is preferably in a range of 50 to 1000 and more preferably in a range of 50 to 600.

In the compound (A3), the coordinating atom to be coordinated with an unshared electron pair is identical to that described in the section of the above-described compound (A2), and the preferred range thereof is also identical.

The compound (A3) is also preferably represented by General Formula (V) described below.

$$Y^1\text{-}L^1\text{-}Y^2 \qquad \text{General Formula (V)}$$

(In General Formula (V), each of $Y^1$ and $Y^2$ independently represents a ring including the coordinating atom to be coordinated with an unshared electron pair or the partial structure represented by the group (UE). $L^1$ represents a single bond or a divalent linking group.)

In General Formula (V), $Y^1$ and $Y^2$ are identical to rings including the above-described coordinating atom to be coordinated with an unshared electron pair or partial structures including the above-described coordinating atom to be coordinated with an unshared electron pair, and the preferred range thereof is also identical.

In General Formula (V), in a case in which $L^1$ represents a divalent linking group, an alkylene group having 1 to 12 carbon atoms, an arylene group having 6 to 12 carbon atoms, —SO—, —O—, —SO$_2$—, or a group formed of a combination thereof is preferred, and an alkylene group having 1 to 3 carbon atoms, a phenylene group, or —SO$_2$— is preferred.

More detailed examples of the compound (A3) also include compounds represented by General Formula (V-1) or (V-2) described below.

$$Y^3\text{-}L^2\text{-}Y^4\text{-}L^3\text{-}Y^5 \qquad (V\text{-}1)$$

$$Y^6\text{-}L^6\text{-}Y^7\text{-}L^7\text{-}Y^8\text{-}L^8\text{-}Y^9 \qquad (V\text{-}2)$$

In General Formulae (V-1) and (V-2), each of $Y^3$, $Y^5$, $Y^6$, and $Y^9$ independently represents a ring including the coordinating atom to be coordinated with an unshared electron pair or the partial structure represented by the group (UE).

In addition, each of $Y^4$, $Y^7$, and $Y^8$ is independently a ring including the coordinating atom to be coordinated with an unshared electron pair or at least one selected from the group (UE-1) in the above-described compound (A2).

In General Formulae (V-1) and (V-2), each of $L^2$ to $L^8$ independently represents a single bond or a divalent linking group. The divalent linking group is identical to that in a case in which $L^1$ in General Formula (V) represents a divalent linking group, and the preferred range thereof is also identical.

The compound (A3) is also preferably a compound having a 5-membered or 6-membered ring and is identical to the above-described compound (A2), and the preferred range thereof is also identical.

Specific examples of the compound (A3) include the following compounds, but the compound (A3) is not limited thereto.

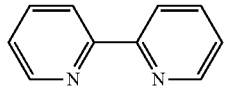

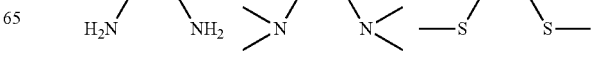

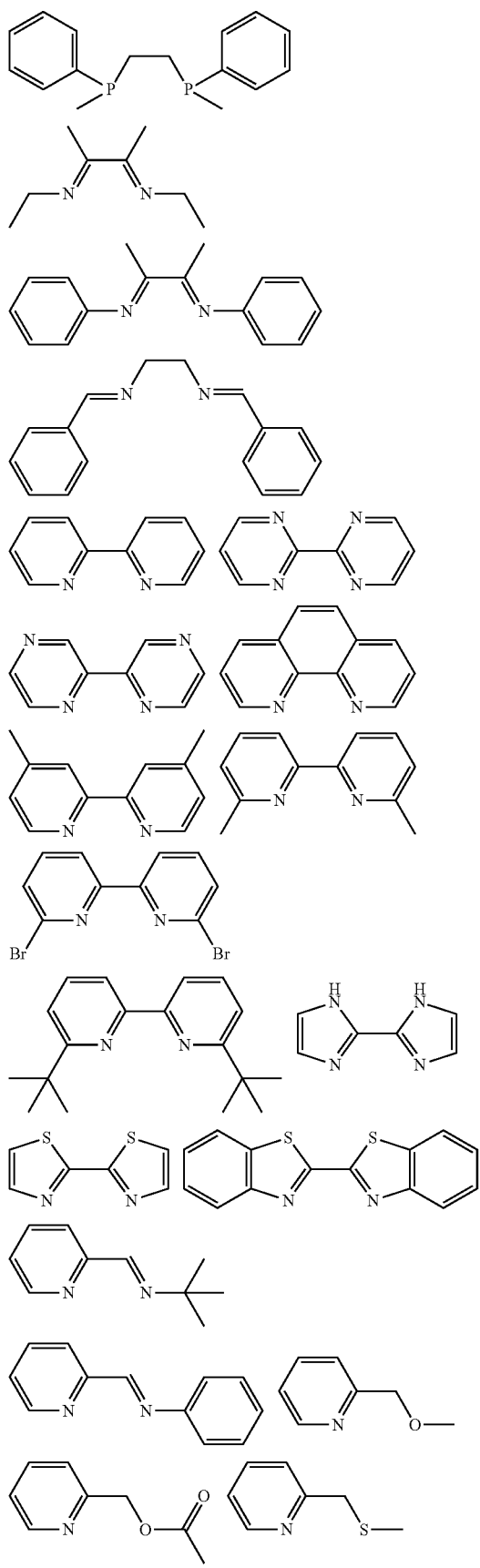
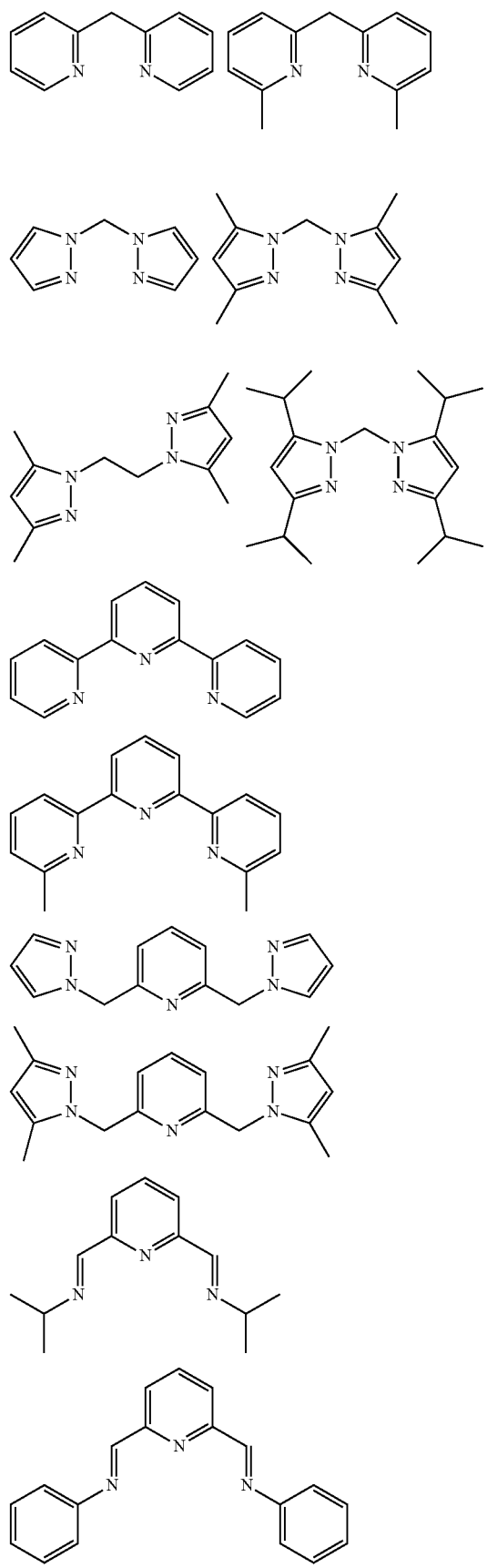

-continued

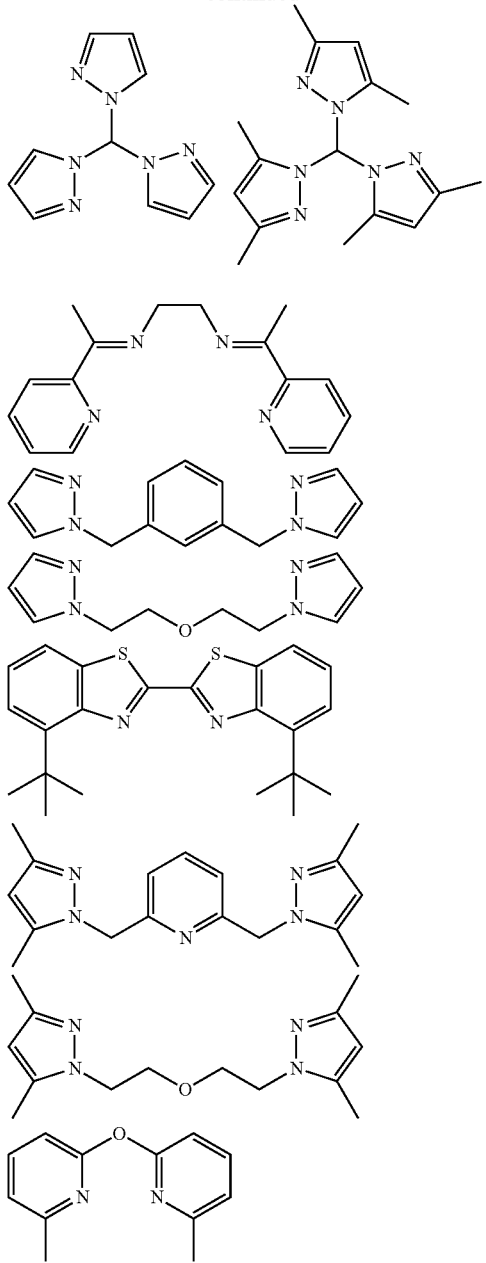

<<Copper Component>>

As the copper component in the copper complex used in the present invention, it is possible to use copper or a compound including copper. As the compound including copper, it is possible to use, for example, copper oxide or a copper salt. For the copper salt, monovalent or divalent copper is preferred and divalent copper is more preferred. The copper salt is more preferably copper acetate, copper chloride, copper formate, copper hydroxide, copper stearate, copper benzoate, copper ethylacetoacetate, copper pyrophosphate, copper naphthenate, copper citrate, copper nitrate, copper sulfate, copper carbonate, copper chlorate, copper (meth)acrylate, copper perchlorate, copper phosphinate, copper diphenylphosphinate, or copper methane sulfonate. Particularly, the copper salt used in the compound (A1) and the compound (A2) is preferably copper acetate, copper chloride, copper sulfate, copper hydroxide, copper benzoate, or copper (meth)acrylate. The copper salt used in the compound (A3) is preferably copper acetate, copper chloride, copper phosphinate, copper diphenylphosphinate, or copper methane sulfonate and more preferably copper acetate, copper phosphinate, copper diphenylphosphinate, or copper methane sulfonate.

<<Reaction Between Compound (A) and Copper Component>>

The reaction ratio in a reaction between the copper component and the above-described compound (A) or a compound having a salt thereof is preferably set in a range of 1:0.5 to 1:8 and more preferably set in a range of 1:0.5 to 1:4 in terms of molar ratio.

In addition, the reaction conditions for the reaction between the copper component and the above-described compound A or a compound having a salt thereof are preferably set to, for example, a temperature in a range of 20° C. to 50° C. and 0.5 hours or longer.

Regarding the molar ratio in a case in which two or more compounds (A) used in the present invention are used, for example, in a case in which two compounds (A) used in the present invention (the compound (A10) of the present invention and the compound (A11) of the present invention) are used, the molar ratio ((A10)/(A11)) is preferably in a range of 1/9 to 9/1, more preferably in a range of 1/5 to 5/1, still more preferably in a range of 1/2 to 2/1, and particularly preferably 1/1.

The reaction ratio in a reaction between the copper component and the above-described compound (A) or a compound having a salt thereof is preferably set in a range of 1:0.5 to 1:8 and more preferably set in a range of 1:0.5 to 1:4 in terms of molar ratio.

In addition, the reaction conditions for the reaction between the copper component and the above-described compound (A) or a compound having a salt thereof are preferably set to, for example, a temperature in a range of 20° C. to 50° C. and 0.5 hours or longer.

Specific examples of the copper complex used in the present invention include copper complexes in which any one or more of exemplary compounds (A-1) to (A-191) of the compound (A) used in the present invention and salts thereof are used. Examples thereof include exemplary compounds (Cu-1) to (Cu-444) of the following copper complexes. The copper complex included in the composition of the present invention is not limited to the following exemplary compounds. (A-6) and the like in the following tables correspond to the exemplary compounds (A-1) to (A-106) of the compound (A1) used in the present invention. For example, a copper complex Cu-1 represents a copper complex obtained by reacting the compound (A-1) used in the present invention with the copper component. In addition, a copper complex Cu-25 represents a copper complex obtained by reacting the compounds (A-82) and (A-83) used in the present invention with the copper component.

In addition, specific examples of the copper complex used in the present invention also include the following copper complexes Cu-445 to 452, copper complexes Cu-1-1 to Cu 1-52, and copper complexes Cu-2-1 to Cu 2-49. In the following tables, Compounds A2-1-1 to A2-1-22 represents Compounds A2-1-1 to A2-1-22 illustrated below. In addition, in the following tables, Compounds A2-2-1 to A2-2-44 represent Compounds A2-2-1 to A2-2-44 described above.

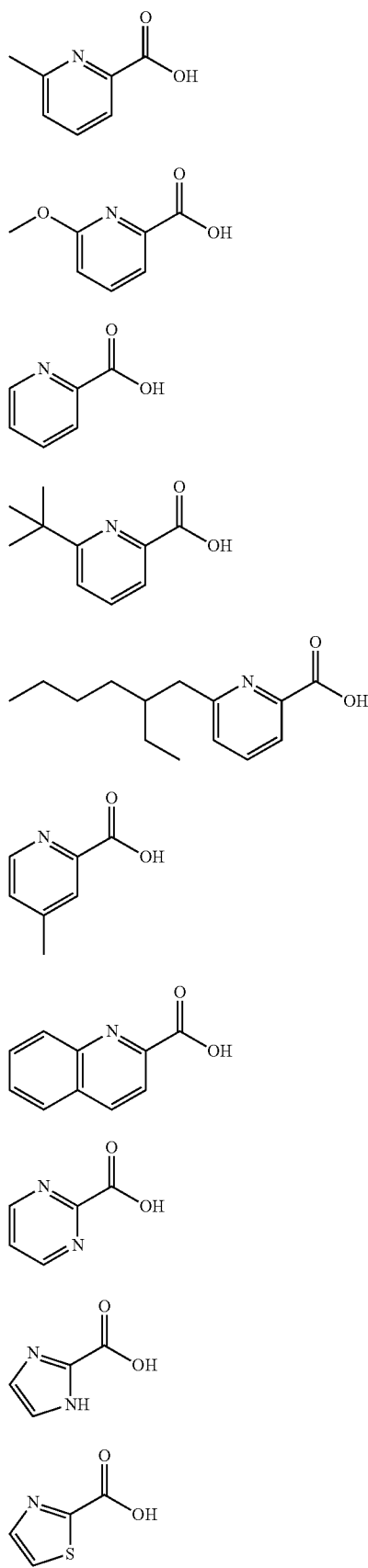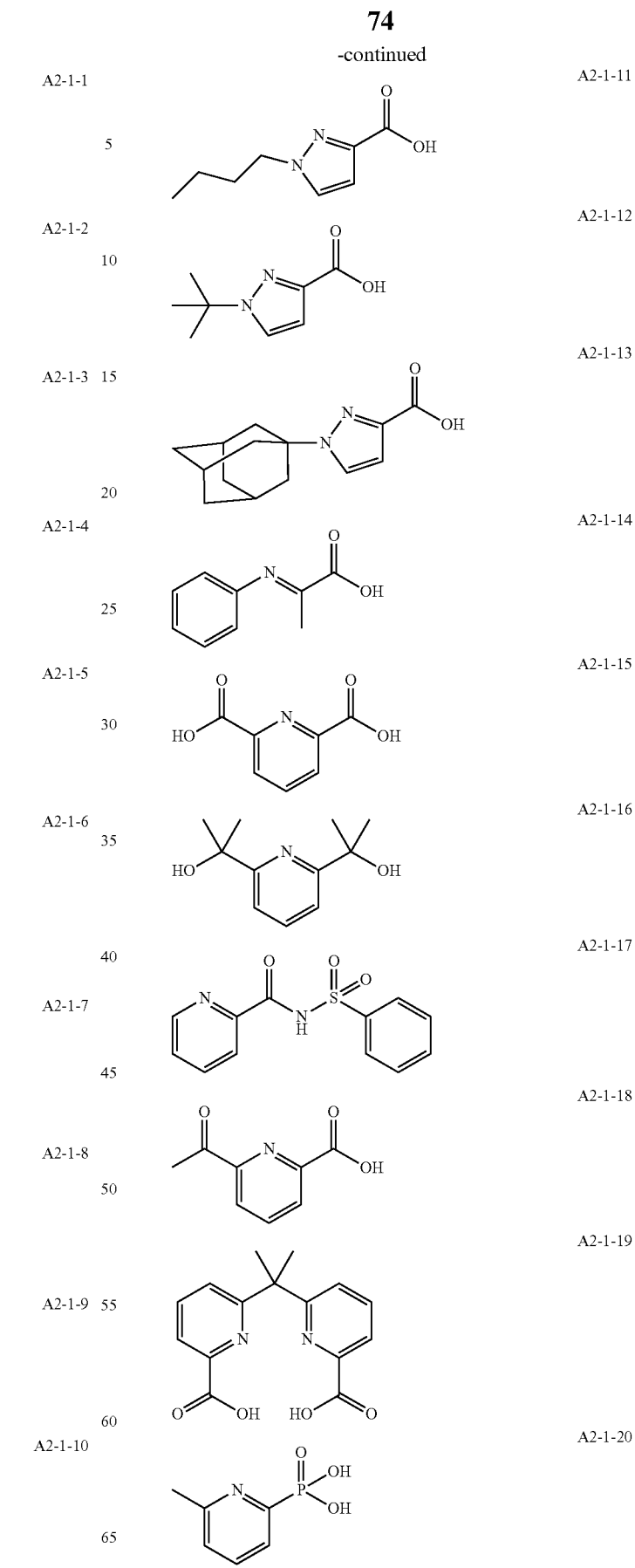

-continued

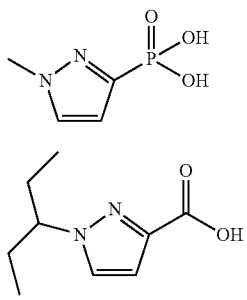

A2-1-21

A2-1-22

TABLE 1

| Copper complex | Ligand (1) | Ligand (2) |
|---|---|---|
| Cu-1 | A-1 | — |
| Cu-2 | A-7 | — |
| Cu-3 | A-12 | — |
| Cu-4 | A-24 | — |
| Cu-5 | A-25 | — |
| Cu-6 | A-31 | — |
| Cu-7 | A-50 | — |
| Cu-8 | A-52 | — |
| Cu-9 | A-65 | — |
| Cu-10 | A-73 | — |
| Cu-11 | A-77 | — |
| Cu-12 | A-82 | — |
| Cu-13 | A-83 | — |
| Cu-14 | A-88 | — |
| Cu-15 | A-92 | — |
| Cu-16 | A-96 | — |
| Cu-17 | A-109 | — |
| Cu-18 | A-112 | — |
| Cu-19 | A-126 | — |
| Cu-20 | A-132 | — |
| Cu-21 | A-135 | — |
| Cu-22 | A-138 | — |
| Cu-23 | A-142 | — |
| Cu-24 | A-146 | — |
| Cu-25 | A-82 | A-83 |
| Cu-26 | A-2 | — |
| Cu-27 | A-3 | — |
| Cu-28 | A-4 | — |
| Cu-29 | A-5 | — |
| Cu-30 | A-6 | — |
| Cu-31 | A-8 | — |
| Cu-32 | A-9 | — |
| Cu-33 | A-10 | — |
| Cu-34 | A-11 | — |
| Cu-35 | A-13 | — |
| Cu-36 | A-14 | — |
| Cu-37 | A-15 | — |
| Cu-38 | A-16 | — |
| Cu-39 | A-17 | — |
| Cu-40 | A-18 | — |
| Cu-41 | A-19 | — |
| Cu-42 | A-20 | — |
| Cu-43 | A-21 | — |
| Cu-44 | A-22 | — |
| Cu-45 | A-23 | — |
| Cu-46 | A-26 | — |
| Cu-47 | A-27 | — |
| Cu-48 | A-28 | — |
| Cu-49 | A-29 | — |
| Cu-50 | A-30 | — |
| Cu-51 | A-32 | — |
| Cu-52 | A-33 | — |
| Cu-53 | A-34 | — |
| Cu-54 | A-35 | — |
| Cu-55 | A-36 | — |
| Cu-56 | A-37 | — |
| Cu-57 | A-38 | — |
| Cu-58 | A-39 | — |
| Cu-59 | A-40 | — |
| Cu-60 | A-41 | — |
| Cu-61 | A-42 | — |
| Cu-62 | A-43 | — |
| Cu-63 | A-44 | — |
| Cu-64 | A-45 | — |
| Cu-65 | A-46 | — |
| Cu-66 | A-47 | — |
| Cu-67 | A-48 | — |
| Cu-68 | A-49 | — |
| Cu-69 | A-51 | — |
| Cu-70 | A-53 | — |
| Cu-71 | A-54 | — |
| Cu-72 | A-55 | — |
| Cu-73 | A-56 | — |
| Cu-74 | A-57 | — |
| Cu-75 | A-58 | — |
| Cu-76 | A-59 | — |
| Cu-77 | A-60 | — |
| Cu-78 | A-61 | — |
| Cu-79 | A-62 | — |
| Cu-80 | A-63 | — |

TABLE 2

| Copper complex | Ligand (1) | Ligand (2) |
|---|---|---|
| Cu-81 | A-64 | — |
| Cu-82 | A-66 | — |
| Cu-83 | A-67 | — |
| Cu-84 | A-68 | — |
| Cu-85 | A-69 | — |
| Cu-86 | A-70 | — |
| Cu-87 | A-71 | — |
| Cu-88 | A-72 | — |
| Cu-89 | A-74 | — |
| Cu-90 | A-75 | — |
| Cu-91 | A-76 | — |
| Cu-92 | A-78 | — |
| Cu-93 | A-79 | — |
| Cu-94 | A-80 | — |
| Cu-95 | A-81 | — |
| Cu-96 | A-84 | — |
| Cu-97 | A-85 | — |
| Cu-98 | A-86 | — |
| Cu-99 | A-87 | — |
| Cu-100 | A-89 | — |
| Cu-101 | A-90 | — |
| Cu-102 | A-91 | — |
| Cu-103 | A-93 | — |
| Cu-104 | A-94 | — |
| Cu-105 | A-95 | — |
| Cu-106 | A-97 | — |
| Cu-107 | A-98 | — |
| Cu-108 | A-99 | — |
| Cu-109 | A-100 | — |
| Cu-110 | A-101 | — |
| Cu-111 | A-102 | — |
| Cu-112 | A-103 | — |
| Cu-113 | A-104 | — |
| Cu-114 | A-105 | — |
| Cu-115 | A-106 | — |
| Cu-116 | A-107 | — |
| Cu-117 | A-108 | — |
| Cu-118 | A-110 | — |
| Cu-119 | A-111 | — |
| Cu-120 | A-113 | — |
| Cu-121 | A-114 | — |
| Cu-122 | A-115 | — |
| Cu-123 | A-116 | — |
| Cu-124 | A-117 | — |
| Cu-125 | A-118 | — |
| Cu-126 | A-119 | — |
| Cu-127 | A-120 | — |
| Cu-128 | A-121 | — |
| Cu-129 | A-122 | — |

TABLE 2-continued

| Copper complex | Ligand (1) | Ligand (2) |
|---|---|---|
| Cu-130 | A-123 | — |
| Cu-131 | A-124 | — |
| Cu-132 | A-125 | — |
| Cu-133 | A-127 | — |
| Cu-134 | A-128 | — |
| Cu-135 | A-129 | — |
| Cu-136 | A-130 | — |
| Cu-137 | A-131 | — |
| Cu-138 | A-133 | — |
| Cu-139 | A-134 | — |
| Cu-140 | A-136 | — |
| Cu-141 | A-137 | — |
| Cu-142 | A-139 | — |
| Cu-143 | A-140 | — |
| Cu-144 | A-141 | — |
| Cu-145 | A-143 | — |
| Cu-146 | A-144 | — |
| Cu-147 | A-145 | — |
| Cu-148 | A-147 | — |
| Cu-149 | A-148 | — |
| Cu-150 | A-149 | — |
| Cu-151 | A-150 | — |
| Cu-152 | A-151 | — |
| Cu-153 | A-152 | — |
| Cu-154 | A-153 | — |
| Cu-155 | A-154 | — |
| Cu-156 | A-155 | — |
| Cu-157 | A-156 | — |
| Cu-158 | A-157 | — |
| Cu-159 | A-158 | — |
| Cu-160 | A-159 | — |

TABLE 3

| Copper complex | Ligand (1) | Ligand (2) |
|---|---|---|
| Cu-161 | A-160 | — |
| Cu-162 | A-161 | — |
| Cu-163 | A-162 | — |
| Cu-164 | A-163 | — |
| Cu-165 | A-164 | — |
| Cu-166 | A-165 | — |
| Cu-167 | A-166 | — |
| Cu-168 | A-167 | — |
| Cu-169 | A-168 | — |
| Cu-170 | A-1 | A-7 |
| Cu-171 | A-1 | A-12 |
| Cu-172 | A-1 | A-24 |
| Cu-173 | A-1 | A-25 |
| Cu-174 | A-1 | A-31 |
| Cu-175 | A-1 | A-50 |
| Cu-176 | A-1 | A-52 |
| Cu-177 | A-1 | A-65 |
| Cu-178 | A-1 | A-73 |
| Cu-179 | A-1 | A-77 |
| Cu-180 | A-1 | A-82 |
| Cu-181 | A-1 | A-83 |
| Cu-182 | A-1 | A-88 |
| Cu-183 | A-1 | A-92 |
| Cu-184 | A-1 | A-96 |
| Cu-185 | A-1 | A-109 |
| Cu-186 | A-1 | A-112 |
| Cu-187 | A-1 | A-126 |
| Cu-188 | A-1 | A-132 |
| Cu-189 | A-1 | A-135 |
| Cu-190 | A-1 | A-138 |
| Cu-191 | A-1 | A-142 |
| Cu-192 | A-1 | A-146 |
| Cu-193 | A-7 | A-12 |
| Cu-194 | A-7 | A-24 |
| Cu-195 | A-7 | A-25 |
| Cu-196 | A-7 | A-31 |
| Cu-197 | A-7 | A-50 |
| Cu-198 | A-7 | A-52 |
| Cu-199 | A-7 | A-65 |

TABLE 3-continued

| Copper complex | Ligand (1) | Ligand (2) |
|---|---|---|
| Cu-200 | A-7 | A-73 |
| Cu-201 | A-7 | A-77 |
| Cu-202 | A-7 | A-82 |
| Cu-203 | A-7 | A-83 |
| Cu-204 | A-7 | A-88 |
| Cu-205 | A-7 | A-92 |
| Cu-206 | A-7 | A-96 |
| Cu-207 | A-7 | A-109 |
| Cu-208 | A-7 | A-112 |
| Cu-209 | A-7 | A-126 |
| Cu-210 | A-7 | A-132 |
| Cu-211 | A-7 | A-135 |
| Cu-212 | A-7 | A-138 |
| Cu-213 | A-7 | A-142 |
| Cu-214 | A-7 | A-146 |
| Cu-215 | A-12 | A-24 |
| Cu-216 | A-12 | A-25 |
| Cu-217 | A-12 | A-31 |
| Cu-218 | A-12 | A-50 |
| Cu-219 | A-12 | A-52 |
| Cu-220 | A-12 | A-65 |
| Cu-221 | A-12 | A-73 |
| Cu-222 | A-12 | A-77 |
| Cu-223 | A-12 | A-82 |
| Cu-224 | A-12 | A-83 |
| Cu-225 | A-12 | A-88 |
| Cu-226 | A-12 | A-92 |
| Cu-227 | A-12 | A-96 |
| Cu-228 | A-12 | A-109 |
| Cu-229 | A-12 | A-112 |
| Cu-230 | A-12 | A-126 |
| Cu-231 | A-12 | A-132 |
| Cu-232 | A-12 | A-135 |
| Cu-233 | A-12 | A-138 |
| Cu-234 | A-12 | A-142 |
| Cu-235 | A-12 | A-146 |
| Cu-236 | A-24 | A-25 |
| Cu-237 | A-24 | A-31 |
| Cu-238 | A-24 | A-50 |
| Cu-239 | A-24 | A-52 |
| Cu-240 | A-24 | A-65 |

TABLE 4

| Copper complex | Ligand (1) | Ligand (2) |
|---|---|---|
| Cu-241 | A-24 | A-73 |
| Cu-242 | A-24 | A-77 |
| Cu-243 | A-24 | A-82 |
| Cu-244 | A-24 | A-83 |
| Cu-245 | A-24 | A-88 |
| Cu-246 | A-24 | A-92 |
| Cu-247 | A-24 | A-96 |
| Cu-248 | A-24 | A-109 |
| Cu-249 | A-24 | A-112 |
| Cu-250 | A-24 | A-126 |
| Cu-251 | A-24 | A-132 |
| Cu-252 | A-24 | A-135 |
| Cu-253 | A-24 | A-138 |
| Cu-254 | A-24 | A-142 |
| Cu-255 | A-24 | A-146 |
| Cu-256 | A-25 | A-31 |
| Cu-257 | A-25 | A-50 |
| Cu-258 | A-25 | A-52 |
| Cu-259 | A-25 | A-65 |
| Cu-260 | A-25 | A-73 |
| Cu-261 | A-25 | A-77 |
| Cu-262 | A-25 | A-82 |
| Cu-263 | A-25 | A-83 |
| Cu-264 | A-25 | A-88 |
| Cu-265 | A-25 | A-92 |
| Cu-266 | A-25 | A-96 |
| Cu-267 | A-25 | A-109 |
| Cu-268 | A-25 | A-112 |
| Cu-269 | A-25 | A-126 |

TABLE 4-continued

| Copper complex | Ligand (1) | Ligand (2) |
|---|---|---|
| Cu-270 | A-25 | A-132 |
| Cu-271 | A-25 | A-135 |
| Cu-272 | A-25 | A-138 |
| Cu-273 | A-25 | A-142 |
| Cu-274 | A-25 | A-146 |
| Cu-275 | A-31 | A-50 |
| Cu-276 | A-31 | A-52 |
| Cu-277 | A-31 | A-65 |
| Cu-278 | A-31 | A-73 |
| Cu-279 | A-31 | A-77 |
| Cu-280 | A-31 | A-82 |
| Cu-281 | A-31 | A-83 |
| Cu-282 | A-31 | A-88 |
| Cu-283 | A-31 | A-92 |
| Cu-284 | A-31 | A-96 |
| Cu-285 | A-31 | A-109 |
| Cu-286 | A-31 | A-112 |
| Cu-287 | A-31 | A-126 |
| Cu-288 | A-31 | A-132 |
| Cu-289 | A-31 | A-135 |
| Cu-290 | A-31 | A-138 |
| Cu-291 | A-31 | A-142 |
| Cu-292 | A-31 | A-146 |
| Cu-293 | A-50 | A-52 |
| Cu-294 | A-50 | A-65 |
| Cu-295 | A-50 | A-73 |
| Cu-296 | A-50 | A-77 |
| Cu-297 | A-50 | A-82 |
| Cu-298 | A-50 | A-83 |
| Cu-299 | A-50 | A-88 |
| Cu-300 | A-50 | A-92 |
| Cu-301 | A-50 | A-96 |
| Cu-302 | A-50 | A-109 |
| Cu-303 | A-50 | A-112 |
| Cu-304 | A-50 | A-126 |
| Cu-305 | A-50 | A-132 |
| Cu-306 | A-50 | A-135 |
| Cu-307 | A-50 | A-138 |
| Cu-308 | A-50 | A-142 |
| Cu-309 | A-50 | A-146 |
| Cu-310 | A-52 | A-65 |
| Cu-311 | A-52 | A-73 |
| Cu-312 | A-52 | A-77 |
| Cu-313 | A-52 | A-82 |
| Cu-314 | A-52 | A-83 |
| Cu-315 | A-52 | A-88 |
| Cu-316 | A-52 | A-92 |
| Cu-317 | A-52 | A-96 |
| Cu-318 | A-52 | A-109 |
| Cu-319 | A-52 | A-112 |
| Cu-320 | A-52 | A-126 |

TABLE 5

| Copper complex | Ligand (1) | Ligand (2) |
|---|---|---|
| Cu-321 | A-52 | A-132 |
| Cu-322 | A-52 | A-135 |
| Cu-323 | A-52 | A-138 |
| Cu-324 | A-52 | A-142 |
| Cu-325 | A-52 | A-146 |
| Cu-326 | A-65 | A-73 |
| Cu-327 | A-65 | A-77 |
| Cu-328 | A-65 | A-82 |
| Cu-329 | A-65 | A-83 |
| Cu-330 | A-65 | A-88 |
| Cu-331 | A-65 | A-92 |
| Cu-332 | A-65 | A-96 |
| Cu-333 | A-65 | A-109 |
| Cu-334 | A-65 | A-112 |
| Cu-335 | A-65 | A-126 |
| Cu-336 | A-65 | A-132 |
| Cu-337 | A-65 | A-135 |
| Cu-338 | A-65 | A-138 |
| Cu-339 | A-65 | A-142 |

TABLE 5-continued

| Copper complex | Ligand (1) | Ligand (2) |
|---|---|---|
| Cu-340 | A-65 | A-146 |
| Cu-341 | A-73 | A-77 |
| Cu-342 | A-73 | A-82 |
| Cu-343 | A-73 | A-83 |
| Cu-344 | A-73 | A-88 |
| Cu-345 | A-73 | A-92 |
| Cu-346 | A-73 | A-96 |
| Cu-347 | A-73 | A-109 |
| Cu-348 | A-73 | A-112 |
| Cu-349 | A-73 | A-126 |
| Cu-350 | A-73 | A-132 |
| Cu-351 | A-73 | A-135 |
| Cu-352 | A-73 | A-138 |
| Cu-353 | A-73 | A-142 |
| Cu-354 | A-73 | A-146 |
| Cu-355 | A-77 | A-82 |
| Cu-356 | A-77 | A-83 |
| Cu-357 | A-77 | A-88 |
| Cu-358 | A-77 | A-92 |
| Cu-359 | A-77 | A-96 |
| Cu-360 | A-77 | A-109 |
| Cu-361 | A-77 | A-112 |
| Cu-362 | A-77 | A-126 |
| Cu-363 | A-77 | A-132 |
| Cu-364 | A-77 | A-135 |
| Cu-365 | A-77 | A-138 |
| Cu-366 | A-77 | A-142 |
| Cu-367 | A-77 | A-146 |
| Cu-368 | A-82 | A-88 |
| Cu-369 | A-82 | A-92 |
| Cu-370 | A-82 | A-96 |
| Cu-371 | A-82 | A-109 |
| Cu-372 | A-82 | A-112 |
| Cu-373 | A-82 | A-126 |
| Cu-374 | A-82 | A-132 |
| Cu-375 | A-82 | A-135 |
| Cu-376 | A-82 | A-138 |
| Cu-377 | A-82 | A-142 |
| Cu-378 | A-82 | A-146 |
| Cu-379 | A-83 | A-88 |
| Cu-380 | A-83 | A-92 |
| Cu-381 | A-83 | A-96 |
| Cu-382 | A-83 | A-109 |
| Cu-383 | A-83 | A-112 |
| Cu-384 | A-83 | A-126 |
| Cu-385 | A-83 | A-132 |
| Cu-386 | A-83 | A-135 |
| Cu-387 | A-83 | A-138 |
| Cu-388 | A-83 | A-142 |
| Cu-389 | A-83 | A-146 |
| Cu-390 | A-88 | A-92 |
| Cu-391 | A-88 | A-96 |
| Cu-392 | A-88 | A-109 |
| Cu-393 | A-88 | A-112 |
| Cu-394 | A-88 | A-126 |
| Cu-395 | A-88 | A-132 |
| Cu-396 | A-88 | A-135 |
| Cu-397 | A-88 | A-138 |
| Cu-398 | A-88 | A-142 |
| Cu-399 | A-88 | A-146 |
| Cu-400 | A-92 | A-96 |

TABLE 6

| Copper complex | Ligand (1) | Ligand (2) |
|---|---|---|
| Cu-401 | A-92 | A-109 |
| Cu-402 | A-92 | A-112 |
| Cu-403 | A-92 | A-126 |
| Cu-404 | A-92 | A-132 |
| Cu-405 | A-92 | A-135 |
| Cu-406 | A-92 | A-138 |
| Cu-407 | A-92 | A-142 |
| Cu-408 | A-92 | A-146 |
| Cu-409 | A-96 | A-109 |

TABLE 6-continued

| Copper complex | Ligand (1) | Ligand (2) |
|---|---|---|
| Cu-410 | A-96 | A-112 |
| Cu-411 | A-96 | A-126 |
| Cu-412 | A-96 | A-132 |
| Cu-413 | A-96 | A-135 |
| Cu-414 | A-96 | A-138 |
| Cu-415 | A-96 | A-142 |
| Cu-416 | A-96 | A-146 |
| Cu-417 | A-109 | A-112 |
| Cu-418 | A-109 | A-126 |
| Cu-419 | A-109 | A-132 |
| Cu-420 | A-109 | A-135 |
| Cu-421 | A-109 | A-138 |
| Cu-422 | A-109 | A-142 |
| Cu-423 | A-109 | A-146 |
| Cu-424 | A-112 | A-126 |
| Cu-425 | A-112 | A-132 |
| Cu-426 | A-112 | A-135 |
| Cu-427 | A-112 | A-138 |
| Cu-428 | A-112 | A-142 |
| Cu-429 | A-112 | A-146 |
| Cu-430 | A-126 | A-132 |
| Cu-431 | A-126 | A-135 |
| Cu-432 | A-126 | A-138 |
| Cu-433 | A-126 | A-142 |
| Cu-434 | A-126 | A-146 |
| Cu-435 | A-132 | A-135 |
| Cu-436 | A-132 | A-138 |
| Cu-437 | A-132 | A-142 |
| Cu-438 | A-132 | A-146 |
| Cu-439 | A-135 | A-138 |
| Cu-440 | A-135 | A-142 |
| Cu-441 | A-135 | A-146 |
| Cu-442 | A-138 | A-142 |
| Cu-443 | A-138 | A-146 |
| Cu-444 | A-142 | A-146 |

TABLE 7

| Copper complex | Ligand (1) | Ligand (2) |
|---|---|---|
| Cu-445 | 2,2'-bipyridine | bis(2-sulfo-4-methylphenyl) ether |
| Cu-446 | 2,2'-bipyridine | 2-sulfobenzoic acid |
| Cu-447 | 2,2'-bipyridine | bis[(hydroxy(phenyl)phosphoryl)methyl] ether |
| Cu-448 | 2,2'-bipyridine | pyridine-2,6-dicarboxylic acid |
| Cu-449 | bis(3,5-dimethylpyrazol-1-yl)methane | pyridine-2,6-dicarboxylic acid |
| Cu-450 | bis(3,5-dimethylpyrazol-1-yl)methane | 2,2'-(ethylenedioxy)diacetic acid |
| Cu-451 | 1,2-bis(2-(pyrazol-1-yl)ethoxy)ethane | pyridine-2,6-dicarboxylic acid |

TABLE 7-continued

| Copper complex | Ligand (1) | Ligand (2) |
|---|---|---|
| Cu-452 | 3,5-dimethylpyrazolyl-methyl substituted pyridine ligand | 2,6-pyridinedicarboxylic acid |

TABLE 8

| Copper complex | Compound (A2)-1 | Compound (A2)-2 | Compound (A2)-3 | Compound (A2)-4 | 1:2:3:4 | Copper component | Ratio between compound (A2) and copper |
|---|---|---|---|---|---|---|---|
| Cu1-1 | A2-1-1 | — | — | — | 1:0:0:0 | Copper sulfate | 2:1 |
| Cu1-2 | A2-1-2 | — | — | — | 1:0:0:0 | Copper sulfate | 2:1 |
| Cu1-3 | A2-1-3 | — | — | — | 1:0:0:0 | Copper sulfate | 2:1 |
| Cu1-4 | A2-1-4 | — | — | — | 1:0:0:0 | Copper sulfate | 2:1 |
| Cu1-5 | A2-1-5 | — | — | — | 1:0:0:0 | Copper sulfate | 2:1 |
| Cu1-6 | A2-1-6 | — | — | — | 1:0:0:0 | Copper sulfate | 2:1 |
| Cu1-7 | A2-1-7 | — | — | — | 1:0:0:0 | Copper sulfate | 2:1 |
| Cu1-8 | A2-1-8 | — | — | — | 1:0:0:0 | Copper sulfate | 2:1 |
| Cu1-9 | A2-1-9 | — | — | — | 1:0:0:0 | Copper sulfate | 2:1 |
| Cu1-10 | A2-1-10 | — | — | — | 1:0:0:0 | Copper sulfate | 2:1 |
| Cu1-11 | A2-1-11 | — | — | — | 1:0:0:0 | Copper sulfate | 2:1 |
| Cu1-12 | A2-1-12 | — | — | — | 1:0:0:0 | Copper sulfate | 2:1 |
| Cu1-13 | A2-1-13 | — | — | — | 1:0:0:0 | Copper sulfate | 2:1 |
| Cu1-14 | A2-1-14 | — | — | — | 1:0:0:0 | Copper sulfate | 2:1 |
| Cu1-15 | A2-1-15 | — | — | — | 1:0:0:0 | Copper sulfate | 2:1 |
| Cu1-16 | A2-1-16 | — | — | — | 1:0:0:0 | Copper sulfate | 2:1 |
| Cu1-17 | A2-1-17 | — | — | — | 1:0:0:0 | Copper sulfate | 2:1 |
| Cu1-18 | A2-1-18 | — | — | — | 1:0:0:0 | Copper sulfate | 2:1 |
| Cu1-19 | A2-1-19 | — | — | — | 1:0:0:0 | Copper sulfate | 2:1 |
| Cu1-20 | A2-1-1 | — | — | — | 1:0:0:0 | Copper sulfate | 1:2 |
| Cu1-21 | A2-1-1 | — | — | — | 1:0:0:0 | Copper sulfate | 1:1 |
| Cu1-22 | A2-1-1 | — | — | — | 1:0:0:0 | Copper sulfate | 3:1 |
| Cu1-23 | A2-1-1 | — | — | — | 1:0:0:0 | Copper sulfate | 3:2 |
| Cu1-24 | A2-1-1 | A2-1-2 | — | — | 1:1:0:0 | Copper sulfate | 2:1 |
| Cu1-25 | A2-1-1 | A2-1-2 | — | — | 1:2:0:0 | Copper sulfate | 2:1 |
| Cu1-26 | A2-1-1 | A2-1-2 | — | — | 2:1:0:0 | Copper sulfate | 2:1 |
| Cu1-27 | A2-1-1 | A2-1-2 | A2-1-10 | — | 1:1:1:0 | Copper sulfate | 2:1 |
| Cu1-28 | A2-1-1 | A2-1-2 | A2-1-10 | A2-1-18 | 1:1:1:1 | Copper sulfate | 2:1 |
| Cu1-29 | A2-1-1 | A2-1-2 | A2-1-10 | A2-1-18 | 1:1:1:3 | Copper sulfate | 2:1 |
| Cu1-30 | A2-1-1 | — | — | — | 1:0:0:0 | Copper acetate | 2:1 |
| Cu1-31 | A2-1-1 | — | — | — | 1:0:0:0 | Copper hydroxide | 2:1 |
| Cu1-32 | A2-1-1 | — | — | — | 1:0:0:0 | Copper chloride | 2:1 |
| Cu1-33 | A2-1-1 | — | — | — | 1:0:0:0 | Copper nitrate | 2:1 |
| Cu1-34 | A2-1-20 | — | — | — | 1:0:0:0 | Copper sulfate | 2:1 |
| Cu1-35 | A2-1-21 | — | — | — | 1:0:0:0 | Copper sulfate | 2:1 |
| Cu1-36 | A2-1-1 | A2-1-5 | — | — | 1:1:0:0 | Copper sulfate | 2:1 |
| Cu1-37 | A2-1-1 | A2-1-11 | — | — | 1:1:0:0 | Copper sulfate | 2:1 |
| Cu1-38 | A2-1-1 | A2-1-12 | — | — | 1:1:0:0 | Copper sulfate | 2:1 |
| Cu1-39 | A2-1-1 | A2-1-13 | — | — | 1:1:0:0 | Copper sulfate | 2:1 |
| Cu1-40 | A2-1-1 | A2-1-15 | — | — | 1:1:0:0 | Copper sulfate | 2:1 |
| Cu1-41 | A2-1-1 | A2-1-18 | — | — | 1:1:0:0 | Copper sulfate | 2:1 |
| Cu1-42 | A2-1-1 | A2-1-20 | — | — | 1:1:0:0 | Copper sulfate | 2:1 |
| Cu1-43 | A2-1-1 | A2-1-21 | — | — | 1:1:0:0 | Copper sulfate | 2:1 |
| Cu1-44 | A2-1-3 | A2-1-5 | — | — | 1:1:0:0 | Copper sulfate | 2:1 |
| Cu1-45 | A2-1-5 | A2-1-11 | — | — | 1:1:0:0 | Copper sulfate | 2:1 |
| Cu1-46 | A2-1-5 | A2-1-12 | — | — | 1:1:0:0 | Copper sulfate | 2:1 |
| Cu1-47 | A2-1-5 | A2-1-13 | — | — | 1:1:0:0 | Copper sulfate | 2:1 |
| Cu1-48 | A2-1-11 | A2-1-12 | — | — | 1:1:0:0 | Copper sulfate | 2:1 |
| Cu1-49 | A2-1-12 | A2-1-13 | — | — | 1:1:0:0 | Copper sulfate | 2:1 |
| Cu1-50 | A2-1-1 | A2-1-5 | A2-1-13 | — | 1:1:1:0 | Copper sulfate | 2:1 |
| Cu1-51 | A2-1-11 | A2-1-12 | A2-1-13 | — | 1:1:1:0 | Copper sulfate | 2:1 |
| Cu1-52 | A2-1-1 | A2-1-5 | A2-1-12 | A2-1-13 | 1:1:1:1 | Copper sulfate | 2:1 |
| Cu1-53 | A2-1-22 | — | — | — | 1:0:0:0 | Copper sulfate | 2:1 |

TABLE 9

| Copper complex | Compound (A2)-1 | Compound (A2)-2 | Compound (A2)-3 | Compound (A2)-4 | 1:2:3:4 | Copper component | Ratio between compound (A2) and copper |
|---|---|---|---|---|---|---|---|
| Cu2-1 | A2-2-1 | — | — | — | 1:0:0:0 | Copper hydroxide | 2:1 |
| Cu2-2 | A2-2-3 | — | — | — | 1:0:0:0 | Copper hydroxide | 2:1 |
| Cu2-3 | A2-2-4 | — | — | — | 1:0:0:0 | Copper hydroxide | 2:1 |
| Cu2-4 | A2-2-7 | — | — | — | 1:0:0:0 | Copper hydroxide | 2:1 |
| Cu2-5 | A2-2-10 | — | — | — | 1:0:0:0 | Copper hydroxide | 2:1 |
| Cu2-6 | A2-2-12 | — | — | — | 1:0:0:0 | Copper hydroxide | 2:1 |
| Cu2-7 | A2-2-13 | — | — | — | 1:0:0:0 | Copper hydroxide | 2:1 |
| Cu2-8 | A2-2-18 | — | — | — | 1:0:0:0 | Copper hydroxide | 2:1 |
| Cu2-9 | A2-2-19 | — | — | — | 1:0:0:0 | Copper hydroxide | 2:1 |
| Cu2-10 | A2-2-21 | — | — | — | 1:0:0:0 | Copper hydroxide | 2:1 |
| Cu2-11 | A2-2-22 | — | — | — | 1:0:0:0 | Copper hydroxide | 2:1 |
| Cu2-12 | A2-2-23 | — | — | — | 1:0:0:0 | Copper hydroxide | 2:1 |
| Cu2-13 | A2-2-24 | — | — | — | 1:0:0:0 | Copper hydroxide | 2:1 |
| Cu2-14 | A2-2-28 | — | — | — | 1:0:0:0 | Copper hydroxide | 2:1 |
| Cu2-15 | A2-2-29 | — | — | — | 1:0:0:0 | Copper hydroxide | 2:1 |
| Cu2-16 | A2-2-31 | — | — | — | 1:0:0:0 | Copper hydroxide | 2:1 |
| Cu2-17 | A2-2-33 | — | — | — | 1:0:0:0 | Copper hydroxide | 2:1 |
| Cu2-18 | A2-2-34 | — | — | — | 1:0:0:0 | Copper hydroxide | 2:1 |
| Cu2-19 | A2-2-35 | — | — | — | 1:0:0:0 | Copper hydroxide | 2:1 |
| Cu2-20 | A2-2-36 | — | — | — | 1:0:0:0 | Copper hydroxide | 2:1 |
| Cu2-21 | A2-2-37 | — | — | — | 1:0:0:0 | Copper hydroxide | 2:1 |
| Cu2-22 | A2-2-40 | — | — | — | 1:0:0:0 | Copper hydroxide | 2:1 |
| Cu2-23 | A2-2-41 | — | — | — | 1:0:0:0 | Copper hydroxide | 2:1 |
| Cu2-24 | A2-2-42 | — | — | — | 1:0:0:0 | Copper hydroxide | 2:1 |
| Cu2-25 | A2-2-44 | — | — | — | 1:0:0:0 | Copper hydroxide | 2:1 |
| Cu2-26 | A2-2-3 | — | — | — | 1:0:0:0 | Copper acetate | 2:1 |
| Cu2-27 | Sodium salt of A2-2-3 | — | — | — | 1:0:0:0 | Copper sulfate | 2:1 |
| Cu2-28 | A2-2-40 | — | — | — | 1:0:0:0 | Copper hydroxide | 1:1 |
| Cu2-29 | A2-2-41 | — | — | — | 1:0:0:0 | Copper hydroxide | 1:1 |
| Cu2-30 | A2-2-42 | — | — | — | 1:0:0:0 | Copper hydroxide | 1:1 |
| Cu2-31 | A2-2-44 | — | — | — | 1:0:0:0 | Copper hydroxide | 1:1 |
| Cu2-32 | A2-2-1 | A2-2-3 | — | — | 1:1:0:0 | Copper hydroxide | 2:1 |
| Cu2-33 | A2-2-1 | A2-2-4 | — | — | 1:1:0:0 | Copper hydroxide | 2:1 |
| Cu2-34 | A2-2-1 | A2-2-7 | — | — | 1:1:0:0 | Copper hydroxide | 2:1 |
| Cu2-35 | A2-2-1 | A2-2-19 | — | — | 1:1:0:0 | Copper hydroxide | 2:1 |
| Cu2-36 | A2-2-1 | A2-2-29 | — | — | 1:1:0:0 | Copper hydroxide | 2:1 |
| Cu2-37 | A2-2-1 | A2-2-30 | — | — | 1:1:0:0 | Copper hydroxide | 2:1 |
| Cu2-38 | A2-2-1 | A2-2-32 | — | — | 1:1:0:0 | Copper hydroxide | 2:1 |
| Cu2-39 | A2-2-1 | A2-2-33 | — | — | 1:1:0:0 | Copper hydroxide | 2:1 |
| Cu2-40 | A2-2-1 | A2-2-35 | — | — | 1:1:0:0 | Copper hydroxide | 2:1 |
| Cu2-41 | A2-2-1 | A2-2-36 | — | — | 1:1:0:0 | Copper hydroxide | 2:1 |
| Cu2-42 | A2-2-1 | A2-2-39 | — | — | 2:1:0:0 | Copper hydroxide | 3:2 |
| Cu2-43 | A2-2-1 | A2-2-42 | — | — | 2:1:0:0 | Copper hydroxide | 2:1 |
| Cu2-44 | A2-2-1 | A2-2-44 | — | — | 2:1:0:0 | Copper hydroxide | 2:1 |
| Cu2-45 | A2-2-1 | A2-2-3 | A2-2-36 | — | 1:1:1:0 | Copper hydroxide | 2:1 |
| Cu2-46 | A2-2-1 | A2-2-7 | A2-2-36 | — | 1:1:1:0 | Copper hydroxide | 2:1 |
| Cu2-47 | A2-2-1 | A2-2-33 | A2-2-36 | — | 1:1:1:0 | Copper hydroxide | 2:1 |
| Cu2-48 | A2-2-1 | A2-2-3 | A2-2-7 | A2-2-36 | 1:1:1:1 | Copper hydroxide | 2:1 |
| Cu2-49 | A2-2-1 | A2-2-7 | A2-2-33 | A2-2-36 | 1:1:1:1 | Copper hydroxide | 2:1 |

<<Characteristics of Copper Complex>>

The copper complex used in the present invention preferably has a maximum absorption wavelength ($\lambda_{max}$) in a near-infrared wavelength range of 700 nm to 2500 nm, more preferably has a maximum absorption wavelength in a range of 720 nm to 890 nm, and still more preferably has a maximum absorption wavelength in a range of 730 nm to 880 nm. The maximum absorption wavelength can be measured using, for example, a Cary 5000 UV-Vis-NIR (spectrophotometer, manufactured by Agilent Technologies Japan, Ltd.).

When the above-described copper complex used in the present invention is used, it is possible to provide a near-infrared-ray-absorbing composition having strong near-infrared shielding properties when a cured film is produced. In addition, when the copper complex used in the present invention is used, it is possible to provide a near-infrared-ray-absorbing composition including a copper complex having an excellent solubility in a solvent. While it is not confined by any theories, it is assumed that the structure of the copper complex obtained using the compound (A) used in the present invention or a salt thereof becomes distorted, and the color valency improves (light in a visible range is not absorbed, and the light-absorbing capability in the near-infrared range (spectral characteristics) improves), and consequently, the near-infrared-shielding properties can be enhanced when a cured film is produced, and it is possible to provide a near-infrared-ray-absorbing composition including a copper complex having an excellent solubility in a solvent.

In addition, when the copper complex used in the present invention is used, it is also possible to improve the heat resistance of the near-infrared-ray-absorbing composition.

The content of the copper complex in the total solid content of the composition of the present invention is preferably 15% by mass or higher, more preferably 20% by mass or higher, and still more preferably 30% by mass or higher. In addition, the content thereof is preferably in a range of 15% by mass to 60% by mass, more preferably in a range of 20% by mass to 50% by mass, and still more preferably in a range of 25% by mass to 45% by mass. When the content of the copper complex is increased, it is possible to improve near-infrared shielding performance.

The content of the copper complex obtained by reacting the compound (A) and the copper component in the composition of the present invention is preferably in a range of 1% by mass to 60% by mass, more preferably in a range of 5% by mass to 40% by mass, and still more preferably in a range of 5% by mass to 20% by mass in relation to the composition of the present invention.

The content of a copper complex (near-infrared-ray-absorbing substance) other than the copper complex obtained by reacting the compound (A) and the copper component in the composition of the present invention is preferably in a range of 0% by mass to 20% by mass, more preferably in a range of 0% by mass to 10% by mass, and still more preferably in a range of 0% by mass to 5% by mass in relation to the composition of the present invention.

In the near-infrared-ray-absorbing substance included in the composition of the present invention, the proportion of the compound obtained by reacting the compound (A) and the copper component is preferably 80% by mass or higher, more preferably 90% by mass or higher, and still more preferably 95% by mass or higher.

The total solid content of the near-infrared-ray-absorbing composition of the present invention is preferably in a range of 1% by mass to 50% by mass, more preferably in a range of 1% by mass to 40% by mass, and still more preferably in a range of 10% by mass to 35% by mass in relation to the composition.

In the composition of the present invention, the above-described copper complex used in the present invention may be used singly or two or more copper complexes may be jointly used. In a case in which two or more copper complexes used in the present invention may be jointly used, the total amount thereof is preferably in the above-described range.

The near-infrared-ray-absorbing composition of the present invention preferably includes the above-described copper complex, and, as necessary, other near-infrared-ray-absorbing compounds, a solvent, a curable compound, a binder polymer, a surfactant, and a polymerization initiator, and other components may be blended into the near-infrared-ray-absorbing composition.

<<Other Near-infrared-ray-absorbing Compounds>>

As other near-infrared-ray-absorbing compounds that can be used in the present invention, it is possible to use a copper compound obtained from a reaction between a polymer including an acid group or a salt thereof and the copper component or a copper compound obtained from a reaction between a compound including a low-molecular-weight (for example, with a molecular weight of 1000 or lower) acid group or a salt thereof, which is other than the compound having two monoanionic coordination sites, and the copper component.

The copper compound obtained from a reaction between a polymer including an acid group or a salt thereof and the copper component is, for example, a polymer-type copper compound including a polymer having an acid group ion portion and a copper ion, and a preferred aspect thereof is a polymer-type copper compound having an acid group ion portion in the polymer as a ligand. This polymer-type copper compound generally has an acid group ion portion in a side chain of the polymer, the acid group ion portion is bonded (for example, forming a coordination bond) to copper, and a crosslinking structure is formed between side chains from copper as a starting point.

The copper component is preferably a compound including divalent copper. The content of copper in the copper component is preferably in a range of 2% by mass to 40% by mass and more preferably in a range of 5% by mass to 40% by mass. The copper component may be used singly or two or more copper components may be jointly used. As the compound including copper, it is possible to use, for example, copper oxide or a copper salt. The copper salt is preferably divalent copper. The copper salt is particularly preferably copper hydroxide, copper acetate, or copper sulfate.

The acid group included in the polymer including an acid group or a salt thereof is not particularly limited as long as the acid group is capable of reacting with the above-described copper component, but is preferably an acid group forming a coordination bond with the copper component. Specific examples thereof include acid groups having an acid dissociation constant (pKa) of 12 or lower, and a sulfonic acid group, a carboxylic acid group, a phosphoric acid group, a phosphonic acid group, a phosphinic acid group, an imide acid group, and the like are preferred. The polymer may have only one acid group or two or more acid groups.

Examples of an atom or an atomic group configuring the salt of the acid group used in the present invention include a metal atom (particularly, an alkali metal atom) such as sodium and an atomic group such as tetrabutyl ammonium. Furthermore, in the polymer including the acid group or a salt thereof, the acid group or the salt thereof may be included in either or both the main chain and the side chain and is preferably included in at least the side chain.

The polymer including the acid group or a salt thereof is preferably a polymer including a carboxylic acid group or a salt thereof and/or a sulfonic acid group or a salt thereof and more preferably a polymer including a sulfonic acid group or a salt thereof.

<<<Polymer Including First Acid Group or Salt Thereof>>>

A preferred example of the polymer including the acid group or a salt thereof is a structure having a carbon-carbon bond in the main chain and preferably includes a configuration unit represented by Formula (A1-1) described below.

(A1-1)

(In Formula (A1-1), $R^1$ represents a hydrogen atom or a methyl group, $L^1$ represents a single bond or a divalent linking group, and $M^1$ represents a hydrogen atom or an atom or an atomic group configuring a sulfonic acid group or a salt thereof.)

In Formula (A1-1), $R^1$ is preferably a hydrogen atom.

In Formula (A1-1), in a case in which $L^1$ represents a divalent linking group, the divalent linking group is not particularly limited, and examples thereof include —a divalent hydrocarbon group, a heteroarylene group, —O—, —S—, —CO—, —COO—, —OCO—, —SO$_2$—, —NX— (X represents a hydrogen atom or an alkyl group and is preferably a hydrogen atom), or a group formed of a combination thereof.

Examples of the divalent hydrocarbon group include linear, branched, or cyclic alkylene groups and arylene groups. The hydrocarbon group may have a substituent, but is preferably not substituted.

The number of carbon atoms in the linear alkylene group is preferably in a range of 1 to 30, more preferably in a range of 1 to 15, and still more preferably in a range of 1 to 6. In addition, the number of carbon atoms in the branched alkylene group is preferably in a range of 3 to 30, more preferably in a range of 3 to 15, and still more preferably in a range of 3 to 6.

The cyclic alkylene group may be either a monocyclic ring or a polycyclic ring. The number of carbon atoms in the cyclic alkylene group is preferably in a range of 3 to 20, more preferably in a range of 4 to 10, and still more preferably in a range of 6 to 10.

The number of carbon atoms in the arylene group is preferably in a range of 6 to 18, more preferably in a range of 6 to 14, and still more preferably in a range of 6 to 10, and a phenylene group is particularly preferred.

The heteroarylene group is not particularly limited, but is preferably a 5-membered or 6-membered ring. In addition, the heteroarylene group may be a monocyclic ring or a condensed ring, is preferably a monocyclic ring or a condensed ring having 2 to 8 condensations and more preferably a monocyclic ring or a condensed ring having 2 to 4 condensations.

In Formula (A1-1), an atom or an atomic group configuring a sulfonic acid group or a salt thereof represented by $M^1$ is identical to the above-described atom or atomic group configuring a salt of the acid group, and is preferably a hydrogen atom or an alkali metal atom.

Regarding configuration units other than the configuration unit represented by Formula (A1-1), the description of the copolymer component disclosed in Paragraphs [0068] to [0075] ([0112] to [0118] in the specification of the corresponding US2011/0124824A) of JP2010-106268A can be referred to, and the content thereof is incorporated into the present specification.

Examples of the preferred other configuration units include configuration units represented by Formula (A1-2) described below.

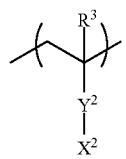

(A1-2)

In Formula (A1-2), $R^3$ represents a hydrogen atom or a methyl group and is preferably a hydrogen atom.

$Y^2$ represents a single bond or a divalent linking group, and the divalent linking group is identical to the divalent linking group in Formula (A1) described above. Particularly, $Y^2$ is preferably —COO—, —CO—, —NH—, a linear or branched alkylene group, or a group formed of a combination thereof or a single bond.

In Formula (A1-2), $X^2$ represents —PO$_3$H—, —PO$_3$H$_2$, —OH, or —COOH, and is preferably —COOH.

In a case in which the polymer including the configuration unit represented by Formula (A1-1) includes other configuration units (preferably the configuration unit represented by Formula (A1-2)), the molar ratio between the configuration unit represented by Formula (A1-1) and the configuration unit represented by Formula (A1-2) is preferably in a range of 95:5 to 20:80 and more preferably in a range of 90:10 to 40:60.

<<<Polymer Including Second Acid Group or Salt Thereof>>>

As the copper compound that can be used in the present invention, a polymer-type copper compound obtained from a reaction between a polymer having an acid group or a salt thereof and having an aromatic hydrocarbon group and/or an aromatic heterocyclic group in the main chain (hereinafter, referred to as the aromatic group-containing polymer) and a copper component may be used. The aromatic group-containing polymer may have at least one of an aromatic hydrocarbon group and/or an aromatic heterocyclic group in the main chain or may have two or more thereof. The acid group or the salt thereof and the copper component are identical to those in the above-described copper compound obtained from a reaction between the polymer including the acid group or the salt thereof and the copper component, and the preferred range thereof is also identical.

The aromatic hydrocarbon group is preferably, for example, an aryl group. The number of carbon atoms in the aryl group is preferably in a range of 6 to 20, more preferably in a range of 6 to 15, and still more preferably in a range of 6 to 12. Particularly, a phenyl group, a naphthyl group, or a biphenyl group is preferred. The aromatic hydrocarbon group may be a monocyclic ring or a polycyclic ring, but is preferably a monocyclic ring.

As the aromatic heterocyclic group, it is possible to use, for example, an aromatic heterocyclic group having 2 to 30 carbon atoms. The aromatic heterocyclic group is preferably a 5-membered ring or a 6-membered ring. In addition, the aromatic heterocyclic group may be a monocyclic ring or a condensed ring and is, for example, a monocyclic ring or a condensed ring having 2 to 8 condensations. Examples of the hetero atom included in the heterocycle include nitrogen, oxygen, sulfur atoms, and the hetero atom is preferably nitrogen or oxygen.

In a case in which the aromatic hydrocarbon group and/or the aromatic heterocyclic group have a substituent T, examples of the substituent T include an alkyl group, a polymerizable group (preferably a polymerizable group having a carbon-carbon double bond), a halogen atom (a fluorine atom, a chlorine atom, a bromine atom, or an iodine atom), a carboxylic acid ester group, a halogenated alkyl group, an alkoxy group, a methacryloyloxy group, an acryloyloxy group, an ether group, a sulfonyl group, a sulfide group, an amide group, an acyl group, a hydroxy group, a carboxyl group, and an aralkyl group, and an alkyl group (particularly, an alkyl group having 1 to 3 carbon atoms) is preferred.

Particularly, the aromatic group-containing polymer is preferably at least one polymer selected from a polyether sulfone-based polymer, a polysulfone-based polymer, a polyether ketone-based polymer, a polyphenylene ether-based polymer, a polyimide-based polymer, a polybenzimidazole-based polymer, a polyphenylene-based polymer, a phenol resin-based polymer, a polycarbonate-based polymer, a polyamide-based polymer, and a polyester-based polymer. Hereinafter, examples of the respective polymers will be described.

Polyether sulfone-based polymer: a polymer having a main chain structure represented by (—O-Ph-SO$_2$-Ph-) (Ph represents a phenylene group, which shall apply below)

Polysulfone-based polymer: a polymer having a main chain structure represented by (—O-Ph-Ph-O-Ph-SO$_2$-Ph-)

Polyether ketone-based polymer: a polymer having a main chain structure represented by (—O-Ph-O-Ph-C(=O)-Ph-)

Polyphenylene ether-based polymer: a polymer having a main chain structure represented by (-Ph-O—, -Ph-S—)

Polyphenylene-based polymer: a polymer having a main chain structure represented by (-Ph-)

Phenol resin-based polymer: a polymer having a main chain structure represented by (-Ph(OH)—CH$_2$—)

Polycarbonate-based polymer: a polymer having a main chain structure represented by (-Ph-O—C(=O)—O—)

as the polyamide-based polymer, for example, a polymer having a main chain structure represented by (-Ph-C(=O)—NH—)

as the polyester-based polymer, for example, a polymer having a main chain structure represented by (-Ph-C(=O) O—)

Regarding the polyether sulfone-based polymer, the polysulfone-based polymer, and the polyether ketone-based polymer, for example, the main chain structures described in Paragraph [0022] of JP2006-310068A and Paragraph [0028] of JP2008-27890A can be referred to, and the content thereof is incorporated into the present specification.

Regarding the polyimide-based polymer, the main chain structures described in Paragraphs [0047] to [0058] of JP2002-367627A and Paragraphs [0018] and [0019] of JP2004-35891A can be referred to, and the content thereof is incorporated into the present specification.

A preferred example of the aromatic group-containing polymer preferably includes a configuration unit represented by Formula (A1-3) described below.

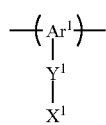
(A1-3)

(In Formula (A1-3), Ar$^1$ represents an aromatic hydrocarbon group and/or an aromatic heterocyclic group, Y$^1$ represents a monocyclic ring or a divalent linking group, and X$^1$ represents an acid group or a salt thereof.)

In Formula (A1-3), in a case in which Ar$^1$ represents an aromatic hydrocarbon group, the aromatic hydrocarbon group is identical to the above-described aromatic hydrocarbon group, and, in a case in which Ar$^1$ represents an aromatic heterocyclic group, the aromatic heterocyclic group is identical to the above-described aromatic heterocyclic group, and the preferred ranges thereof are also identical.

Ar$^1$ may have a substituent in addition to —Y$^1$—X$^1$ in Formula (A1-3). In a case in which Ar$^1$ has a substituent, the substituent is identical to the above-described substituent T, and the preferred range thereof is also identical.

In Formula (A1-3), Y$^1$ is preferably a monocyclic ring. In a case in which Y$^1$ is a divalent linking group, examples of the divalent hydrocarbon group include a hydrocarbon group, an aromatic heterocyclic group, —O—, —S—, —SO$_2$—, —CO—, —C(=O)—O—, —NX— (X represents a hydrogen atom or an alkyl group and is preferably a hydrogen atom), —C(R$^{Y1}$)(R$^{Y2}$)—, or a group formed of a combination thereof. Here, each of R$^{Y1}$ and R$^{Y2}$ independently represents a hydrogen atom, a fluorine atom, or an alkyl group.

Examples of the hydrocarbon group include a linear, branched, or cyclic alkylene group or arylene group. The number of carbon atoms in the linear alkylene group is preferably in a range of 1 to 20, more preferably in a range of 1 to 10, and still more preferably in a range of 1 to 6. In addition, the number of carbon atoms in the branched alkylene group is preferably in a range of 3 to 20, more preferably in a range of 3 to 10, and still more preferably in a range of 3 to 6. The cyclic alkylene group may be either a monocyclic ring or a polycyclic ring. The number of carbon atoms in the cyclic alkylene group is preferably in a range of 3 to 20, more preferably in a range of 4 to 10, and still more preferably in a range of 6 to 10. In these linear, branched, or cyclic alkylene groups, the hydrogen atom in the alkylene group may be substituted with a fluorine atom.

The arylene group is identical to that in a case in which the above-described divalent linking group in Formula (A1-1) is an arylene group.

The aromatic heterocyclic group is not particularly limited, but is preferably a 5-membered ring or a 6-membered ring. In addition, the aromatic heterocyclic group may be a monocyclic ring or a condensed ring, is preferably a monocyclic ring or a condensed ring having 2 to 8 condensations and more preferably a monocyclic ring or a condensed ring having 2 to 4 condensations.

In Formula (A1-3), the acid group or the salt thereof represented by X$^1$ is identical to the above-described acid group or the salt thereof, and the preferred range thereof is also identical.

The weight-average molecular weight of the polymer including the configuration unit represented by Formula (A1-1), (A1-2), or (A1-3) is preferably 1000 or higher, more preferably in a range of 1000 to 10,000,000, more preferably in a range of 3000 to 1,000,000, and particularly preferably in a range of 4000 to 400,000.

Specific examples of the polymer including the configuration unit represented by Formula (A1-1), (A1-2), or (A1-3) include compounds described below and salts of the compounds described below, but the polymer is not limited thereto.

TABLE 10

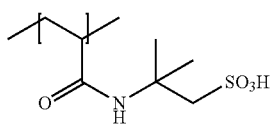

P-1

Mw = 100,000

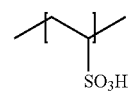

P-2

Mw = 10,000

TABLE 10-continued
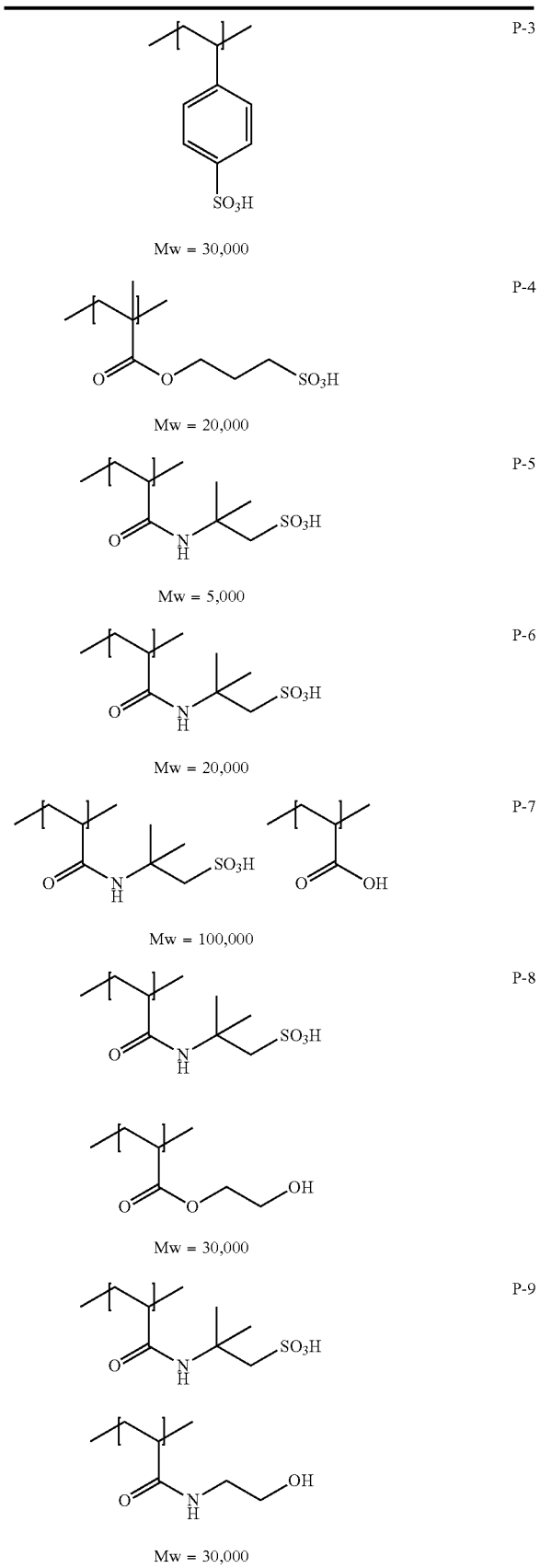
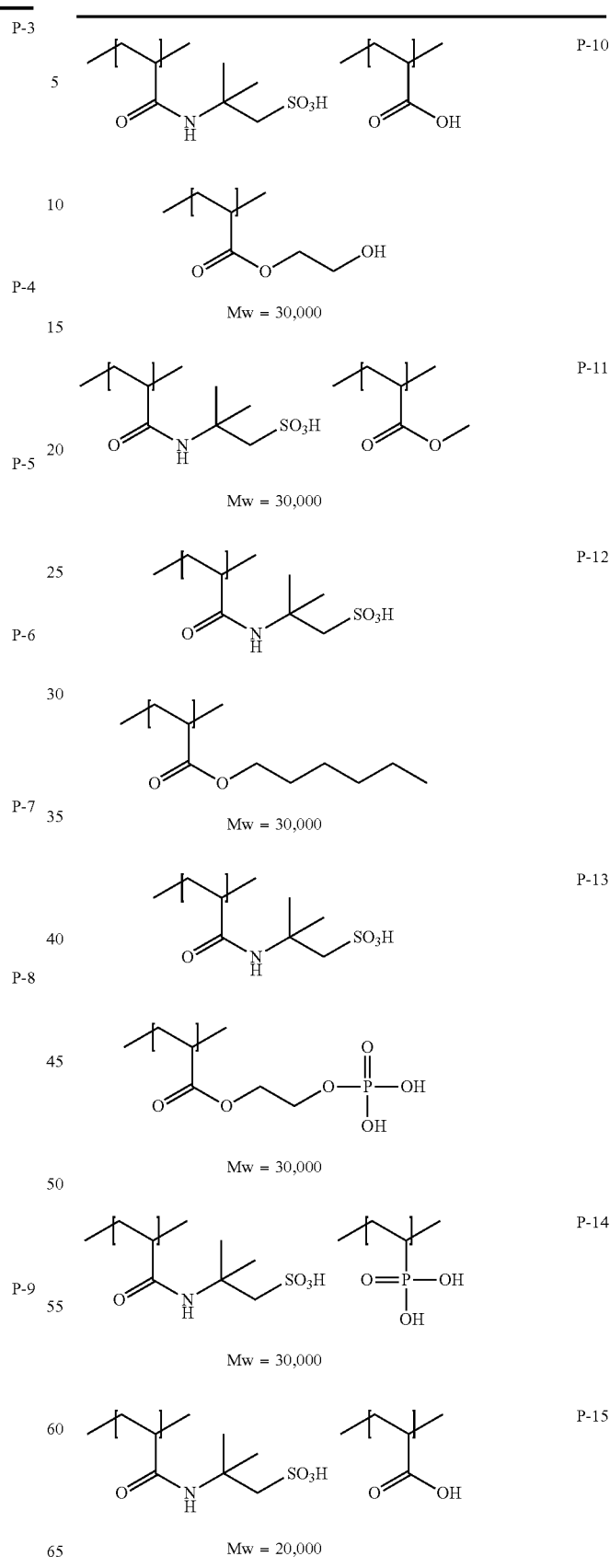

95 96
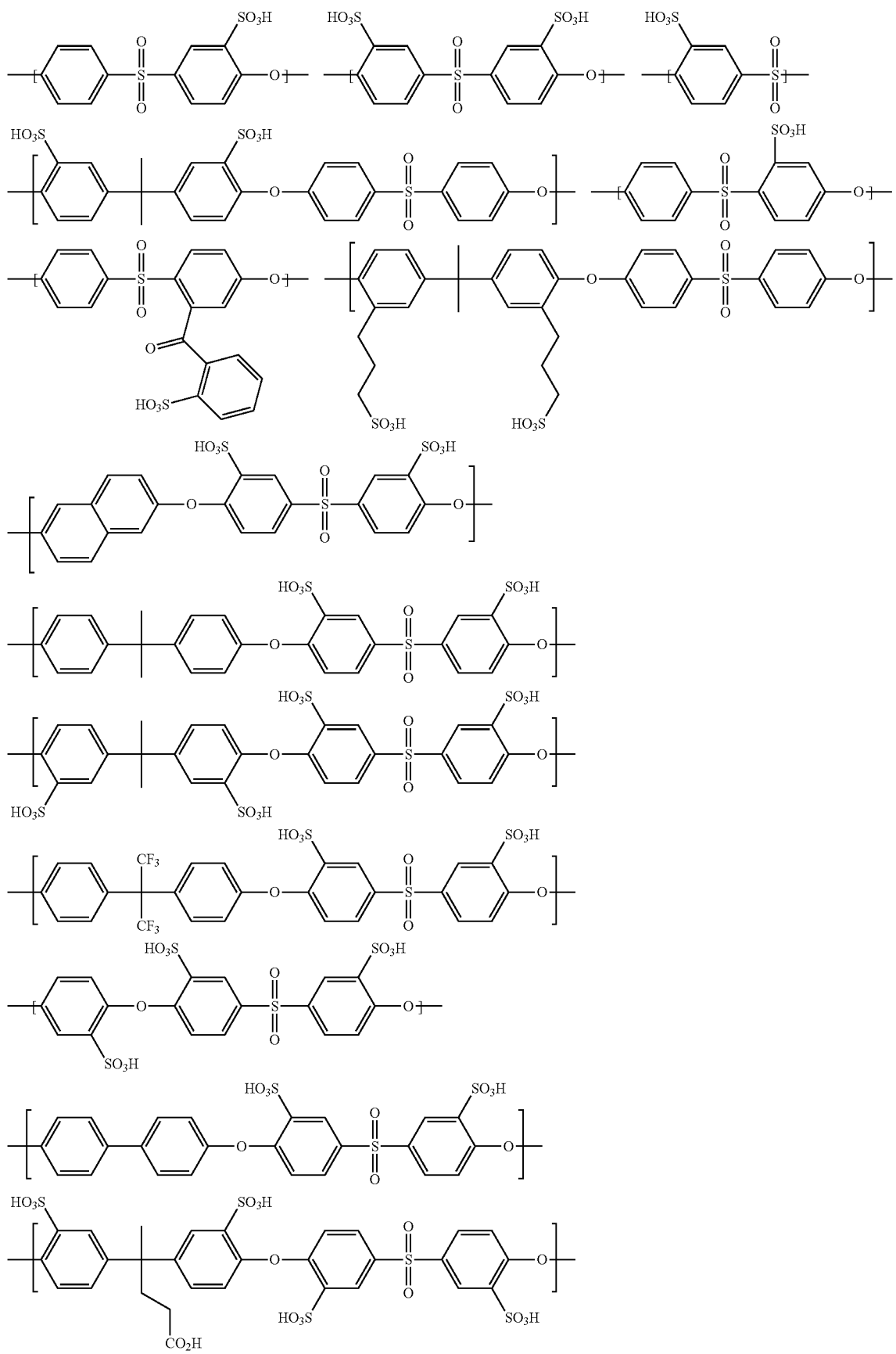

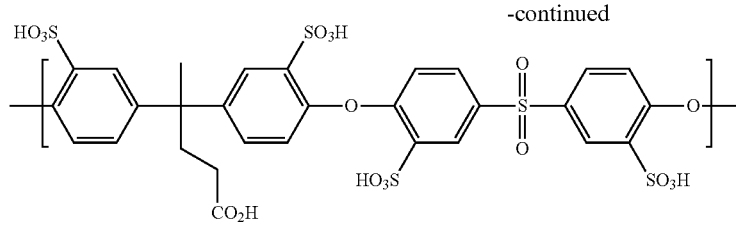
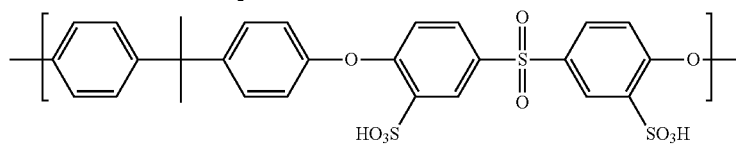
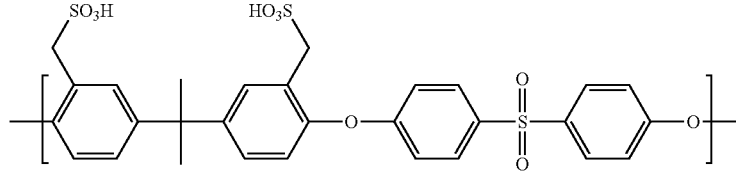
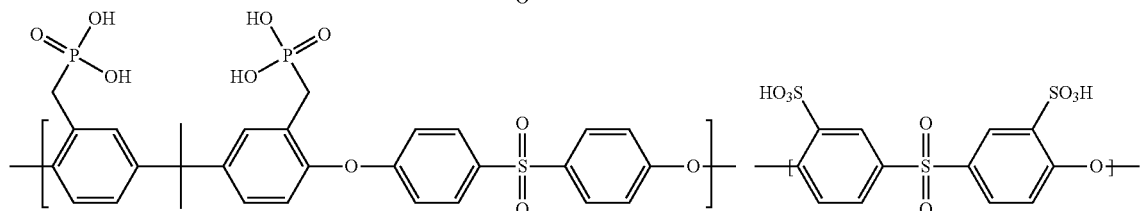
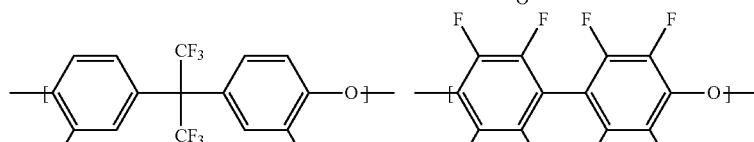
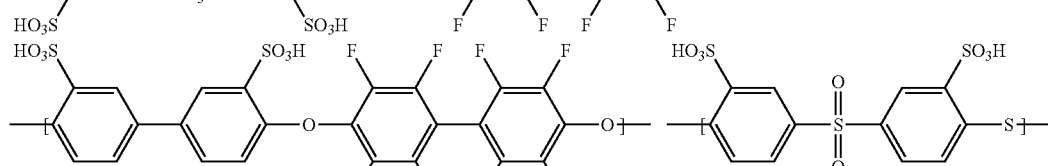
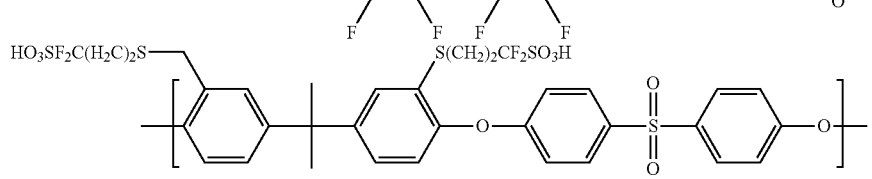
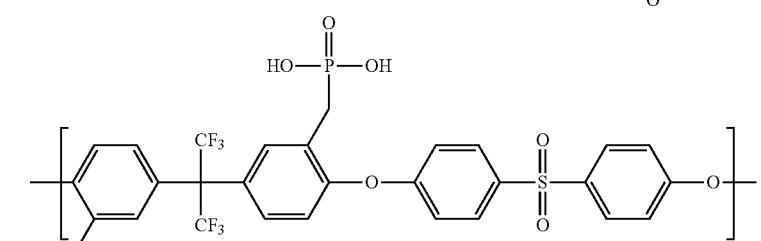
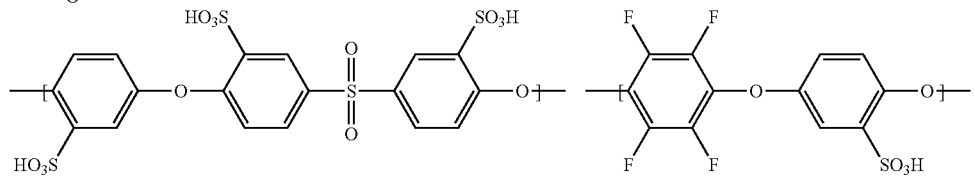

-continued
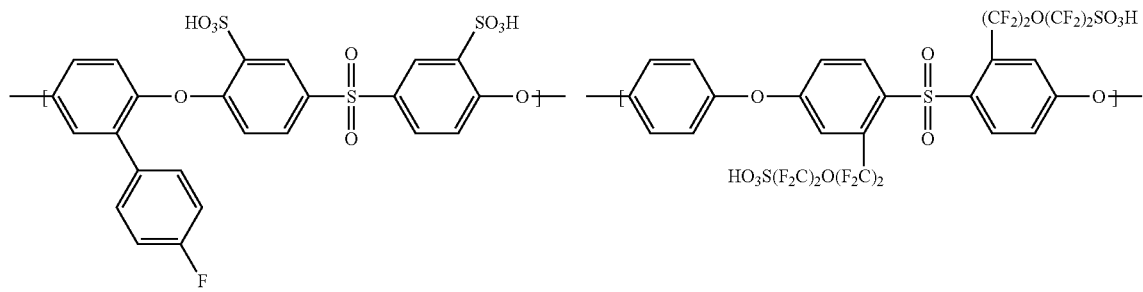
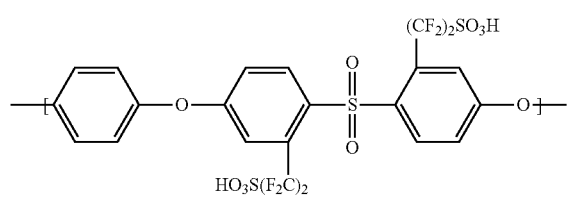
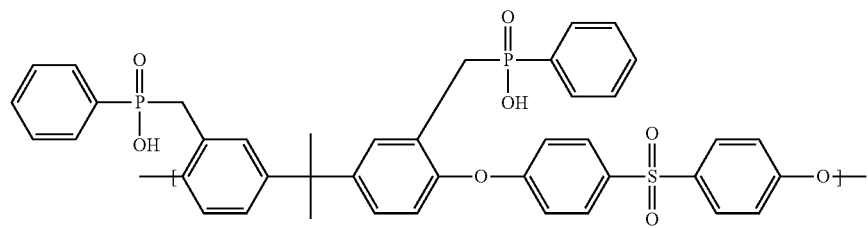
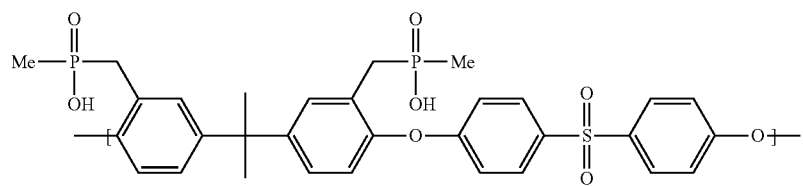
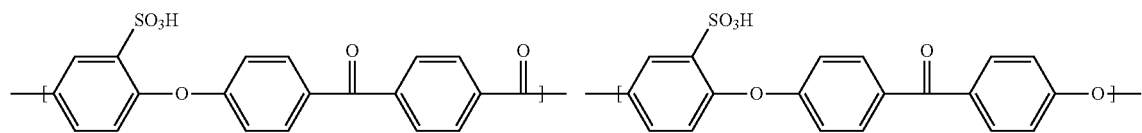
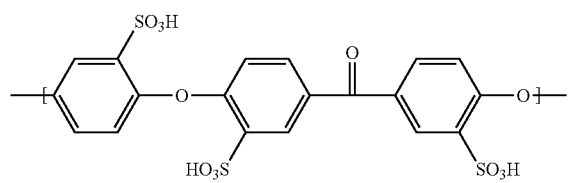
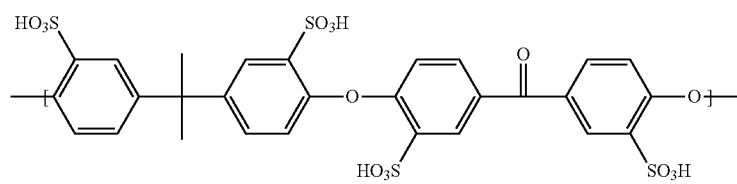

-continued
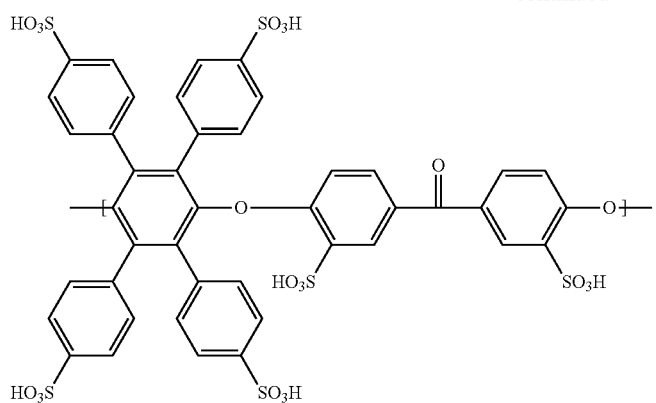
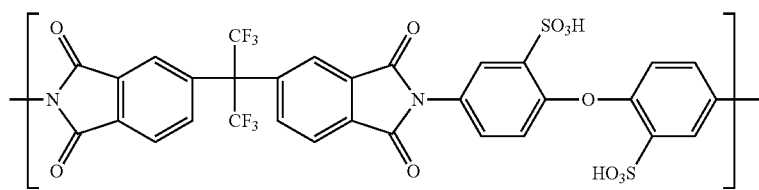
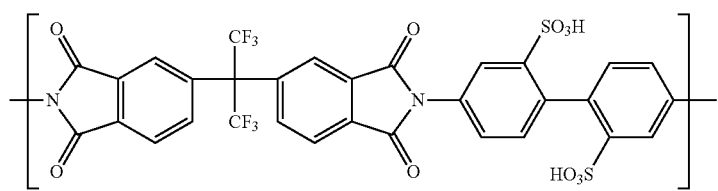
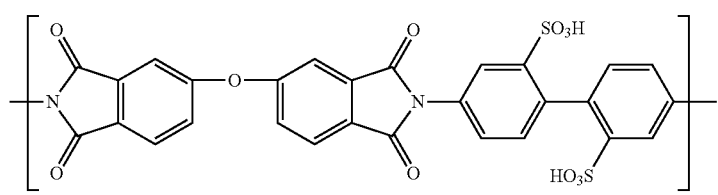
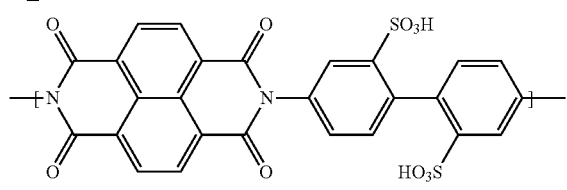
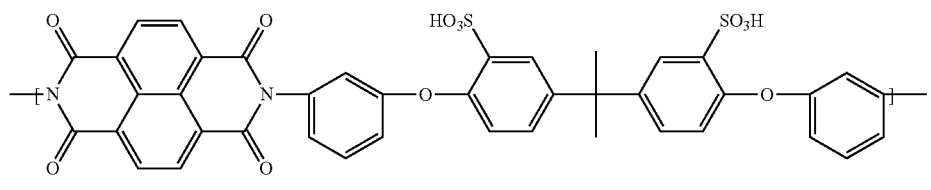
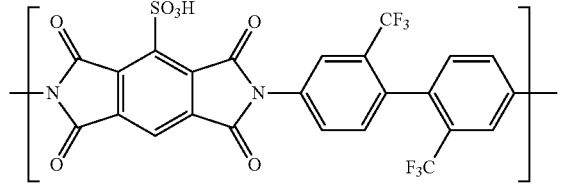

-continued
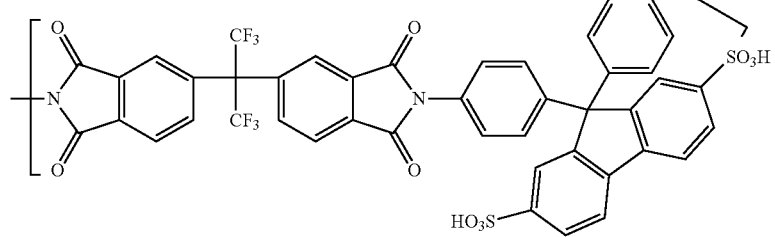
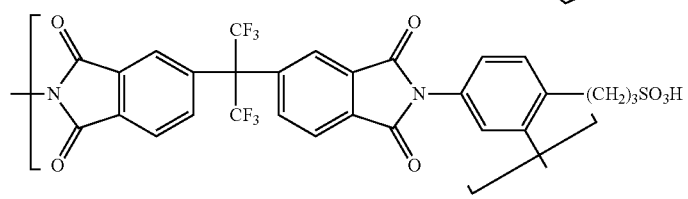
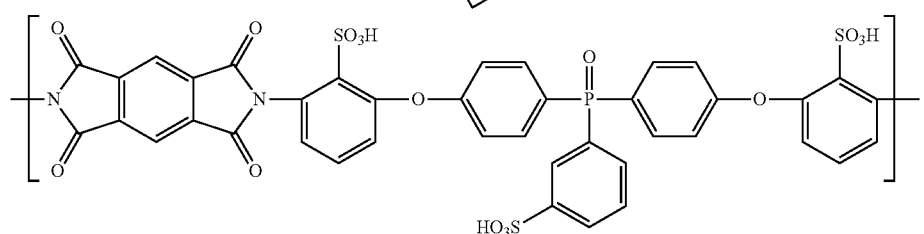
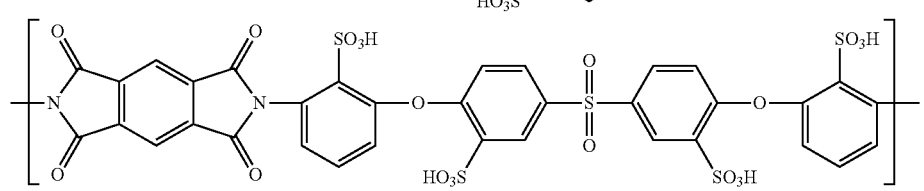
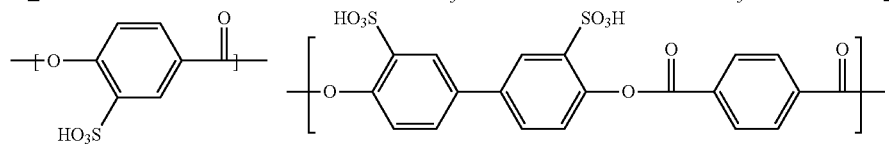
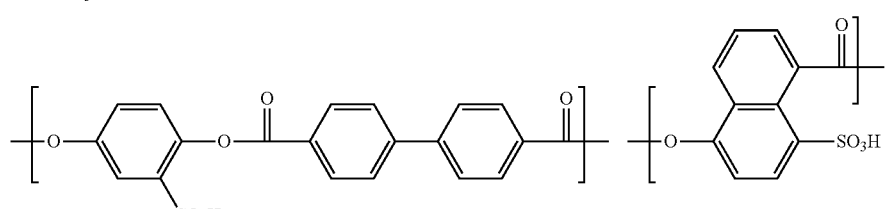
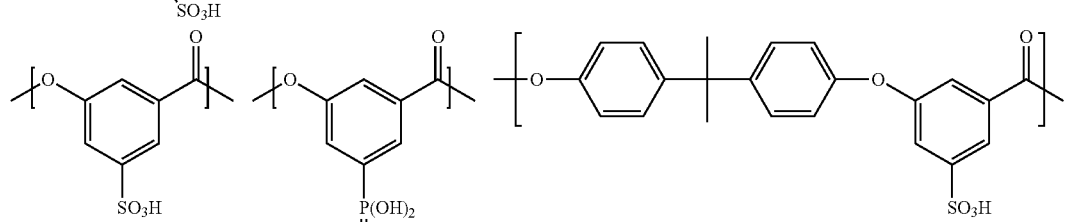
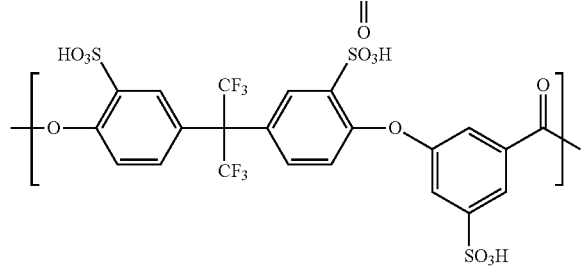

105 106
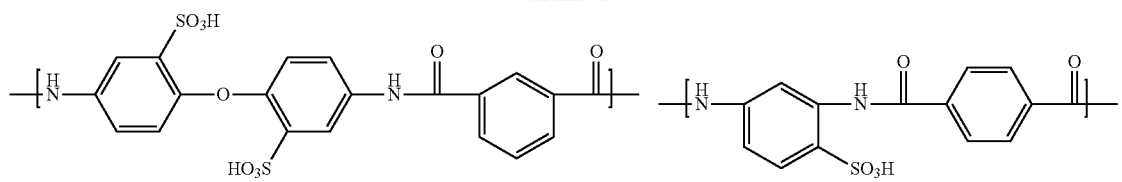
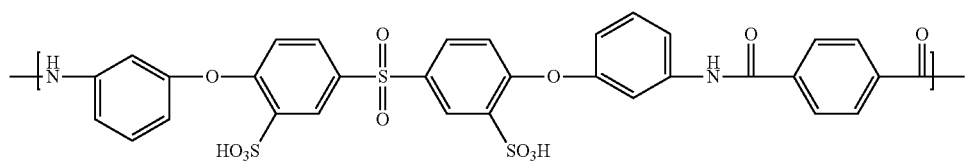
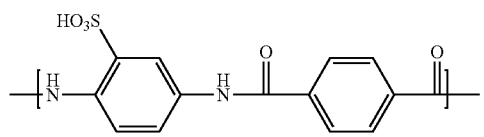
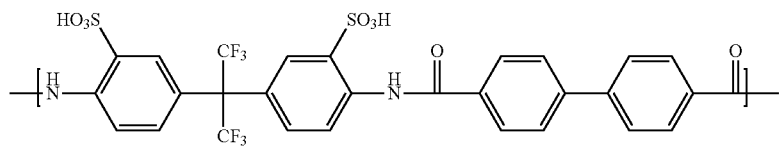
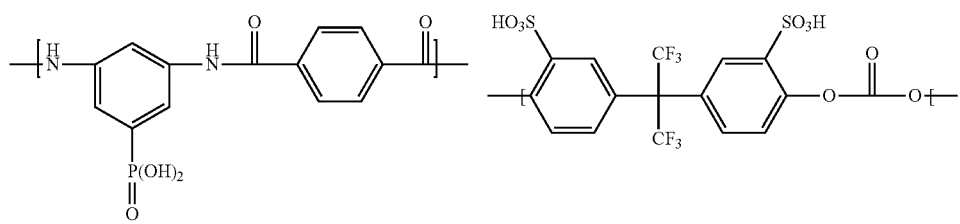
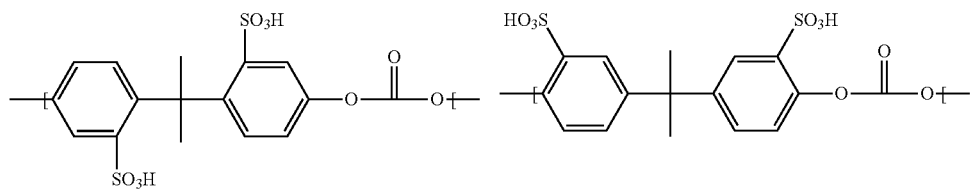
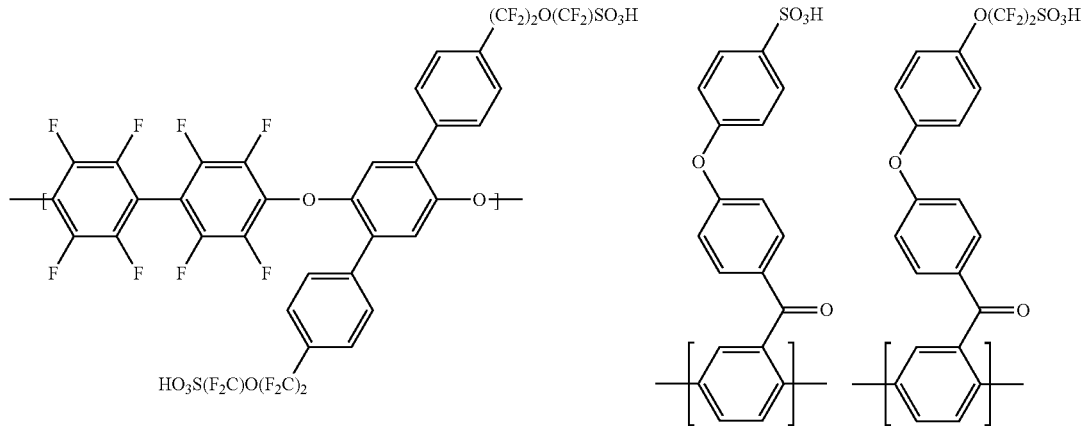

-continued

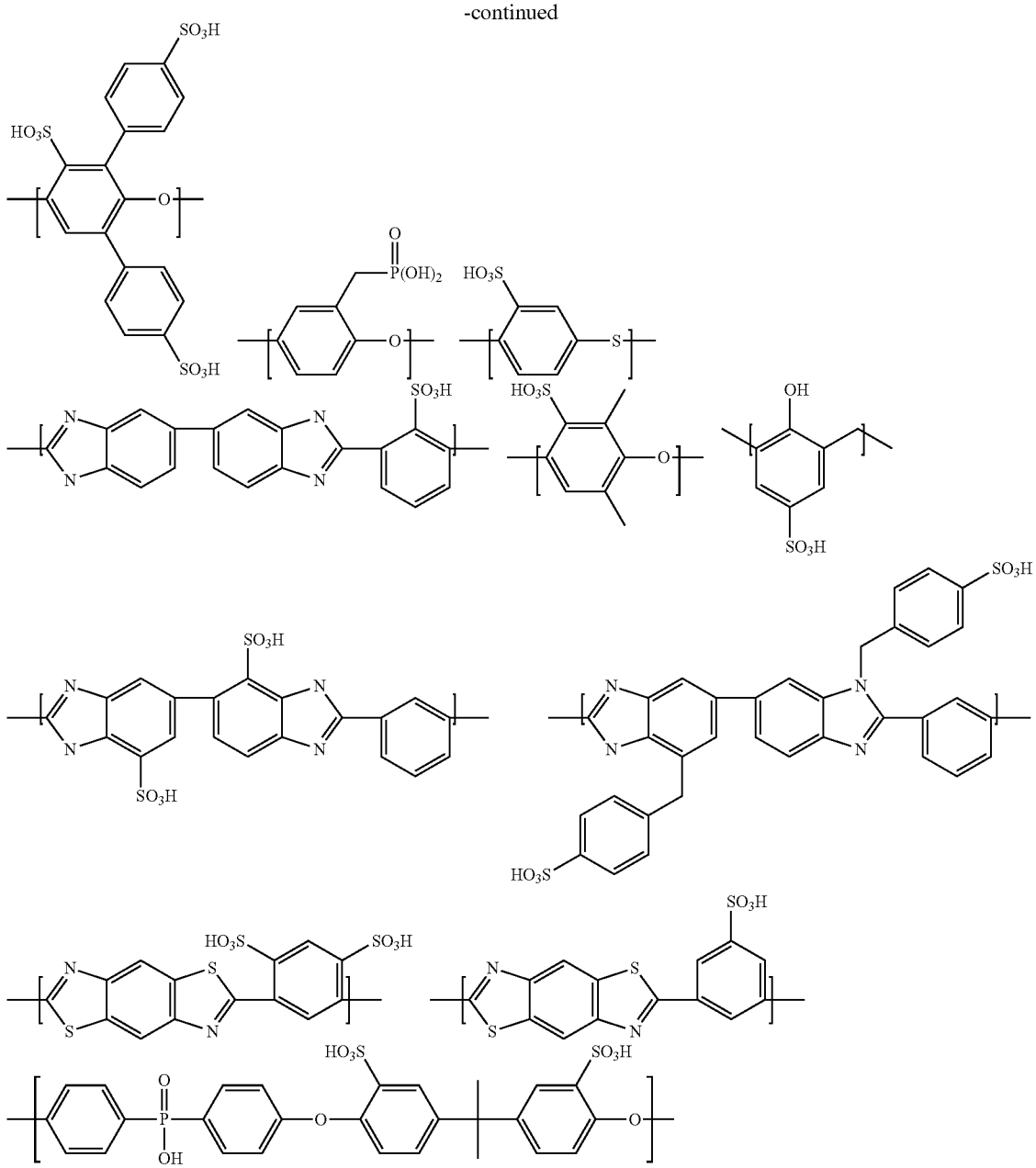

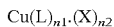

The compound obtained from the reaction between the compound including a low-molecular-weight acid group or a salt thereof other than the compound having two mono-anionic coordination sites and the copper component is preferably a copper complex which is obtained from a reaction between a compound having an acid group or a salt thereof and the copper component and is represented by Formula (i) below.

$$Cu(L)_{n1}\cdot(X)_{n2} \quad \text{Formula (i)}$$

In Formula (i), L represents a ligand coordinating copper, X is not present or represents a halogen atom, $H_2O$, $NO_3$, $ClO_4$, $SO_4$, CN, SCN, $BF_4$, $PF_6$, $BPh_4$ (Ph represents a phenyl group) or an alcohol. Each of n1 and n2 independently represents an integer from 1 to 4.

The ligand L has a substituent including C, N, O, and S as an atom capable of coordinating copper and more preferably has a group having a lone electron pair such as N, O, or S. The number of kinds of the group capable of coordinating copper in the molecule is not limited to one and may be two or more, and the group may or may not be dissociated. In a case in which the group is dissociated, X is not present.

The copper complex is a copper compound in which a copper central metal is coordinated with a ligand, and copper is generally divalent copper. The copper complex can be obtained by, for example, mixing, reacting, and the like a compound or a salt thereof which serves as the ligand with the copper component.

The compound or the salt thereof which serves as the ligand is not particularly limited, and examples thereof preferably include an organic acid compound (for example, a sulfonic acid compound, a carboxylic acid compound, or a phosphoric acid compound) or salts thereof.

The compound or the salt thereof which serves as the ligand is preferably a compound represented by General Formula (ii).

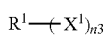

General Formula (ii)

(In General Formula (ii), $R^1$ represents an n-valent organic group, $X^1$ represents an acid group, and n3 represents an integer from 1 to 6.)

In General Formula (ii), the n-valent organic group is preferably a hydrocarbon group or an oxyalkylene group and more preferably an aliphatic hydrocarbon group or an aromatic hydrocarbon group. The hydrocarbon group may have a substituent, and examples of the substituent include a halogen atom (for example, a fluorine atom), a (meth) acryloyl group, and groups having an unsaturated double bond. In addition, examples of the substituent also include an alkyl group, a polymerizable group (for example, a vinyl group, an epoxy group, an oxetane group, or the like), a sulfonic acid group, a carboxylic acid group, an acid group having a phosphorus atom, a carboxylic acid ester group (for example, —$CO_2CH_3$), a hydroxyl group, an alkoxy group (for example, a methoxy group), an amino group, a carbamoyl group, a carbamoyloxy group, and a halogenated alkyl group (for example, a fluoroalkyl group or a chloroalkyl group). In a case in which the hydrocarbon group has a substituent, the hydrocarbon group may have another substituent, and examples thereof include an alkyl group, the above-described polymerizable group, and a halogen atom. In a case in which the hydrocarbon group is monovalent, an alkyl group or an aryl group is preferred, and an aryl group is more preferred. In addition, in a case in which the hydrocarbon group is monovalent, the hydrocarbon group may be an alkenyl group. In a case in which the hydrocarbon group is divalent, an alkylene group, an arylene group, or an oxyalkylene group is preferred, and an arylene group is more preferred. In a case in which the hydrocarbon group is trivalent, groups corresponding to the monovalent hydrocarbon group or the divalent hydrocarbon group are preferred.

The number of carbon atoms in the alkyl group and the alkylene group is preferably in a range of 1 to 20 and more preferably in a range of 1 to 10. The alkyl group and the alkylene group may have any of a linear shape, a branched shape, and a ring shape. The number of carbon atoms in the linear alkyl or alkylene group is preferably in a range of 1 to 20, more preferably in a range of 1 to 12, and still more preferably in a range of 1 to 8. The number of carbon atoms in the branched alkyl or alkylene group is preferably in a range of 3 to 20, more preferably in a range of 3 to 12, and still more preferably in a range of 3 to 8. The cyclic alkylene group may be either a monocyclic ring or a polycyclic ring. The number of carbon atoms in the cyclic alkyl or alkylene group is preferably in a range of 3 to 20, more preferably in a range of 4 to 10, and still more preferably in a range of 6 to 10.

The number of carbon atoms in the alkenyl group is preferably in a range of 2 to 10, more preferably in a range of 2 to 8, and still more preferably in a range of 2 to 4.

The number of carbon atoms in the aryl group or the arylene group is preferably in a range of 6 to 18, more preferably in a range of 6 to 14, still more preferably in a range of 6 to 12, and particularly preferably in a range of 6 to 10.

In General Formula (ii), $X^1$ is preferably at least one of a sulfonic acid group, a carboxylic acid group, and acid groups including a phosphorus atom and is preferably a group including a sulfonic acid group and a carboxyl group. The number of kinds of $X^1$ may be one or more, but is preferably two or more.

In General Formula (ii), n3 is preferably in a range of 1 to 3, more preferably 2 or 3, and still more preferably 3.

The molecular weight of the compound or the salt thereof (compound including the acid group or a salt thereof) which serves as a ligand is preferably 1000 or lower, preferably in a range of 70 to 1000, and more preferably in a range of 0 to 500.

Preferred aspects of the compound including the acid group or the salt thereof include (1) a compound having at least one of a sulfonic acid group, a carboxylic acid group, and acid groups including a phosphorus atom.

(1) Specific examples of the compound having at least one of a sulfonic acid group, a carboxylic acid group, and acid groups including a phosphorus atom include the following compounds.

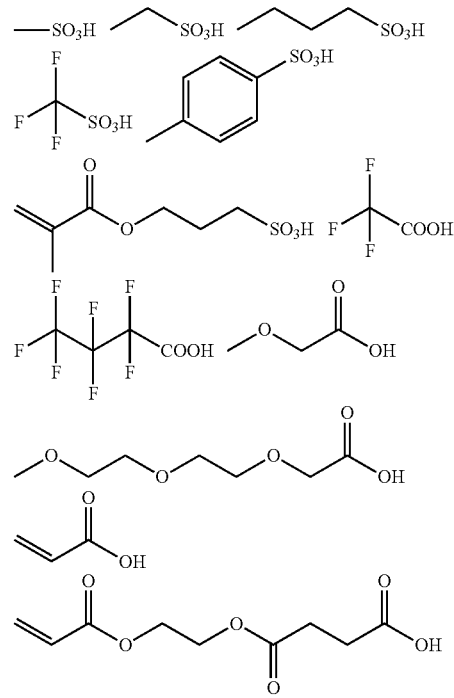

(Inorganic Fine Particles)

The composition of the present invention may include inorganic fine particles as another near-infrared-ray-absorbing substance. Only one kind of inorganic fine particles may be used or two or more kinds of inorganic fine particles may be used.

The inorganic fine particles refer to particles that play a role of shielding (absorbing) infrared rays. The inorganic fine particles are preferably at least one selected from the group consisting of metal oxide particles and metal particles in terms of more favorable infrared shielding properties.

Examples of the inorganic fine particles include metal oxide particles such as indium tin oxide (ITO) particles, antimony tin oxide (ATO) particles, particles of zinc oxide which may be doped with aluminum (ZnO which may be doped with aluminum), fluorine-doped tin dioxide (F-doped $SnO_2$) particles, and niobium-doped titanium dioxide (Nb-doped $TiO_2$) and metal particles such as silver (Ag) particles, gold (Au) particles, copper (Cu) particles, and nickel (Ni) particles. Meanwhile, in order to satisfy both infrared shielding properties and photolithographic properties, inorganic fine particles having a high transmissivity at an exposure wavelength (365 nm to 405 nm) are desired and indium tin oxide (ITO) particles or antimony tin oxide (ATO) particles are preferred.

The shapes of the inorganic fine particles are not particularly limited, may be any of non-spherical and spherical, and may be sheet shapes, wire shapes, or tube shapes.

In addition, as the inorganic fine particles, a tungsten oxide-based compound can be used and, specifically, the inorganic fine particles are more preferably a tungsten oxide-based compound represented by General Formula (Composition Formula) (I) described below.

$$M_xW_yO_z \quad (I)$$

M represents a metal, W represents tungsten, and O represents oxygen.

Examples of the metal M include alkali metals, alkaline earth metals, Mg, Zr, Cr, Mn, Fe, Ru, Co, Rh, Ir, Ni, Pd, Pt, Cu, Ag, Au, Zn, Cd, Al, Ga, In, Tl, Sn, Pb, Ti, Nb, V, Mo, Ta, Re, Be, Hf, Os, and Bi. The metal M is preferably an alkali metal, preferably Rb or Cs, and more preferably Cs. The number of the metals M may be one or more.

When x/y is 0.001 or more, it is possible to sufficiently shield infrared rays and, when x/y is 1.1 or less, it is possible to more reliably avoid the generation of impurity phases in the tungsten oxide-based compound.

When z/y is 2.2 or more, it is possible to further improve chemical stability as a material and, when z/y is 3.0 or less, it is possible to sufficiently shield infrared rays.

The metal oxide is preferably cesium tungsten oxide.

Specific examples of the tungsten oxide-based compound represented by Formula (I) include $Cs_{0.33}WO_3$, $Rb_{0.33}WO_3$, $K_{0.33}WO_3$, $Ba_{0.33}WO_3$, and the like, $Cs_{0.33}WO_3$ or $Rb_{0.33}WO_3$ is preferred, and $Cs_{0.33}WO_3$ is more preferred.

The metal oxide preferably has a fine particle form. The average particle diameter of the fine particles of the metal oxide is preferably 800 nm or less, more preferably 400 nm or less, and still more preferably 200 nm or less. When the average particle diameter is in the above-described range, the metal oxide is not capable of easily shielding visible light through light scattering and thus it is possible to more reliably transmit light in the visible light range. From the viewpoint of avoiding light scattering, the average particle diameter is preferably small; however, in consideration of ease of handling during the manufacturing of the metal oxide, the average particle diameter of the metal oxide is generally 1 nm or more.

The tungsten oxide-based compound can be produced in a form of, for example, a dispersion of tungsten fine particles such as YMF-02, YMF-02A, YMS-01A-2, or YMF-10A-1 manufactured by Sumitomo Metal Mining Co., Ltd.

The content of the metal oxide is preferably in a range of 0.01% by mass to 30% by mass, more preferably in a range of 0.1% by mass to 20% by mass, and still more preferably in a range of 1% by mass to 10% by mass in relation to the total solid content mass of the composition including the metal oxide.

In the composition of the present invention, as other near-infrared-ray-absorbing compounds, the phthalocyanine compound described in Paragraphs [0013] to [0029] of JP2013-195480A can be used, and the content thereof is incorporated into the present specification.

<Solvent>

The composition of the present invention may include a solvent.

Regarding the solvent used in the present invention, there is no particular limitation, any solvent can be appropriately selected depending on the purpose as long as the solvent is capable of uniformly dissolving or dispersing the respective components of the composition of the present invention, and, for example, water or an organic solvent can be used. Since the composition of the present invention uses the above-described compound (A), it is possible to weaken the influence on spectral characteristics even in a case in which an organic solvent is used as the solvent. Preferred examples of the solvent include alcohols, ketones, esters, aromatic hydrocarbons, halogenated hydrocarbons, dimethylformamide, dimethylacetamide, dimethylsulfoxide, sulfolane, and the like. In this case, a mixed solution made up of two or more solvents selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, ethylene glycol monobutyl ether acetate, propylene glycol monomethyl ether, and propylene glycol monomethyl ether acetate is particularly preferred.

Specific examples of the alcohols, the aromatic hydrocarbons, and the halogenated hydrocarbons include those described in Paragraph [0136] and the like in JP2012-194534A and the content thereof is incorporated into the specification of the present application by reference. In addition, specific examples of the esters, the ketones, and the ethers include those described in Paragraph [0497] in JP2012-208494A (Paragraph [0609] in the corresponding US2012/0235099A) and further include n-amyl acetate, ethyl propionate, dimethyl phthalate, ethyl benzoate, methyl sulfate, acetone, methyl isobutyl ketone, diethyl ether, ethylene glycol monobutyl ether acetate, and the like.

The content of the solvent is preferably 10% by mass or higher, more preferably 20% by mass or higher, still more preferably 30% by mass or higher, and far still more preferably 40% by mass or higher. In addition, the proportion of the solvent in the composition of the present invention is preferably in a range of 10% by mass to 90% by mass, more preferably in a range of 20% by mass to 80% by mass, and particularly preferably in a range of 30% by mass to 70% by mass. The number of kinds of the solvent may be one or more, and, in a case in which two or more solvents are used, the total amount thereof falls in the above-described range.

In addition, in a case in which the composition of the present invention includes water or a water-based solvent, the number of kinds of water or the water-based solvents may be one or more. The proportion of water or the water-based solvent in the composition of the present invention is preferably 20% by mass or higher, more preferably in a range of 20% by mass to 90% by mass, and still more preferably in a range of 25% by mass to 85% by mass.

<Curable Compound>

The composition of the present invention preferably includes a curable compound. In a case in which the copper complex is a curable compound having a polymerizable group, the composition of the present invention may not include the curable compound. The curable compound may be a polymerizing compound or a non-polymerizing compound such as a binder. In addition, the curable compound may be a thermosetting compound or a photocrosslinkable compound and is preferably a thermosetting composition due to its high reaction rate.

<Compound Having Polymerizable Group>

The composition of the present invention preferably includes a compound having a polymerizable group (hereinafter, in some cases, referred to as the "polymerizing compound") as a curable composition. The above-described compound group is widely known in the corresponding industrial field and, in the present invention, the above-described compounds can be used without any particular limitation. The compounds may have any chemical form of, for example, a monomer, an oligomer, a prepolymer, a polymer, and the like.

The polymerizing compound may be monofunctional or polyfunctional and is preferably polyfunctional. The inclusion of a polyfunctional compound makes it possible to improve near-infrared shielding properties and heat resistance. The number of functional groups is not particularly specified, but is preferably in a range of 2 to 8 and more preferably in a range of 3 to 6.

In a case in which the composition of the present invention includes the curable composition together with the copper complex, a preferred aspect of the curable compound includes the following. The present invention is not limited to the following aspects. Examples of the curable compound include a monofunctional (meth)acrylate, a polyfunctional (meth)acrylate (preferably tri- to hexafunctional (meth)acrylate), a polybasic acid-denatured acryl oligomer, an epoxy resin, and a polyfunctional epoxy resin.

<<Polymerizing Monomer and Polymerizing Oligomer>>

A first preferred embodiment of the composition of the present invention includes a monomer having a polymerizable group (polymerizing monomer) or an oligomer having a polymerizable group (polymerizing oligomer) (hereinafter, in some cases, the polymerizing monomer and the polymerizing oligomer will be collectively referred to as "the polymerizing monomer and the like") as the polymerizing compound.

Examples of the polymerizing monomer and the like include unsaturated carboxylic acids (for example, acrylic acid, methacrylic acid, itaconic acid, crotonic acid, isocrotonic acid, maleic acid, and the like), esters thereof, and amides thereof and esters of an unsaturated carboxylic acid and an aliphatic polyvalent alcohol compound and amides of an unsaturated carboxylic acid and an aliphatic polyvalent amine compound are preferred. In addition, addition reactants of an unsaturated carboxylic acid ester or amide having a nucleophilic substituent such as a hydroxyl group, an amino group, or a mercapto group and a monofunctional or polyfunctional isocyanate or epoxy, dehydration and condensation reactants of an unsaturated carboxylic acid ester or amide and a monofunctional or polyfunctional carboxylic acid, and the like are also preferably used. In addition, addition reactants of an unsaturated carboxyl ester or an amide having an electrophilic substituent such as an isocyanate group or an epoxy group and a monofunctional or polyfunctional alcohol, amine, or thiol and, furthermore, substitution reactants of an unsaturated carboxylic acid ester or amide having a desorbable substituent such as a halogen group or a tosyloxy group and a monofunctional or polyfunctional alcohol, amine, or thiol are also preferred.

As additional examples, it is also possible to use a compound group in which the above-described unsaturated carboxylic acid is substituted with an unsaturated phosphonic acid, a vinyl benzene derivative such as styrene, a vinyl ether, an aryl ether, or the like.

As the specific compounds thereof, the compounds described in Paragraphs [0095] to [0108] in JP2009-288705A can be preferably used even in the present invention.

In addition, the polymerizing monomer and the like are also preferably compounds having an ethylenic unsaturated group which has at least one addition-polymerizing ethylene group and a boiling point of 100° C. or higher at normal pressure and monofunctional (meth)acrylates, difunctional (meth)acrylates, and tri- or higher-functional (meth)acrylates (for example, tri- to hexafunctional (meth)acrylate) are preferred.

Examples thereof include monofunctional acrylates or methacrylates such as polyethylenene glycol mono(meth)acrylate, polypropylene glycol mono(meth)acrylate, and phenoxyethyl (meth)acrylate;

substances obtained by adding ethylene oxide or propylene oxide to a polyfunctional alcohol such as polyethylene glycol di(meth)acrylate, trimethylolethane tri(meth)acrylate, neopentyl glycol di(meth)acrylate, pentaerythritol tri(meth)acrylate, pentaerythritol tetra(meth)acrylate, dipentaerythritol penta(meth)acrylate, dipentaerythritol hexa(meth)acrylate, hexanediol (meth)acrylate, trimethylolpropane tri(acryloyloxypropyl) ether, tri(acryloyloxyethyl)isocyanurate, glycerin, or trimethylolethane and then (meth)acrylating the mixture; and polyfunctional acrylate or methacrylate such as urethane (meth)acrylates as respectively described in JP1973-41708B (JP-S48-41708B), and JP1975-6034B (JP-S50-6034B), JP1976-37193A (JP-S51-37193A), polyester acrylates respectively described in JP1973-64183A (JP-S48-64183A), JP1974-43191B (JP-S49-43191B), and JP1977-30490B (JP-S52-30490B), epoxy acrylates that are reaction products of an epoxy polymer and (meth)acrylic acid and mixtures thereof.

Among these, the polymerizing compound is preferably ethyleneoxy-denatured pentaerythritol tetraacrylate (NK ester ATM-35E as a commercially available product: manufactured by Shin-Nakamura Chemical Co., Ltd.), dipentaerythritol triacrylate (KAYARAD D-330 as a commercially available product; manufactured by Nippon Kayaku Co., Ltd.), dipentaerythritol tetraacrylate (KAYARAD D-320 as a commercially available product; manufactured by Nippon Kayaku Co., Ltd.), dipentaerythritol penta(meth)acrylate (KAYARAD D-310 as a commercially available product; manufactured by Nippon Kayaku Co., Ltd.), dipentaerythritol hexa(meth)acrylate (KAYARAD DPHA as a commercially available product; manufactured by Nippon Kayaku Co., Ltd.), and structures in which the above-described (meth)acryloyl groups are bonded to each other through ethylene glycol and propylene glycol residues. In addition, the oligomer types thereof can also be used.

Examples of the polymerizing compound include polyfunctional (meth)acrylates and the like obtained by reacting a polyfunctional carboxylic acid and a compound having a cyclic ether group such as glycidyl (meth)acrylate and an ethylenic unsaturated group.

In addition, as other preferred polymerizing monomers and the like, it is also possible to use compounds and cardo polymers having a fluorene ring and a di- or higher-functional ethylenic polymerizable group which are described in JP2010-160418A, JP2010-129825A, JP4364216B, and the like.

In addition, the compounds having a boiling point of 100° C. or higher at normal pressure and having at least one addition-polymerizing ethylenic unsaturated group are also preferably the compounds described in Paragraphs [0254] to [0257] in JP2008-292970A.

In addition, a compound obtained by adding ethylene oxide or propylene oxide to polyfunctional alcohol, which are described as General Formulae (1) and (2) together with specific examples thereof in JP1998-62986A (JP-H10-62986A), and then causing (meth)acrylation can also be used as the polymerizing monomer.

Furthermore, the polymerizing monomer used in the present invention is preferably a polymerizing monomer represented by General Formulae (MO-1) to (MO-6).

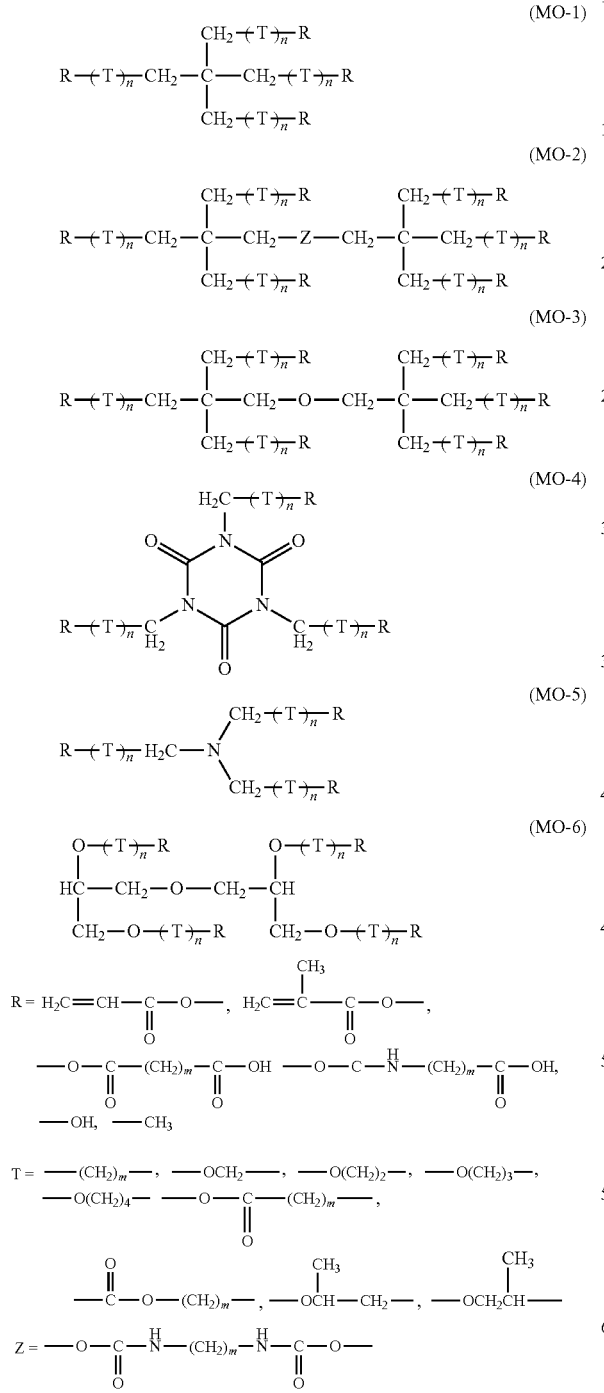

(In the formulae, n is 0 to 14 and m is 1 to 8. The multiple R's, T's, and Z's present in a molecule may be identical to or different from each other. In a case in which T is an oxyalkylene group, the terminal on the carbon atom side is bonded to R. At least one of the R's is a polymerizable group.)

n is preferably 0 to 5 and more preferably 1 to 3.
m is preferably 1 to 5 and more preferably 1 to 3.
Rs are preferably the following four structures.

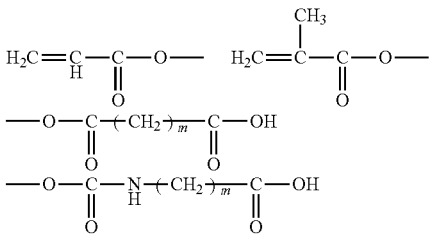

Rs are more preferably the following two structures out of the above-illustrated four structures.

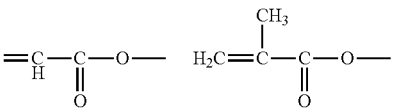

As specific examples of a radical polymerizing monomer represented by Formulae (MO-1) to (MO-6), the compounds described in Paragraphs [0248] to [0251] in JP2007-269779A can also be preferably used in the present invention.

Among these, examples of the polymerizing monomer and the like include the polymerizing monomer and the like described in Paragraph [0477] in JP2012-208494A (Paragraph [0585] in the corresponding US2012/0235099A) and the content thereof is incorporated into the specification of the present application. In addition, DIGLYCERIN EO (ethylene oxide)-denatured (meth)acrylate (M-460 as a commercially available product; manufactured by Toagosei Co., Ltd.) is preferred. Pentaerythritol tetraacrylate (manufactured by Shin-Nakamura Chemical Co., Ltd., A-TMMT) and 1,6-hexanediol diacrylate (manufactured by Nippon Kayaku Co., Ltd., KAYARAD HDDA) are also preferred. The oligomer types thereof can also be used.

Examples thereof include RP-1040 (manufactured by Nippon Kayaku Co., Ltd.).

The polymerizing monomer and the like are polyfunctional monomers and may have an acid group such as a carboxyl group, a sulfonic acid group, or a phosphoric acid group. Therefore, an ethylenic compound can be used as it is as long as the compound has an unreacted carboxyl group like a mixture-form compound as described above. If necessary, it is also possible to introduce an acid group by reacting a hydroxyl group of the above-described ethylenic compound and a non-aromatic carboxy anhydride. In this case, specific examples of the non-aromatic carboxy anhydride being used include anhydrous tetrahydrophthalic acid, alkylated anhydrous tetrahydrophthalic acid, anhydrous hexahydrophthalic acid, alkylated anhydrous hexahydrophthalic acid, anhydrous succinic acid, and anhydrous maleic acid.

In the present invention, the monomer having an acid group is preferably an ester of an aliphatic polyhydroxy compound and an unsaturated carboxylic acid which is a polyfunctional monomer provided with an acid group by reacting an unreacted hydroxyl group in an aliphatic polyhydroxy compound and a non-aromatic carboxy anhydride and particularly preferably an ester in which the aliphatic polyhydroxy compound is pentaerythritol and/or dipentaerythritol. Examples of commercially available products thereof include ARONIX series M-305, M-510, M-520, and the like which are polybasic acid-denatured acryl oligomers manufactured by Toagosei Co., Ltd.

The acid value of the polyfunctional monomer having an acid group is preferably in a range of 0.1 mg-KOH/g to 40 mg-KOH/g and particularly preferably in a range of 5 mg-KOH/g to 30 mg-KOH/g. In a case in which two or more polyfunctional monomers having different acid groups are jointly used or polyfunctional monomers having no acid groups are jointly used, the polyfunctional monomers are preferably prepared so that all the acid values of the polyfunctional monomers fall within the above-described range.

In addition, the polymerizing monomer and the like preferably include a polyfunctional monomer having a caprolactone-denatured structure.

The polyfunctional monomer having a caprolactone-denatured structure is not particularly limited as long as the polyfunctional monomer has a caprolactone-denatured structure in the molecule. Examples of the polyfunctional monomer having a caprolactone-denatured structure include ε-caprolactone-denatured polyfunctional (meth)acrylates obtained by esterifying a polyvalent alcohol such as trimethylolethane, ditrimethylolethane, trimethylolpropane, ditrimethylolpropane, pentaerythritol, dipentaerythritol, tripentaerythritol, glycerin, diglycerol, or trimethylol melamine, (meth)acrylic acid, and s-caprolactone. Among these, polyfunctional monomers having a caprolactone-denatured structure represented by Formula (20) described below are preferred.

Formula (20)

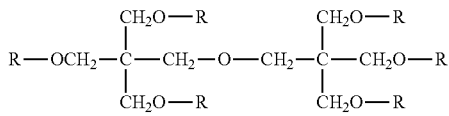

(In the formula, all of the six Rs are groups represented by Formula (21) described below or one to five of the six Rs are the groups represented by Formula (21) described below and the remaining Rs are groups represented by Formula (22) described below.)

Formula (21)

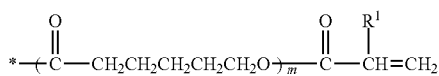

(In the formula, $R^1$ represents a hydrogen atom or a methyl group, m represents a number of 1 or 2, and "*" indicates a direct bond.)

Formula (22)

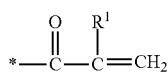

(In the formula, $R^1$ represents a hydrogen atom or a methyl group and "*" indicates a direct bond.)

Examples of the polyfunctional monomer having a caprolactone-denatured structure include DPCA-20 (compound in which m=1 in Formulae (20) to (22), the number of the groups represented by Formula (21)=2, and all the $R^1$s are hydrogen atoms), DPCA-30 (compound in which m=1 in the same formulae, the number of the groups represented by Formula (21)=3, and all the $R^1$s are hydrogen atoms), DPCA-60 (compound in which m=1 in the same formulae, the number of the groups represented by Formula (21)=6, and all the $R^1$s are hydrogen atoms), DPCA-120 (compound in which m=2 in the same formulae, the number of the groups represented by Formula (21)=6, and all the $R^1$s are hydrogen atoms), and the like which have been marketed as the KAYARAD DPCA series by Nippon Kayaku Co., Ltd.

In the present invention, the polyfunctional monomer having a caprolactone-denatured structure can be used singly or a mixture of two or more monomers can be used.

Examples of the commercially available products of the polymerizing monomer and the like include SR-494 manufactured by Sartomer Co., Ltd. which is a tetrafunctional acrylate having four ethyleneoxy chains, DPCA-60 which is a hexafunctional acrylate having six pentyleneoxy chains, and TPA-330 which is a trifunctional acrylate having three isobutyleneoxy chains both of which are manufactured by Nippon Kayaku Co., Ltd.

<<Compound Having Epoxy Group or Oxetanyl Group>>

A third preferred aspect of the present invention includes a compound having an epoxy group or an oxetanyl group as the polymerizing compound. Examples of the compound having an epoxy group or an oxetanyl group include polymers having an epoxy group in the side chain and polymerizing monomers or oligomers having two or more epoxy groups in the molecule and specific examples thereof include bisphenol A-type epoxy resins, bisphenol F-type epoxy resins, phenol novolac-type epoxy resins, cresol novolac-type epoxy resins, aliphatic epoxy resins, and the like. A monofunctional or polyfunctional glycidyl ether compound can also be used as the compound having an epoxy group or an oxetanyl group and a polyfunctional aliphatic glycidyl ether compound is preferred.

As the above-described compound, a commercially available product may be used or the compound can be obtained by introducing an epoxy group into the side chain in the polymer.

Regarding the commercially available product, for example, the description of Paragraphs [0191] and the like in JP2012-155288A can be referred to and the content thereof is incorporated into the specification of the present application by reference.

Examples of the commercially available product include polyfunctional aliphatic glycidyl ether compounds such as DENACOL EX-212L, EX-214L, EX-216L, EX-321L, and EX-850L (all manufactured by Nagase ChemteX Corporation). The above-described products are low-chlorine products and EX-212, X-214, EX-216, EX-321, EX-850, and the like, which are not low-chlorine products, can also be used in a similar manner.

Additionally, examples thereof include ADEKA RESIN EP-4000S, ADEKA RESIN EP-4003S, ADEKA RESIN EP-4010S, ADEKA RESIN EP-4011S (all manufactured by Adeka Corporation), NC-2000, NC-3000, NC-7300, XD-1000, EPPN-501, EPPN-502 (all manufactured by Adeka Corporation), JER1031S, and the like.

Furthermore, examples of the commercially available product of the phenol novolac-type epoxy resins include JER-157S65, JER-152, JER-154, JER-157S70 (all manufactured by Mitsubishi Chemical Corporation), and the like.

As a specific example of a polymer having an oxetanyl group in the side chain and the above-described polymerizing monomer or oligomer having two or more oxetanyl groups in the molecule, it is possible to use ARON OXETANE OXT-121, OXT-221, OX-SQ, and PNOX (all manufactured by Toagosei Co., Ltd.).

The molecular weight is in a range of 500 to 5000000 and, furthermore, preferably in a range of 1000 to 500000 in terms of weight average.

As the epoxy unsaturated compound, it is also possible to use a compound having a glycidyl group as an epoxy group such as glycidyl (meth)acrylate or allyl glycidyl ether and the epoxy unsaturated compound is preferably an unsaturated compound having an alicyclic epoxy group. Regarding the above-described unsaturated compound, the description of Paragraphs [0045] and the like in JP2009-265518A and the like can be referred to and the content thereof is incorporated into the specification of the present application by reference.

The composition of the present invention may include a polymer having a crosslinked group such as an unsaturated double bond, an epoxy group, or an oxetanyl group. Specific examples thereof include polymers (copolymers) having a repeating unit described below. The polymer having the following repeating unit is preferably a polymer having an epoxy group.

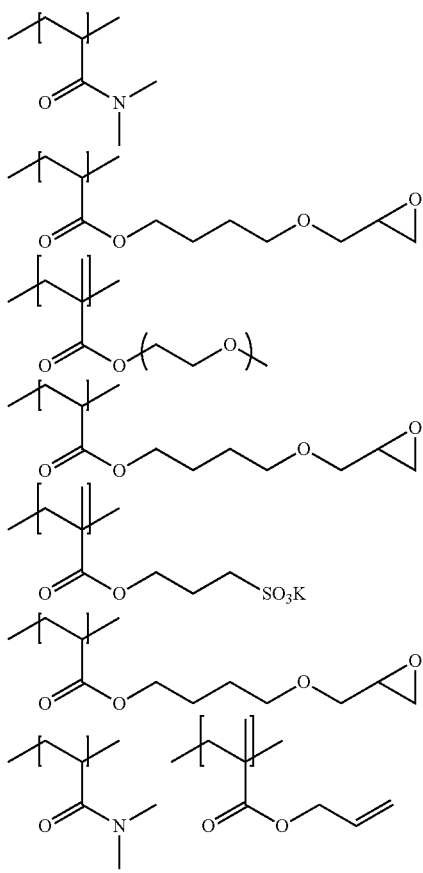

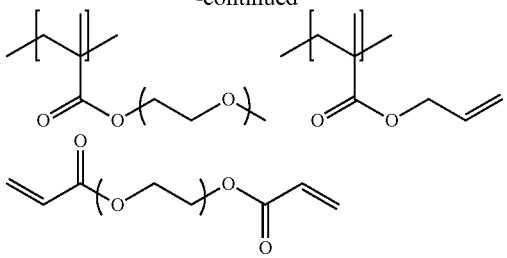

<<Compound Having Partial Structure Represented by Formula (30)>>

The curable compound used in the present invention also may have a partial structure represented by Formula (30) and the curable compound may have a crosslinked group such as an unsaturated double bond, an epoxy group, or an oxetanyl group.

General formula (30)

(In Formula (30), $R^1$ represents a hydrogen atom or an organic group.)

When the above-described compound is included, it is possible to further improve near-infrared shielding properties and further improve moisture resistance when a cured film is produced using the near-infrared-ray-absorbing composition of the present invention.

In Formula (30), $R^1$ represents a hydrogen atom or an organic group. Examples of the organic group include hydrocarbon groups, specifically, alkyl groups and aryl groups and the organic group is preferably an alkyl group having 1 to 20 carbon atoms, an aryl group having 6 to 20 carbon atoms, or a group obtained by combining the above-described group and a divalent linking group.

Specific examples of the above-described organic group include —OR', —SR', and groups obtained by combining the above-described group and at least one of —$(CH_2)_m$— (m is an integer from 1 to 10), a cyclic alkylene group having 5 to 10 carbon atoms, —O—, —CO—, —COO—, and —NH—. Here, R' is preferably a hydrogen atom, a linear alkyl group having 1 to 10 carbon atoms, a branched or cyclic alkyl group having 3 to 10 carbon atoms (preferably a linear alkyl group having 1 to 7 carbon atoms or a branched or cyclic alkyl group having 3 to 7 carbon atoms), an aryl group having 6 to 10 carbon atoms, or a group obtained by combining an aryl group having 6 to 10 carbon atoms and an alkylene group having 1 to 10 carbon atoms.

In addition, in Formula (30), $R^1$ and C may be bonded together and thus form a ring structure (heterocyclic structure). A hetero atom in the heterocyclic structure is a nitrogen atom in Formula (30). The heterocyclic structure is preferably a 5- or 6-membered ring structure and more preferably a 5-membered ring structure. The heterocyclic structure may be a condensed ring, but is preferably a monocyclic ring.

Specific examples of a particularly preferred $R^1$ include a hydrogen atom, an alkyl group having 1 to 3 carbon atoms, groups obtained by combining —OR' (R' is a linear alkyl group having 1 to 5 carbon atoms) and —$(CH_2)_m$— (m is an integer from 1 to 10 and preferably an integer from 1 to 5), and groups in which $R^1$ and C in Formula (30) are bonded together and thus form a heterocyclic structure (preferably a 5-membered ring structure).

The compound having the partial structure represented by Formula (30) is preferably represented by (the main chain structure of the polymer—the partial structure of the above-illustrated (30)—$R^1$) or (A—the partial structure of the above-illustrated (30)—B). Here, A is a linear alkyl group having 1 to 10 carbon atoms, a branched alkyl group having 3 to 10 carbon atoms, or a cyclic alkyl group having 3 to 10 carbon atoms. In addition, B is a group obtained by combining —$(CH_2)_m$— (m is an integer from 1 to 10 and preferably an integer from 1 to 5), the partial structure of the above-illustrated (30), and a polymerizable group.

In addition, the compound having the partial structure represented by Formula (30) is a structure represented by any one of Formulae (1-1) to (1-5) described below.

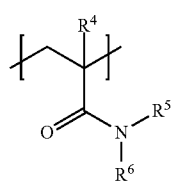

General Formula (1-1)

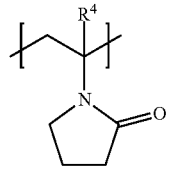

General Formula (1-2)

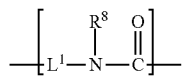

General Formula (1-3)

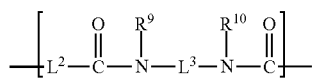

General Formula (1-4)

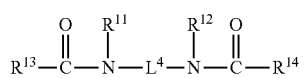

General Formula (1-5)

(In Formula (1-1), $R^4$ represents a hydrogen atom or a methyl group and each of $R^5$ and $R^6$ independently represents a hydrogen atom or an organic group. In Formula (1-2), $R^7$ represents a hydrogen atom or a methyl group. In Formula (1-3), $L^1$ represents a divalent linking group and $R^8$ represents a hydrogen atom or an organic group. In Formula (1-4), each of $L^2$ and $L^3$ independently represents a divalent linking group and each of $R^9$ and $R^{10}$ independently represents a hydrogen atom or an organic group. In Formula (1-5), $L^4$ represents a divalent linking group and each of $R^{11}$ to $R^{14}$ independently represents a hydrogen atom or an organic group.)

In Formula (1-1), each of $R^5$ and $R^6$ independently represents a hydrogen atom or an organic group. The organic group is identical to $R^1$ in Formula (30), and the preferred range thereof is also identical.

In Formulae (1-3) to (1-5), $L^1$ to $L^4$ represent divalent linking groups. The divalent linking group is preferably a divalent linking group obtained through a combination with at least one of —$(CH_2)_m$— (m is an integer from 1 to 10), a cyclic alkylene group having 5 to 10 carbon atoms, —O—, —CO—, —COO—, and —NH— and more preferably —$(CH_2)_m$— (m is an integer from 1 to 8).

In Formulae (1-3) to (1-5), each of $R^8$ to $R^{14}$ independently represents a hydrogen atom or an organic group. The organic group is preferably a hydrocarbon group, specifically, an alkyl group or an alkenyl group.

The alkyl group may be substituted. In addition, the alkyl group may have a linear shape, a branched shape, or a ring shape, but preferably has a linear shape or a ring shape. The alkyl group is preferably an alkyl group having 1 to 10 carbon atoms, more preferably an alkyl group having 1 to 8 carbon atoms, and still more preferably an alkyl group having 1 to 6 carbon atoms.

The alkenyl group may be substituted. The alkenyl group is preferably an alkenyl group having 1 to 10 carbon atoms, more preferably an alkenyl group having 1 to 4 carbon atoms, and particularly preferably a vinyl group.

Examples of the substituent include a polymerizable group, a halogen atom, an alkyl group, a carboxylic acid ester group, a halogenated alkyl group, an alkoxy group, a methacryloyloxy group, an acryloyloxy group, an ether group, a sulfonyl group, a sulfide group, an amide group, an acyl group, a hydroxy group, a carboxyl group, or the like. Among the above-described substituents, a polymerizable group (for example, a vinyl group, a (meth)acryloyloxy group, a (meth)acryloyl group, an epoxy group, an aziridinyl group, or the like) is preferred and a vinyl group is more preferred.)

In addition, the compound having the partial structure represented by Formula (30) may be a monomer or a polymer, but is preferably a polymer. The compound having the partial structure represented by Formula (30) is preferably a compound represented by Formula (1-1) or (1-2).

In addition, in a case in which the compound having the partial structure represented by Formula (30) is a polymer, the compound preferably has the partial structure in the side chain of the polymer.

The molecular weight of the compound having the partial structure represented by Formula (30) is preferably in a range of 50 to 1000000 and more preferably in a range of 500 to 500,000. When the molecular weight is set in the above-described range, it is possible to more effectively achieve the effects of the present invention.

The content of the compound having the partial structure represented by Formula (30) is preferably in a range of 5% by mass to 80% by mass and more preferably in a range of 10% by mass to 60% by mass in the composition of the present invention.

Specific examples of the compound having the partial structure represented by Formula (30) include compounds having structures described below or exemplary compounds described below, but the compound is not limited thereto. In the present invention, particularly, the compound having the partial structure represented by Formula (30) is preferably polyacrylamide.

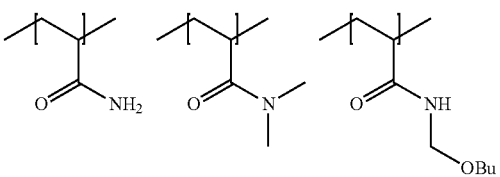

-continued

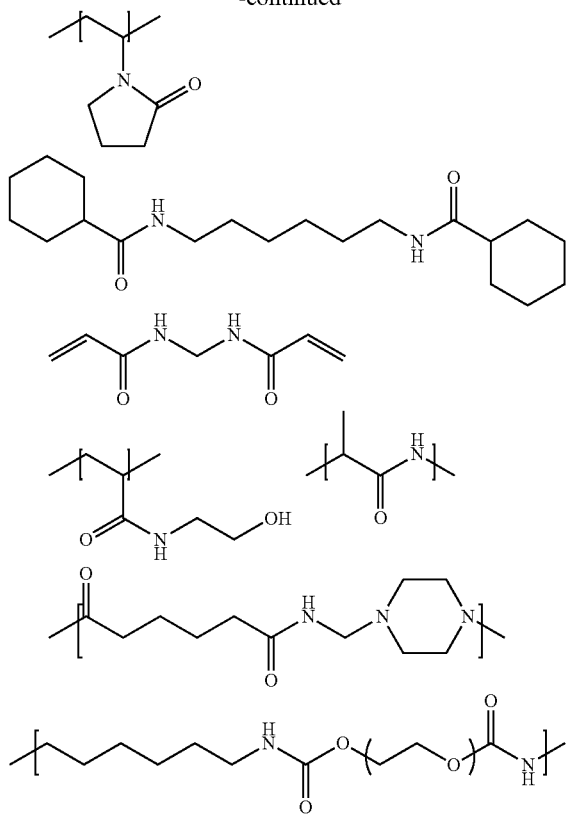

In addition, specific examples of the compound having the partial structure represented by Formula (30) include water-soluble polymers and examples of the preferred main chain structure include polyvinylpyrrolidone, poly(meth)acrylamide, polyamide, polyurethane, and polyurea. The water-soluble polymer may be a copolymer and the copolymer may be a random copolymer.

As the polyvinylpyrrolidone, trade names K-30, K-85, K-90, K-30W, K-85W, and K-90W (manufactured by Nippon Shokubai Co., Ltd.) can be used.

Examples of the poly(meth)acrylamide include polymers and copolymers of (meth)acrylamide. Specific examples of the acrylamide include acrylamide, N-methylacrylamide, N-ethylacrylamide, N-propylacrylamide, N-butylacrylamide, N-benzylacrylamide, N-hydroxyethylacrylamide, N-phenylacrylamide, N-tolylacrylamide, N-(hydroxyphenyl)acrylamide, N-(sulfamoylphenyl)acrylamide, N-(phenylsulfonyl)acrylamide, N-(tolylsulfonyl)acrylamide, N,N-dimethylacrylamide, N-methyl-N-phenylacrylamide, N-hydroxyethyl-N-methylacrylamide, and the like. In addition, methacrylamides corresponding to the above-described poly(meth)acrylamides can also be used in a similar manner.

Examples of the water-soluble polyamide resin particularly include compounds obtained by copolymerizing a polyamide resin and a hydrophilic compound. A derivative of the water-soluble polyamide resin refers to a compound in which the structure of an amide bond is changed by the substitution or addition reaction of an atom in the water-soluble polyamide resin molecule such as a compound in which a water-soluble polyamide resin is used as a raw material and a hydrogen atom in an amide bond (—CONH—) is substituted with a methoxymethyl group (—CH$_2$OCH$_3$).

Examples of the polyamide resin include so-called "n-nylon" that is synthesized by the polymerization of ω amino acids and so-called "n,m-nylon" that is synthesized by the copolymerization of a diamine and a dicarboxylic acid. Among these, from the viewpoint of imparting hydrophilic properties, a copolymer of a diamine and a dicarboxylic acid is preferred and a reaction product of ε-caprolactam and a dicarboxylic acid is more preferred.

Examples of a hydrophilic compound include hydrophilic nitrogen-containing cyclic compounds, polyalkylene glycols, and the like.

Here, the hydrophilic nitrogen-containing cyclic compound refers to a compound including a ternary amine component in the side chain or the main chain and examples thereof include aminoethyl piperazine, bisaminopropyl piperazine, α-dimethylamino ε caprolactam, and the like.

Meanwhile, in the compound in which the polyamide resin and the hydrophilic compound are copolymerized together, for example, at least one selected from the group consisting of hydrophilic nitrogen-containing cyclic compounds and polyalkylene glycols is copolymerized in the main chain of the polyamide resin. Therefore, the hydrogen bonding capability at the amide-bonded portion in the polyamide resin is strong with respect to N-methoxymethylated nylon.

Among the compounds in which the polyamide resin and the hydrophilic compound are copolymerized together, 1) the reaction products of ε-caprolactam, the hydrophilic nitrogen-containing cyclic compound, and a dicarboxylic acid and 2) the reaction products of ε-caprolactam, polyalkylene glycol, and a dicarboxylic acid are preferred.

The above-described compounds are commercially available under a trademark of, for example, "AQ NYLON" from Toray Fine Chemicals Co., Ltd. The reaction products of ε-caprolactam, the hydrophilic nitrogen-containing cyclic compound, and dicarboxylic acid can be procured from AQ NYLON A-90 manufactured by Toray Fine Chemicals Co., Ltd., and the reaction products of ε-caprolactam, polyalkylene glycol, and dicarboxylic acid can be procured from AQ NYLON P-70 manufactured by Toray Fine Chemicals Co., Ltd. AQ NYLON A-90, P-70, P-95, and T-70 (manufactured by Toray Fine Chemicals Co., Ltd.) can be used.

The molar ratio of a polymer having a repeating unit that includes the partial structure represented by Formula (30) and a repeating unit that includes an epoxy group is preferably in a range of 10/90 to 90/10 and more preferably in a range of 30/70 to 70/30. The weight-average molecular weight of the copolymer is preferably in a range of 3,000 to 1,000,000 and more preferably in a range of 5,000 to 200,000.

The amount of the polymerizing compound added to the composition of the present invention is in a range of 1% by mass to 90% by mass, more preferably in a range of 15% by mass to 80% by mass, and particularly preferably in a range of 40% by mass to 75% by mass in relation to the total solid content excluding the solvent.

In addition, in a case in which the polymer having a repeating unit that includes a crosslinked group is used as the polymerizing compound, the amount of the polymerizing compound added is set to a range of 10% by mass to 75% by mass, more preferably to a range of 20% by mass to 65% by mass, and particularly preferably to a range of 20% by mass to 60% by mass in relation to the total solid content of the composition of the present invention excluding the solvent.

The number of the polymerizing compounds may be one or more and, in a case in which two or more polymerizing compounds are used, the total amount thereof needs to fall into the above-described range.

<Binder Polymer>

The present invention may further include a binder polymer as necessary in addition to the above-described polymerizing compound for the purpose of improving coating characteristics. As the binder polymer, an alkali-soluble resin is preferably used. When the present invention includes an alkali-soluble resin, heat resistance and the like are improved and coating appropriateness can be finely adjusted.

Regarding the alkali-soluble resin, the description of Paragraphs [0558] to [0571] ([0685] to [0700] in the specification of the corresponding US2012/0235099A) and thereafter of JP2012-208494A can be referred to, and the content thereof is incorporated into the present specification.

The content of the binder polymer in the present invention is preferably in a range of 1 mass % to 80 mass %, more preferably in a range of 5 mass % to 50 mass %, and still more preferably in a range of 7 mass % to 30 mass % in relation to the total solid content of the composition.

<Surfactant>

The composition of the present invention may include a surfactant. Only one surfactant may be used or a combination of two or more surfactants may be used. The amount of the surfactant added is preferably in a range of 0.0001% by mass to 2% by mass, more preferably in a range of 0.005% by mass to 1.0% by mass, and still more preferably in a range of 0.01% by mass to 0.1% by mass in relation to the solid content of the composition of the present invention.

As the surfactant, a variety of surfactants such as a fluorine-based surfactant, a nonionic surfactant, a cationic surfactant, an anionic surfactant, and a silicone-based surfactant can be used.

Particularly, when the composition of the present invention includes at least any of fluorine-based surfactants and silicone-based surfactants, the liquid characteristics (particularly, fluidity) are further improved when a coating fluid is produced. Therefore, the uniformity of the coating thickness or liquid-saving properties are further improved.

That is, in a case in which a film is formed using a coating fluid to which the composition including at least any one of fluorine-based surfactants and silicone-based surfactants is applied, the surface tension between a surface to be coated and the coating fluid decreases and thus the wetting properties with respect to the surface to be coated are improved and the coating properties with respect to the surface to be coated are improved. Therefore, in a case in which a thin film having a thickness of approximately several micrometers is formed using a small amount of the fluid as well, the inclusion of the surfactant is effective since a film having a uniform thickness with little thickness variation is more preferably formed.

The content ratio of fluorine in the fluorine-based surfactant is preferably in a range of 3% by mass to 40% by mass, more preferably in a range of 5% by mass to 30% by mass, and particularly preferably in a range of 7% by mass to 25% by mass. A fluorine-based surfactant having a content ratio of fluorine in the above-described range is effective in terms of the uniformity of the thickness of a coated film or liquid-saving properties and also has favorable solubility in a colored photosensitive composition.

Specific examples of the fluorine-based surfactant include the surfactants described in Paragraph [0552] in JP2012-208494A ([0678] in the specification of US2012/0235099A) and the content thereof is incorporated into the specification of the present application.

Examples of nonionic surfactants include polyoxyethylene alkyl ethers, polyoxyethylene alkyl allyl ethers, polyoxyethylene aliphatic acid esters, sorbitan aliphatic acid esters, polyoxyethylene sorbitan aliphatic acid esters, polyoxyethylene alkyl amines, glycerin aliphatic acid esters, oxyethylene oxypropylene block copolymers, acetylene glycol-based surfactants, acetylene-based polyoxyethylene oxides, and the like. The above-described surfactants can be used singly or two or more surfactants can be used.

Examples of specific commercially available products thereof include SURFYNOL 61, 82, 104, 104E, 104H, 104A, 104BC, 104DPM, 104PA, 104PG-50, 104S, 420, 440, 465, 485, 504, CT-111, CT-121, CT-131, CT-136, CT-141, CT-151, CT-171, CT-324, DF-37, DF-58, DF-75, DF-110D, DF-210, GA, OP-340, PSA-204, PSA-216, PSA-336, SE, SE-F, TG, GA, DYNOL 604 (all manufactured by Nissin Chemical Co., Ltd. and Air Products & Chemicals, Inc.), OLFINE A, B, AK-02, CT-151W, E1004, E1010, P, SPC, STG, Y, 32W, PD-001, PD-002W, PD-003, PD-004, EXP. 4001, EXP. 4036, EXP. 4051, AF-103, AF-104, SK-14, AE-3 (all manufactured by Nissin Chemical Co., Ltd.), ACETYLENOL E00, E13T, E40,E60, E81, E100, E200 (all are trade names and are manufactured by Kawaken Fine Chemicals Co., Ltd.), and the like. Among these, OLFINE E1010 is preferred.

Additionally, regarding the nonionic surfactants, specifically, the nonionic surfactants described in Paragraph [0553] in JP2012-208494A ([0679] in the specification of the corresponding US2012/0235099A) can be referred to and the contents thereof can be incorporated into the specification of the present application by reference.

Specific examples of cationic surfactants include the cationic surfactants described in Paragraph [0554] in JP2012-208494A ([0680] in the specification of the corresponding US2012/0235099A) and the contents thereof can be incorporated into the specification of the present application by reference.

Specific examples of the anionic surfactants include W004, W005, W017 (manufactured by Yusho Co., Ltd.), and the like.

Examples of silicone-based surfactants include the silicone-based surfactants described in Paragraph [0556] in JP2012-208494A ([0682] in the specification of the corresponding US2012/0235099A) and the contents thereof can be incorporated into the specification of the present application by reference. In addition, examples thereof also include "TORAY SILICONE SF8410", TORAY SILICONE SF8427", TORAY SILICONE SF8400", "ST80PA", "ST83PA", "ST86PA" all manufactured by Dow Corning Toray Co., Ltd., "TSF-400", "TSF-401", "TSF-410", "TSF-4446" manufactured by Momentive Performance Materials Worldwide Inc., "KP321", "KP323", "KP324", "KP340" manufactured by Shin-Etsu Chemical Co., Ltd. and the like.

<Polymerization Initiator>

The composition of the present invention may include a polymerization initiator. The number of the polymerization initiators included may be one or more and, in a case in which the composition includes two or more polymerization initiators, the total amount thereof falls into the following range. The content of the polymerization initiator is preferably in a range of 0.01% by mass to 30% by mass, more preferably in a range of 0.1% by mass to 20% by mass, and particularly preferably in a range of 0.1% by mass to 15% by mass.

The polymerization initiator is not particularly limited as long as the polymerization initiator has the capability of initiating the polymerization of the polymerizing compounds using either or both light and heat and can be appropriately selected depending on the purpose, but is preferably a photopolymerizing compound. In a case in which polymerization is initiated using light, the polymerization initiator preferably has photosensitivity to light rays in an ultraviolet to visible light range.

In addition, in a case in which polymerization is initiated using heat, a polymerization initiator that is decomposed at a temperature in a range of 150° C. to 250° C. is preferred.

The polymerization initiator that can be used in the present invention is preferably a compound having at least an aromatic group and examples thereof include acylphosphine compounds, acetophenone-based compounds, α-aminoketone compounds, benzophenone-based compounds, benzoin ether-based compounds, ketal derivative compounds, thioxanthone compounds, oxime compounds, hexaaryl biimidazole compounds, trihalomethyl compounds, azo compounds, organic peroxides, diazonium compounds, iodonium compounds, sulfonium compounds, azinium compounds, onium salt compounds such as metallocene compounds, organic boron salt compounds, disulfone compounds, thiol compounds, and the like.

Regarding the acetophenone-based compounds, the trihalomethyl compounds, the hexaaryl biimidazole compounds, and the oxime compounds, specifically, the description in Paragraphs [0506] to [0510] in JP2012-208494A ([0622] to [0628] in the specification of the corresponding US2012/0235099A) and the like can be referred to and the content thereof is incorporated into the specification of the present application by reference.

In addition, the polymerization initiator can also be preferably used for the cyclic oxime compounds described in JP2007-231000A (the specification of the corresponding US2011/0123929A) and JP2007-322744A.

Additional examples thereof include the oxime compounds having a specific substituent described in JP2007-269779A (the specification of the corresponding US2010/0104976A) and the oxime compounds having a thioaryl group described in JP2009-191061A (the specification of the corresponding US2009/023085A).

The description of the compound represented by Formula (OX-1), (OX-2), or (OX-3) in Paragraphs [0513] ([0632] in the specification of the corresponding US2012/235099A) and thereafter in JP2012-208494A can be referred to and the content thereof is incorporated into the specification of the present application by reference.

Regarding the specific examples of the oxime compounds, the descriptions of Paragraphs [0090] to [0106] in JP2009-191061A (Paragraph [0393] in the specification of the corresponding US2009/023085A), Paragraph [0054] in JP2012-032556A, and Paragraph [0054] in JP2012-122045A can be referred to and the content thereof is incorporated into the specification of the present application by reference.

The photopolymerization initiator is more preferably an oxime compound, an acetophenone-based compound, or an acylphosphine compound. More specifically, for example, it is also possible to use the aminoacetophenone-based initiators described in JP1998-291969A (JP-H10-291969A), the acylphosphine oxide-based initiators described in JP4225898B, the above-described oxime-based initiators, and, furthermore, as the oxime-based initiators, the compounds described in JP2001-233842A.

As the oxime compound, it is possible to use a commercially available product IRGACURE-OXE01 (manufactured by BASF) or IRGACURE-OXE02 (manufactured by BASF). As the acetophenone-based initiator, it is possible to use commercially available products IRGACURE-907, IRGACURE-369, and IRGACURE-379 (trade name, all manufactured by BASF Japan). In addition, as the acylphosphine-based initiator, it is possible to use a commercially available product IRGACURE-819 or DAROCUR-TPO (trade name, all manufactured by BASF Japan).

<Other Components>

Examples of the other components that can be jointly used in the composition of the present invention include a dispersing agent, a sensitizer, a crosslinking agent, a curing accelerator, a filler, a thermal curing accelerator, a thermopolymerization inhibitor, a plasticizer, and the like and, furthermore, an accelerator of adhesion to the surface of a base material and other auxiliary agents (for example, conductive particles, a filler, a defoamer, a flame retardant, a levelling agent, a peeling accelerator, an antioxidant, a fragrance, a surface tension adjuster, a chain transfer agent, and the like) may also be jointly used.

When the composition of the present invention appropriately includes the above-described components, it is possible to adjust properties such as stability and film properties of the target near-infrared-ray cut filter.

Regarding the above-described components, for example, the descriptions in Paragraphs [0183] and thereafter in JP2012-003225A (the specification of the corresponding US2010/0034812A), Paragraphs [0101] and [0102], Paragraphs [0103] and [0104] and Paragraphs [0107] to [0109] in JP2008-250074A, Paragraphs [0159] to [0184] in JP2013-195480A, and the like can be referred to and the contents thereof can be incorporated into the specification of the present application by reference.

The use of the near-infrared-ray-absorbing composition of the present invention is not particularly limited, and examples thereof include a near-infrared-ray cut filter in the light-receiving side of a solid-state imaging element (for example, a near-infrared-ray cut filter for a wafer-level lens, or the like), a near-infrared-ray cut filter in the back surface side (the side opposite to the light-receiving side) of a solid-state imaging element, and the like. The near-infrared-ray-absorbing composition of the present invention is preferably used for a near-infrared-ray cut filter in the light-receiving side of a solid-state imaging element. In addition, the near-infrared-ray-absorbing composition of the present invention is preferably directly applied onto a solid-state imaging sensor so as to form a coated film.

In a case in which an infrared-ray-cut layer is formed through coating, the viscosity of the near-infrared-ray-absorbing composition of the present invention is preferably in a range of 1 mPa·s to 3000 mPa·s, more preferably in a range of 10 mPa·s to 2000 mPa·s, and still more preferably in a range of 100 mPa·s to 1500 mPa·s.

Since the composition of the present invention can be supplied in a state of being capable of being applied, it is possible to easily form a near-infrared-ray cut filter at a desired member or location in a solid-state imaging element.

In the near-infrared-ray cut filter obtained using the composition of the present invention, the optical transmissivity thereof preferably satisfies at least one of the following conditions (1) to (9), more preferably satisfies all of the following conditions (1) to (8), and still more preferably satisfies all of the following conditions (1) to (9).

(1) The optical transmissivity at a wavelength of 400 nm is preferably 80% or higher, more preferably 90% or higher, still more preferably 92% or higher, and particularly preferably 95% or higher.

(2) The optical transmissivity at a wavelength of 450 nm is preferably 80% or higher, more preferably 90% or higher, still more preferably 92% or higher, and particularly preferably 95% or higher.

(3) The optical transmissivity at a wavelength of 500 nm is preferably 80% or higher, more preferably 90% or higher, still more preferably 92% or higher, and particularly preferably 95% or higher.

(4) The optical transmissivity at a wavelength of 550 nm is preferably 80% or higher, more preferably 90% or higher, still more preferably 92% or higher, and particularly preferably 95% or higher.

(5) The optical transmissivity at a wavelength of 700 nm is preferably 20% or lower, more preferably 15% or lower, still more preferably 10% or lower, and particularly preferably 5% or lower.

(6) The optical transmissivity at a wavelength of 750 nm is preferably 20% or lower, more preferably 15% or lower, still more preferably 10% or lower, and particularly preferably 5% or lower.

(7) The optical transmissivity at a wavelength of 800 nm is preferably 20% or lower, more preferably 15% or lower, still more preferably 10% or lower, and particularly preferably 5% or lower.

(8) The optical transmissivity at a wavelength of 850 nm is preferably 20% or lower, more preferably 15% or lower, still more preferably 10% or lower, and particularly preferably 5% or lower.

(9) The optical transmissivity at a wavelength of 900 nm is preferably 20% or lower, more preferably 15% or lower, still more preferably 10% or lower, and particularly preferably 5% or lower.

While the near-infrared cur-off filter can be appropriately selected depending on the purpose, the film thickness thereof is preferably set to 300 µm or smaller, more preferably set to 200 µm or smaller, and still more preferably set to 100 µm or smaller. The lower limit of the film thickness is, for example, preferably 1 µm or larger, more preferably 5 µm or larger, and preferably 20 µm or larger. According to the composition of the present invention, since the composition has strong near-infrared-shielding properties, it is possible to decrease the film thickness of the near-infrared-ray cut filter.

In the near-infrared-ray cut filter, at a film thickness of 300 µm or smaller, the visible light transmissivity in the entire wavelength range of 400 nm to 550 nm is preferably 85% or higher and more preferably 90% or higher. In addition, the optical transmissivity in at least one point in a wavelength range of 700 nm to 800 nm is preferably 20% or lower, and the optical transmissivity in the entire wavelength range of 700 nm to 800 nm is more preferably 20% or lower. According to the present invention, it is possible to ensure a wide visible light range with a high transmissivity and to provide a near-infrared-ray cut filter having strong near-infrared shielding properties.

The near-infrared-ray cut filter is used for a lens (a camera lens in a digital camera, a mobile phone, an in-vehicle camera, or the like or an optical lens such as a f-θ lens or a pickup lens) and an optical filter for a semiconductor light-receiving element which have a function of absorbing and cutting near-infrared rays, a near-infrared-ray-absorbing film or a near-infrared-ray-absorbing sheet which shields heat rays for energy saving, an agricultural coating agent which aims the selective use of sunlight, a recording medium which uses near-infrared-ray-absorbing heat, a near-infrared filter for an electronic device or a photograph, protective glasses, sunglasses, a heat ray shielding film, an optical letter-reading record, the prevention of copying a confidential document, an electrophotographic photoreceptor, laser fusion, and the like. In addition, the near-infrared-ray cut filter is also useful for a noise cut filter for a CCD camera and a filter for a CMOS image sensor.

The present invention also relates to a method for manufacturing a near-infrared-ray cut filter including a step of forming a film by applying the near-infrared-ray-absorbing composition of the present invention (preferably through a dropwise addition method, coating, or printing) to a light-receiving side of a solid-state imaging element and a step of drying the film. The film thickness, the laminate structure, and the like can be appropriately selected depending on the purpose.

A supporter to which the composition of the present invention is applied may be a transparent substrate made of glass, a solid-state imaging element, another substrate provided in the light-receiving side of the solid-state imaging element, or a layer such as a flattened layer provided in the light-receiving side of the solid-state imaging element.

The near-infrared-ray cut filter can be formed using a method such as, for example, a dropwise addition method (drop casting), spin coating, slit spin coating, slit coating, screen printing, applicator application, or the like. In the case of the dropwise addition method (drop casting), it is preferable to form a dropwise addition region for the near-infrared-ray-absorbing composition including a photoresist as a partition wall on a glass substrate so that a uniform film can be formed with a predetermined film thickness.

Meanwhile, it is possible to adjust the amount of the composition added dropwise using the film thickness, the concentration of the solid content, and the area of the dropwise addition region.

In addition, the conditions for drying the coated film vary depending on the kind and proportions of individual components and a solvent; however, generally, the coated film is dried at a temperature in a range of 60° C. to 150° C. for approximately 30 seconds to 15 minutes.

A method for forming a near-infrared-ray cut filter using the near-infrared-ray-absorbing composition of the present invention may include other steps. The other steps are not particularly limited and can be appropriately selected depending on the purpose. Examples thereof include a surface treatment step of the base material, a pretreatment step (prebaking step), a curing treatment step, a post heating step (post baking step), and the like.

<Preheating Step and Post Heating Step>

The heating temperatures in the preheating step and the post heating step are generally in a range of 80° C. to 200° C. and preferably in a range of 90° C. to 150° C. The heating times in the preheating step and the post heating step are generally in a range of 30 seconds to 240 seconds and preferably in a range of 60 seconds to 180 seconds.

<Curing Treatment Step>

The curing treatment step refers to a step of carrying out a curing treatment on the formed film as necessary and the curing treatment improves the mechanical strength of the near-infrared-ray cut filter.

The curing treatment step is not particularly limited and can be appropriately selected depending on the purpose and preferred examples thereof include a full-surface exposure treatment, a full-surface thermal treatment, and the like. In the present invention, the meaning of "exposure" includes the irradiation of the surface with radioactive rays such as electron beams or X rays as well as light rays having a variety of wavelengths.

The exposure is preferably carried out through irradiation with radioactive rays and, as the radioactive rays that can be used in the exposure, particularly, ultraviolet rays such as electron beams, KrF, ArF, g-rays, h-rays, or i-rays or visible light are preferably used.

Examples of the exposure method include stepper exposure, exposure using a high-pressure mercury lamp, and the like.

The exposure amount is preferably in a range of 5 J/cm$^2$ to 3000 mJ/cm$^2$, more preferably in a range of 10 J/cm$^2$ to 2000 mJ/cm$^2$, and particularly preferably in a range of 50 J/cm$^2$ to 1000 mJ/cm$^2$.

Examples of a method for the full-surface exposure treatment include a method in which the full surface of the above-described formed film is exposed. In a case in which the near-infrared-ray-absorbing composition includes the polymerizing compound, the full-surface exposure accelerates the curing of a polymerizing component in the film formed of the composition, makes the film cured to a greater extent, and improves the mechanical strength and the durability.

An apparatus for carrying out the full-surface exposure is not particularly limited and can be appropriately selected depending on the purpose, and preferred examples thereof include UV steppers such as ultrahigh-pressure mercury lamps.

In addition, examples of the method for the full-surface thermal treatment include a method in which the full surface of the above-described formed film is heated. The heating of the full surface increases the film strength of a pattern.

The heating temperature during the full-surface heating is preferably in a range of 120° C. to 250° C. and more preferably in a range of 160° C. to 220° C. When the heating temperature is 120° C. or higher, the film strength is improved by the heating treatment and, when the heating temperature is 250° C. or lower, components in the film are decomposed and it is possible to prevent the film from becoming weak and brittle.

The heating time in the full-surface heating is preferably in a range of 3 minutes to 180 minutes and more preferably in a range of 5 minutes to 120 minutes.

An apparatus for carrying out the full-surface heating is not particularly limited and can be appropriately selected from well-known apparatuses depending on the purpose, and examples thereof include a drying oven, a hot plate, an IR heater, and the like.

The camera module of the present invention is a camera module having a solid-state imaging element and a near-infrared-ray cut filter disposed in the light-receiving side of the solid-state imaging element, in which the near-infrared-ray cut filter is the above-described near-infrared-ray cut filter.

In addition, a method for manufacturing a camera module of the present invention is a method for manufacturing a camera module having a solid-state imaging element and a near-infrared-ray cut filter disposed in a light-receiving side of the solid-state imaging element, including a step of forming a film by applying the near-infrared-ray-absorbing composition of the present invention to a light-receiving side of a solid-state imaging element.

FIG. 1 is a schematic sectional view illustrating the configuration of a camera module including the near-infrared-ray cut filter according to an embodiment of the present invention.

A camera module 10 includes, for example, a solid-state imaging element 11, a flattening layer 12 provided on the solid-state imaging element 11, a near-infrared-ray cut filter 13, and a lens holder 15 which is disposed above the near-infrared-ray cut filter and includes an imaging lens 14 in a space inside thereof.

In the camera module 10, incident light hv from the outside sequentially permeates through the imaging lens 14, the near-infrared-ray cut filter 13, and the flattening layer 12 and then reaches an imaging element unit 16 in the solid-state imaging element 11.

The solid-state imaging element 11 includes, for example, the imaging element unit 16, an interlayer insulating film (not illustrated), a base layer (not illustrated), a color filter 17, an overcoat (not illustrated), and a micro lens 18 in this order on the main surface of a silicon substrate which is a base body. The color filter 17 (a red color filter, a green color filter, or a blue color filter) or the micro lens 18 are respectively disposed so as to correspond to the imaging element unit 16.

In addition, instead of providing the near-infrared-ray cut filter 13 on the surface of the flattening layer 12, the near-infrared-ray cut filter 13 may be provided on the surface of the micro lens 18, between the base layer and the color filter 17, or between the color filter 17 and the overcoat. For example, the near-infrared-ray cut filter 13 may be provided at a location 2 mm or less (more preferably 1 mm or less) distant from the surface of the micro lens. When the near-infrared-ray cut filter is provided at this location, a step of forming the near-infrared-ray cut filter can be simplified, and it is possible to sufficiently cut unnecessary near-infrared rays travelling toward the micro lens, and thus it is possible to further enhance the near-infrared shielding properties.

The near-infrared-ray cut filter of the present invention can be subjected to a solder reflow step. When the camera module is manufactured through the solder reflow step, the automatic mounting of an electronic component-mounted substrate or the like which requires soldering becomes possible, and it is possible to extremely improve the productivity compared with a case in which the solder reflow step is not used. Furthermore, since the solder reflow step is automatically carried out, it is also possible to reduce the cost. In a case in which the near-infrared-ray cut filter is subjected to the solder reflow step, the near-infrared-ray cut filter is exposed to a temperature in a range of approximately 250° C. to 270° C., and thus the near-infrared-ray cut filter is preferably heat-resistant enough to withstand the solder reflow step (hereinafter, also referred to as the "solder reflowability").

In the present specification, "having solder reflowability" means that the infrared-ray cut filter maintains its characteristics before and after being heated at 200° C. for 10 minutes. More preferably, the infrared-ray cut filter maintains its characteristics before and after being heated at 230° C. for 10 minutes. Still more preferably, the infrared-ray cut filter maintains its characteristics before and after being heated at 250° C. for three minutes. In a case in which the near-infrared-ray cut filter does not have solder reflowability, when being held under the above-described conditions, there are cases in which the infrared-ray-absorbing performance of the infrared-ray cut filter degrades or the functions become insufficient for films.

In addition, the present invention also relates to a method for manufacturing a camera module including a step of a reflow treatment. Even when the reflow step is provided, the infrared-ray cut filter of the present invention is capable of maintaining its near-infrared-ray-absorbing performance, there are no cases in which the characteristics of the camera module having reduced size and weight and having improved performance are impaired.

Figure 2:
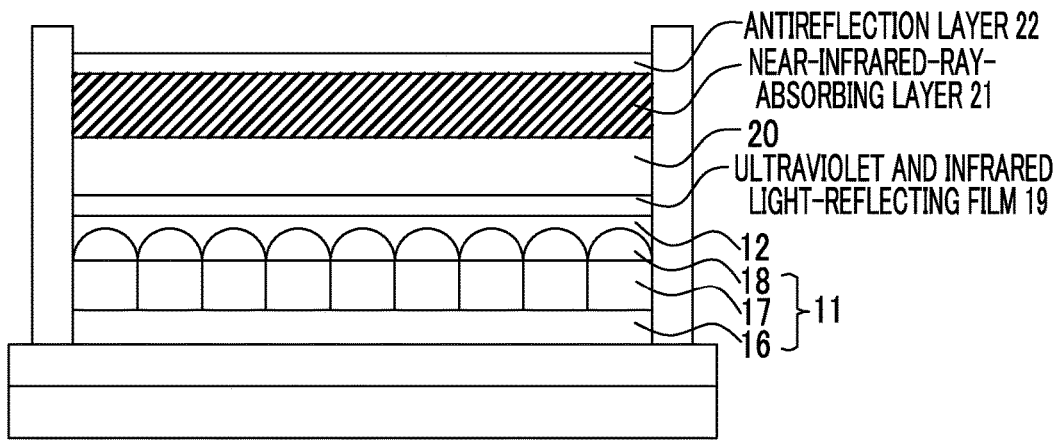
FIG. 2 is a schematic sectional view illustrating an example of a near-infrared-ray cut filter peripheral portion in the camera module.
Figure 3:
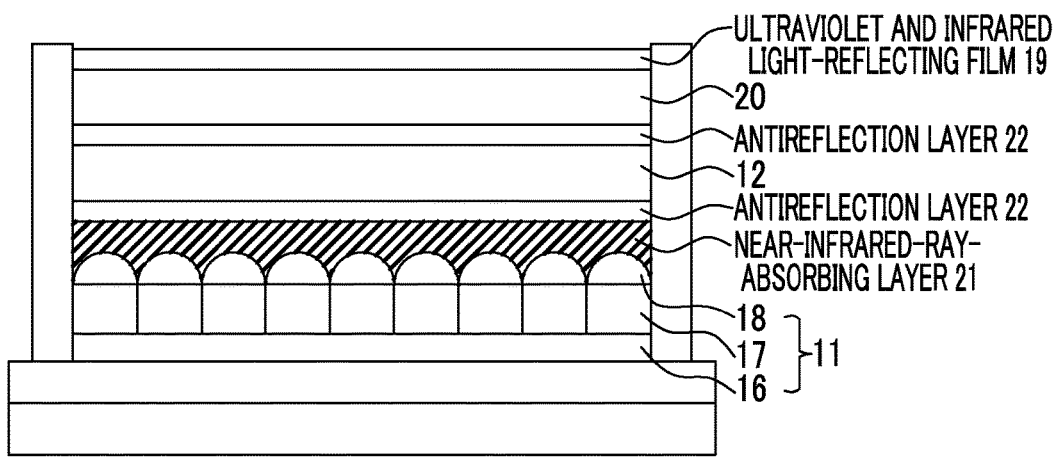
FIG. 3 is a schematic sectional view illustrating an example of the near-infrared-ray cut filter peripheral portion in the camera module.
Figure 4:
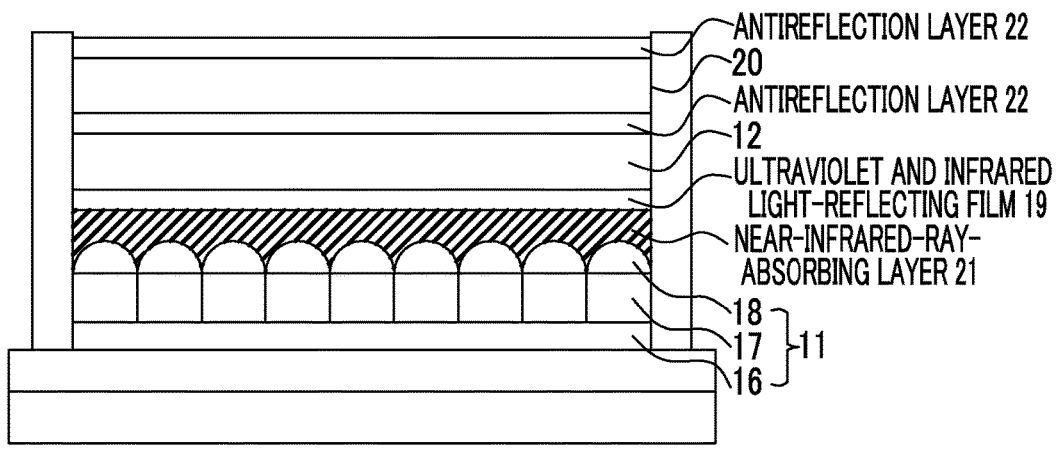
FIG. 4 is a schematic sectional view illustrating an example of the near-infrared-ray cut filter peripheral portion in the camera module.

FIGS. 2 to 4 are schematic sectional views illustrating examples of a near-infrared-ray cut filter peripheral portion in the camera module.

As illustrated in FIG. 2, the camera module may have the solid-state imaging element 11, the flattening layer 12, an ultraviolet and infrared light-reflecting film 19, a transparent base material 20, a near-infrared-ray-absorbing layer 21, and an antireflection layer 22 in this order.

The ultraviolet and infrared light-reflecting film 19 has an effect of imparting and enhancing the functions of the near-infrared-ray cut filter, and, for example, Paragraphs [0033] to [0039] in JP2013-68688A can be referred to, and the content thereof is incorporated into the present specification.

The transparent base material 20 transmits light having wavelengths in the visible light range, and, for example, Paragraphs [0026] to [0032] in JP2013-68688A can be referred to, and the content thereof is incorporated into the present specification.

The near-infrared-ray-absorbing layer 21 can be formed by applying the above-described near-infrared-ray-absorbing composition of the present invention.

The antireflection layer 22 has a function of preventing the reflection of light incident on the near-infrared-ray cut filter so as to improve the transmissivity and allowing efficient use of the incident light, and, for example, Paragraph [0040] in JP2013-68688A can be referred to, and the content thereof is incorporated into the present specification.

As illustrated in FIG. 3, the camera module may have the solid-state imaging element 11, the near-infrared-ray-absorbing layer 21, the antireflection layer 22, the flattening layer 12, the antireflection layer 22, the transparent base material 20, and the ultraviolet and infrared light-reflecting film 19 in this order.

As illustrated in FIG. 4, the camera module may have the solid-state imaging element 11, the near-infrared-ray-absorbing layer 21, the ultraviolet and infrared light-reflecting film 19, the flattening layer 12, the antireflection layer 22, the transparent base material 20, and the antireflection layer 22 in this order.

EXAMPLES

Hereinafter, the present invention will be more specifically described using examples. Materials, amounts used, proportions, treatment contents, treatment orders, and the like described in the following examples can be appropriately changed within the scope of the gist of the present invention. Therefore, the scope of the present invention is not limited to specific examples described below. Particularly, unless particularly otherwise described, "%" and "parts" are on the basis of mass.

In the present examples, the following abbreviations will be employed.

<Curable Composition>

KAYARAD DPHA: (manufactured by Nippon Kayaku Co., Ltd., a mixture of dipentaerythritol pentaacrylate and dipentaerythritol hexaacrylate)

JER157S65: (manufactured by Mitsubishi Chemical Corporation, special novolac-type epoxy resin)

KAYARAD D-320: (manufactured by Nippon Kayaku Co., Ltd., dipentaerythritol tetraacrylate)

M-510: (manufactured by Toagosei Co., Ltd., polybasic acid-denatured acryl oligomer)

M-520: (manufactured by Toagosei Co., Ltd., polybasic acid-denatured acryl oligomer)

DPCA-60: (manufactured by Nippon Kayaku Co., Ltd., hexafunctional acrylate having six pentyleneoxy chains)

<Solvent>

PGMEA: Propylene glycol monomethyl ether acetate

First Example

<Synthesis Example>

<Synthesis of Compounds A1>

(Syntheses of Compounds A1-1 and A1-7)

Chlorosulfonic acid (14.11 g, 121.1 mmol) was diluted with dichloromethane (30 ml) and was cooled to 5° C. in an ice water bath. After a dichloromethane solution (20 ml) of di-(para-tolyl)ether (10.0 g, 50.44 mmol) was added dropwise to this solution, the reaction liquid was returned to room temperature and was stirred for two hours. Distilled water (10 ml) was added dropwise to the reaction liquid, and dichloromethane was distilled away using an evaporator. The obtained solution was added dropwise to saturated salt water (500 ml), and the obtained precipitate was filtered off and recovered and then was heated and dissolved in distilled water (400 ml). This solution was cooled in ice water, and the obtained precipitate was filtrated and recovered. The obtained solid was dissolved in methanol (50 ml), Amberlite IR120 hydrogen form (20 g) (manufactured by Sigma-Aldrich Co. LLC.) was added, and the components were stirred at room temperature for 30 minutes. Next, the reaction liquid was filtered, and the obtained liquid was concentrated and dried, thereby obtaining Compound A1-1 (4.7 g, 14.23 mmol).

Compound (A1-7) was also synthesized using the same method.

(Synthesis of Compound A1-12)

Compound (a-1) illustrated below was obtained from di-(para-tolyl)ether according to the method described in Tetrahedron 54, (1998) 10111 to 10118. Next, hexane (100 ml) and pyridine (7.91 g, 100.0 mmol) were added to Compound (a-1) (10.0 g, 25.0 mmol), and the compound was cooled to 5° C. in an ice water bath. 2-Propanol (6.01 g, 10.0 mmol) was added dropwise to this solution, the reaction liquid was returned to room temperature and was stirred for two hours. The reaction liquid was celite-filtered, and the filtrate was concentrated, thereby obtaining Compound a-2 (11.75 g, 23.75 mmol). Next, Compound a-2 (7.0 g, 14.15 mmol) was heated at 130° C. in a nitrogen atmosphere, and 2-iodopropane (4.81 g, 28.30 mmol) was added dropwise thereto. After the reaction liquid was cooled to room temperature, the reaction liquid was purified using column chromatography, thereby obtaining Compound a-3 (6.17 g, 12.88 mmol). Next, a 3 N aqueous solution of hydrochloric acid (30 ml) was added to Compound a-3 (5.0 g, 10.43 mmol), and the mixture was refluxed for 12 hours. After the reaction liquid was returned to room temperature, the reaction liquid was concentrated, thereby obtaining Compound A1-12 (4.28 g, 10.43 mmol).

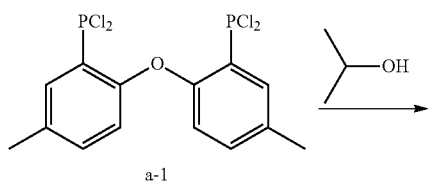

a-1

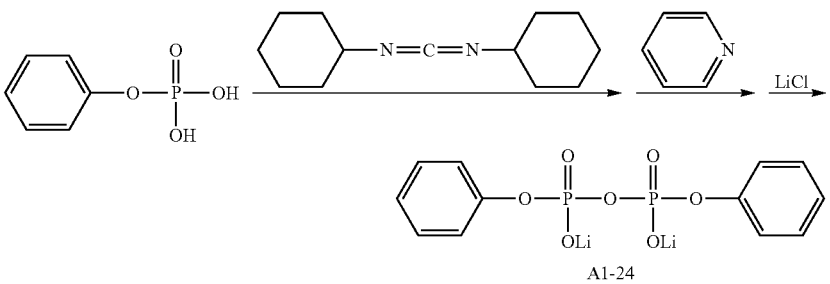

A1-24

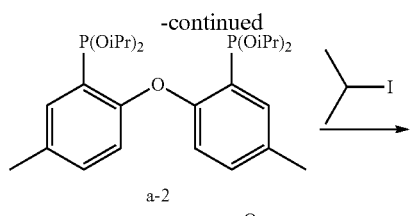

a-2

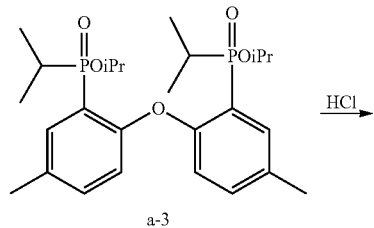

a-3

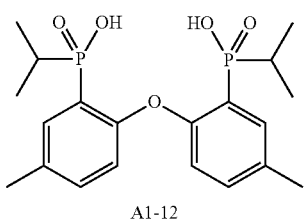

A1-12

(Syntheses of Compounds A1-24, A1-25, and A1-31)

Phenylphosphonic acid (15.0 g, 86.16 mmol) was dissolved in tetrahydrofuran (THF) (80 ml), and the solution was cooled to 5° C. in an ice water bath. A THF solution (30 ml) of dicyclohexylcarbodiimide (9.77 g, 47.35 mmol) was added dropwise thereto, and the reaction liquid was returned to room temperature and was stirred for three hours. The generated precipitate was filtered off, and the filtrate was concentrated using an evaporator. The obtained liquid was dissolved in acetonitrile (100 ml), and pyridine (13.63 g, 172.31 mmol) was added dropwise thereto. The generated precipitate was filtered off, and the filtrate was concentrated using an evaporator. The obtained reaction product was dissolved in acetonitrile (100 ml), and an aqueous solution of lithium chloride (3.66 g, 86.4 mmol) (10 ml) was added dropwise thereto, and thus a white precipitate was generated. The obtained precipitate was filtered off, recovered, and purified through recrystallization using methanol (100 ml), thereby obtaining a lithium salt of Compound A1-24 (5.5 g, 16.08 mmol).

In addition, Compounds A1-25 and A1-31 were also synthesized using the same method.

(Syntheses of Compounds A1-50, A1-52, and A1-65)

Ethanol (76.54 g, 2.10 mmol) was cooled to 5° C. in an ice water bath, and dichlorophenylphosphine (75.0 g, 419.0 mmol) was added dropwise thereto. The reaction liquid was returned to room temperature and was stirred for three hours, and then the reaction liquid was concentrated using an evaporator. The obtained liquid was diluted with ethyl acetate, and an aqueous solution of saturated sodium bicarbonate was added dropwise thereto. After a water layer was removed using a separating funnel, the organic layer was dried with anhydrous magnesium sulfate and was concentrated using an evaporator, thereby obtaining Compound a-4 (65.60 g, 385.52 mmol) illustrated below.

Next, Compound a-4 (8.5 g, 48.25 mmol), cyclohexylamine (2.39 g, 24.12 mmol), paraformaldehyde (1.45 g, 48.25 mmol), and distilled water (40 ml) were mixed together and were refluxed for eight hours. After the reaction liquid was returned to room temperature, the reaction liquid was moved to a separating funnel, and was extracted by adding ethyl acetate (150 ml) and an aqueous solution of 1.2% potassium carbonate (150 ml) thereto. After a water layer was removed, the organic layer was dried with anhydrous magnesium sulfate and was concentrated using an evaporator. The obtained liquid was purified using column chromatography, thereby obtaining Compound a-5 (4.70 g, 10.13 mmol).

Next, a 3 N aqueous solution of hydrochloric acid (15 ml) was added to Compound a-5 (2.0 g, 4.58 mmol) and the solution was stirred at 80° C. for eight hours. After the reaction liquid was returned to room temperature, saturated salt water (30 ml) and ethyl acetate (50 ml) were added to the reaction liquid, and the reaction liquid was moved to a separating funnel and was extracted. After a water layer was removed, the organic layer was dried with anhydrous magnesium sulfate and was concentrated using an evaporator. The obtained solid was purified through recrystallization with THF (150 ml), thereby obtaining a hydrochloride salt of Compound A1-50 (1.92 g, 4.58 mmol). Distilled water (5 ml) and potassium carbonate (467.1 mg, 3.38 mmol) were added to this hydrochloride salt (1.0 g, 2.25 mmol), the components were stirred for 10 minutes, and then the distilled water was removed at a reduced pressure. A liquid mixture (20 ml) of methanol/ethyl acetate (1/1) was added to the reaction liquid, a salt remaining after the dissolution of the hydrochloride salt was filtered off. The filtrate was concentrated, thereby obtaining a potassium salt (1.09 g, 2.25 mmol) of Compound A1-5.

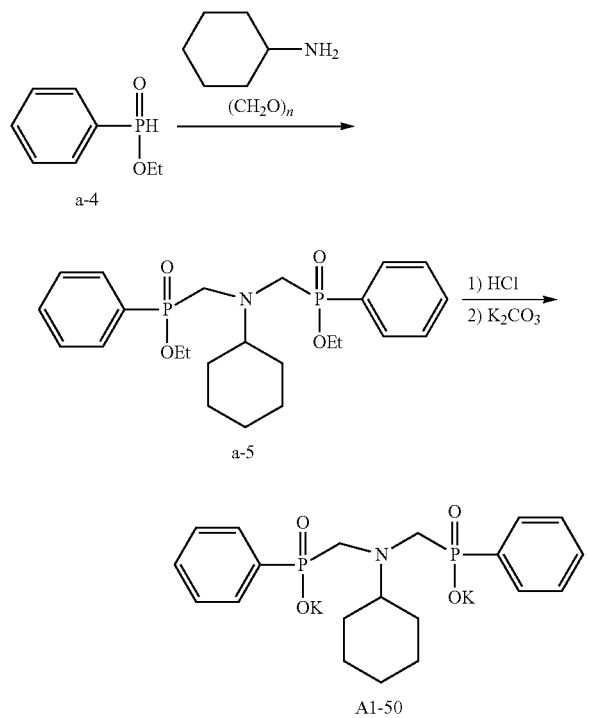

(Synthesis of Compound A1-73)

A sodium salt of Compound A1-73 was obtained from p-methylaniline according to the method described in Tetrahedron Letters 47, (2006) 8279 to 8284.

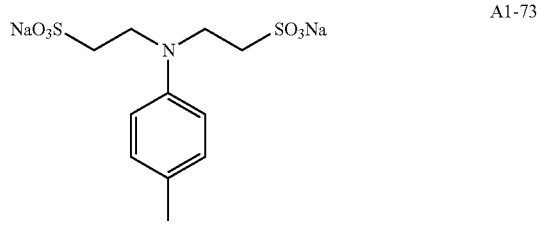

(Synthesis of Compound A1-77)

Compound A-77 was obtained from 2,4,6-triisopropylaniline according to the method described in Polyhedron 21, (2002) 2719 to 2725.

(Syntheses of Compounds A1-82, A1-83, A1-88, A1-92, and A1-96)

Bis(2-iodoethyl)ether (4.56 g, 14.0 mmol) was heated at 120° C. in a nitrogen flow, and dimethoxyphenylphosphine (5.72 g, 33.6 mmol) was slowly added dropwise thereto so that the temperature of the reaction liquid fell in a range of 120° C. to 125° C. After the end of the dropwise addition, the components were stirred for one hour, and then were returned to room temperature. The obtained liquid was purified using column chromatography, thereby obtaining Compound a-6 (1.12 g, 2.93 mmol).

Next, a 3 N aqueous solution of hydrochloric acid (15 ml) was added to Compound a-6 (1.0 g, 2.62 mmol), and the mixture was refluxed for six hours. After the reaction liquid was returned to room temperature, the reaction liquid was concentrated, thereby obtaining Compound A1-83 (0.93 g, 2.62 mmol).

Compounds A1-82, A1-88, A1-92, and A1-96 were also synthesized using the same method.

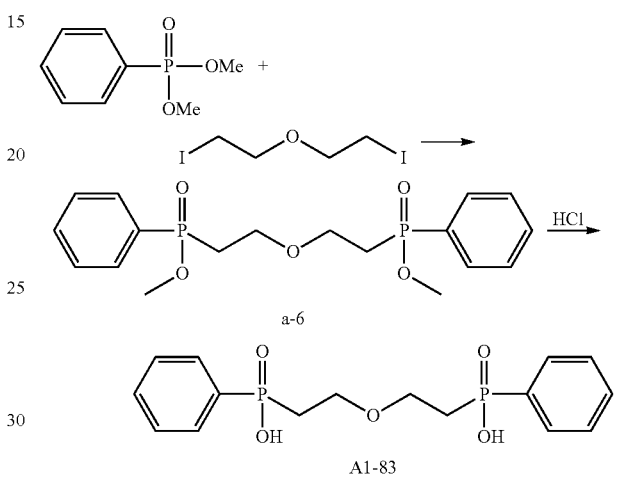

(Synthesis of Compounds A1-109 and A1-138)

Phenyl dichlorophosphate (40.0 g, 189.6 mmol) was diluted with THF (100 ml) and was cooled to 5° C. in an ice water bath. Diethylene glycol (10.06 g, 94.80 mmol) and a THF solution (100 ml) of pyridine (7.50 g, 94.80 mmol) were added dropwise thereto, and the reaction liquid was returned to room temperature and was stirred for five hours. An aqueous solution of sodium bicarbonate was added to the reaction liquid so that the pH of the solution reached 8 or higher, and THF was distilled away using an evaporator. This solution was moved to a separating funnel and was washed with ethyl acetate (200 ml), and then concentrated hydrochloric acid was added to a water layer, thereby setting the pH of the solution to 1 or lower. Ethyl acetate (200 ml) and methanol (20 ml) were added, and extraction was carried out. An organic layer was washed twice with 1 N hydrochloric acid (200 ml), was dried using magnesium sulfate, and then was concentrated using an evaporator, thereby obtaining Compound A1-109 (7.2 g, 17.21 mmol).

Compound A1-138 was also synthesized using the same method.

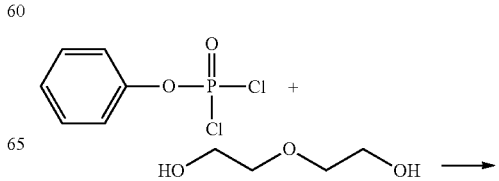

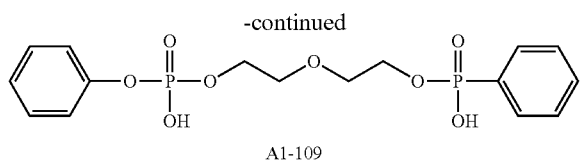

A1-109

(Synthesis of Compound A1-112)

Compound A1-112 was obtained using the method described in Zh. Obshch Khim. 59, (1989) 62.

(Synthesis of Compound A1-126)

Compound a-7 illustrated below was synthesized using the method described in Org. Lett. 14, 13, (2012) 3404-3407. Next, THF (30 ml) was added to sodium hydroxide (50% oily, 1.48 g, 30.86 mmol), the reaction liquid was cooled to 5° C. in an ice water bath in a nitrogen atmosphere, and a THF solution (10 ml) of Compound a-8 illustrated below (5.83 g, 29.39 mmol) was added dropwise thereto. The reaction liquid was returned to room temperature, and was stirred for 30 minutes, and then a THF solution (10 ml) of Compound a-7 (11.24 g, 29.39 mmol) was added dropwise thereto. After a reaction at room temperature for two hours, an aqueous solution of saturated ammonium chloride was added dropwise thereto, the generated salt was dissolved, and then THF was distilled away using an evaporator. The reaction product was diluted with ethyl acetate (200 ml) and was washed with an aqueous solution of saturated ammonium chloride (200 ml), and an organic layer was dried with magnesium sulfate and then was concentrated. The obtained liquid was purified using column chromatography, thereby obtaining Compound a-9 (5.82 g, 14.25 mmol). Next, phosphinic acid ester was hydrolyzed in the same manner as in the synthesis of Compound A-83, thereby obtaining Compound A1-126.

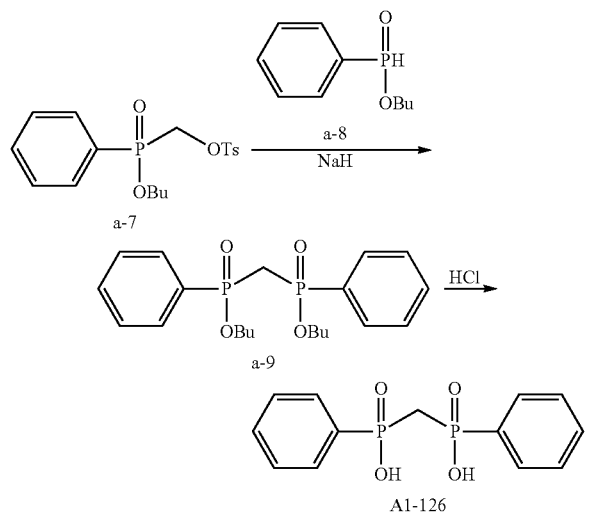

a-7 a-9

A1-126

(Synthesis of Compound A1-132)

Compound A1-132 was obtained using the method described in Synth. Commun. 34, 2, (2004) 331 to 334.

(Synthesis of Compound A1-135)

Compound A1-135 was obtained using the method described in Synth. Commun. 9, (1979) 261 to 266.

(Synthesis of Compound A1-142)

Compound a-10 illustrated below was synthesized using the method described in Macromol. 11, 5, (1978) 1027 to 1030, and then the phosphinic acid ester and a sulfonic acid ester were hydrolyzed in the same manner as in the synthesis of Compound A-83, thereby obtaining Compound A1-142.

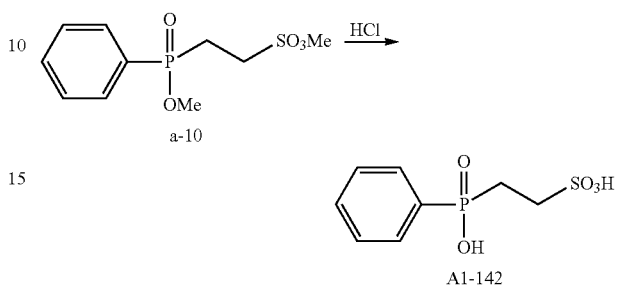

a-10

A1-142

(Synthesis of Compound A1-146)

Compound A1-146 was obtained from diethoxy(2,6-dimethylphenyl)phosphine according to the method described in Bull. Acad. Sci. USSR, Chem. Sci. 37, 4, (1988) 800 to 803.

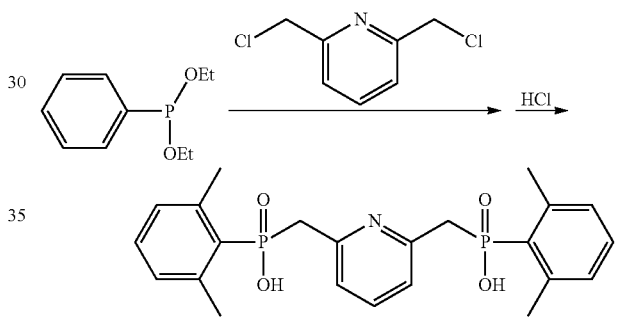

A1-146

<Synthesis of Copper Complex>

(Synthesis of Copper Complex 1-1)

Compound A1-1 (886 mg, 2.47 mmol) was dissolved in methanol (20 ml). After this solution was heated at 50° C., a methanol solution (160 ml) of copper acetate (449 mg, 2.47 mmol) was added dropwise thereto, and a reaction was caused at 50° C. for two hours. After the end of the reaction, the generated acetic acid and the solvent were distilled away using an evaporator, thereby obtaining Copper Complex 1-1 (1.00 g).

(Syntheses of Copper Complexes 1-2, 1-3, and 1-11 to 1-25)

Copper Complexes 1-2, 1-3, and 1-11 to 1-25 were obtained using a method according to the synthesis method for Copper Complex 1-1.

(Synthesis of Copper Complex 1-4)

A lithium salt (1.00 g, 2.92 mmol) of Compound A1-24 was dissolved in methanol (20 ml) and then was heated at 50° C., and then a methanol solution (20 ml) of copper sulfate pentahydrate (0.73 g, 2.92 mmol) was added dropwise thereto. The solution was heated at 50° C. for one hour, then, the reaction liquid was cooled to 5° C. in an ice water bath and was filtered. The filtrate was concentrated using an evaporator, thereby obtaining Copper Complex 1-4 (1.14 g).

(Syntheses of Copper Complexes 1-5 to 1-10)

Copper Complexes 1-5 to 1-10 were obtained using a method according to the synthesis method for Copper Complex 1-4.

<Comparative Synthesis Examples>
<Syntheses of Copper Complexes 1-26 and 1-27>

Copper Complex 1-26 and Copper Complex 1-27 were obtained with a method according to the synthesis method for Copper Complex 1 using Compound R-1 illustrated below and Compound R-2 illustrated below respectively as ligands.

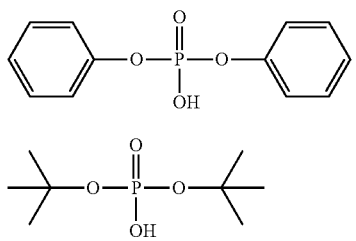

R-1

R-2

<Evaluation>
<<Evaluation of Solubility of Copper Complex>>

The copper complex (0.5 g) was put into a testing tube, PGMEA was added thereto so that the concentration of the solid content reached 40% by mass, 30% by mass, and 20% by mass, and the components were vibrated for 10 minutes. The concentration of the solid content at which the mixture became visually turbid was evaluated on the basis of the following standards.

A: the concentration of the solid content is 40% by mass
B: the concentration of the solid content is 30% by mass
C: the concentration of the solid content is 20% by mass <<Evaluation of Heat Resistance of Copper Complex>>

The copper complex (3 mg) was taken and a thermogravimetric measurement was carried out using a thermal analysis instrument Q-500 (manufactured by TA Instruments Japan Inc.). The 5% weight decrease temperature ($Td_5$) was measured, and the heat resistance was evaluated on the basis of the following standards.

A: 200° C.<$Td_5$
B: 180° C.<$Td_5$≤200° C.
C: $Td_5$≤180° C.

<<Evaluation of Near-infrared-ray-absorbing Composition>>

(Preparation of Near-infrared-ray-absorbing Composition)

(Example A1-1)

The following compounds were mixed together, thereby preparing a near-infrared-ray-absorbing composition of Example 1.

| | |
|---|---|
| Copper Complex 1-1 | 20 parts by mass |
| KAYARAD DPHA | 20 parts by mass |
| JER157S65 | 20 parts by mass |
| PGMEA | 120 parts by mass |

Near-infrared-ray-absorbing compositions of individual examples and individual comparative examples were prepared by providing the same composition as that of Example A1-1 except for the fact that Copper Complex 1-1 was changed to Copper Complexes 1-2 to 1-27.

(Production of Near-infrared-ray Cut Filter)

A photoresist was applied onto a glass substrate, and patterning was carried out through lithography, thereby forming a dropwise addition region for the near-infrared-ray-absorbing composition. 3 ml of each of the near-infrared-ray-absorbing compositions prepared in the examples and the comparative examples was added dropwise thereto. The coated film-attached substrate was left to stand at room temperature for 24 hours so as to be dried, and then the thickness of the coated film was evaluated and was found to be 192 μm.

(Evaluation of Near-infrared Shielding Properties)

The transmissivities at a wavelength of 800 nm of the near-infrared-ray cut filters obtained as described above were measured using a spectrophotometer U-4100 (manufactured by Hitachi High-Technologies Corporation). The near-infrared shielding properties were evaluated on the basis of the following standards.

A: transmissivity at 800 nm≤5%
B: 5%<transmissivity at 800 nm≤7%
C: 7%<transmissivity at 800 nm≤10%
D: 10%<transmissivity at 800 nm

TABLE 11

| | Compound A (molar ratio) | Molar ratio of Compound A/copper | Copper complex | Copper complex Solubility | Evaluation Heat resistance | Infrared-ray cut filter Near-infrared shielding properties |
|---|---|---|---|---|---|---|
| Example A1-1 | A1-1 | 1/1 | 1-1 | B | B | B |
| Example A1-2 | A1-7 | 1/1 | 1-2 | A | C | A |
| Example A1-3 | A1-12 | 4/3 | 1-3 | B | A | A |
| Example A1-4 | A1-24 | 1/1 | 1-4 | B | B | B |
| Example A1-5 | A1-25 | 2/1 | 1-5 | B | B | B |
| Example A1-6 | A1-31 | 1/1 | 1-6 | A | A | A |
| Example A1-7 | A1-50 | 4/3 | 1-7 | A | A | A |
| Example A1-8 | A1-52 | 1/1 | 1-8 | A | A | A |
| Example A1-9 | A1-65 | 1/1 | 1-9 | A | B | A |
| Example A1-10 | A1-73 | 1/1 | 1-10 | C | B | B |
| Example A1-11 | A1-77 | 1/1 | 1-11 | B | B | B |
| Example A1-12 | A1-82 | 4/3 | 1-12 | B | A | A |
| Example A1-13 | A1-83 | 1/1 | 1-13 | B | A | A |
| Example A1-14 | A1-88 | 1/1 | 1-14 | A | A | B |
| Example A1-15 | A1-92 | 1/1 | 1-15 | A | A | B |
| Example A1-16 | A1-96 | 4/3 | 1-16 | B | A | A |

TABLE 11-continued

| | Copper complex | | | Evaluation | | Infrared-ray cut filter |
|---|---|---|---|---|---|---|
| | Compound A | Molar ratio of | | Copper complex | | Near-infrared |
| | (molar ratio) | Compound A/copper | Copper complex | Solubility | Heat resistance | shielding properties |
| Example A1-17 | A1-109 | 5/4 | 1-17 | B | C | B |
| Example A1-18 | A1-112 | 1/1 | 1-18 | B | B | B |
| Example A1-19 | A1-126 | 2/1 | 1-19 | B | A | B |
| Example A1-20 | A1-132 | 4/3 | 1-20 | B | B | B |
| Example A1-21 | A1-135 | 4/3 | 1-21 | B | A | B |
| Example A1-22 | A1-138 | 1/1 | 1-22 | B | B | B |
| Example A1-23 | A1-142 | 1/1 | 1-23 | B | A | B |
| Example A1-24 | A1-146 | 1/1 | 1-24 | A | A | A |
| Example A1-25 | A1-82/A1-83 (1/1) | 1/1 | 1-25 | A | A | A |
| Comparative Example A1-1 | R-1 | 2/1 | 1-26 | C | C | D |
| Comparative Example A1-2 | R-2 | 2/1 | 1-27 | C | C | D |

As is clear from the table shown above, the near-infrared-ray-absorbing compositions of the examples were capable of enhancing the near-infrared shielding properties when a cured film was produced. In addition, the near-infrared-ray-absorbing compositions of the examples were capable of improving the solubility of the copper complex in a solvent. In addition, it was found that the near-infrared-ray-absorbing compositions of the examples made the heat resistances of the copper complexes favorable.

On the other hand, for the near-infrared-ray-absorbing compositions of the comparative examples, compared with the examples, it was difficult to enhance the near-infrared shielding properties when a cured film was produced. In addition, it was difficult to improve the solubility of the copper complex in a solvent.

In addition, near-infrared-ray cut filters of Examples A1-26 to A1-29 were obtained in the same manner as in Example 1 except for the fact that 20 parts by mass of the polymerizing compound (KAYARAD DPHA) was changed to the equivalent amount of a polymerizing compound shown in the following table in the near-infrared-ray-absorbing composition of Example A1-1. In these near-infrared-ray cut filters as well, it could be confirmed that it was possible to enhance the near-infrared shielding properties when a cured film was produced. In addition, it could be confirmed that it was possible to improve the solubility of the copper complex in a solvent.

TABLE 12

| | Polymerizing compound |
|---|---|
| Example A1-26 | KAYARAD D-320 |
| Example A1-27 | M-510 |
| Example A1-28 | M-520 |
| Example A1-29 | DPCA-60 |

Excellent effects could be obtained in the same manner as in the near-infrared-ray cut filter of Example A1-1 even in a case in which Copper Complex 1-1 was changed to a copper complex having the following compound as a ligand in the near-infrared-ray-absorbing composition obtained in Example A1-1.

TABLE 13

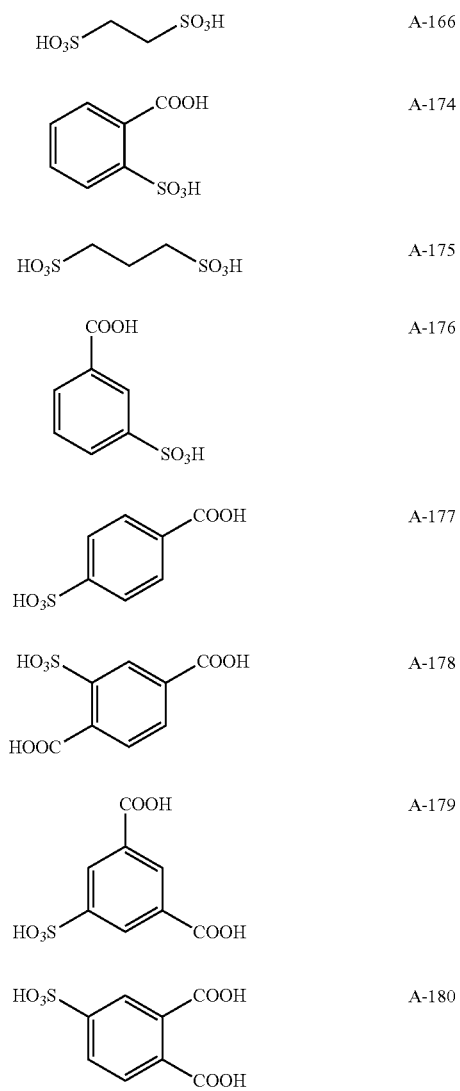

TABLE 13-continued

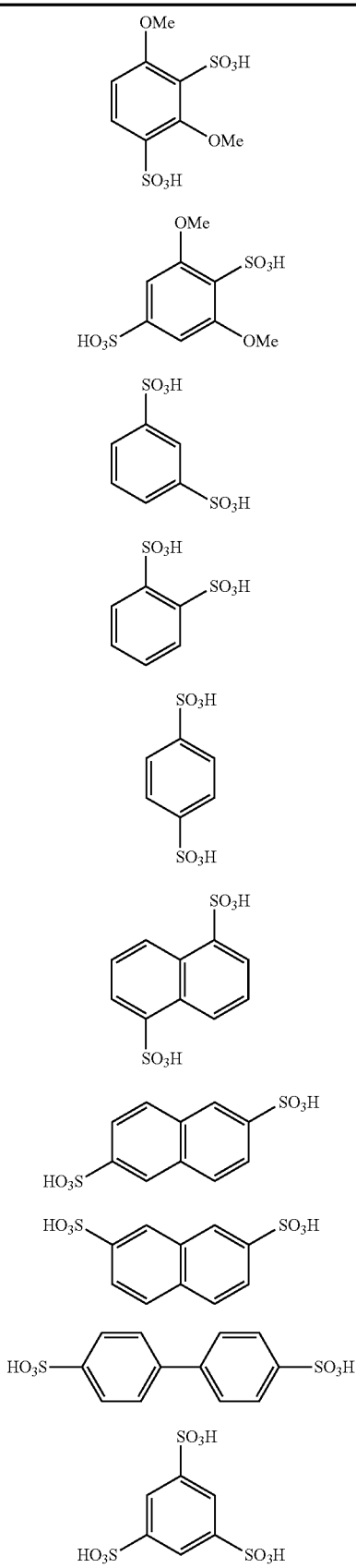

In addition, excellent effects could be obtained in the same manner as those in Examples A1-1 to A1-25 even in a case in which 20 parts by mass of the polymerizing compound (KAYARAD DPHA) was changed to the equivalent amount of KAYARAD D-310, D-330, DPCA-20, DPCA-30, DPCA-120 (all manufactured by Nippon Kayaku Co., Ltd.), M-305, M-460 (manufactured by Toagosei Co., Ltd.), A-TMMT (manufactured by Shin-Nakamura Chemical Co., Ltd.), SR-494 (manufactured by Sartomer Americas), DENACOL EX-212L (manufactured by Nagase ChemteX Corporation) or JER-157S65 (manufactured by Mitsubishi Chemical Corporation) Examples A1-1 to A1-25.

In addition, even in a case in which the content of the copper complex in relation to the total solid content of the composition was respectively set to 15% by mass, 20% by mass, 30% by mass, or 40% by mass in the near-infrared-ray-absorbing compositions of Examples A1-1 to A1-25, excellent near-infrared shielding performance could be obtained in the same manner as those in Examples A1-1 to A1-25.

In addition, even in a case in which the content of the solvent (PGMEA) was respectively set to 10% by mass, 20% by mass, 30% by mass, or 40% by mass in the near-infrared-ray-absorbing compositions of Examples A1-1 to A1-25, excellent coatability could be obtained in the same manner as those in Examples A1-1 to A1-25.

Second Example

<Synthesis Examples>

Compounds A2-1-1 to A2-1-3, A2-1-6, A2-1-7, A2-1-9, A2-1-15, A2-2-1, A2-2-33, A2-2-35, and A2-2-37 have been marketed as chemicals by Tokyo Chemical Industry Co., Ltd., Wako Pure Chemical Industries, Ltd., and Sigma-Aldrich Co. LLC., and these compounds were used as they were without being further purified. As A2-2-39 and A2-2-45, commercially available products were used.

Synthesis Example of Compound A2-1-4

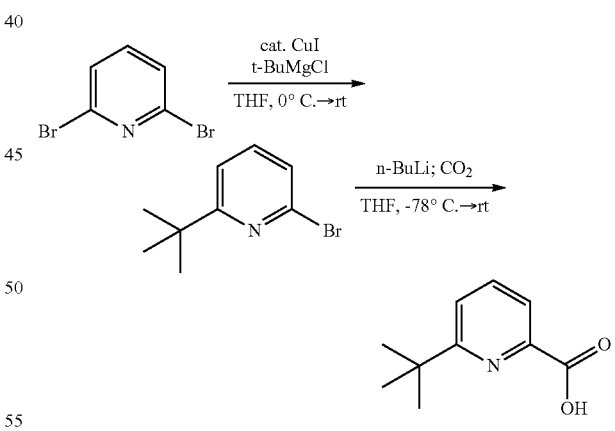

2,6-Dibromopyridine (14.24 g), copper iodide (I) (0.61 g), and tetrahydrofuran (a commercially available dried solvent) (180 mL) were introduced into a three-neck flask in a nitrogen atmosphere and were cooled to 0° C. A 1.0 M tetrahydrofuran solution (70 mL) of t-butylmagnesium chloride was added dropwise thereto, and the components were stirred at room temperature for one hour. An aqueous solution of saturated ammonium chloride (100 mL) and ethyl acetate (100 mL) were added thereto, and a coarse product obtained by concentrating an organic layer obtained through extraction and separation was purified through silica gel column chromatography (solvent: hexane), thereby obtaining 2-bromo-6-t-butylpyridine (10 g).

Subsequently, the 2-bromo-6-t-butylpyridine synthesized above (3.65 g) and tetrahydrofuran (a commercially available dried solvent) (50 mL) were introduced into a three-neck flask in a nitrogen atmosphere, and the solution was cooled to −78° C. A 1.6 M hexane solution (10.0 mL) of n-butyl lithium was added dropwise thereto, and the components were stirred at −78° C. for 30 minutes. A significant excess of crushed dry ice was slowly added thereto, and the components were stirred at room temperature for two hours. Water (100 mL) and ethyl acetate (50 mL) were added thereto, and a water layer (with a pH of 11 or lower) was recovered through extraction and separation. Concentrated hydrochloric acid was added to this water layer little by little so as to obtain a pH of 2 or lower, and an organic layer obtained through extraction three times using ethyl acetate (50 mL) was concentrated, thereby obtaining Compound A2-1-4 (2 g).

Synthesis Example of Compound A2-1-5

A compound was synthesized using the same method as for Compound A2-1-4 using 2-ethylhexyl magnesium bromide instead of t-butylmagnesium chloride.

Synthesis Example of Compound A2-1-8

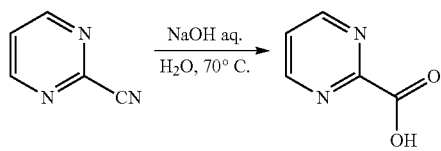 [SMILES: N#Cc1ncccn1 ; O=C(O)c1ncccn1]

2-Cyanopyrimidine (0.10 g) and an aqueous solution of 12% by mass of sodium hydroxide (13 mL) were added to a flask and were stirred at 70° C. for 30 minutes. 1 N diluted hydrochloric acid was added thereto little by little so as to obtain a pH of 3 or lower, and an organic layer obtained through extraction three times using ethyl acetate (10 mL) was concentrated, thereby obtaining Compound A2-1-8 (0.10 g).

Synthesis Example of Compound A2-1-10

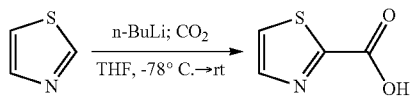

Thiazole (8.5 g) and tetrahydrofuran (a commercially available dried solvent) (150 mL) were introduced into a three-neck flask in a nitrogen atmosphere and the solution was cooled to −78° C. A 1.6 M hexane solution (60 mL) of n-butyl lithium was added dropwise thereto, and the components were stirred at −78° C. for 30 minutes. A significant excess of crushed dry ice was slowly added thereto, and the components were stirred at room temperature for two hours. Water (100 mL) and ethyl acetate (50 mL) were added thereto, and a water layer (with a pH of 11 or lower) was recovered through extraction and separation. Concentrated hydrochloric acid was added to this water layer little by little so as to obtain a pH of 2 or lower, and an organic layer obtained through extraction three times using ethyl acetate (50 mL) was concentrated, thereby obtaining Compound A2-1-10 (12 g).

Synthesis Example of Compound A2-1-11

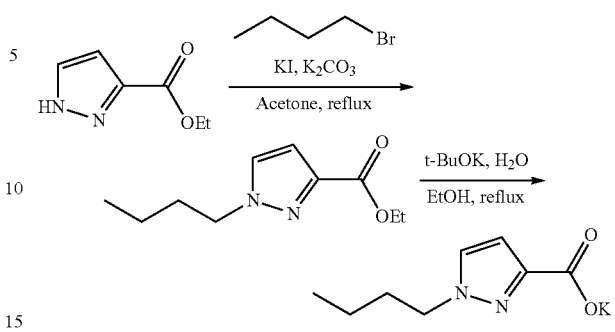

Ethyl pyrazole-3-carboxylate (3.0 g), potassium iodide (3.55 g), potassium carbonate (4.44 g), 1-bromobutane (4.40 g), and acetone (48 mL) were added to a three-neck flask in a nitrogen atmosphere and were heated and refluxed for 10 hours. After the solution was cooled to room temperature, impurities were removed through filtration, and the coarse product obtained by concentrating the filtrate was purified using silica gel column chromatography (solvent: hexane/ ethyl acetate), thereby obtaining ethyl 1-butylpyrazole-3-carboxylate (2.8 g).

The above-described product (0.39 g) and ethanol (3 mL) were added to a flask, water (0.05 g) and potassium t-butoxy (0.22 g) were added thereto under stirring at room temperature, and the components were stirred at 70° C. for 30 minutes. A solid obtained by concentrating these components at a reduced pressure was a corresponding potassium carboxylate, and the solid was used to form a copper complex as it was.

Synthesis Example of Compound A2-1-12

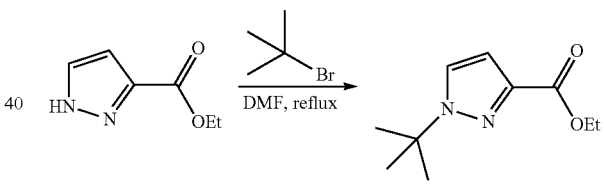

Ethyl pyrazole-3-carboxylate (3.0 g), 2-bromo-2-methylpropane (4.40 g), and dimethylformamide (48 mL) were added to a three-neck flask in a nitrogen atmosphere and were heated and refluxed for 72 hours. After the solution was cooled to room temperature, impurities were removed through filtration, and the coarse product obtained by concentrating the filtrate was purified using silica gel column chromatography (solvent: hexane/ethyl acetate), thereby obtaining 1-t-butylpyrazole-3-ethyl carboxylate (0.8 g).

An ester was hydrolyzed using the same method as for Compound A2-1-11, thereby obtaining Compound A2-1-12.

Synthesis Example of Compound A2-1-13

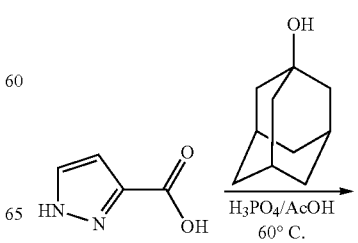

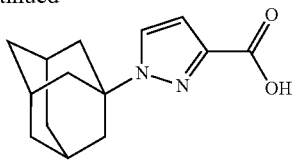

Pyrazole-3-carboxylate (5.5 g), 1-adamantanol (7.5 g), phosphoric acid (100 mL), and acetic acid (25 mL) were added to a three-neck flask in a nitrogen atmosphere and were stirred at 60° C. for seven hours. After the solution was cooled to room temperature, a white solid precipitated by adding water (200 mL) was recovered through filtration. Water (300 mL) and ethyl acetate (100 mL) were added to this white solid at room temperature, and an aqueous solution of 50% by mass of sodium hydroxide was added thereto under stirring so that the pH thereof reached 12 or lower. A water layer was recovered through extraction and separation and washed four times with ethyl acetate (100 mL). When concentrated hydrochloric acid was added to this water layer little by little so as to obtain a pH of 2 or lower, a white solid was precipitated. The white solid was filtered off and washed with water, thereby obtaining 1-(1-adamantyl)pyrazole-3-carboxylate (3.9 g).

Synthesis Example of Compound A2-1-14

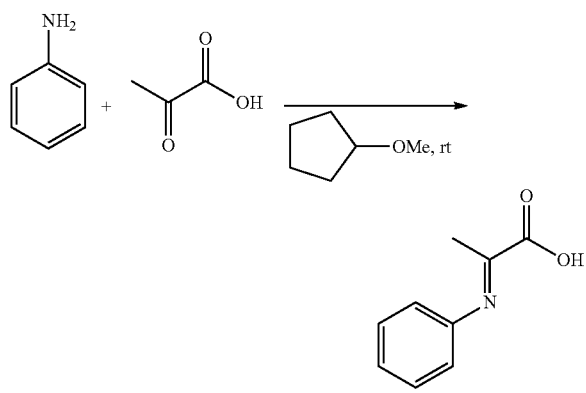

Pyruvic acid (4.4 g) and cyclopentyl methyl ether (10 mL) were added to a three-neck flask in a nitrogen atmosphere and were stirred at room temperature. Aniline (4.7 g) was added dropwise thereto, and the components were stirred for 10 minutes, and then a solid precipitated by cooling the solution to 0° C. was recovered through filtration, thereby obtaining Compound A2-1-14 (3.6 g).

Synthesis Example of Compound A2-1-16

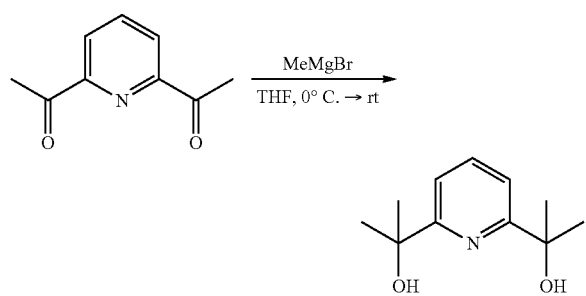

2,6-Diacetylpyridine (16.3 g) and tetrahydrofuran (a commercially available dried solvent) (160 mL) were introduced into a three-neck flask in a nitrogen atmosphere, and the solution was cooled to 0° C. A 3 M diethyl ether solution (33 mL) of n-butyl lithium methyl magnesium bromide was added dropwise thereto, and the components were stirred at room temperature for three hours. An aqueous solution of saturated ammonium chloride (100 mL) and ethyl acetate (100 mL) were added thereto, and an organic layer obtained through extraction and separation was concentrated, thereby obtaining Compound A2-1-16 (19.5 g).

Synthesis Example of Compound A2-1-17

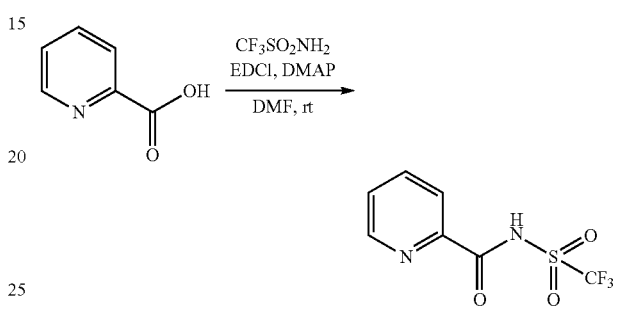

Picolinic acid (2.46 g), trifluoromethanesulfonamide (3.0 g), N,N-dimethylaminopyridine (DMAP) (3.66 g), and dimethylformamide (150 mL) were added to a three-neck flask in a nitrogen atmosphere and were stirred at room temperature. 1-Ethyl-3-(3-dimethylaminopropyl)carbodiimide hydrochloride (EDCI) (5.73 g) was added thereto, and the components were stirred at room temperature for four hours. Water (100 mL) and ethyl acetate (100 mL) were added thereto, a water layer was recovered through extraction and separation, and concentrated hydrochloric acid was added to this water layer little by little so as to obtain a pH of 2 or lower. Ethyl acetate (100 mL) was added, and an organic layer obtained through extraction and separation was concentrated, thereby obtaining Compound A2-1-17 (1.56 g).

Synthesis Example of Compound A2-1-18

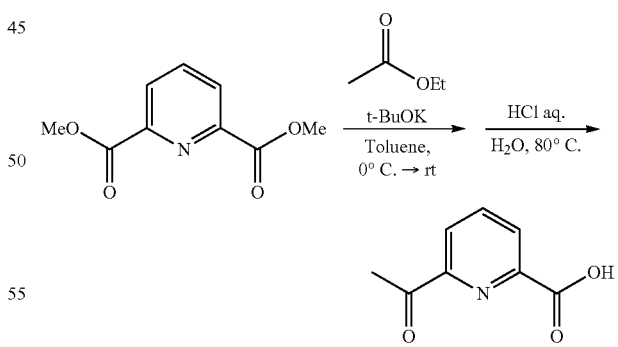

Potassium t-butoxy (11.20 g) and toluene (100 mL) were added to a three-neck flask in a nitrogen atmosphere, and the solution was cooled to 0° C. After ethyl acetate (5.30 g) was added dropwise thereto, dimethyl dipicolinate (9.75 g) was introduced, and the components were stirred at room temperature for two hours. An aqueous solution of saturated ammonium chloride (200 mL) was added thereto, an organic layer obtained through extraction and separation was concentrated, 2 N diluted hydrochloric acid (50 mL) was added thereto, and the components were stirred at 80° C. for two hours. Ethyl acetate (50 mL) was added thereto, and a coarse product obtained by concentrating an organic layer obtained through extraction and separation was recrystallized twice with hot water, thereby obtaining Compound A2-1-18 (10 g).

Synthesis Example of Compound A2-1-19

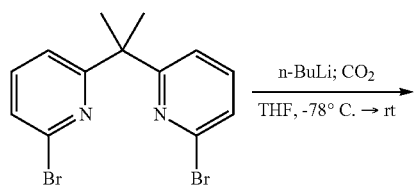

2,2-Bis(6-bromo-2-pyridyl)propane (5.6 g) synthesized using the method described in WO2006098505A and tetrahydrofuran (a commercially available dried solvent) (150 mL) were introduced into a three-neck flask in a nitrogen atmosphere, and the solution was cooled to −78° C. A 1.6 M hexane solution (20 mL) of n-butyl lithium was added dropwise thereto, and the components were stirred at −78° C. for 30 minutes. A significant excess of crushed dry ice was slowly added thereto, and the components were stirred at room temperature for two hours. Water (100 mL) and ethyl acetate (50 mL) were added thereto, and a water layer (with a pH of 11 or lower) was recovered through extraction and separation. Concentrated hydrochloric acid was added to this water layer little by little so as to obtain a pH of 2 or lower, and an organic layer obtained through extraction three times using ethyl acetate (50 mL) was concentrated, thereby obtaining Compound A2-1-19 (4.2 g).

Synthesis Example of Compound A2-1-20

The compound was synthesized using the method described in J. Org. Chem. 1970, 35, 4114.

Synthesis Example of Compound A2-1-21

The compound was synthesized with the same method as for Compound A2-1-14 using diethyl pyrazole-3-phosphonate synthesized using the method described in Tetrahedron 1999, 55, 14791 instead of ethyl pyrazole-3-carboxylate and using methyl p-toluenesulfonate instead of 1-bromobutane.

Synthesis Example of Compound A2-1-22

The compound was synthesized with the same method as for Compound A2-1-11 using 3-bromopentane instead of 1-bromobutane and cesium carbonate instead of potassium carbonate.

Synthesis Example of Compound A2-2-3

2-Ethylhexanol (13.0 g) and tetrahydrofuran (a commercially available dried solvent) (200 mL) were introduced into a three-neck flask in a nitrogen atmosphere, and the solution was cooled to 0° C. Sodium hydride (60% dispersion) (4.0 g) was introduced thereinto, and the components were stirred at 0° C. for 30 minutes. Bromoacetic acid (15.0 g) was added dropwise thereto, and the components were stirred at room temperature for five hours. Saturated ammonium chloride (200 mL) and ethyl acetate (100 mL) were added thereto, and an organic layer obtained through extraction and separation was concentrated, thereby obtaining Compound A2-2-3 (18.4 g).

Synthesis Example of Compound A2-2-4

The compound was synthesized with the same method as for Compound A2-2-3 using t-butyl alcohol instead of 2-ethylhexanol.

Synthesis Example of Compound A2-2-7

The compound was synthesized with the same method as for Compound A2-2-3 using diethylene glycol monoethyl ether instead of 2-ethylhexanol.

Synthesis Example of Compound A2-2-10

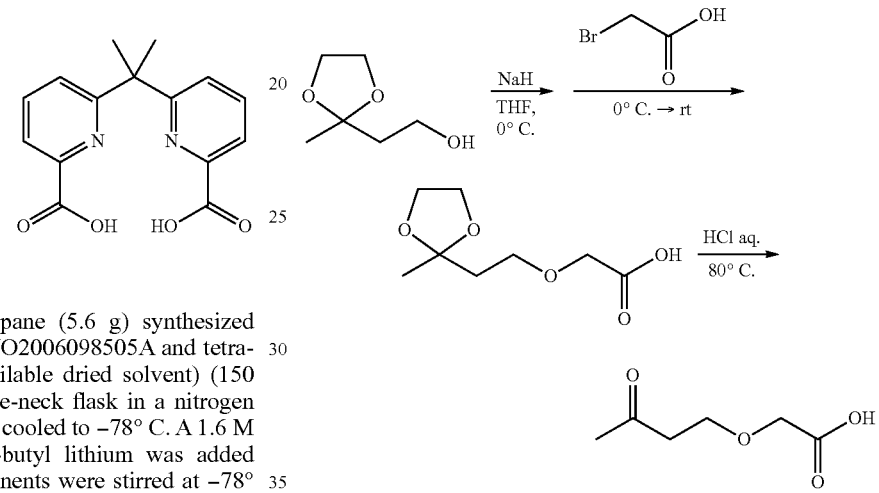

A product obtained by reacting 2-(2-methyl-1,3-dioxan-2-yl)ethanol synthesized using the method described in J. Org. Chem. 1989, 54, 3625 with bromoacetic acid using the same method as for Compound A2-2-3 was heated and refluxed at 80° C. for two hours in concentrated hydrochloric acid, thereby carrying out acetal deprotection. A deprotection reaction liquid was neutralized by being added dropwise to an aqueous solution of saturated sodium hydrogen carbonate, and an organic layer obtained through extraction and separation with ethyl acetate was concentrated, thereby obtaining Compound A2-2-10.

Synthesis Example of Compound A2-2-12

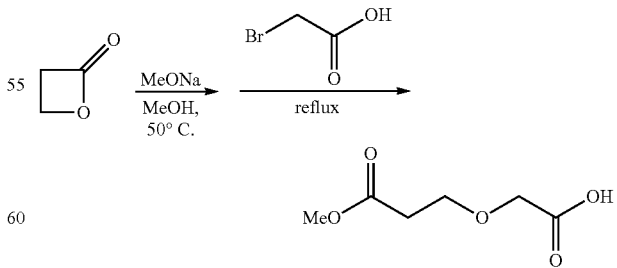

β-Propiolactone (7.2 g) and methanol (100 mL) were introduced into a three-neck flask, sodium methoxide (a 28% methanol solution) (19.3 g) was added dropwise under stirring at room temperature, and the solution was heated and refluxed at 50° C. for two hours. After the solution was cooled to room temperature, bromoacetic acid (13.9 g) was added dropwise thereto, and the solution was heated and refluxed for five hours. Saturated ammonium chloride (200 mL) and ethyl acetate (100 mL) were added thereto, and an organic layer obtained through extraction and separation was concentrated, thereby obtaining Compound A2-2-12 (12.4 g).

Synthesis Example of Compound A2-2-13

The compound was synthesized with the same method as for Compound A2-2-3 using 2,2,2-trifluoroethanol instead of 2-ethylhexanol.

Synthesis Example of Compound A2-2-18

The compound was synthesized with the same method as for Compound A2-2-3 using methyl salicylate instead of 2-ethylhexanol.

Synthesis Example of Compound A2-2-19

The compound was synthesized with the same method as for Compound A2-2-3 using tetrahydropyran-2-methanol instead of 2-ethylhexanol.

Synthesis Example of Compound A2-2-21

The compound was synthesized with the same method as for Compound A2-2-3 using tetrahydrofurfuryl alcohol instead of 2-ethylhexanol.

Synthesis Example of Compound A2-2-22

The compound was synthesized with the same method as for Compound A2-2-3 using furfuryl alcohol instead of 2-ethylhexanol.

Synthesis Example of Compound A2-2-23

The compound was synthesized with the method described in Polymer 2013, 54, 2924.

Synthesis Example of Compound A2-2-24

The compound was synthesized with the same method as for Compound A2-2-3 using 3-buten-1-ol instead of 2-ethylhexanol.

Synthesis Example of Compound A2-2-28

The compound was synthesized with the same method as for Compound A2-2-3 using 1,6-heptadien-4-ol instead of 2-ethylhexanol.

Synthesis Example of Compound A2-2-29

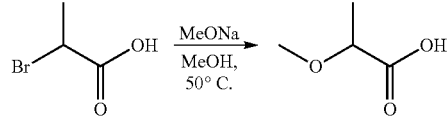

2-Bromopropionate (15.3 g) and methanol (100 mL) were introduced into a three-neck flask, sodium methoxide (28% methanol solution) (19.3 g) was added dropwise thereto under stirring at room temperature, and the solution was heated and refluxed at 50° C. for 12 hours. The reaction liquid was concentrated at a reduced pressure, 1 N diluted hydrochloric acid (100 mL) and ethyl acetate (100 mL) were added thereto, and an organic layer obtained through extraction and separation was concentrated, thereby obtaining Compound A2-2-29 (10.4 g).

Synthesis Example of Compound A2-2-31

The compound was synthesized with the method described in J. Am. Chem. Soc. 1948, 70, 1157.

Synthesis Example of Compound A2-2-34

The compound was synthesized with the same method as for Compound A2-2-29 using bromofluoroacetate synthesized using the method described in J. Org. Chem. 1957, 23, 1785 instead of DL-2-bromopropionic acid.

Synthesis Example of Compound A2-2-36

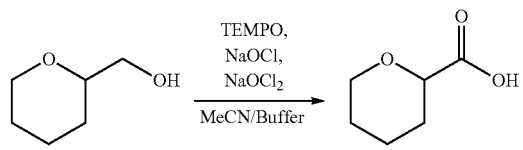 [SMILES: OCC1CCCCO1 ; O=C(O)C1CCCCO1]

Tetrahydropyran-2-methanol (25.0 g) and acetonitrile (375 g) were introduced into a three-neck flask in a nitrogen atmosphere, and 2,2,6,6-tetramethylpiperidine 1-oxyl (TEMPO) (2.4 g), a phosphoric acid buffer with a pH of 6.8 (375 g), and sodium chlorite (38.9 g) were introduced thereinto in this order under stirring at room temperature. After an aqueous solution of 4% by mass sodium chlorite (200.3 g) was slowly added dropwise, the components were stirred at 40° C. for six hours. After the reaction liquid was cooled to room temperature, an aqueous solution of saturated sodium hydrogen carbonate (700 mL) and sodium sulfite (68 g) were introduced thereinto. The reaction liquid was washed with ethyl acetate three times (400 mL, 300 mL, and 300 mL), and concentrated hydrochloric acid was slowly added thereto until the pH reached 2 or lower. An organic layer obtained through extraction and separation three times (300 mL×3) with ethyl acetate was washed with water (300 mL) and then with an aqueous solution of saturated sodium chloride (300 mL), and the organic layer was concentrated at a reduced pressure, thereby obtaining a compound A2-2-36 (22.3 g).

Synthesis Example of Compound A2-2-40

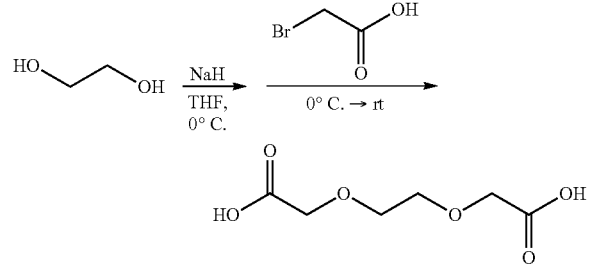

Ethylene glycol (12.4 g) and tetrahydrofuran (a commercially available dried solvent) (200 mL) were introduced into a three-neck flask in a nitrogen atmosphere, and the solution was cooled to 0° C. Sodium hydride (60% dispersion) (16.0 g) was introduced thereinto, and the components were stirred at 0° C. for 30 minutes. Bromoacetic acid (55.6 g) was added dropwise thereto, and the components were stirred at room temperature for five hours. Saturated ammonium chloride (200 mL) and ethyl acetate (100 mL) were added thereto, and an organic layer obtained through extraction and separation was concentrated, thereby obtaining Compound A2-2-40 (32.4 g).

Synthesis Example of Compound A2-2-41

The compound was synthesized with the same method as for Compound A2-2-40 using diethylene glycol instead of ethylene glycol.

Synthesis Example of Compound A2-2-42

The compound was synthesized with the same method as for Compound A2-2-40 using 2,2-diethyl-1,3-propanediol instead of ethylene glycol.

Synthesis Example of Compound A2-2-44

The compound was synthesized with the same method as for Compound A2-2-40 using cis-1,2,-cyclohexanediol instead of ethylene glycol.

Synthesis Example of Compound A2-2-45
The compound was synthesized with the same method as for Compound A2-2-40 using catechol instead of ethylene glycol.
In the present examples, the following abbreviations were employed.
<Compound (A)>
Compounds A2-1-1 to A2-1-22 represent Compounds A2-1-1 to A2-1-22 described above.
Compounds A2-2-1 to A2-2-45 represent the following compounds.
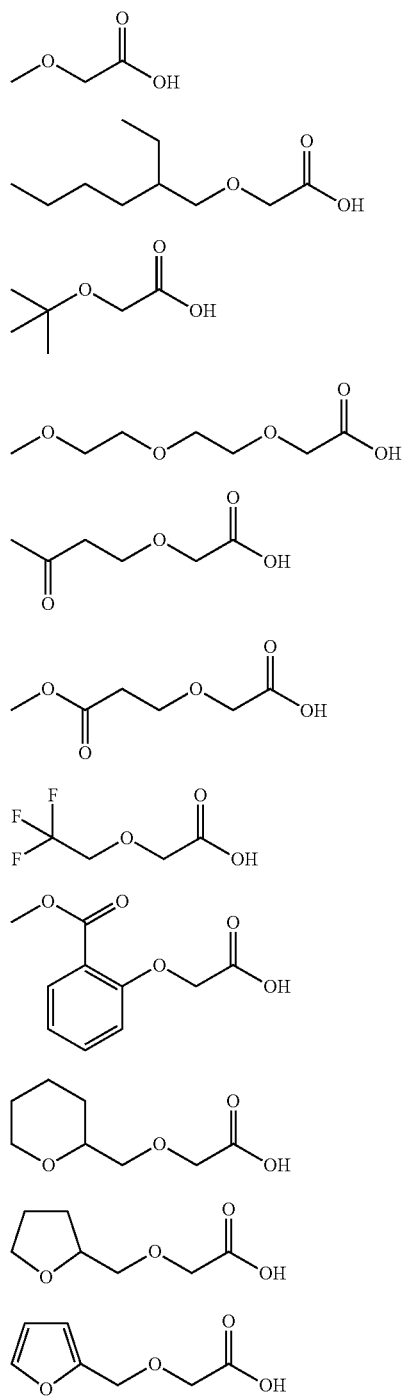
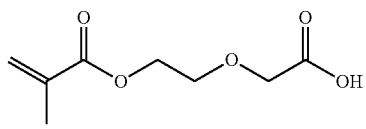
(A2-2-23)
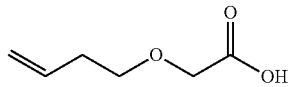
(A2-2-24)
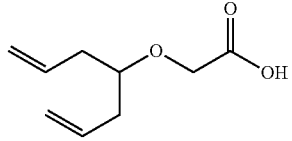
(A2-2-28)
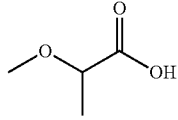
(A2-2-29)
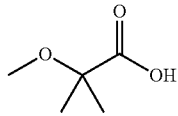
(A2-2-31)
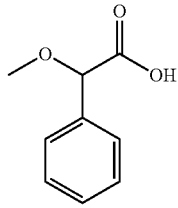
(A2-2-33)
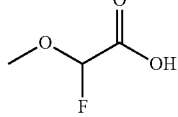
(A2-2-34)
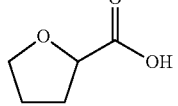
(A2-2-35)
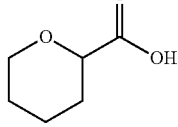
(A2-2-36)
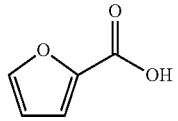
(A2-2-37)
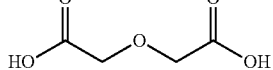
(A2-2-39)

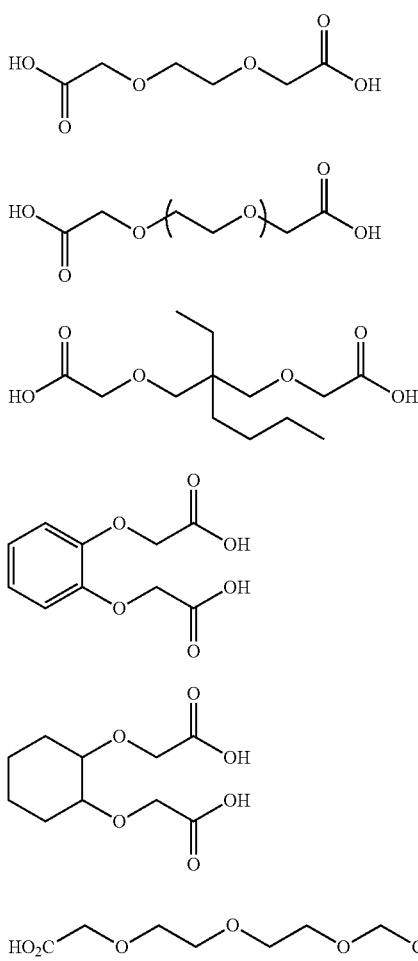

(Synthesis of Copper Complex A2-2-30)

A sodium salt (1.00 g, 4.76 mmol) of Compound A2-2-3 was dissolved in methanol (20 ml), the solution was heated at 50° C., and then a methanol solution (20 ml) of copper sulfate pentahydrate (0.73 g, 2.92 mmol) was added dropwise thereto. After the reaction liquid was heated at 50° C. for one hour, the reaction liquid was cooled to 5° C. in an ice water bath, and the reaction liquid was filtered. The filtrate was concentrated using an evaporator, thereby obtaining Copper Complex A2-2-30 (1.14 g).

<Evaluation of Near-infrared-ray-absorbing Composition>

<<Preparation of Near-infrared-ray-absorbing Composition>>

(Example A2-1-1)

The following compounds were mixed together, thereby preparing a near-infrared-ray-absorbing composition of Example A2-1-1.

| Copper Complex A2-1-1 | 20 parts by mass |
| KAYARAD DPHA | 20 parts by mass |
| JER157S65 | 20 parts by mass |
| PGMEA | 120 parts by mass |

Near-infrared-ray-absorbing compositions of individual examples and individual comparative examples were prepared by producing the same composition as that of Example A2-1-1 except for the fact that Copper Complex A2-1-1 was changed to Copper Complexes A2-1-2 to A2-1-35.

(Example A2-2-1)

The following compounds were mixed together, thereby preparing a near-infrared-ray-absorbing composition of Example A2-2-1.

| Copper Complex A2-2-1 | 20 parts by mass |
| KAYARAD DPHA | 20 parts by mass |
| JER157S65 | 20 parts by mass |
| PGMEA | 120 parts by mass |

Near-infrared-ray-absorbing compositions of individual examples and individual comparative examples were prepared by producing the same composition as that of Example A2-2-1 except for the fact that Copper Complex A2-2-1 was changed to Copper Complexes A2-2-2 to A2-2-30 or copper acetate.

<<Production of Near-infrared-ray Cut Filter>>

A near-infrared-ray cut filter was produced in the same manner as in the first example.

<<Evaluation of Near-infrared Shielding Properties>>

The near-infrared shielding properties were evaluated on the basis of the same evaluation standards as in the evaluation of the near-infrared shielding properties in the first example.

<<Evaluation of Heat Resistance>>

The near-infrared-ray cut filters obtained as described above were left to stand at 200° C. for 5 minutes. The maximum absorbance (Absλmax) at a wavelength of 700 nm to 1400 nm and the minimum absorbance (Absλmin) at a wavelength of 400 nm to 700 nm were measured using a spectrophotometer U-4100 (manufactured by Hitachi High-Technologies Corporation) respectively before and after the heat resistance test and the absorbance ratios represented by "Absλmax/Absλmin" were obtained.

<Synthesis of Copper Complex>

(Synthesis of Copper Complex A2-1-1)

Compound A2-1-1 (886 mg, 2.47 mmol) was dissolved in methanol (20 ml). After this solution was heated at 50° C., a methanol solution (160 ml) of copper hydroxide (449 mg, 2.47 mmol) was added dropwise thereto, and the components were reacted at 50° C. for two hours. After the end of the reaction, the generated water and a solvent were distilled away using an evaporator, thereby obtaining Copper Complex A2-1-1 (1.00 g).

(Syntheses of Copper Complexes A2-1-2 to A2-1-36)

Copper Complexes A2-1-2 to A2-1-36 were obtained with the method according to the synthesis method for Copper Complex A2-1-1.

(Synthesis of Copper Complex A2-2-1)

A sodium salt (814 mg, 2.97 mmol) of Compound A2-2-1 was dissolved in water (50 ml). After this solution was heated at 50° C., an aqueous solution (50 ml) of copper sulfate pentahydrate (739 mg, 2.97 mmol) was added dropwise thereto, and the components were reacted at 50° C. for two hours. After the end of the reaction, the reaction liquid was cooled to room temperature, and the precipitated solid was recovered through filtration, thereby obtaining a Copper Complex A2-2-1 (1.00 g).

(Syntheses of Copper Complexes A2-2-2 to A2-2-29)

Copper Complexes A2-2-2 to A2-2-29 were obtained with the method according to the synthesis method for Copper Complex A2-2-1.

The rates of absorbance ratio change represented by |(the absorbance ratio before the test−the absorbance ratio after the test)/the absorbance ratio before the test×100|(%) were evaluated on the basis of the following standards. The results are described in the following tables.

A: rate of absorbance ratio change≤2%
B: 2%<rate of absorbance ratio change≤4%
C: 4%<rate of absorbance ratio change≤7%
D: 7%<rate of absorbance ratio change

TABLE 14

| | Compound (A2) | | | | | Copper component | Copper complex | Ratio between Compound (A) and copper | Near-infrared shielding properties | Heat resistance |
|---|---|---|---|---|---|---|---|---|---|---|
| | Compound (A2)-1 | Compound (A2)-2 | Compound (A2)-3 | Compound (A2)-4 | 1:2:3:4 | | | | | |
| Example A2-1-1 | A2-1-1 | — | — | — | 1:0:0:0 | Copper sulfate | A2-1-1 | 2:1 | A | A |
| Example A2-1-2 | A2-1-2 | — | — | — | 1:0:0:0 | Copper sulfate | A2-1-2 | 2:1 | A | A |
| Example A2-1-3 | A2-1-3 | — | — | — | 1:0:0:0 | Copper sulfate | A2-1-3 | 2:1 | A | B |
| Example A2-1-4 | A2-1-4 | — | — | — | 1:0:0:0 | Copper sulfate | A2-1-4 | 2:1 | A | B |
| Example A2-1-5 | A2-1-5 | — | — | — | 1:0:0:0 | Copper sulfate | A2-1-5 | 2:1 | A | B |
| Example A2-1-6 | A2-1-6 | — | — | — | 1:0:0:0 | Copper sulfate | A2-1-6 | 2:1 | A | B |
| Example A2-1-7 | A2-1-7 | — | — | — | 1:0:0:0 | Copper sulfate | A2-1-7 | 2:1 | A | B |
| Example A2-1-8 | A2-1-8 | — | — | — | 1:0:0:0 | Copper sulfate | A2-1-8 | 2:1 | A | A |
| Example A2-1-9 | A2-1-9 | — | — | — | 1:0:0:0 | Copper sulfate | A2-1-9 | 2:1 | A | B |
| Example A2-1-10 | A2-1-10 | — | — | — | 1:0:0:0 | Copper sulfate | A2-1-10 | 2:1 | A | A |
| Example A2-1-11 | A2-1-11 | — | — | — | 1:0:0:0 | Copper sulfate | A2-1-11 | 2:1 | A | B |
| Example A2-1-12 | A2-1-12 | — | — | — | 1:0:0:0 | Copper sulfate | A2-1-12 | 2:1 | A | B |
| Example A2-1-13 | A2-1-13 | — | — | — | 1:0:0:0 | Copper sulfate | A2-1-13 | 2:1 | A | B |
| Example A2-1-14 | A2-1-14 | — | — | — | 1:0:0:0 | Copper sulfate | A2-1-14 | 2:1 | A | B |
| Example A2-1-15 | A2-1-15 | — | — | — | 1:0:0:0 | Copper sulfate | A2-1-15 | 2:1 | A | B |
| Example A2-1-16 | A2-1-16 | — | — | — | 1:0:0:0 | Copper sulfate | A2-1-16 | 2:1 | A | A |
| Example A2-1-17 | A2-1-17 | — | — | — | 1:0:0:0 | Copper sulfate | A2-1-17 | 2:1 | A | A |
| Example A2-1-18 | A2-1-18 | — | — | — | 1:0:0:0 | Copper sulfate | A2-1-18 | 2:1 | A | B |
| Example A2-1-19 | A2-1-19 | — | — | — | 1:0:0:0 | Copper sulfate | A2-1-19 | 2:1 | A | B |
| Example A2-1-20 | A2-1-1 | — | — | — | 1:0:0:0 | Copper sulfate | A2-1-20 | 1:2 | A | A |
| Example A2-1-21 | A2-1-1 | — | — | — | 1:0:0:0 | Copper sulfate | A2-1-21 | 1:1 | A | A |
| Example A2-1-22 | A2-1-1 | — | — | — | 1:0:0:0 | Copper sulfate | A2-1-22 | 3:1 | A | B |
| Example A2-1-23 | A2-1-1 | — | — | — | 1:0:0:0 | Copper sulfate | A2-1-23 | 3:2 | A | A |
| Example A2-1-24 | A2-1-1 | A2-1-2 | — | — | 1:1:0:0 | Copper sulfate | A2-1-24 | 2:1 | A | A |
| Example A2-1-25 | A2-1-1 | A2-1-2 | — | — | 1:2:0:0 | Copper sulfate | A2-1-25 | 2:1 | A | B |
| Example A2-1-26 | A2-1-1 | A2-1-2 | — | — | 2:1:0:0 | Copper sulfate | A2-1-26 | 2:1 | A | B |
| Example A2-1-27 | A2-1-1 | A2-1-2 | A2-1-10 | — | 1:1:1:0 | Copper sulfate | A2-1-27 | 2:1 | A | A |
| Example A2-1-28 | A2-1-1 | A2-1-2 | A2-1-10 | A2-1-18 | 1:1:1:1 | Copper sulfate | A2-1-28 | 2:1 | A | B |
| Example A2-1-29 | A2-1-1 | A2-1-2 | A2-1-10 | A2-1-18 | 1:1:1:3 | Copper sulfate | A2-1-29 | 2:1 | A | B |
| Example A2-1-30 | A2-1-1 | — | — | — | 1:0:0:0 | Copper acetate | A2-1-30 | 2:1 | A | A |
| Example A2-1-31 | A2-1-1 | — | — | — | 1:0:0:0 | Copper hydroxide | A2-1-31 | 2:1 | A | A |
| Example A2-1-32 | A2-1-1 | — | — | — | 1:0:0:0 | Copper chloride | A2-1-32 | 2:1 | A | A |
| Example A2-1-33 | A2-1-1 | — | — | — | 1:0:0:0 | Copper nitrate | A2-1-33 | 2:1 | A | A |

TABLE 14-continued

| | Compound (A2) | | | | | Copper component | Copper complex | Ratio between Compound (A) and copper | Near-infrared shielding properties | Heat resistance |
|---|---|---|---|---|---|---|---|---|---|---|
| | Compound (A2)-1 | Compound (A2)-2 | Compound (A2)-3 | Compound (A2)-4 | 1:2:3:4 | | | | | |
| Example A2-1-34 | A2-1-20 | — | — | — | 1:0:0:0 | Copper sulfate | A2-1-34 | 2:1 | B | B |
| Example A2-1-35 | A2-1-21 | — | — | — | 1:0:0:0 | Copper sulfate | A2-1-35 | 2:1 | B | B |
| Example A2-1-36 | A2-1-22 | — | — | — | 1:0:0:0 | Copper sulfate | A2-1-36 | 2:1 | A | A |

TABLE 15

| | Compound (A2) or salt thereof | Copper component | Copper complex | Near-infrared shielding properties |
|---|---|---|---|---|
| Example A2-2-1 | A2-2-1 | Copper hydroxide | A2-2-1 | A |
| Example A2-2-2 | A2-2-3 | Copper hydroxide | A2-2-2 | B |
| Example A2-2-3 | A2-2-4 | Copper hydroxide | A2-2-3 | B |
| Example A2-2-4 | A2-2-7 | Copper hydroxide | A2-2-4 | B |
| Example A2-2-5 | A2-2-10 | Copper hydroxide | A2-2-5 | B |
| Example A2-2-6 | A2-2-12 | Copper hydroxide | A2-2-6 | B |
| Example A2-2-7 | A2-2-13 | Copper hydroxide | A2-2-7 | B |
| Example A2-2-8 | A2-2-18 | Copper hydroxide | A2-2-8 | B |
| Example A2-2-9 | A2-2-19 | Copper hydroxide | A2-2-9 | B |
| Example A2-2-10 | A2-2-21 | Copper hydroxide | A2-2-10 | B |
| Example A2-2-11 | A2-2-22 | Copper hydroxide | A2-2-11 | B |
| Example A2-2-12 | A2-2-23 | Copper hydroxide | A2-2-12 | B |
| Example A2-2-13 | A2-2-24 | Copper hydroxide | A2-2-13 | B |
| Example A2-2-14 | A2-2-28 | Copper hydroxide | A2-2-14 | B |
| Example A2-2-15 | A2-2-29 | Copper hydroxide | A2-2-15 | A |
| Example A2-2-16 | A2-2-31 | Copper hydroxide | A2-2-16 | A |
| Example A2-2-17 | A2-2-33 | Copper hydroxide | A2-2-17 | B |
| Example A2-2-18 | A2-2-34 | Copper hydroxide | A2-2-18 | A |
| Example A2-2-19 | A2-2-35 | Copper hydroxide | A2-2-19 | A |
| Example A2-2-20 | A2-2-36 | Copper hydroxide | A2-2-20 | A |
| Example A2-2-21 | A2-2-37 | Copper hydroxide | A2-2-21 | B |
| Example A2-2-22 | A2-2-40 | Copper hydroxide | A2-2-22 | A |
| Example A2-2-23 | A2-2-41 | Copper hydroxide | A2-2-23 | B |
| Example A2-2-24 | A2-2-42 | Copper hydroxide | A2-2-24 | A |
| Example A2-2-25 | A2-2-44 | Copper hydroxide | A2-2-25 | A |
| Example A2-2-26 | A2-2-39 | Copper hydroxide | A2-2-26 | B |
| Example A2-2-27 | A2-2-43 | Copper hydroxide | A2-2-27 | B |
| Example A2-2-28 | A2-2-45 | Copper hydroxide | A2-2-28 | A |
| Example A2-2-29 | A2-2-3 | Copper acetate | A2-2-29 | B |
| Example A2-2-30 | Na salt of A2-2-3 | Copper sulfate | A2-2-30 | B |
| Comparative Example A2-2-1 | Copper acetate | — | — | B |

As is clear from the tables shown above, it was found that the near-infrared-ray-absorbing compositions of the examples were capable of enhancing shielding properties in the near-infrared range when a cured film was produced. Furthermore, it was found that the near-infrared-ray cut filters of the examples all had a transmissivity of 80% or higher at a wavelength of 550 nm and were capable of enhancing the transmissivity in the visible light range and the shielding properties in the near-infrared range. In addition, it was also found that the near-infrared-ray cut filters of the examples were capable of ensuring a wide visible light range with a high transmissivity and had excellent spectral characteristics.

On the other hand, it was found that, in the near-infrared-ray-absorbing compositions of the comparative examples, compared with the examples, it was difficult to satisfy both the transmissivity in the visible light range and the shielding properties in the near-infrared range when a cured film was produced.

In addition, the near-infrared-ray cut filters can be obtained in the same manner as those in Examples A2-1-1 to A2-2-30 except for the fact that 20 parts by mass of the polymerizing compound (KAYARAD DPHA) was changed to the equivalent amount of KAYARAD D-320, M-510, M-520, or DPCA-60 in the near-infrared-ray-absorbing compositions of Examples A2-1-1 to A2-2-30. In these near-infrared-ray cut filters as well, it is possible to increase the transmissivity in the visible light range and enhance the shielding properties in the near-infrared range when a cured film is produced.

In addition, the near-infrared-ray cut filters can be obtained in the same manner as those in Examples A2-1-1 to A2-2-30 except for the fact that 20 parts by mass of the polymerizing compound (KAYARAD DPHA) was changed to the equivalent amount of KAYARAD D-310, D-330, DPCA-20, DPCA-30, DPCA-120 (all manufactured by manufactured by Nippon Kayaku Co., Ltd.), M-305, M-460 (manufactured by Toagosei Co., Ltd.), A-TMMT (manufactured by Shin-Nakamura Chemical Co., Ltd.), SR-494 (manufactured by Sartomer Americas), DENACOL EX-212L (manufactured by Nagase ChemteX Corporation), or JER-157S65 (manufactured by Mitsubishi Chemical Corporation) in the near-infrared-ray-absorbing compositions of Examples A2-1-1 to A2-2-30. In these near-infrared-ray cut filters as well, excellent effects can be obtained in the same manner as in the near-infrared-ray cut filter of Example A2-1-1.

In addition, even in a case in which the content of Copper Complex A2-1-1 in relation to the total solid content of the composition was changed to 15% by mass, 20% by mass, 30% by mass, or 40% by mass in the near-infrared-ray-absorbing compositions of Examples A2-1-1 to A2-2-30, excellent near-infrared shielding performance can be obtained in the same manner as in that copper complex.

In addition, even in a case in which the content of the solvent (PGMEA) was set to 10% by mass, 20% by mass, 30% by mass, or 40% by mass in the near-infrared-ray-absorbing compositions of Examples A2-1-1 to A2-2-30, excellent coatability can be obtained in the same manner as in the near-infrared-ray-absorbing composition of Example A2-1-1.

Third Example

In the present examples, the following abbreviations will be employed.

<Compound (A)>
Compounds A3-1 to A3-10

A3-1 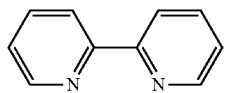

A3-2 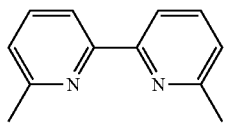

A3-3 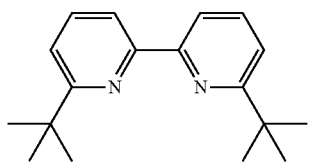

A3-4 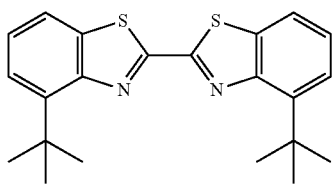

A3-5 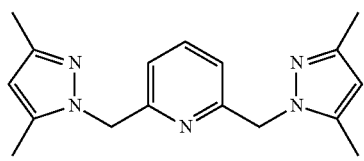

A3-6 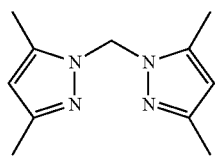

A3-7 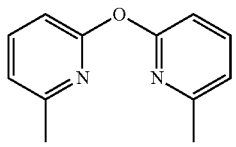

A3-8 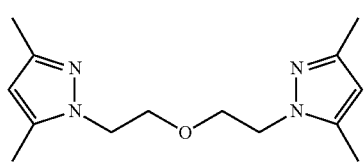

A3-9 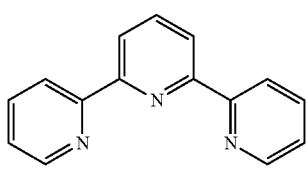

-continued

A3-10 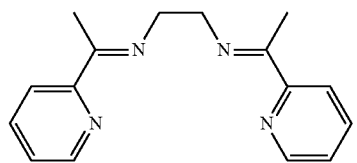

<Compounds A3-1 to A3-10>

Compound A3-1: 2,2'-bipyridyl, manufactured by Tokyo Chemical Industry Co., Ltd. Compound A3-2: 6,6'-dimethyl-2,2'-bipyridyl, manufactured by Tokyo Chemical Industry Co., Ltd.

Compound A3-3 was synthesized using the method described in Angewandte Chemie-International Edition, 2008, 47, 8246 to 8250.

Compound A3-4 was synthesized using the method described in HELVETICA CHMICA ACTA, 2000, 83, 1161 to 1167.

Compound A3-5 was synthesized using the method described in Journal of Organometallic Chemistry, 2009, 694, 2636 to 2641.

Compound A3-6 was synthesized using the method described in POLYHEDRON, 2008, 27, 1432 to 1446.

Compound A3-7 was synthesized as described below.

2-Bromo-6-methylpyridine (10 g, 58.1 mol) manufactured by Tokyo Chemical Industry Co., Ltd., 2-hydroxy-6-methyl pyridine (7.6 g, 69.8 mmol) manufactured by Tokyo Chemical Industry Co., Ltd., tetramethylethylenediamine (1.02 g, 8.72 mmol) manufactured by Tokyo Chemical Industry Co., Ltd., potassium carbonate (16.0 g, 116.3 mmol) manufactured by Wako Pure Chemical Industries, Ltd., and copper iodide (0.56 g, 2.91 mmol) manufactured by Wako Pure Chemical Industries, Ltd. were heated and refluxed in DMF (200 mL) for 12 hours. Water was added thereto, and extraction using ethyl acetate, washing with water, and dehydration of magnesium sulfate were carried out. After concentration, column-purification was carried out, and a target substance (4.0 g) was obtained.

400 MHz (CDCl$_3$, 7.60 (2H, t), 6.94 (2H, d), 6.83 (2H, d), 1.59 (6H, s))

Compound A3-8 was synthesized using the method described in European Journal of Organic Chemistry, 2007, 30, 5112 to 5116.

Compound A3-9: α,α',α''-tripyridyl manufactured by Tokyo Chemical Industry Co., Ltd.

Compound A3-10 was synthesized using the method described in European Journal of Inorganic Chemistry, 2004, 12, 2533 to 2541.

<Synthesis Example of Copper Component>

Copper methane sulfonate was synthesized by reacting methanesulfonic acid (0.1 g, 2.05 mmol) and copper hydroxide (0.197 g, 1.03 mmol) in ethanol at 70° C. for 0.5 hours.

Copper diphenylphosphate was synthesized by reacting diphenylphosphoric acid (0.5 g, 2.29 mmol) and copper acetate (0.21 g, 1.15 mmol) in ethanol at 70° C. for 0.5 hours.

<Synthesis of Copper Complex>

(Synthesis of Copper Complex A3-1)

Compound A3-1 (0.2 g, 1.1 mmol) was dissolved in ethanol (5 ml). After this solution was heated at 70° C., an ethanol solution (5 ml) of copper acetate (0.2 g, 1.1 mmol) was added dropwise, and the components were reacted with each other at 70° C. for two hours. After the end of the reaction, the generated water and a solvent were distilled away using an evaporator, thereby obtaining Copper Complex A3-1 (0.6 g).

Copper Complexes A3-2 to A3-17 were obtained in the same manner as Copper Complex A3-1 except for the fact that the compound (A) or the copper component were changed as shown in the following table.

<<Production of Near-infrared-ray Cut Filter>>

A near-infrared-ray cut filter was produced in the same manner as in the first example.

<<Evaluation of Near-infrared Shielding Properties>>

The near-infrared shielding properties were evaluated on the basis of the same evaluation standards as in the evaluation of the near-infrared shielding properties in the first example.

<<Evaluation of Heat Resistance>>

The heat resistance was evaluated on the basis of the same evaluation standards as in the evaluation of the heat resistance in the second example.

TABLE 16

|  | Compound (A3) | Copper component | Copper complex | Molar ratio between Compound (A3) and copper compound | Near-infrared shielding properties | Heat resistance |
| --- | --- | --- | --- | --- | --- | --- |
| Example A3-1 | A3-1 | Copper acetate | A3-1 | 1:1 | A | B |
| Example A3-2 | A3-1 | Copper acetate | A3-2 | 2:1 | B | B |
| Example A3-3 | A3-1 | Copper chloride | A3-3 | 1:1 | B | A |
| Example A3-4 | A3-1 | Copper phosphinate | A3-4 | 1:1 | A | A |
| Example A3-5 | A3-1 | Copper diphenylphosphate | A3-5 | 1:1 | A | B |
| Example A3-6 | A3-1 | Copper methane sulfonate | A3-6 | 1:1 | A | A |
| Example A3-7 | A3-2 | Copper methane sulfonate | A3-7 | 1:1 | A | A |
| Example A3-8 | A3-3 | Copper methane sulfonate | A3-8 | 1:1 | A | A |
| Example A3-9 | A3-4 | Copper methane sulfonate | A3-9 | 1:1 | A | A |
| Example A3-10 | A3-5 | Copper methane sulfonate | A3-10 | 1:1 | B | B |
| Example A3-11 | A3-6 | Copper methane sulfonate | A3-11 | 1:1 | A | A |
| Example A3-12 | A3-7 | Copper methane sulfonate | A3-12 | 1:1 | A | A |
| Example A3-13 | A3-8 | Copper methane sulfonate | A3-13 | 1:1 | B | B |
| Example A3-14 | A3-9 | Copper methane sulfonate | A3-14 | 1:1 | B | B |
| Example A3-15 | A3-10 | Copper methane sulfonate | A3-15 | 1:1 | B | B |
| Comparative Example A3-1 | — | Copper acetate | A3-16 | — | C | B |
| Comparative Example A3-2 | — | Copper chloride | A3-17 | — | C | A |

<Evaluation of Near-infrared-ray-absorbing Composition>

<<Preparation of Near-infrared-ray-absorbing Composition>>

(Example A3-1)

The following compounds were mixed together, thereby preparing a near-infrared-ray-absorbing composition of Example 1.

| Copper Complex A3-1 | 20 parts by mass |
| --- | --- |
| KAYARAD DPHA | 20 parts by mass |
| JER157S65 | 20 parts by mass |
| PGMEA | 120 parts by mass |

Near-infrared-ray-absorbing compositions of individual examples and individual comparative examples were prepared by producing the same composition as that of Example A3-1 except for the fact that Copper Complex A3-1 was changed to Copper Complexes A3-2 to A3-17.

As is clear from the tables shown above, it was found that the near-infrared-ray-absorbing compositions of the examples were capable of enhancing shielding properties in the near-infrared range even when a cured film was produced. Furthermore, it was found that the near-infrared-ray cut filters of the examples all had a transmissivity of 80% or higher at a wavelength of 550 nm and were capable of enhancing the transmissivity in the visible light range and the shielding properties in the near-infrared range. In addition, it was also found that the near-infrared-ray cut filters of the examples were capable of ensuring a wide visible light range with a high transmissivity and had excellent spectral characteristics.

On the other hand, it was found that, in the near-infrared-ray-absorbing compositions of the comparative examples, the shielding properties in the near-infrared range were insufficient when a cured film was produced.

In addition, the near-infrared-ray cut filters can be obtained in the same manner as those in Examples A3-1 to A3-15 except for the fact that 20 parts by mass of the polymerizing compound (KAYARAD DPHA) was changed to the equivalent amount of KAYARAD D-320, M-510, M-520, or DPCA-60 in the near-infrared-ray-absorbing compositions of Examples A3-1 to A3-15. In these near-infrared-ray cut filters as well, it is possible to enhance the shielding properties in the near-infrared range when a cured film is produced.

In addition, the near-infrared-ray cut filters can be obtained in the same manner as those in Examples A3-1 to A3-15 except for the fact that 20 parts by mass of the polymerizing compound (KAYARAD DPHA) was changed to the equivalent amount of KAYARAD D-310, D-330, DPCA-20, DPCA-30, DPCA-120 (all manufactured by Nippon Kayaku Co., Ltd.), M-305, M-460 (manufactured by Toagosei Co., Ltd.), A-TMMT (manufactured by Shin-Nakamura Chemical Co., Ltd.), SR-494 (manufactured by Sartomer Americas), DENACOL EX-212L (manufactured by Nagase ChemteX Corporation), or JER-157S65 (manufactured by Mitsubishi Chemical Corporation) in the near-infrared-ray-absorbing compositions of Examples A3-1 to A3-15. In these near-infrared-ray cut filters as well, excellent effects can be obtained in the same manner as in the near-infrared-ray cut filter of Example A3-1.

In addition, even in a case in which the content of Copper Complex A3-1 in relation to the total solid content of the composition was changed to 15% by mass, 20% by mass, 30% by mass, or 40% by mass in the near-infrared-ray-absorbing compositions of Examples A3-1 to A3-15, excellent near-infrared shielding performance can be obtained in the same manner as in the near-infrared-ray cut filter of Example A3-1.

In addition, even in a case in which the content of the solvent (PGMEA) was set to 10% by mass, 20% by mass, 30% by mass, or 40% by mass in the near-infrared-ray-absorbing compositions of Examples A3-1 to A3-15, excellent coatability can be obtained in the same manner as in the near-infrared-ray-absorbing composition of Example A3-1.

EXPLANATION OF REFERENCES

10: camera module
11: solid-state imaging element
12: flattening layer
13: near-infrared-ray cut filter
14: imaging lens
15: lens holder
16: imaging element unit
17: color filter
18: micro lens
19: ultraviolet and infrared light-reflecting film
20: transparent base material
21: near-infrared-ray-absorbing layer
22: antireflection layer

What is claimed is:

1. A near-infrared-ray-absorbing composition comprising:
a copper complex obtained by reacting a compound (A) having at least two coordination sites with a copper component, wherein the compound (A) is a compound (A3) having three or more coordinating atoms to be coordinated with an unshared electron pair and the coordinating atoms are nitrogen atoms; and wherein the composition further comprises a curable compound which contains at least one of a trifunctional or higher acrylate, a trifunctional or higher methacrylate, and a trifunctional or higher epoxy resin.

2. The near-infrared-ray-absorbing composition according to claim 1, further comprising:
a curable compound and a solvent.

3. A near-infrared-ray-absorbing composition comprising:
a curable compound, a solvent, and a copper complex obtained by reacting a compound (A) having at least two coordination sites with a copper component, wherein the compound (A) is a compound (A3) having three or more coordinating atoms to be coordinated with an unshared electron pair and the coordinating atoms are nitrogen atoms,
wherein the curable compound is at least one of a trifunctional or higher acrylate, a trifunctional or higher methacrylate, and a trifunctional or higher epoxy resin.

4. A near-infrared-ray cut filter obtained using the near-infrared-ray-absorbing composition according to claim 1.

5. A method for manufacturing a near-infrared-ray cut filter, comprising:
forming a film by applying the near-infrared-ray-absorbing composition according to claim 1 to a light-receiving side of a solid-state imaging element.

6. A camera module comprising:
a solid-state imaging element; and
a near-infrared-ray cut filter disposed in a light-receiving side of the solid-state imaging element,
wherein the near-infrared-ray cut filter is formed by curing the near-infrared-ray-absorbing composition according to claim 1.

7. A method for manufacturing a camera module having a solid-state imaging element and a near-infrared-ray cut filter disposed in a light-receiving side of the solid-state imaging element, the method comprising:
forming the near-infrared-ray cut filter by applying the near-infrared-ray-absorbing composition according to claim 1 to the light-receiving side of the solid-state imaging element.

8. A near-infrared-ray-absorbing composition comprising:
a copper complex obtained by reacting a compound (A) having at least two coordination sites with a copper component, wherein the compound (A) is a compound (A3) having three or more coordinating atoms to be coordinated with an unshared electron pair and the coordinating atoms are nitrogen atoms, and wherein the near-infrared-ray-absorbing composition further comprises a curable compound which contains a compound having a trifunctional or higher epoxy group or an oxetanyl group.

9. The near-infrared-ray-absorbing composition according to claim 1, wherein the number of atoms linking the coordinating atoms to be coordinated with an unshared electron pair is in a range of 3 to 6.

10. The near-infrared-ray-absorbing composition according to claim 1, wherein the number of atoms linking the coordinating atoms to be coordinated with an unshared electron pair is 3.

11. The near-infrared-ray-absorbing composition according to claim 1, wherein the compound (A3) is represented by the following General Formula (V):

   General Formula (V)

wherein each of $Y^1$ and $Y^2$ independently represents a ring including the coordinating nitrogen atom to be coordinated with an unshared electron pair or a partial structure selected from the following group (UE) of partial structures; and $L_1$ represents a single bond or a divalent linking group:

Group (UE)

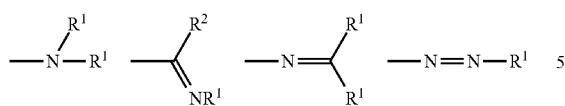

wherein each of R¹s independently represents a hydrogen atom, an alkyl group, an alkenyl group, an alkynyl group, an aryl group, or a heteroaryl group, and each of R²s independently represents a hydrogen atom, an alkyl group, an alkenyl group, an alkynyl group, an aryl group, a heteroaryl group, an alkoxy group, an aryloxy group, a heteroaryloxy group, an alkylthio group, an arylthio group, a heteroarylthio group, an amino group, or an acyl group.

12. The near-infrared-ray-absorbing composition according to claim 1, wherein the compound (A3) is represented by the following General Formula (V-1) or (V-2):

 (V-1)

 (V-2)

wherein each of $Y^3$, $Y^5$, $Y^6$, and $Y^9$ independently represents a ring including the coordinating nitrogen atom to be coordinated with an unshared electron pair or a partial structure selected from the following group (UE) of partial structures;

each of $Y^4$, $Y^7$, and $Y^8$ independently represents a ring including the coordinating nitrogen atom to be coordinated with an unshared electron pair or at least one group selected from following group (UE-1) of partial structures; and each of $L^2$ to $L^8$ independently represents a single bond or a divalent linking group, wherein the divalent linking group is an alkylene group having 1 to 12 carbon atoms, an arylene group having 6 to 12 carbon atoms, —SO—, —O—, —SO₂— or a group formed of a combination thereof;

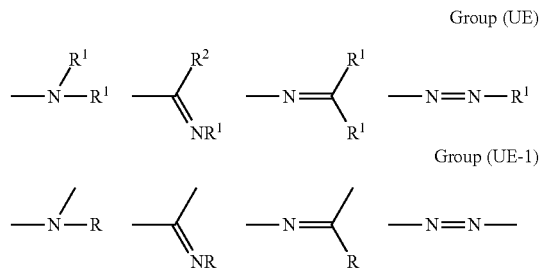

wherein in Group (UE), each of R¹s independently represents a hydrogen atom, an alkyl group, an alkenyl group, an alkynyl group, an aryl group, or a heteroaryl group, and each of R²s independently represents a hydrogen atom, an alkyl group, an alkenyl group, an alkynyl group, an aryl group, a heteroaryl group, an alkoxy group, an aryloxy group, a heteroaryloxy group, an alkylthio group, an arylthio group, a heteroarylthio group, an amino group, or an acyl group, and wherein in Group (UE-1), each of Rs independently represents a hydrogen atom, an alkyl group, an alkenyl group, an alkynyl group, an aryl group, or a heteroaryl group.

* * * * *